(12) United States Patent
Wan et al.

(10) Patent No.: US 11,130,958 B2
(45) Date of Patent: Sep. 28, 2021

(54) PLANTS HAVING INCREASED TOLERANCE TO HEAT STRESS

(71) Applicant: PERFORMANCE PLANTS, INC., Kingston (CA)

(72) Inventors: Jiangxin Wan, Bath (CA); Yafan Huang, Bath (CA); Monika M. Kuzma, Battersea (CA)

(73) Assignee: Performance Plants, Inc., Kingston (CA)

( * ) Notice: Subject to any disclaimer, the term of this patent is extended or adjusted under 35 U.S.C. 154(b) by 0 days.

(21) Appl. No.: 15/418,412

(22) Filed: Jan. 27, 2017

(65) Prior Publication Data

US 2017/0145435 A1 May 25, 2017

Related U.S. Application Data

(63) Continuation of application No. 12/148,548, filed on Apr. 18, 2008, now abandoned.

(60) Provisional application No. 60/925,312, filed on Apr. 18, 2007, provisional application No. 60/965,582, filed on Aug. 20, 2007.

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01); *C12N 15/8261* (2013.01); *C12N 15/8271* (2013.01)

(58) Field of Classification Search
None
See application file for complete search history.

(56) References Cited

U.S. PATENT DOCUMENTS

| | | | |
|---|---|---|---|
| 5,240,842 | A | 8/1993 | Mets |
| 5,349,124 | A | 9/1994 | Fischhoff et al. |
| 5,683,439 | A | 11/1997 | Jensen |
| 6,809,232 | B1 | 10/2004 | Held et al. |
| 2006/0183137 | A1 | 8/2006 | Harper et al. |
| 2009/0158466 | A1 | 6/2009 | Wan et al. |

FOREIGN PATENT DOCUMENTS

| | | | |
|---|---|---|---|
| EP | 1085684 A2 | | 3/2001 |
| WO | WO-9630530 A1 | | 10/1996 |
| WO | WO-0132002 A1 | | 5/2001 |
| WO | WO-0216655 A2 | | 2/2002 |
| WO | WO-03014327 A2 | | 2/2003 |
| WO | WO-07028165 A2 | | 3/2007 |

OTHER PUBLICATIONS

Feng et al. (Plant Science, 167:1099-1107, Published 2004).*
Kranz et al., Plant Journal, 16:263-276, 1998.*
McCarthy et al. (Plant Cell Physiol., 51:1084-1090; 2010).*
Song et al. (Nature Biotechnology, 21:914-919, 2003).*
Jako et al. (Plant Physiology, 126:861-874, 2001).*
Wu et al. (Plant Cell Physiol., 45:600-607, 2004).*
Bradeen et al. (MPMI, 22:437-446, 2009).*
Ku et al. (Nature Biotechnology, 17:76-80, 1990).*
Wang (Studies on *Arabidopsis* MYB Transcription Factor Genes: Potential Regulators of the Phenylpropanoid Pathway and Analysis of the Root Preferentially Expressed Gene AtMYB68, PhD thesis, pp. 1-122, University of British Columbia, Vancouver, Canada, Published May 14, 2003).*
Abdul-Baki A, A. "Tolerance of Tomato Cultivars and Selected Germplasm to Heat Stress", Journal of the American Society for Horticultural Science, vol. 116, No. 6, 1991, pp. 1113-1116.
An et al., "Functional Analysis of the 3' Control Region of the Potato Wound-Inducible Proteinase Inhibitor II Gene", *Plant Cell*, 1:115-122 (1989).
Angadi et al., "Response of three *Brassica* species to high temperature stress during reproductive growth", *Canadian J. Plant Sci.*, 80:693-701 (2000).
Atanassvoa et al., "A 126 bp fragment of a plant histone gene promoter confers preferential Expression in meristems of transgenic *Arabidopsis*", *Plant J.*, 2(3):291-300 (1992).
Baloch, M.J. "In vitro gametophytic selection for heat tolerance in upland cotton", Proc. Pakistan Acad. Sci., vol. 41, Apr. 16, 2007 (Apr. 16, 2007), pp. 9-15.
Bevan et al., "Structure and transcription of the nopaline synthase gene region of T-DNA", *Nucl. Acids Res.*, 12:369-385 (1983).
Bevan, M. et al., "The structure and transcription start site of a major potato tuber protein gene", *Nucl. Acids Res.*, 14:4625-4636 (1986).
Borevitz et al., "Activation Tagging Identifies a Conserved MYB Regulator of Phenylpropanoid Biosynthesis", *Plant Cell*, 12:2383-2394 (2000).
Burke et al., "Isolation of *Arabidopsis* mutants lacking components of acquired thermotolerance", *Plant Physiol.*, 123(2):575-587 (2000).
Carlson, "Heat stress, plant-available soil moisture, and corn yields in Iowa: a short and long-term view", *J. Production Agriculture*, 3:293-297 (1990).
Christensen et al., "Sequence analysis and transcriptional regulation by heat shock of polyubiquitin transcripts from maize", *Plant Mol. Biol.*, 12:619-632 (1992).

(Continued)

*Primary Examiner* — Vinod Kumar
(74) *Attorney, Agent, or Firm* — Cooley LLP; Cynthia A. Kozakiewicz; Chen Chen

(57) ABSTRACT

The invention relates to methods of producing a desired phenotype in a plant by manipulation of gene expression within the plant. The method relates to means which increase the level of expression of a MYB-subgroup14 polynucleotide or a MYB68 polypeptide. The method also relates to expression of a nucleic acid sequence encoding a MYB-subgroup14 or a MYB68 transcriptional factor. The methods are directed to elevating the levels of a MYB-subgroup14 or a MYB68 expression, wherein a desired phenotype such as reduced flower abortion and increased yield during heat stress is observed. The invention also relates to nucleic acid sequences useful in such methods.

2 Claims, No Drawings

Specification includes a Sequence Listing.

(56) References Cited

OTHER PUBLICATIONS

DeLoose et al., "The extension signal peptide allows secretion of a heterologous protein from protoplasts", Gene, 99:95-100 (1991).
Dong et al., "Functional Conservation of Plant Secondary Metabolic Enzymes Revealed by Complementation of Arabidopsis Flavonoid Mutants with Maize Genes", Plant Physiol., 127:46-47 (2001).
Dratewka-Kos et al., "Polypeptide Structure of Germin as Deduced from cDNA Sequencing", J. Biol. Chem., 264:4896-4900 (1989).
Elomaa et al., "A bHLH transcription factor mediates organ, region and flower type specific signals on dihydroflavonol-4-reductase (dfr) gene expression in the inflorescence of Gerbera hybrida (Asteraceae)", Plant J., 16(1):93-99.
Feng et al., "Arabidopsis MYB68 in development and responses to environmental cues", Plant Sci., 167:1099-1107 (2004).
Flahaut et al., "Impact of thermal variations on biochemical and physiological traits in Pectinatus sp.", Int. J. Food Microbiol., 55:53-61.
Fraley et al., "Expression of bacterial genes in plant cells", Proc. Natl. Acad. Sci. U.S.A., 80:4803-4807 (1983).
Gocal et al., "GAMYB-like Genes, Flowering, and Gibberellin Signaling in Arabidopsis", Plant Physiol., 127:1682-1693 (2001).
Goldberg, P., "Regulation of plant gene expression", Trans. R. Soc. London, B314:343-353 (1986).
Guilioni, L. et al. "Heat Stress-induced Abortion of Buds and Flowers in Pea: Is Sensitivity Linked to Organ Age or to Relations between Reproductive Organs?", Annals of Botany 80: 159-168, 1997.
Guo et al. "Plant Responses to Ethylene Gas are Mediated by SCFEBF1/EBF2-Dependent Proteolysis of EIN3 Transcription Factor." Cell. 115(2003):667-677.
Hong et al., "Mutants of Arabidopsis thaliana defective in the acquisition of tolerance to high temperature stress", Proc. Natl. Acad. Sci. U.S.A., 97(8):4392-4397 (2000).
Horsch et al., "A Simple and General Method for Transferring Genes into Plants", Science, 227:1229-1231 (1985).
Huang et al., "Identification and characterization of proteins associated with plant tolerance to heat stress", J Integrative Plant, 50(10):1230-1237 (2008).
Jin et al., "Multifunctionality and diversity within the plant MYB-gene family", Plant Mol. Biol., 41:577-585 (1999).
Kado, C.I. "Molecular Mechanisms of Crown Gall Tumorigenesis", Grit. Rev. Plant Sci., 10(1):1-32 (1991).
Kapoor et al., "Development of thermotolerance in Neurospora crassa by heat shock and other stresses eliciting peroxidase induction", J Bacteriol., 172(5):2798-2801 (1990).
Keil et al., "Primary structure of a proteinase inhibitor II gene from potato (Solanum tuberosum)", Nucl. Acids Res., 14:5641-5650 (1986).
Keller, Thomas et al. "Arabidopsis Regulator of Axillary Meristems1 controls a leaf axil stem cell niche and modulates vegetative development" Plant Cell, vol. 18, No. 3, Mar. 2006 (Mar. 2006), pp. 598-611.
Kirik et al., "Two novel MYB homologues with changed expression in late embryogenesis-defective Arabidopsis mutants", Plant Mol. Biol., 37(5):819-827 (1998).
Kranz et al., "Towards functional characterisation of the members of the R2R3-MYB gene family from Arabidopsis thaliana", Plant J., 16(2):263-276 (1998).
Larkindale et al., "Heat stress phenotypes of Arabidopsis mutants implicate multiple signaling pathways in the acquisition of thermotolerance", Plant Physiol., 138(2):882-897 (2005).
Last et al., "pEmu: an improved promoter for gene expression in cereal cells", Theor. Appl. Genet., 81:581-588 (1991).
Lepetit et al., "A plant histone gene promoter can direct both replication-dependent and -independent gene expression in transgenic plants", Mol. Gen. Genet., 231-276-285 (1992).
Liou, Susan S. C. et al. "Sorting the Heated Mess: Screening Tulip Cultivars for Sensitivity to Heat", Hortscience, vol. 39, No. 4, Jul.

2004 (Jul. 2004), p. 894, & 101st Annual Meeting of the American-Society-of Horticultural-Science; Austin, TX, USA; July 17-20, 2004.
Lobell et al., "Climate and management contributions to recent trends in U.S. agricultural yields", Science, 299:1032 (2003).
Lohar, D. P. et al. "Floral characteristics of heat-tolerant and heat-sensitive tomato (Lycopersicon esculentum Mill.) cultivars at high temperature", Scientia Horticulturae (Amsterdam), vol. 73, No. 1, Mar. 12, 1998 (Mar. 12, 1998), pp. 53-60.
Lund et al., "A plant signal sequence enhances the secretion of bacterial ChiA in transgenic tobacco", Plant Mol. Biol., 18:47-53 (1992).
Massie et al., "Exposure to the metabolic inhibitor sodium azide induces stress protein expression and thermotolerance in the nematode Caenorhabditis elegans", Cell Stress Chaperones, 8(1):1-7 (2003).
Matsuoka et al., "Propeptide of a precursor to a plant vacuolar protein required for vacuolar targeting", Proc. Natl. Acad. Sci. USA, 88:834-838 (1991).
McElroy et al., "Isolation of an Efficient Actin Promoter for Use in Rice Transformation", Plant Cell, 2:163-171 (1990).
Meissner et al., "Function Search in a Large Transcription Factor Gene Family in Arabidopsis: Assessing the Potential of Reverse Genetics to Identify Insertional Mutations in R2R3 MYB Genes", Plant Cell, 11:1827-1840 (1999).
Mogen et al.,"Upstream Sequences Other than AAUAAA Are Required for Efficient Messenger RNA 3'-End Formation in Plants", Plant Cell, 2:1261-1272 (1990).
Moloney et al., "High efficiency transformation of Brassica napus using Agrobacterium vectors", Plant Cell Reports, 8:238-242 (1989).
Muller et al., "Blind Homologous R2R3 Myb Genes Control the Pattern of Lateral Meristem Initiation in Arabidopsis", Plant Cell, 18:586-597 (2006).
Odell et al., "Identification of DNA sequences required for activity of the cauliflower mosaic virus 35S promoter", Nature, 313:810-812 (1985).
Ogata et al., "Solution structure of a DNA-binding unit of Myb: a helix-turn-helix-related motif with conserved tryptophans forming a hydrophobic core", Proc. Natl. Acad. Sci. U.S.A., 89:6428-6432 (1992).
Oppenheimer et al., "A myb gene required for leaf trichome differentiation in Arabidopsis is expressed in stipules", Cell, 67(3):483-93 (1991).
Paz-Ares et al., "The regulatory c1 locus of Zea mays encodes a protein with homology to myb proto-oncogene products and with structural similarities to transcriptional activators", EMBO J., 6(12):3553-3558 (1987).
Sanford et al., "Delivery of Substances into Cells and Tissues Using a Particle Bombardment Process", Part. Sci. Technol., 5:27-37 (1987).
Sato et al., "Moderate Increase of Mean Daily Temperature Adversely Affects Fruit Set of Lycopersicon esculentum by Disrupting Specific Physiological Processes in Male Reproductive Development", Ann. Bot., 97:731-738 (2006).
Schmitz, Gregor et al. "The tomato Blind gene encodes a MYB transcription factor that controls the formation of lateral meristems" Proceedings of the National Academy of Sciences of the United States of America, vol. 99, No. 2, Jan. 22, 2002 (Jan. 22, 2002), pp. 1064-1069.
Stepanova et al. "TAA1-Mediated Auxin Biosynthesis is Essential for Hormone Crosstalk and Plant Development." Cell. 133(2008):177-191.
Stockinger et al., "A Linkage Map of Sweet Cherry Based on RAPD Analysis of a Microspore-Derived Callus Culture Population", J. Heredity, 87:214-218 (1996).
Stracke et al., "The R2R3-MYB gene family in Arabidopsis thaliana", Curr. Opin. Biol., 4:447-456 (2001).
Takahashi et al., Plant J., 2:751-761 (1992).
Takahashi et al., "Characterization of two genes encoding small heat-shock proteins in Arabidopsis thaliana", Mol. Gen. Genet., 219:365-372 (1989).
Ueda et al., "Characterization and subcellular localization of a small GTP-binding protein (Ara-4) from Arabidopsis: conditional expres-

(56) References Cited

OTHER PUBLICATIONS sion under control of the promoter of the gene for heat-shock protein HSP81-1", *Mol. Gen. Genet.*, 250:533-539 (1996).

Van der Meer et al., "Promoter analysis of the chalcone synthase (chsA) gene of *Petunia hybrida*: a 67 bp promoter region directs flower-specific expression", *Plant Mol. Biol.*, 15(1):95-109 (1990).

Velten et al., "Isolation of a dual plant promoter fragment from the Ti plasmid of *Agrobacterium tumefaciens*", *EMBO J.*, 3(12):2723-2730 (1984).

Verwoert et al., "Developmental specific expression and organelle targeting of the *Escherichia coli* fabD gene, encoding malonyl coenzyme A-acyl carrier protein transacylase in transgenic rape of tobacco seeds", *Plant Mol. Biol.*, 26:189-202, (1994).

Vierling et aL, "Plant responses to environmental stress", *Curr Opin Biotechnol.*, 3(2):164-70 (1992).

Visser et al., "Expression of a chimaeric granule-bound starch synthase-GUS gene in transgenic potato plants", *Plant Mol. Biol.*, 17:691-699 (1991).

Wahid et al., "Heat tolerance in plants: An overview", *Environ. Exp. Bot.*, 61:199-223 (2007).

Walling et al., "Isolation, characterization and evolutionary relatedness of three members from the soybean multigene family encoding chlorophyll a/b binding proteins", *Nucl. Acids Res.*, 16(22):10477-10492 (1988).

Weigel et al., "Activation Tagging in *Arabidopsis*", *Plant Physiol.*, 122:1003-1013 (2000).

Wilkins et al., "Role of Propeptide Glycan in Post-Translational Processing and Transport of Barley Lectin to Vacuoles in Transgenic Tobacco", *Plant Cell*, 2:301-313 (1990).

Williams et al., "Differences between plant and animal Myb domains are fundamental for DNA binding activity, and chimeric Myb domains have novel DNA binding specificities", *J Biol. Chem.*, 272(1):563-571 (1997).

Yanhui et al., "The MYB transcription factor superfamily of *Arabidopsis*: expression analysis and phylogenetic comparison with the rice MYB family", *Plant Mol. Biol.*, 60(1):107-124 (2006).

Yoshida et al., "Heat-inducible expression system for a foreign gene in cultured tobacco cells using the HSP18.2 promoter of *Arabidopsis thaliana*", *Appl. Microbiol. Biotechnol.*, 44:466-472 (1995).

Young et al., "High temperature stress of *Brassica napus* during flowering reduces micro-and megagametophyte fertility, induces fruit abortion, and disrupts seed production", *J. Exp. Botany*, 55(396):485-495 (2004).

Ziegelhoffer et al. "Cloning of the *Arabidopsis WIGGUM* Gene Identifies a Role for Farnesylation in Meristem Development." *PNAS.* 97.13(2000):7633-7638.

Blanco, F. A. et al. (2009) "A small GTPase of the Rab family is required for root hair formation and preinfection stages of the common bean-Rhizobium symbiotic association", Plant Cell. Sep. 2009;21(9):2797-2810. doi: 10.1105/tpc.108.063420. Epub Sep. 11, 2009.

Liu, L. et al. (2018) "Coding-Sequence Identification and Transcriptional Profiling of Nine AMTs and Four NRTs From Tobacco Revealed Their Differential Regulation by Developmental Stages, Nitrogen Nutrition, and Photoperiod", Front Plant Sci. Mar. 5, 2018;9:210:1-17. doi: 10.3389/fpls.2018.00210. eCollection 2018.

Mittler, R. et al. (2006) "Gain- and loss-of-function mutations in Zat10 enhance the tolerance of plants to abiotic stress", FEBS Lett. Dec. 11, 2006;580(28-29):6537-6542. Epub Nov. 9, 2006.

Samuel, M. A. et al. (2002) "Double jeopardy: both overexpression and suppression of a redox-activated plant mitogen-activated protein kinase render tobacco plants ozone sensitive", Plant Cell. Sep. 2002;14(9):2059-2069.

Smalle, J. et al. (2002) "Cytokinin growth responses in *Arabidopsis* involve the 26S proteasome subunit RPN12", Plant Cell. Jan. 2002;14(1):17-32.

Wang, P. et al. (2014) "Both decreased and increased SRPK1 levels promote cancer by interfering with PHLPP-mediated dephosphorylation of Akt", Mol. Cell. May 8, 2014;54(3):378-391. doi: 10.1016/j.molcel.2014.03.007. Epub Apr. 3, 2014.

Yoshihara, T. et al (2007) "Identification of the Gravitropism-Related Rice Gene LAZY1 and Elucidation of LAZY1-Dependent and -Independent Gravity Signaling Pathways", Plant Cell Physiol. 48(5):678-688.

Alberts, B. et al. "Studying Gene Expression and Function," Molecular Biology of the Cell, 4th edition, New York: Garland Science; 18 pages (2002).

Katju, V. et al. "Copy-number changes in evolution: rates, fitness effects and adaptive significance," Frontiers in Genetics; 4(273):1-12 (Dec. 10, 2013).

Tang, Y. C. et al. "Gene copy number alterations: A cost-benefit analysis," Cell; 152(3):394-405 (Jan. 31, 2013).

\* cited by examiner

SEQUENCE LISTING

```
<160> NUMBER OF SEQ ID NOS: 325

<210> SEQ ID NO 1
<211> LENGTH: 1125
<212> TYPE: DNA
<213> ORGANISM: Arabidopsis thaliana

<400> SEQUENCE: 1
atgggaagag caccgtgttg tgataaggcc aacgtgaaga aagggccttg gtctcctgag      60
gaagacgcca aactcaaaga ttacatcgag aatagtggca caggaggcaa ctggattgct     120
ttgcctcaga aaattggttt aaggagatgt gggaagagtt gcaggctaag gtggctcaac     180
tatttgagac caaacatcaa acatggtggc ttctccgagg aagaagacaa catcatttgt     240
aacctctatg ttactattgg tagcaggtgg tctataattg ctgcacaatt gccgggaaga     300
accgacaacg atatcaaaaa ctattggaac acgaggctga agaagaagct tctgaacaaa     360
caaaggaaag agttccaaga agcgcgaatg aagcaagaga tggtgatgat gaaaaggcaa     420
caacaaggac aaggacaagg tcaaagtaat ggtagtacgg atctttatct taacaacatg     480
tttggatcat caccatggcc attactacca caacttcctc ctccacatca tcaaatacct     540
cttggaatga tggaaccaac aagctgtaac tactaccaaa cgacaccgtc ttgtaaccta     600
gaacaaaagc cattgatcac actcaagaac atggtcaaga ttgaagaaga acaggaaagg     660
acaaaccctg atcatcatca tcaagattct gtcacaaacc cttttgattt ctctttctct     720
cagcttttgt tagatcccaa ttactatctg ggatcaggag gggaggaga aggagatttt     780 gctatcatga gcagcagcac aaaactcacca ttaccaaaca caagtagtga tcaacatcca     840
agtcaacagc aagagattct tcaatggttt gggagcagta actttcagac agaagcaatc     900
aacgatatgt tcataaacaa caacaacaac atagtgaatc ttgagaccat cgagaacaca     960
aaagtctatg gagacgcctc agtagccgga gccgctgtcc gagcagcttt gggcggaggg    1020
acaacgagta catcggcgga tcaaagtaca ataagttggg aggatataac ttctctagtt    1080
aattccgaag atgcaagtta cttcaatgcg ccaaatcatg tgtaa                     1125

<210> SEQ ID NO 2
<211> LENGTH: 374
<212> TYPE: PRT
<213> ORGANISM: Arabidopsis thaliana

<400> SEQUENCE: 2

Met Gly Arg Ala Pro Cys Cys Asp Lys Ala Asn Val Lys Lys Gly Pro
1               5                   10                  15

Trp Ser Pro Glu Glu Asp Ala Lys Leu Lys Asp Tyr Ile Glu Asn Ser
            20                  25                  30

Gly Thr Gly Gly Asn Trp Ile Ala Leu Pro Gln Lys Ile Gly Leu Arg
        35                  40                  45

Arg Cys Gly Lys Ser Cys Arg Leu Arg Trp Leu Asn Tyr Leu Arg Pro
    50                  55                  60
```

```
Asn Ile Lys His Gly Gly Phe Ser Glu Glu Glu Asp Asn Ile Ile Cys
 65                  70                  75                  80

Asn Leu Tyr Val Thr Ile Gly Ser Arg Trp Ser Ile Ile Ala Ala Gln
                 85                  90                  95

Leu Pro Gly Arg Thr Asp Asn Asp Ile Lys Asn Tyr Trp Asn Thr Arg
            100                 105                 110

Leu Lys Lys Lys Leu Leu Asn Lys Gln Arg Lys Glu Phe Gln Glu Ala
        115                 120                 125

Arg Met Lys Gln Glu Met Val Met Met Lys Arg Gln Gln Gln Gly Gln
130                 135                 140

Gly Gln Gly Gln Ser Asn Gly Ser Thr Asp Leu Tyr Leu Asn Asn Met
145                 150                 155                 160

Phe Gly Ser Ser Pro Trp Pro Leu Leu Pro Gln Leu Pro Pro His
                165                 170                 175

His Gln Ile Pro Leu Gly Met Met Glu Pro Thr Ser Cys Asn Tyr Tyr
            180                 185                 190

Gln Thr Thr Pro Ser Cys Asn Leu Glu Gln Lys Pro Leu Ile Thr Leu
        195                 200                 205

Lys Asn Met Val Lys Ile Glu Glu Gln Glu Arg Thr Asn Pro Asp
210                 215                 220

His His His Gln Asp Ser Val Thr Asn Pro Phe Asp Phe Ser Phe Ser
225                 230                 235                 240

Gln Leu Leu Leu Asp Pro Asn Tyr Tyr Leu Gly Ser Gly Gly Gly
                245                 250                 255

Glu Gly Asp Phe Ala Ile Met Ser Ser Ser Thr Asn Ser Pro Leu Pro
            260                 265                 270

Asn Thr Ser Ser Asp Gln His Pro Ser Gln Gln Gln Glu Ile Leu Gln
        275                 280                 285

Trp Phe Gly Ser Ser Asn Phe Gln Thr Glu Ala Ile Asn Asp Met Phe
290                 295                 300

Ile Asn Asn Asn Asn Asn Ile Val Asn Leu Glu Thr Ile Glu Asn Thr
305                 310                 315                 320

Lys Val Tyr Gly Asp Ala Ser Val Ala Gly Ala Ala Val Arg Ala Ala
                325                 330                 335

Leu Gly Gly Gly Thr Thr Ser Thr Ser Ala Asp Gln Ser Thr Ile Ser
            340                 345                 350

Trp Glu Asp Ile Thr Ser Leu Val Asn Ser Glu Asp Ala Ser Tyr Phe
        355                 360                 365

Asn Ala Pro Asn His Val
    370

<210> SEQ ID NO 3
<211> LENGTH: 933
<212> TYPE: DNA
<213> ORGANISM: Arabidopsis thaliana

<400> SEQUENCE: 3
atgggaagag caccgtgttg tgacaaagca aacgtgaaga aagggccttg gtctcctgag      60
gaagatgcaa aactcaaatc ttacattgaa aatagtggca ccggaggcaa ttggatcgct     120
ttgcctcaaa agattggttt aaagagatgt ggaaagagtt gcaggctgag gtggcttaac     180
tatcttagac aaacatcaa acatggtggc ttctctgagg aagaagaaaa catcatttgt     240
agcctttacc ttacaattgg tagcaggtgg tctataatcg ctgctcaatt gccgggacga     300
```

-continued

```
acagacaacg atataaaaaa ctattggaac acgaggctca agaagaaact cattaacaaa    360
caacgcaagg agcttcaaga agcttgtatg gagcagcaag agatgatggt gatgatgaag    420
agacaacacc aacaacaaca aatccaaact tcttttatga tgagacaaga ccaaacaatg    480
ttcacatggc cactacatca tcataatgtt caagttccag ctcttttcat gaatcaaacc    540
aactcgtttt gcgaccaaga agatgttaag ccagtgctca tcaagaacat ggtcaagatc    600
gaagatcaag aactggagaa aacaaaccct catcatcatc aagattcaat gacaaacgct    660
tttgatcatc tctctttctc tcaactcttg ttagatccta atcataacca cttaggatca    720
ggcgagggtt tctccatgaa ctctatcttg agcgccaaca caaactctcc attgcttaat    780
acaagtaatg ataatcagtg gttcgggaat ttccaggccg aaaccgtaaa cttgttctca    840
ggagcctcca caagtacttc ggcagatcaa agcactataa gttgggaaga cataagctct    900
cttgtttatt ctgattcaaa gcaattttt taa                                  933
```

<210> SEQ ID NO 4
<211> LENGTH: 310
<212> TYPE: PRT
<213> ORGANISM: Arabidopsis thaliana

<400> SEQUENCE: 4

```
Met Gly Arg Ala Pro Cys Cys Asp Lys Ala Asn Val Lys Lys Gly Pro
1               5                  10                  15

Trp Ser Pro Glu Glu Asp Ala Lys Leu Lys Ser Tyr Ile Glu Asn Ser
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Glu Asn Ile Ile Cys
65                  70                  75                  80

Ser Leu Tyr Leu Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Ile Asn Lys Gln Arg Lys Glu Leu Gln Glu Ala
        115                 120                 125

Cys Met Glu Gln Gln Glu Met Met Val Met Met Lys Arg Gln His Gln
    130                 135                 140

Gln Gln Gln Ile Gln Thr Ser Phe Met Met Arg Gln Asp Gln Thr Met
145                 150                 155                 160

Phe Thr Trp Pro Leu His His His Asn Val Gln Val Pro Ala Leu Phe
                165                 170                 175

Met Asn Gln Thr Asn Ser Phe Cys Asp Gln Glu Asp Val Lys Pro Val
            180                 185                 190

Leu Ile Lys Asn Met Val Lys Ile Glu Asp Gln Glu Leu Glu Lys Thr
        195                 200                 205

Asn Pro His His His Gln Asp Ser Met Thr Asn Ala Phe Asp His Leu
    210                 215                 220

Ser Phe Ser Gln Leu Leu Leu Asp Pro Asn His Asn His Leu Gly Ser
225                 230                 235                 240

Gly Glu Gly Phe Ser Met Asn Ser Ile Leu Ser Ala Asn Thr Asn Ser
                245                 250                 255

Pro Leu Leu Asn Thr Ser Asn Asp Asn Gln Trp Phe Gly Asn Phe Gln
```

```
            260                 265                 270
Ala Glu Thr Val Asn Leu Phe Ser Gly Ala Ser Thr Ser Thr Ser Ala
                275                 280                 285

Asp Gln Ser Thr Ile Ser Trp Glu Asp Ile Ser Ser Leu Val Tyr Ser
        290                 295                 300

Asp Ser Lys Gln Phe Phe
305                 310
```

<210> SEQ ID NO 5
<211> LENGTH: 1002
<212> TYPE: DNA
<213> ORGANISM: Arabidopsis thaliana

<400> SEQUENCE: 5

```
atgggaagag ctccatgctg cgacaaggca aacgtgaaga aaggaccatg gtcaccggaa      60
gaagatgtga agctcaagga ttacatcgac aaatatggca ctggtggcaa ctggatcgca     120
ctgcctcaga aaattgggct gaagagatgt ggtaagagtt gcagactgag atggcttaat     180
tacttaagac caaacatcaa acatggtggt ttttctgagg aagaagatag aatcatcttg     240
agtctctaca ttagcattgg aagccggtgg tccataattg cagctcagct tcctggaagg     300
actgacaatg atatcaagaa ttattggaac acaaaactga agaagaaact tctaggaaga     360
cagaaacaaa tgaatcgtca agactccata accgattcta ctgagaacaa cctcagcaac     420
aataacaaca ataagagtcc tcagaatctg agcaattcgg cactggagag gctccagctt     480
cacatgcagc ttcagaatct acagagccct ttctctagtt tctacaacaa ccctatcttg     540
tggcccaagc ttcatccatt gctccagagc actacaacta atcaaaaccc taagcttgca     600
tctcaagaaa gcttccaccc tttaggagtt aacgttgatc atcagcacaa caataccaag     660
ctagctcaga taaacaatgg agcctcttct ctctattcgg agaacgtaga gcaatcccaa     720
aaccctgctc atgaatttca acctaatttc ggttttttcac aggaccttcg attagataat     780
cataacatgg actttatgaa cagaggggtt tctaaagaac tgtttcaagt gggcaacgag     840
tttgagctaa cgaacggttc gagttggtgg tcagaggaag tggaactaga gaggaaaacg     900
acgtcgtcga gttcttgggg gtcagcttct gtgcttgatc agacaactga gggaatggtt     960
atgcttcaag attacgctca gatgagctac cacagtgttt aa                       1002
```

<210> SEQ ID NO 6
<211> LENGTH: 333
<212> TYPE: PRT
<213> ORGANISM: Arabidopsis thaliana

<400> SEQUENCE: 6

```
Met Gly Arg Ala Pro Cys Cys Asp Lys Ala Asn Val Lys Lys Gly Pro
1               5                   10                  15

Trp Ser Pro Glu Glu Asp Val Lys Leu Lys Asp Tyr Ile Asp Lys Tyr
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Glu Asp Arg Ile Ile Leu
65                  70                  75                  80

Ser Leu Tyr Ile Ser Ile Gly Ser Arg Trp Ser Ile Ile Ala Ala Gln
                85                  90                  95
```

```
Leu Pro Gly Arg Thr Asp Asn Asp Ile Lys Asn Tyr Trp Asn Thr Lys
                100                 105                 110
Leu Lys Lys Lys Leu Leu Gly Arg Gln Lys Gln Met Asn Arg Gln Asp
            115                 120                 125
Ser Ile Thr Asp Ser Thr Glu Asn Asn Leu Ser Asn Asn Asn Asn Asn
        130                 135                 140
Lys Ser Pro Gln Asn Leu Ser Asn Ser Ala Leu Glu Arg Leu Gln Leu
145                 150                 155                 160
His Met Gln Leu Gln Asn Leu Gln Ser Pro Phe Ser Ser Phe Tyr Asn
                165                 170                 175
Asn Pro Ile Leu Trp Pro Lys Leu His Pro Leu Leu Gln Ser Thr Thr
            180                 185                 190
Thr Asn Gln Asn Pro Lys Leu Ala Ser Gln Glu Ser Phe His Pro Leu
        195                 200                 205
Gly Val Asn Val Asp His Gln His Asn Asn Thr Lys Leu Ala Gln Ile
210                 215                 220
Asn Asn Gly Ala Ser Ser Leu Tyr Ser Glu Asn Val Glu Gln Ser Gln
225                 230                 235                 240
Asn Pro Ala His Glu Phe Gln Pro Asn Phe Gly Phe Ser Gln Asp Leu
                245                 250                 255
Arg Leu Asp Asn His Asn Met Asp Phe Met Asn Arg Gly Val Ser Lys
            260                 265                 270
Glu Leu Phe Gln Val Gly Asn Glu Phe Glu Leu Thr Asn Gly Ser Ser
        275                 280                 285
Trp Trp Ser Glu Glu Val Glu Leu Glu Arg Lys Thr Thr Ser Ser Ser
    290                 295                 300
Ser Trp Gly Ser Ala Ser Val Leu Asp Gln Thr Thr Glu Gly Met Val
305                 310                 315                 320
Met Leu Gln Asp Tyr Ala Gln Met Ser Tyr His Ser Val
                325                 330

<210> SEQ ID NO 7
<211> LENGTH: 1092
<212> TYPE: DNA
<213> ORGANISM: Brassica rapa

<400> SEQUENCE: 7
atgggaagag caccgtgttg tgacaaggct aacgtgaaga aagggccgtg gtctcctgaa      60
gaagacgcaa aactcaaaga ttacatcgag aataatggca caggcggcaa ctggattgcg     120
ttgcctcaga agattggtct aagaagatgt gggaagagtt gcagactaag gtggctcaac     180
tatttgagac caaacatcaa acatggtggc ttctctgagg aagaggacaa catcatttgt     240
aatctctatg ttaccattgg tagcaggtgg tctataattg ctgcacaatt gcctggaaga     300
acagacaatg atatcaagaa ctattggaac acgaggctga agaagaagct tcttaacaaa     360
caaagaaaag agtaccaaga agctcggatg aagcaagata tggtgatgat aaagcgacaa     420
gaacaaggga caggccaaag taatgctagt agggatcttt attcgaacaa catgtttgga     480
tcatcaccat ggccattact acaacagctt cctcctcatc atcaagtacc tcttgtgatg     540
atggaaccaa caagttgtaa ctactaccaa acgtcaccct cttgtaacct agaacaaaag     600
ccactgatca ctttcaagaa catggtcaag attgaagaag aaccggagag aacaaaccct     660
tataatcctc agcatcaaaa ttctatcaca aaccctttg atgtctcctt ctcccagctc     720
ttgttagatc ctaattacta cttaggatca ggaggaggag cagaagggga ttttgctatc     780
```

```
atgagtagca gcacaaattc tccattacca aacacaagtg gtgatcaaaa tgaacatcag    840
cagcaagaga ttcttcaatg gtttgggagt agtaatcttc agacagaagc aagcagtgat    900
atgttcttaa acaacatagg gaatcttgag accaacgagg acacaagatt ctactcatca    960
ttagccggtg ttggagcggc tttggccgga ggaacgacga gtacatcggc agatcaaagc   1020
acaataagtt gggaggacat aacatctctt gttaattccg aagatgcaag ttacttcaat   1080
gggccaaatt aa                                                        1092
```

<210> SEQ ID NO 8
<211> LENGTH: 363
<212> TYPE: PRT
<213> ORGANISM: Brassica rapa

<400> SEQUENCE: 8

```
Met Gly Arg Ala Pro Cys Cys Asp Lys Ala Asn Val Lys Lys Gly Pro
1               5                   10                  15

Trp Ser Pro Glu Glu Asp Ala Lys Leu Lys Asp Tyr Ile Glu Asn Asn
            20                  25                  30

Gly Thr Gly Gly Asn Trp Ile Ala Leu Pro Gln Lys Ile Gly Leu Arg
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Asp Asn Ile Ile Cys
65                  70                  75                  80

Asn Leu Tyr Val Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Asn Lys Gln Arg Lys Glu Tyr Gln Glu Ala
        115                 120                 125

Arg Met Lys Gln Asp Met Val Met Ile Lys Arg Gln Glu Gln Gly Thr
    130                 135                 140

Gly Gln Ser Asn Ala Ser Arg Asp Leu Tyr Ser Asn Asn Met Phe Gly
145                 150                 155                 160

Ser Ser Pro Trp Pro Leu Leu Gln Gln Leu Pro Pro His His Gln Val
                165                 170                 175

Pro Leu Val Met Met Glu Pro Thr Ser Cys Asn Tyr Tyr Gln Thr Ser
            180                 185                 190

Pro Ser Cys Asn Leu Glu Gln Lys Pro Leu Ile Thr Phe Lys Asn Met
        195                 200                 205

Val Lys Ile Glu Glu Glu Pro Glu Arg Thr Asn Pro Tyr Asn Pro Gln
    210                 215                 220

His Gln Asn Ser Ile Thr Asn Pro Phe Asp Val Ser Phe Ser Gln Leu
225                 230                 235                 240

Leu Leu Asp Pro Asn Tyr Tyr Leu Gly Ser Gly Gly Ala Glu Gly
                245                 250                 255

Asp Phe Ala Ile Met Ser Ser Ser Thr Asn Ser Pro Leu Pro Asn Thr
            260                 265                 270

Ser Gly Asp Gln Asn Glu His Gln Gln Gln Glu Ile Leu Gln Trp Phe
        275                 280                 285

Gly Ser Ser Asn Leu Gln Thr Glu Ala Ser Ser Asp Met Phe Leu Asn
    290                 295                 300

Asn Ile Gly Asn Leu Glu Thr Asn Glu Asp Thr Arg Phe Tyr Ser Ser
305                 310                 315                 320
```

Leu Ala Gly Val Gly Ala Ala Leu Ala Gly Gly Thr Thr Ser Thr Ser
            325                 330                 335

Ala Asp Gln Ser Thr Ile Ser Trp Glu Asp Ile Thr Ser Leu Val Asn
            340                 345                 350

Ser Glu Asp Ala Ser Tyr Phe Asn Gly Pro Asn
            355                 360

<210> SEQ ID NO 9
<211> LENGTH: 966
<212> TYPE: DNA
<213> ORGANISM: Oryza sativa

<400> SEQUENCE: 9

```
atggggagag cgccgtgctg cgacaaggcg agcgtgaaga aggggccatg gtcaccggag    60
gaggacgcga agctcaaatc ctacatcgag cagaacggca ccggcggcaa ctggatcgcc   120
ctgccccaga gatcggtttt gaaaaggtgc ggcaagagct gccgcctccg gtggctgaac   180
tacctccggc cgaacatcaa gcacggcggg ttctcggagg aggaagacag gatcatcctc   240
agcctctaca tcagcatagg aagcaggtgg tcgataatag cagcgcagct gccggggcgg   300
acggacaatg acatcaagaa ctattggaac acgaggctca agaagaagct ctttggcaag   360
cagtcgcgca aggatcagag gcagcagcag cacctggcgc gccaggcggc agcagctgcc   420
agcgacttgc agatcaaaca agaagcgagc aggggtgcaa acgaagccga tggcttggct   480
gccggtgcca attacacttg gcatcaccac cacgccatgg ccgtgcctgt gcacccgatg   540
tcggcaccaa tggtggtgga aggaggccgt gtgggagacg atgtcgatga gtcgatccgg   600
aagcttctgt tcaagctcgg agggaaccca ttcgcggcct cgccggcacc gccatgcata   660
cctccaccac caatgtacga ggaagcccca agcttcgtgc caccattggc gcacggcgtg   720
ccgctcaacg aaggcggcat gcagtgctcc agcgtgctgc cggcgctgga gctggacgag   780
aacttccact tcaaccatgt caagctggac gggctcgagt gcctcttcgg gatgggagat   840
caccaaaaca tgagatggaa tgaggtgagc ccgttggttt gccctaataa cgctgtggcg   900
tccagctccc aagggatgca gcagtactgc ctagttgaag aaccagctga cctcgggatg   960
cagtag                                                              966
```

<210> SEQ ID NO 10
<211> LENGTH: 321
<212> TYPE: PRT
<213> ORGANISM: Oryza sativa

<400> SEQUENCE: 10

Met Gly Arg Ala Pro Cys Cys Asp Lys Ala Ser Val Lys Lys Gly Pro
1               5                   10                  15

Trp Ser Pro Glu Glu Asp Ala Lys Leu Lys Ser Tyr Ile Glu Gln Asn
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Glu Asp Arg Ile Ile Leu
65                  70                  75                  80

Ser Leu Tyr Ile Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg

```
            100                 105                 110
Leu Lys Lys Lys Leu Phe Gly Lys Gln Ser Arg Lys Asp Gln Arg Gln
        115                 120                 125

Gln Gln His Leu Ala Arg Gln Ala Ala Ala Ala Ser Asp Leu Gln
        130                 135                 140

Ile Lys Gln Glu Ala Ser Arg Gly Ala Asn Glu Ala Asp Gly Leu Ala
145                 150                 155                 160

Ala Gly Ala Asn Tyr Thr Trp His His His Ala Met Ala Val Pro
                165                 170                 175

Val His Pro Met Ser Ala Pro Met Val Val Glu Gly Gly Arg Val Gly
                180                 185                 190

Asp Asp Val Asp Glu Ser Ile Arg Lys Leu Leu Phe Lys Leu Gly Gly
                195                 200                 205

Asn Pro Phe Ala Ala Ser Pro Ala Pro Cys Ile Pro Pro Pro
        210                 215                 220

Met Tyr Glu Glu Ala Pro Ser Phe Val Pro Leu Ala His Gly Val
225                 230                 235                 240

Pro Leu Asn Glu Gly Gly Met Gln Cys Ser Ser Val Leu Pro Ala Leu
                245                 250                 255

Glu Leu Asp Glu Asn Phe His Phe Asn His Val Lys Leu Asp Gly Leu
                260                 265                 270

Glu Cys Leu Phe Gly Met Gly Asp His Gln Asn Met Arg Trp Asn Glu
        275                 280                 285

Val Ser Pro Leu Val Cys Pro Asn Asn Ala Val Ala Ser Ser Ser Gln
        290                 295                 300

Gly Met Gln Gln Tyr Cys Leu Val Glu Glu Pro Ala Asp Leu Gly Met
305                 310                 315                 320

Gln
```

<210> SEQ ID NO 11
<211> LENGTH: 1071
<212> TYPE: DNA
<213> ORGANISM: Gossypium

<400> SEQUENCE: 11

```
atgggagag ctccttgttg tgacaaagct aacgtcaaga aaggcccatg gtcacctgaa      60
gaagacacca agctcaaggc atacatcgag cagcatggca ctggcggaaa ctggatcgct     120
ttgcctcaca aaattggcct taagagatgt gggaagagct gccgcctcag atggttaaac     180
tatctccgcc caaatattaa gcatggagga ttctccgaag aagaagataa aattatttgc     240
agcctctata tcagtattgg gagcaggtgg tctattattg ctgcacaatt accggggagg     300
actgataacg atataaagaa ctattggaac acaaggctta agaagaagct tctgggcaag     360
caacgcaaag agcatcagtc tcgaagaggc aacagcctaa gcaagatat gaagagatca     420
tcagctagtg tgggggattc catggttcct gcagataaca tcaatcaaat ccttactgg      480
ccagagctgc ctgtgctggc tgcggcggcg gctcccatac cgcactcaag tcaagaacat     540
cgcattgaca gccaagcctc gatgagaaga ttactaatca gcttgggggg aagattttct     600
gaggatgatc atgtggttaa tgatgggaca actcttcatc agtttcctaa tgatttatcc     660
actactgatc aggatcttta cgagcagact gtctatgtgc cctcttcttc ttcttcttct     720
cccatggatg ccttgagctt aagcaataac atcggttctc agtttgtgaa ctctcagttc     780
gccatagatg gagggaatct gcccattctg caaggacaaa gcactacttt ttcatcagag     840
```

```
ctccaggaaa tgggatatag cagcaaccca cagagattag atggaatgga gttcttatat    900
ggggaaggca tggtcgataa tagaggcgtg aatccttgtg aaagcattgg ctggggtgac    960
actagctctc tggttggccc tccttgtgct tcggaatatg gagtcatgca acaaggaatg   1020
cttcaagaat atggttttag tgagatgagg tacccaggag gagcgcaata g            1071
```

<210> SEQ ID NO 12
<211> LENGTH: 356
<212> TYPE: PRT
<213> ORGANISM: Gossypium

<400> SEQUENCE: 12

```
Met Gly Arg Ala Pro Cys Cys Asp Lys Ala Asn Val Lys Lys Gly Pro
1               5                   10                  15

Trp Ser Pro Glu Glu Asp Thr Lys Leu Lys Ala Tyr Ile Glu Gln His
            20                  25                  30

Gly Thr Gly Gly Asn Trp Ile Ala Leu Pro His Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Asp Lys Ile Ile Cys
65                  70                  75                  80

Ser Leu Tyr Ile Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Gly Lys Gln Arg Lys Glu His Gln Ser Arg
        115                 120                 125

Arg Gly Asn Ser Leu Lys Gln Asp Met Lys Arg Ser Ser Ala Ser Val
    130                 135                 140

Gly Asp Ser Met Val Pro Ala Asp Asn Ile Asn Gln Ile Pro Tyr Trp
145                 150                 155                 160

Pro Glu Leu Pro Val Leu Ala Ala Ala Ala Pro Ile Pro His Ser
                165                 170                 175

Ser Gln Glu His Arg Ile Asp Ser Gln Ala Ser Met Arg Arg Leu Leu
            180                 185                 190

Ile Lys Leu Gly Gly Arg Phe Ser Glu Asp Asp His Val Val Asn Asp
        195                 200                 205

Gly Thr Thr Leu His Gln Phe Pro Asn Asp Leu Ser Thr Thr Asp Gln
    210                 215                 220

Asp Leu Tyr Glu Gln Thr Val Tyr Val Pro Ser Ser Ser Ser Ser
225                 230                 235                 240

Pro Met Asp Ala Leu Ser Leu Ser Asn Asn Ile Gly Ser Gln Phe Val
                245                 250                 255

Asn Ser Gln Phe Ala Ile Asp Gly Gly Asn Leu Pro Ile Leu Gln Gly
            260                 265                 270

Gln Ser Thr Thr Phe Ser Ser Glu Leu Gln Glu Met Gly Tyr Ser Ser
        275                 280                 285

Asn Pro Gln Arg Leu Asp Gly Met Glu Phe Leu Tyr Gly Glu Gly Met
    290                 295                 300

Val Asp Asn Arg Gly Val Asn Pro Cys Glu Ser Ile Gly Trp Gly Asp
305                 310                 315                 320

Thr Ser Ser Leu Val Gly Pro Pro Cys Ala Ser Glu Tyr Gly Val Met
                325                 330                 335
```

```
Gln Gln Gly Met Leu Gln Glu Tyr Gly Phe Ser Glu Met Arg Tyr Pro
            340                 345                 350
Gly Gly Ala Gln
        355

<210> SEQ ID NO 13
<211> LENGTH: 596
<212> TYPE: DNA
<213> ORGANISM: Glycine max

<400> SEQUENCE: 13
atggggaggg caccttgctg tgacaaagca aacgtgaaga aaggtccttg gtcgccagaa      60
gaagatacca aactcaaatc ctacatcgaa cagcacggaa ccggaggaaa ctggatcgct     120
ttgccacaaa agattggcct taaacgatgt ggcaagagtt gccgtctcag gtggctaaac     180
tacctccgcc ctaacatcag acacggtggt ttctccgaag aagaagacaa catcatttgc     240
agcctctacg ttagcattgg aagcaggtgg tcggtcattg cagcacaatt gccgggaaga     300
actgataatg acataaagaa ctattggaac acgaggctga agaagaagct tctagggaaa     360
caccgtaagg aactacaggc acgcaacaaa ggaaacggtg gtatccttaa acaggagaac     420
agttcctcgc tcttgcttca gcaaaacagt gctcaacaat acatccatg ttggccacag      480 attccagtgc tgccactttc atcaccgtac acaaaccaaa gtccaagttt caacgaccaa     540
gattccatta gaaagcttct aatcaagctt ggagggagat tctccgatga ttatca        596

<210> SEQ ID NO 14
<211> LENGTH: 198
<212> TYPE: PRT
<213> ORGANISM: Glycine max

<400> SEQUENCE: 14

Met Gly Arg Ala Pro Cys Cys Asp Lys Ala Asn Val Lys Lys Gly Pro
1               5                   10                  15

Trp Ser Pro Glu Glu Asp Thr Lys Leu Lys Ser Tyr Ile Glu Gln His
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Arg His Gly Gly Phe Ser Glu Glu Asp Asn Ile Ile Cys
65                  70                  75                  80

Ser Leu Tyr Val Ser Ile Gly Ser Arg Trp Ser Val Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Gly Lys His Arg Lys Glu Leu Gln Ala Arg
        115                 120                 125

Asn Lys Gly Asn Gly Gly Ile Leu Lys Gln Glu Asn Ser Ser Ser Leu
    130                 135                 140

Leu Leu Gln Gln Asn Ser Ala Gln Gln Leu His Pro Cys Trp Pro Gln
145                 150                 155                 160

Ile Pro Val Leu Pro Leu Ser Ser Pro Tyr Thr Asn Gln Ser Pro Ser
                165                 170                 175

Phe Asn Asp Gln Asp Ser Ile Arg Lys Leu Leu Ile Lys Leu Gly Gly
            180                 185                 190

Arg Phe Ser Asp Asp Tyr
        195
```

-continued

195

<210> SEQ ID NO 15
<211> LENGTH: 1463
<212> TYPE: DNA
<213> ORGANISM: Glycine max

<400> SEQUENCE: 15

```
aaataacact ctctctctct caattatttc tgccgtaaat agacaagggt tatctcaaat      60
aatcaatcta agctagctga aagcaacaac aacaacatgg ggagggcacc ttgctgtgac     120
aaatcaaacg tgaagaaagg cccttggtcg ccagatgaag atgccaaact caaatcctac     180
atcgaacagc acggaaccgg agggaactgg attgctttgc cacaaaagat tggcctcaaa     240
cgatgtggca agagttgccg tctcaggtgg ctaaactacc tccgccctaa catcagacac     300
ggtggtttct ccgaagaaga agacaacatc atttgcagcc tctacgttag cattggaagc     360
aggtggtcgg tcattgcagc acaattgccg ggaagaactg ataatgacat aaagaactat     420
tggaacacga ggctgaagaa gaagcttcta gggaaacacc gtaaggaact acaggcacgc     480
aacaaaggaa acgtggtat ccttaaacag gagaacagtt cctcgctctt gcttcagcaa      540
aacagtgctc aacaattaca tccatgttgg ccacagattc cagtgctgcc actttcatca     600
ccgtacacaa accaaagtcc aagtttcaac gaccaagatt ccattagaaa gcttctaatc     660
aagcttggag ggagattctc cgatgattat caacccatcc tagatgggtt gaatcttcag     720
ttcccacatg gttcaaattc tctctcatca acacaacaaa ttcaagagga gcaagtccat     780
gttggttctt ctgcactagg gtgcatgaac tctattggcc acaatcaagt acaatttggt     840
cagagtaatg agtactgtgc tgagttggtg caaggacaag ggagtttcat taccacagca     900
attggggaaa tggtttcttc taatgattat tctcgaaggt tattaggtgg gtcgttggag     960
ttcttctatg gggaggaaat gattactgat aataagataa tgggtgcttg tgcttcttca    1020
agttgtgggc aaagtactaa ttggggtgaa accagtagtt ctctgatgta tccttctctt    1080
gttgcttcga attcgagggg tgtgcggcaa gagatgccac gagaatgtgc tttttcaagag   1140
ttgagctacc cgggggcgca atagcatgtg tgtacattat ttgttatcaa ttggtggagg    1200
ttgggattat atgtatccaa attgaagcta gcaaaggga attaactttg tatttgattc     1260
ccatatagat aataaaaatc agcttgattt atatataact agagacttgt ccgctatgtg    1320
agactttctc atgtgctgat cccttagtgg cagtgcagtt taattatctg atttgtttgt    1380
gtattatttg gttgtaatct tgagagtcat ttaaatatat cctttatgt tccaagctaa     1440
aaaaaaaaaa aagaaaaacc ccc                                            1463
```

<210> SEQ ID NO 16
<211> LENGTH: 355
<212> TYPE: PRT
<213> ORGANISM: Glycine max

<400> SEQUENCE: 16

```
Met Gly Arg Ala Pro Cys Cys Asp Lys Ser Asn Val Lys Lys Gly Pro
1               5                   10                  15

Trp Ser Pro Asp Glu Asp Ala Lys Leu Lys Ser Tyr Ile Glu Gln His
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60
```

```
Asn Ile Arg His Gly Gly Phe Ser Glu Glu Asp Asn Ile Ile Cys
 65                  70                  75                  80

Ser Leu Tyr Val Ser Ile Gly Ser Arg Trp Ser Val Ile Ala Ala Gln
             85                  90                  95

Leu Pro Gly Arg Thr Asp Asn Asp Ile Lys Asn Tyr Trp Asn Thr Arg
            100                 105                 110

Leu Lys Lys Lys Leu Leu Gly Lys His Arg Lys Glu Leu Gln Ala Arg
            115                 120                 125

Asn Lys Gly Asn Gly Gly Ile Leu Lys Gln Glu Asn Ser Ser Ser Leu
130                 135                 140

Leu Leu Gln Gln Asn Ser Ala Gln Gln Leu His Pro Cys Trp Pro Gln
145                 150                 155                 160

Ile Pro Val Leu Pro Leu Ser Ser Pro Tyr Thr Asn Gln Ser Pro Ser
            165                 170                 175

Phe Asn Asp Gln Asp Ser Ile Arg Lys Leu Leu Ile Lys Leu Gly Gly
            180                 185                 190

Arg Phe Ser Asp Asp Tyr Gln Pro Ile Leu Asp Gly Leu Asn Leu Gln
            195                 200                 205

Phe Pro His Gly Ser Asn Ser Leu Ser Ser Thr Gln Gln Ile Gln Glu
            210                 215                 220

Glu Gln Val His Val Gly Ser Ser Ala Leu Gly Cys Met Asn Ser Ile
225                 230                 235                 240

Gly His Asn Gln Val Gln Phe Gly Gln Ser Asn Glu Tyr Cys Ala Glu
            245                 250                 255

Leu Val Gln Gly Gln Gly Ser Phe Ile Thr Thr Ala Ile Gly Glu Met
            260                 265                 270

Val Ser Ser Asn Asp Tyr Ser Arg Arg Leu Leu Gly Gly Ser Leu Glu
            275                 280                 285

Phe Phe Tyr Gly Glu Glu Met Ile Thr Asp Asn Lys Ile Met Gly Ala
            290                 295                 300

Cys Ala Ser Ser Ser Cys Gly Gln Ser Thr Asn Trp Gly Glu Thr Ser
305                 310                 315                 320

Ser Ser Leu Met Tyr Pro Ser Leu Val Ala Ser Asn Tyr Glu Gly Val
            325                 330                 335

Arg Gln Glu Met Pro Arg Glu Cys Ala Phe Gln Glu Leu Ser Tyr Pro
            340                 345                 350

Gly Ala Gln
        355

<210> SEQ ID NO 17
<211> LENGTH: 395
<212> TYPE: DNA
<213> ORGANISM: Zea mays

<400> SEQUENCE: 17
atggggagag ctccgtgctg cgacaaggct actgtgaaga agggcccgtg gtcaccggag      60
gaggacgcca agctcaagtc ctacatcgag cagaacggca ccggcggtaa ctggatagcc     120
ctgccgcaga agataggttt gaagaggtgc ggcaagagct gccgcctccg gtggctcaac     180
tacctccggc caaacatcaa gcacggcggg ttctcggatg aggaggacat gataatcctt     240
agcctctaca tcagcatagg cagcaggtgg tcgataatag cggcgcagct gccgggaagg     300
acggacaacg acataaagaa ctactggaac acgaggctca agaagaagct cttcggcaag     360
ccgtttaaaa aaggtattcg gcagggttcc ttttt                                395
```

<210> SEQ ID NO 18
<211> LENGTH: 131
<212> TYPE: PRT
<213> ORGANISM: Zea mays

<400> SEQUENCE: 18

Met Gly Arg Ala Pro Cys Cys Asp Lys Ala Thr Val Lys Lys Gly Pro
1               5                   10                  15

Trp Ser Pro Glu Glu Asp Ala Lys Leu Lys Ser Tyr Ile Glu Gln Asn
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Asp Glu Glu Asp Met Ile Ile Leu
65                  70                  75                  80

Ser Leu Tyr Ile Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Phe Gly Lys Pro Phe Lys Gly Ile Arg Gln
        115                 120                 125

Gly Ser Phe
    130

<210> SEQ ID NO 19
<211> LENGTH: 471
<212> TYPE: DNA
<213> ORGANISM: Sorghum bicolor

<400> SEQUENCE: 19
atggggagag ctccgtgctg cgacaaggct actgtgaaga agggtccgtg gtcgccggag      60
gaggacgcca agctcaagtc ctacatcgag cagaacggca ccggcggtaa ctggatagcc     120
ctgcctcaga gataggtct gaagaggtgt ggcaagagct gccgcctccg gtggctcaac     180
tacctccggc caaacatcaa gcacggtggg ttctccgagg aggaagacag aataatcctt     240
agcctctaca tcagcatagg cagcaggtgg tcgataatag cggcgcagct gccggggagg     300
acggacaatg acataaagaa ctactggaac acgaggctca agaagaagct cttcggcaag     360
caatcgcgca aggatcaacg gcagcatcag ttcatgcgcc agcaggcggc agcggcaaac     420
gatgggatga tgaagcaaga agcagcacac cccgggatgc agcccggagc a              471

<210> SEQ ID NO 20
<211> LENGTH: 157
<212> TYPE: PRT
<213> ORGANISM: Sorghum bicolor

<400> SEQUENCE: 20

Met Gly Arg Ala Pro Cys Cys Asp Lys Ala Thr Val Lys Lys Gly Pro
1               5                   10                  15

Trp Ser Pro Glu Glu Asp Ala Lys Leu Lys Ser Tyr Ile Glu Gln Asn
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Glu Asp Arg Ile Ile Leu
 65                  70                  75                  80

Ser Leu Tyr Ile Ser Ile Gly Ser Arg Trp Ser Ile Ile Ala Ala Gln
                 85                  90                  95

Leu Pro Gly Arg Thr Asp Asn Asp Ile Lys Asn Tyr Trp Asn Thr Arg
             100                 105                 110

Leu Lys Lys Lys Leu Phe Gly Lys Gln Ser Arg Lys Asp Gln Arg Gln
         115                 120                 125

His Gln Phe Met Arg Gln Gln Ala Ala Ala Asn Asp Gly Met Met
    130                 135                 140

Lys Gln Glu Ala Ala His Pro Gly Met Gln Pro Gly Ala
145                 150                 155

<210> SEQ ID NO 21
<211> LENGTH: 525
<212> TYPE: DNA
<213> ORGANISM: Triticum aestivum

<400> SEQUENCE: 21
atggggaggg cgccgtgctg cgacaaggcg acggtgaaga agggcccctg gtcgccggag     60
gaggacgcca agctcaaggc ctacatcgac gagaatggca ccggcggcaa ctggatcgcc    120
ctgccgcaga gatcgggct gaagaggtgc ggcaaaagct gtaggctcag atggctcaac    180
tatctgaggc caaacatcaa gcacggcgac ttcacagagg aagaggaaca catcatttgc    240
agcctctaca ttagcatcgg cagcaggtgg tcgatcatcg cggcgcagct gccgggcaga    300
acggacaacg acatcaagaa ctactggaac accaagctca gaagaagct cctcggcaag    360 cgcgcgccgt cccgccgcct gcagcgcgcc aaccaagacg cgccgatgcc ctactcctac    420
ctggcggcgg gcggcggcag cgccagcagc agcgggaacg ctagcggcac caccgcggca    480
ctcagctcgt cagcgctgga gcggatccag ctccacatgc gcctg                   525

<210> SEQ ID NO 22
<211> LENGTH: 175
<212> TYPE: PRT
<213> ORGANISM: Triticum aestivum

<400> SEQUENCE: 22

Met Gly Arg Ala Pro Cys Cys Asp Lys Ala Thr Val Lys Lys Gly Pro
1               5                   10                  15

Trp Ser Pro Glu Glu Asp Ala Lys Leu Lys Ala Tyr Ile Asp Glu Asn
             20                  25                  30

Gly Thr Gly Gly Asn Trp Ile Ala Leu Pro Gln Lys Ile Gly Leu Lys
         35                  40                  45

Arg Cys Gly Lys Ser Cys Arg Leu Arg Trp Leu Asn Tyr Leu Arg Pro
     50                  55                  60

Asn Ile Lys His Gly Asp Phe Thr Glu Glu Glu His Ile Ile Cys
 65                  70                  75                  80

Ser Leu Tyr Ile Ser Ile Gly Ser Arg Trp Ser Ile Ile Ala Ala Gln
                 85                  90                  95

Leu Pro Gly Arg Thr Asp Asn Asp Ile Lys Asn Tyr Trp Asn Thr Lys
             100                 105                 110

Leu Lys Lys Lys Leu Leu Gly Lys Arg Ala Pro Ser Arg Arg Leu Gln
         115                 120                 125

Arg Ala Asn Gln Asp Ala Pro Met Pro Tyr Ser Tyr Leu Ala Ala Gly
    130                 135                 140

Gly Gly Ser Ala Ser Ser Gly Asn Ala Ser Gly Thr Thr Ala Ala
145                 150                 155                 160

Leu Ser Ser Ser Ala Leu Glu Arg Ile Gln Leu His Met Arg Leu
                165                 170                 175

<210> SEQ ID NO 23
<211> LENGTH: 1035
<212> TYPE: DNA
<213> ORGANISM: Populus

<400> SEQUENCE: 23

```
atgggagag ctccttgctg tgacaaagcc aacgtgaaga aaggtccatg gtctcccgag      60
gaagatgcca tactcaaggc ctatattgag cagcatggaa ccggtggcaa tcggattgcc    120
ttgccacaga agataggcct gaaaaggtgt ggcaagagtt gtcgactag atggttgaat     180
tatctccgtc caaacattaa acatggaggg ttttcagagg aagaagataa cattatttgc    240
agtctctata taagtattgg aagcaggtgg tctatcattg ctgctcagtt acctggaagg    300
accgataatg atataaaaaa ctactggaac acaaggctta agaagaagct cttaggaaaa    360
cagcgcaagg aacaagcagc ccggcgagct agtctcaagc aagaaatcat gacaaagaga    420
gaaataaacg agagcttcat ggttcctggg gctatccctc atcaacaaag cccttactgg    480
ccagaggtac cagctctagt catgaatcaa aaccaagatt ctcatttgat ggatcaagaa    540
tccattagga acttgctgat caaacttggt gggagatttt ctgacaataa tcaagagtca    600
gccctattca ctacagtcaa caattaccct ctcgacggtt caagcagaca agatcaagta    660
ccatacacaa actccataga tgtgctttct tcttcggcac ccatgcgatc aatggatagt    720
actaccagtt gttctcaatt tcctaatagc aactacaacg gtccaaatat gtgtcaagct    780
ggacttgaaa acttgttggt cgagctaggt ggattggtct gtagcaaccc acagcgtgta    840
gaaggttttgg atagtttcta cgggatggac atggctgcca gtggcagcac ggggcgtagt   900
tctgcagaaa gtaacagctg ggacatata agctctcttg gttatcctca gcttgtttct    960
gactatgaaa cttgcttgca aagcatgcca caagattcat cttttgaaga ttcaagcttc   1020
tttgggccac aatga                                                    1035
```

<210> SEQ ID NO 24
<211> LENGTH: 344
<212> TYPE: PRT
<213> ORGANISM: Populus

<400> SEQUENCE: 24

Met Gly Arg Ala Pro Cys Cys Asp Lys Ala Asn Val Lys Lys Gly Pro
1               5                   10                  15

Trp Ser Pro Glu Glu Asp Ala Ile Leu Lys Ala Tyr Ile Glu Gln His
                20                  25                  30

Gly Thr Gly Gly Asn Arg Ile Ala Leu Pro Gln Lys Ile Gly Leu Lys
            35                  40                  45

Arg Cys Gly Lys Ser Cys Arg Leu Arg Trp Leu Asn Tyr Leu Arg Pro
        50                  55                  60

Asn Ile Lys His Gly Gly Phe Ser Glu Glu Asp Asn Ile Ile Cys
65                  70                  75                  80

Ser Leu Tyr Ile Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Gly Lys Gln Arg Lys Glu Gln Ala Ala Arg
         115                 120                 125

Arg Ala Ser Leu Lys Gln Glu Ile Met Thr Lys Arg Glu Ile Asn Glu
    130                 135                 140

Ser Phe Met Val Pro Gly Ala Ile Pro His Gln Gln Ser Pro Tyr Trp
145                 150                 155                 160

Pro Glu Val Pro Ala Leu Val Met Asn Gln Asn Gln Asp Ser His Leu
                165                 170                 175

Met Asp Gln Glu Ser Ile Arg Asn Leu Leu Ile Lys Leu Gly Gly Arg
            180                 185                 190

Phe Ser Asp Asn Asn Gln Glu Ser Ala Leu Phe Thr Thr Val Asn Asn
            195                 200                 205

Tyr Pro Leu Asp Gly Ser Ser Arg Gln Asp Gln Val Pro Tyr Thr Asn
    210                 215                 220

Ser Ile Asp Val Leu Ser Ser Ala Pro Met Arg Ser Met Asp Ser
225                 230                 235                 240

Thr Thr Ser Cys Ser Gln Phe Pro Asn Ser Asn Tyr Asn Gly Pro Asn
                245                 250                 255

Met Cys Gln Ala Gly Leu Glu Asn Leu Leu Val Glu Leu Gly Gly Leu
            260                 265                 270

Val Cys Ser Asn Pro Gln Arg Val Glu Gly Leu Asp Ser Phe Tyr Gly
            275                 280                 285

Met Asp Met Ala Ala Ser Gly Ser Thr Gly Ala Ser Ser Ala Glu Ser
            290                 295                 300

Asn Ser Trp Gly His Ile Ser Ser Leu Gly Tyr Pro Gln Leu Val Ser
305                 310                 315                 320

Asp Tyr Glu Thr Cys Leu Gln Ser Met Pro Gln Asp Ser Ser Phe Glu
                325                 330                 335

Asp Ser Ser Phe Phe Gly Pro Gln
            340

<210> SEQ ID NO 25
<211> LENGTH: 537
<212> TYPE: DNA
<213> ORGANISM: Medicago truncatula

<400> SEQUENCE: 25
atgggaagag ctccttgctg tgacaaagcc aatgtcaaaa aaggtccatg gtcacctgaa    60
gaagatgcta aactcaagtc ttacatagaa caaaatggta ctggtggaaa ttggattgct   120
ctacctcaga agataggact taagagatgt gggaaaagct gtcgtcttag atggttaaat   180
tatcttagac caaatattaa acatggtggt ttctccgaag aagaagacga cattatttgc   240
agcctctatg ttagtatcgg aagcaggtgg tctatcatag cagcacaatt accaggacga   300
acggataatg atataaagaa ctactggaac actaggctga agaagaagct ccttgggaaa   360
caaaggaagg agcaacaagc tcgccgagtt agcaacatga acaagagat gaaaagagaa   420 acaaatcaga atttgatgat ggcggctttg ggtgtcaata gtatgagttc agcaccatat   480
tggcctgcag agtattctgt tcatcctatg ccagtttcaa attcatccat aatttga      537

<210> SEQ ID NO 26
<211> LENGTH: 178
<212> TYPE: PRT
<213> ORGANISM: Medicago truncatula

<400> SEQUENCE: 26

```
Met Gly Arg Ala Pro Cys Cys Asp Lys Ala Asn Val Lys Lys Gly Pro
1               5                   10                  15

Trp Ser Pro Glu Glu Asp Ala Lys Leu Lys Ser Tyr Ile Glu Gln Asn
            20                  25                  30

Gly Thr Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Glu Asp Asp Ile Ile Cys
65                  70                  75                  80

Ser Leu Tyr Val Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Gly Lys Gln Arg Lys Glu Gln Gln Ala Arg
        115                 120                 125

Arg Val Ser Asn Met Lys Gln Glu Met Lys Arg Glu Thr Asn Gln Asn
    130                 135                 140

Leu Met Met Ala Ala Leu Gly Val Asn Ser Met Ser Ser Ala Pro Tyr
145                 150                 155                 160

Trp Pro Ala Glu Tyr Ser Val His Pro Met Pro Val Ser Asn Ser Ser
                165                 170                 175

Ile Ile

<210> SEQ ID NO 27
<211> LENGTH: 948
<212> TYPE: DNA
<213> ORGANISM: Solanum laciniatum

<400> SEQUENCE: 27
atgggaagag ctccatgttg tgataaagca aatgtaaaaa gaggtccatg gtctccagaa      60
gaagatgcaa aacttaaaga ttttattcat aaatttggta ctgctggtaa ttggattgca     120
cttcctcaaa aagcaggact aaggagatgt ggaaaaagtt gtagattgag atggctaaat     180
tatttaaggc ctaatataaa gcatggtgat ttttctgatg atgaagatag agttatttgt     240
aacttatatg ccaatattgg aagcaggtgg tcaattatag cggcgcaatt acctggaaga     300
acagacaatg atatcaaaaa ttattggaac acgaagctca agaaaaagct catgggatta     360
ataaccctaa taacaattc ttcttcttct tataataata ataataataa ttaccaaaaa     420
aaattaccat attttccatc aacttctctt catcaagccc aacaaaatct tgggcctttt     480
attacaggcc cagaacagcc cattattatt ccagcagccc aacaaacaa tttgttcacc      540
aataataaca caacttgat gatgatagcc aataatttgc aaaattatcc aaattttggt     600
gctacaaatt acaatttgca aaattatcca aattttgggg aagttgcaag ttgttcttca     660
tcagatggaa gccaaatgag ttttggtact aataaagata ttattaatat taaaagagaa     720
gaaattatga gttttggtgg tcatcatgat ggtgctattt atgaagaaat taataataac     780
caacaattta attttggtta ttttggaaat actatgcagg agattgctac aagttgttgt     840
accaatggca atagtggtag tactaccaat agtagtaata attttttgtt gtacaataat     900
gatgaaaatt gtaacaagtc aaatgagata gggatgtttt attactaa                   948

<210> SEQ ID NO 28
<211> LENGTH: 315
```

<212> TYPE: PRT
<213> ORGANISM: Solanum lycopersicum

<400> SEQUENCE: 28

Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Phe Ile His Lys Phe
            20                  25                  30

Gly Thr Ala Gly Asn Trp Ile Ala Leu Pro Gln Lys Ala Gly Leu Arg
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Asp Asp Glu Asp Arg Val Ile Cys
65                  70                  75                  80

Asn Leu Tyr Ala Asn Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Met Gly Leu Ile Ile Pro Asn Asn Ser Ser
        115                 120                 125

Ser Ser Tyr Asn Asn Asn Asn Asn Tyr Gln Lys Lys Leu Pro Tyr
    130                 135                 140

Phe Pro Ser Thr Ser Leu His Gln Ala Gln Gln Asn Leu Gly Pro Phe
145                 150                 155                 160

Ile Thr Gly Pro Glu Gln Pro Ile Ile Ile Pro Ala Ala Gln Gln Asn
                165                 170                 175

Asn Leu Phe Thr Asn Asn Asn Asn Leu Met Met Ile Ala Asn Asn
            180                 185                 190

Leu Gln Asn Tyr Pro Asn Phe Gly Ala Thr Asn Tyr Asn Leu Gln Asn
        195                 200                 205

Tyr Pro Asn Phe Gly Glu Val Ala Ser Cys Ser Ser Ser Asp Gly Ser
    210                 215                 220

Gln Met Ser Phe Gly Thr Asn Lys Asp Ile Ile Asn Ile Lys Arg Glu
225                 230                 235                 240

Glu Ile Met Ser Phe Gly Gly His His Asp Gly Ala Ile Tyr Glu Glu
                245                 250                 255

Ile Asn Asn Asn Gln Gln Phe Asn Phe Gly Tyr Phe Gly Asn Thr Met
            260                 265                 270

Gln Glu Ile Ala Thr Ser Cys Cys Thr Asn Gly Asn Ser Gly Ser Thr
        275                 280                 285

Thr Asn Ser Ser Asn Asn Phe Leu Leu Tyr Asn Asn Asp Glu Asn Cys
    290                 295                 300

Asn Lys Ser Asn Glu Ile Gly Met Phe Tyr Tyr
305                 310                 315

<210> SEQ ID NO 29
<211> LENGTH: 714
<212> TYPE: DNA
<213> ORGANISM: Solanum lycopersicum

<400> SEQUENCE: 29
atgggaagag ctccatgttg tgataaagca aatgtgaaga agggccatg gtcaccagaa        60 gaagatgcaa aattaaaaga atatattgac aaatttggca ctggtggaaa ttggattgct      120
cttccacaaa aagctgggct aagaagatgt ggaaaaagct gtcgattaag atggttaaat      180

```
tatcttaggc caaatattaa acacggagag ttttcagacg aagaagacag aatcatttgc      240
agcctttatg ctaacattgg aagcaggtgg tcaatcatag cagctcaatt accaggcagg      300
acagataatg atatcaaaaa ctattggaac acgaagctga agaagaaatt aatgggattt      360
gtctcttcat ctcacaagat taggcctctt aatcaccatg attatcacca ccaaattccc      420
actaattgtt acaataatta ttcctcactt gttcaagctt catctttatt aatctcatca      480
aattatccca acaacacaac tttcccatgc tatgaaacaa atattcctag tacaacccca      540
tcaagtacaa gtttcttaag cgcgggtgca tctactagtt gtacctcagg cattactgct      600
agtactttcg cgggtcgtac tacctcttct gatgagaggt atgacatttc gaattttaat      660
tttcatagct atatgtataa taacaatggt ggttttagtg aaggagaaaa gtga           714
```

<210> SEQ ID NO 30
<211> LENGTH: 237
<212> TYPE: PRT
<213> ORGANISM: Solanum lycopersicum

<400> SEQUENCE: 30

```
Met Gly Arg Ala Pro Cys Cys Asp Lys Ala Asn Val Lys Lys Gly Pro
1               5                   10                  15

Trp Ser Pro Glu Glu Asp Ala Lys Leu Lys Glu Tyr Ile Asp Lys Phe
                20                  25                  30

Gly Thr Gly Gly Asn Trp Ile Ala Leu Pro Gln Lys Ala Gly Leu Arg
            35                  40                  45

Arg Cys Gly Lys Ser Cys Arg Leu Arg Trp Leu Asn Tyr Leu Arg Pro
        50                  55                  60

Asn Ile Lys His Gly Glu Phe Ser Asp Glu Glu Asp Arg Ile Ile Cys
65                  70                  75                  80

Ser Leu Tyr Ala Asn Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Met Gly Phe Val Ser Ser Ser His Lys Ile Arg
        115                 120                 125

Pro Leu Asn His His Asp Tyr His His Gln Ile Pro Thr Asn Cys Tyr
    130                 135                 140

Asn Asn Tyr Ser Ser Leu Val Gln Ala Ser Ser Leu Leu Ile Ser Ser
145                 150                 155                 160

Asn Tyr Pro Asn Asn Thr Thr Phe Pro Cys Tyr Glu Thr Asn Ile Pro
                165                 170                 175

Ser Thr Thr Pro Ser Ser Thr Ser Phe Leu Ser Ala Gly Ala Ser Thr
            180                 185                 190

Ser Cys Thr Ser Gly Ile Thr Ala Ser Thr Phe Ala Gly Arg Thr Thr
        195                 200                 205

Ser Ser Asp Glu Arg Tyr Asp Ile Ser Asn Phe Asn Phe His Ser Tyr
    210                 215                 220

Met Tyr Asn Asn Asn Gly Gly Phe Ser Glu Gly Glu Lys
225                 230                 235
```

<210> SEQ ID NO 31
<211> LENGTH: 918
<212> TYPE: DNA
<213> ORGANISM: Arabidopsis thaliana

<400> SEQUENCE: 31

```
atgggaagag caccgtgctg cgacaagatg gcggtgaaga aagggccatg gtcgacggag      60
gaagatgccg tgcttaagtc ttacatcgaa aaacacggca ccggcaacaa ctggatttcc     120
ctccctcaga gaattgggat aaagaggtgc gggaagagtt gtcgtttgag atggcttaat     180
tacttgaggc ctaacttaaa gcatggaggc ttcaccgatg aagaagatta catcatttgc     240
agcctttaca ttactattgg aagcaggtgg tctatcattg cttcacaatt accgggaaga     300
acagacaacg catcaaaaa ctattggaac acgaggctga agaagaagct attgagcaag     360
caagggaagg catttcatca caacttaat gtcaaatttg agcgtggaac aacatcatca      420
tcatcgagtc agaaccagat ccaaatcttt catgatgaga acaccaaatc gaaccaaaca     480
ttatataatc aagtggtgga tccatcaatg agagcttttg ccatggaaga acaaagcatg     540
atcaagaatc agatattgga accattttct tgggaaccaa acaaggtttt gtttgatgtt     600
gattatgatg cagctgcttc atcttatcat catcatgcat ccccatcatt gaactccatg     660
agcagtacta gtagtattgg tactaataat tcatctttac aaatgtctca ctacaccgtc     720
aatcacaatg atcatgatca accagatatg ttctttatgg acgggtttga gaatttccag     780
gccgagctat ttgatgagat agccaacaac aacacggtag aaaatggctt tgacggaacc     840
gagatcctga tcaataacaa ctacttggat cacgatatta gctccttcat tgattatcct     900
ctatacgata atgagtag                                                   918
```

<210> SEQ ID NO 32
<211> LENGTH: 305
<212> TYPE: PRT
<213> ORGANISM: Arabidopsis thaliana

<400> SEQUENCE: 32

```
Met Gly Arg Ala Pro Cys Cys Asp Lys Met Ala Val Lys Lys Gly Pro
1               5                   10                  15

Trp Ser Thr Glu Glu Asp Ala Val Leu Lys Ser Tyr Ile Glu Lys His
            20                  25                  30

Gly Thr Gly Asn Asn Trp Ile Ser Leu Pro Gln Arg Ile Gly Ile Lys
        35                  40                  45

Arg Cys Gly Lys Ser Cys Arg Leu Arg Trp Leu Asn Tyr Leu Arg Pro
    50                  55                  60

Asn Leu Lys His Gly Gly Phe Thr Asp Glu Glu Asp Tyr Ile Ile Cys
65                  70                  75                  80

Ser Leu Tyr Ile Thr Ile Gly Ser Arg Trp Ser Ile Ile Ala Ser Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Ser Lys Gln Gly Lys Ala Phe His Gln Gln
        115                 120                 125

Leu Asn Val Lys Phe Glu Arg Gly Thr Thr Ser Ser Ser Ser Ser Gln
    130                 135                 140

Asn Gln Ile Gln Ile Phe His Asp Glu Asn Thr Lys Ser Asn Gln Thr
145                 150                 155                 160

Leu Tyr Asn Gln Val Val Asp Pro Ser Met Arg Ala Phe Ala Met Glu
                165                 170                 175

Glu Gln Ser Met Ile Lys Asn Gln Ile Leu Glu Pro Phe Ser Trp Glu
            180                 185                 190

Pro Asn Lys Val Leu Phe Asp Val Asp Tyr Asp Ala Ala Ala Ser Ser
        195                 200                 205
```

```
Tyr His His Ala Ser Pro Ser Leu Asn Ser Met Ser Ser Thr Ser
    210                 215                 220
Ser Ile Gly Thr Asn Asn Ser Ser Leu Gln Met Ser His Tyr Thr Val
225                 230                 235                 240
Asn His Asn Asp His Asp Gln Pro Asp Met Phe Phe Met Asp Gly Phe
                245                 250                 255
Glu Asn Phe Gln Ala Glu Leu Phe Asp Glu Ile Ala Asn Asn Asn Thr
            260                 265                 270
Val Glu Asn Gly Phe Asp Gly Thr Glu Ile Leu Ile Asn Asn Asn Tyr
        275                 280                 285
Leu Asp His Asp Ile Ser Ser Phe Ile Asp Tyr Pro Leu Tyr Asp Asn
    290                 295                 300
Glu
305

<210> SEQ ID NO 33
<211> LENGTH: 990
<212> TYPE: DNA
<213> ORGANISM: Arabidopsis thaliana

<400> SEQUENCE: 33
atgggaagag ctccgtgttg cgacaagaca aaagtgaagc gagggccttg gtcgcctgaa      60
gaagactcta aacttagaga ttacattgaa aagtatggta atggtggaaa ttggatctct     120
ttccccctca aagccggttt gaggagatgt gggaagagtt gtagactgag gtggctaaac     180
tatttgagac caaacataaa gcatggtgac ttctctgagg aagaagacag gatcattttt     240
agtctcttcg ctgccatagg aagcaggtgg tcaataatag cagctcatct accgggacga     300
acagacaacg acataaaaaa ctattggaac acaaagctaa ggaagaaact cttgtcttct     360
tcctctgatt catcatcatc agccatggct tctccttatc taaaccctat ttctcaggat     420
gtgaaaagac caacctcacc aacaacaatc ccatcttctt cttacaatcc gtatgctgaa     480
aaccctaatc aatacccaac aaaatccctc atctccagca tcaatggctt cgaagctggt     540
gacaaacaga taatttccta tattaaccct aattatcctc aagatctcta tctctcggac     600
agcaacaaca cacctcgaa cgcaaatggt ttcttgctca ccacaatat gtgtgatcag      660 tacaagaacc acaccagttt ttcttcagac gtcaatggga taagatcaga gattatgatg     720
aagcaagaag agataatgat gatgatgatg atagaccacc acattgacca gaggacaaaa     780
gggtacaatg gggaattcac acaagggtat tataattact acaatgggca tggggatttg     840
aagcaaatga ttagtggaac aggcactaat tctaacataa acatgggtgg ttcaggttca     900
tcttctagtt cgataagcaa cctagctgag aacaaaagca gtggtagcct cctactagaa     960
tacaaatgct tgccctattt ctactcctag                                      990

<210> SEQ ID NO 34
<211> LENGTH: 329
<212> TYPE: PRT
<213> ORGANISM: Arabidopsis thaliana

<400> SEQUENCE: 34

Met Gly Arg Ala Pro Cys Cys Asp Lys Thr Lys Val Lys Arg Gly Pro
1               5                  10                  15

Trp Ser Pro Glu Glu Asp Ser Lys Leu Arg Asp Tyr Ile Glu Lys Tyr
            20                  25                  30

Gly Asn Gly Gly Asn Trp Ile Ser Phe Pro Leu Lys Ala Gly Leu Arg
        35                  40                  45
```

Arg Cys Gly Lys Ser Cys Arg Leu Arg Trp Leu Asn Tyr Leu Arg Pro
         50                  55                  60

Asn Ile Lys His Gly Asp Phe Ser Glu Glu Asp Arg Ile Ile Phe
 65                  70                  75                  80

Ser Leu Phe Ala Ala Ile Gly Ser Arg Trp Ser Ile Ile Ala Ala His
                 85                  90                  95

Leu Pro Gly Arg Thr Asp Asn Asp Ile Lys Asn Tyr Trp Asn Thr Lys
                100                 105                 110

Leu Arg Lys Lys Leu Leu Ser Ser Ser Asp Ser Ser Ser Ser Ala
        115                 120                 125

Met Ala Ser Pro Tyr Leu Asn Pro Ile Ser Gln Asp Val Lys Arg Pro
    130                 135                 140

Thr Ser Pro Thr Thr Ile Pro Ser Ser Ser Tyr Asn Pro Tyr Ala Glu
145                 150                 155                 160

Asn Pro Asn Gln Tyr Pro Thr Lys Ser Leu Ile Ser Ser Ile Asn Gly
                165                 170                 175

Phe Glu Ala Gly Asp Lys Gln Ile Ile Ser Tyr Ile Asn Pro Asn Tyr
                180                 185                 190

Pro Gln Asp Leu Tyr Leu Ser Asp Ser Asn Asn Thr Ser Asn Ala
        195                 200                 205

Asn Gly Phe Leu Leu Asn His Asn Met Cys Asp Gln Tyr Lys Asn His
    210                 215                 220

Thr Ser Phe Ser Ser Asp Val Asn Gly Ile Arg Ser Glu Ile Met Met
225                 230                 235                 240

Lys Gln Glu Glu Ile Met Met Met Met Ile Asp His His Ile Asp
                245                 250                 255

Gln Arg Thr Lys Gly Tyr Asn Gly Glu Phe Thr Gln Gly Tyr Tyr Asn
        260                 265                 270

Tyr Tyr Asn Gly His Gly Asp Leu Lys Gln Met Ile Ser Gly Thr Gly
        275                 280                 285

Thr Asn Ser Asn Ile Asn Met Gly Gly Ser Gly Ser Ser Ser Ser Ser
    290                 295                 300

Ile Ser Asn Leu Ala Glu Asn Lys Ser Ser Gly Ser Leu Leu Leu Glu
305                 310                 315                 320

Tyr Lys Cys Leu Pro Tyr Phe Tyr Ser
                325

<210> SEQ ID NO 35
<211> LENGTH: 897
<212> TYPE: DNA
<213> ORGANISM: Arabidopsis thaliana

<400> SEQUENCE: 35
atgggtaggg ctccatgttg tgacaaggca aatgtgaaga gaggtccatg gtctcctgaa      60
gaagacgcaa agcttaaaga ttacatcgag aaacaaggaa ctggtggcaa ttggattgct     120
ctccctcaca agctggtttt aaggagatgt gggaagagtt gcagactgag atggttaaat     180
tatttgagac caaacataag acatggagat ttcactgaag aagaagacaa tattatctac     240
agcctctttg cctccattgg aagcaggtgg tcagtaatag cagctcactt gcaaggtaga     300
actgataatg acatcaagaa ctattggaac actaagctca agaagaagct catagccacc     360
atggctcctc ctccacatca ccacttagcc attgctacat catcatcatc agcatcccca     420
tcatcatcat cacattacaa catgatcaat agtcttcttc cgtataaccc atcaacaaac     480

-continued

```
caacttctca cacctcatca gggtatcatg atgacaatga tgggccaaca acaacaacta    540
ttttatcaag aagacatggg caatttggta aattctccaa acagaaacaa tctcataatg    600
agccatcaag aagacaacca agagcaaagt acaaacaagg aataatgtt gttgagtgat     660 gtaagaagtg ggtcgagtac aacaagtaca gtaacaagag tgaagatgga acatcgtgat    720
catgatgatc atcatcatca tcatgaagaa gatgagagat caatgacctc ggtagtgatg    780
gaagattatg gaatggagga gatcaagcaa ttaataagta gtagttgtac gagtagtaac    840
aatagcttgt ggtttgacga aaacaagacg gaggataagt tcatgttgta ctactga       897
```

<210> SEQ ID NO 36
<211> LENGTH: 298
<212> TYPE: PRT
<213> ORGANISM: Arabidopsis thaliana

<400> SEQUENCE: 36

```
Met Gly Arg Ala Pro Cys Cys Asp Lys Ala Asn Val Lys Arg Gly Pro
1               5                  10                  15

Trp Ser Pro Glu Glu Asp Ala Lys Leu Lys Asp Tyr Ile Glu Lys Gln
            20                  25                  30

Gly Thr Gly Gly Asn Trp Ile Ala Leu Pro His Lys Ala Gly Leu Arg
        35                  40                  45

Arg Cys Gly Lys Ser Cys Arg Leu Arg Trp Leu Asn Tyr Leu Arg Pro
    50                  55                  60

Asn Ile Arg His Gly Asp Phe Thr Glu Glu Asp Asn Ile Ile Tyr
65                  70                  75                  80

Ser Leu Phe Ala Ser Ile Gly Ser Arg Trp Ser Val Ile Ala Ala His
                85                  90                  95

Leu Gln Gly Arg Thr Asp Asn Asp Ile Lys Asn Tyr Trp Asn Thr Lys
            100                 105                 110

Leu Lys Lys Lys Leu Ile Ala Thr Met Ala Pro Pro His His His
        115                 120                 125

Leu Ala Ile Ala Thr Ser Ser Ser Ala Ser Pro Ser Ser Ser Ser
    130                 135                 140

His Tyr Asn Met Ile Asn Ser Leu Leu Pro Tyr Asn Pro Ser Thr Asn
145                 150                 155                 160

Gln Leu Leu Thr Pro His Gln Gly Ile Met Met Thr Met Met Gly Gln
                165                 170                 175

Gln Gln Gln Leu Phe Tyr Gln Glu Asp Met Gly Asn Leu Val Asn Ser
            180                 185                 190

Pro Asn Arg Asn Asn Leu Ile Met Ser His Gln Glu Asp Asn Gln Glu
        195                 200                 205

Gln Ser Thr Asn Lys Gly Ile Met Leu Leu Ser Asp Val Arg Ser Gly
    210                 215                 220

Ser Ser Thr Thr Ser Thr Val Thr Arg Val Lys Met Glu His Arg Asp
225                 230                 235                 240

His Asp Asp His His His His Glu Glu Asp Glu Arg Ser Met Thr
                245                 250                 255

Ser Val Val Met Glu Asp Tyr Gly Met Glu Glu Ile Lys Gln Leu Ile
            260                 265                 270

Ser Ser Ser Cys Thr Ser Ser Asn Asn Ser Leu Trp Phe Asp Glu Asn
        275                 280                 285

Lys Thr Glu Asp Lys Phe Met Leu Tyr Tyr
    290                 295
```

<210> SEQ ID NO 37
<211> LENGTH: 622
<212> TYPE: DNA
<213> ORGANISM: Aegilops speltoides

<400> SEQUENCE: 37

```
ggcgccgagc tgcaacaagg cgaccgtgaa gagggcgcca tgctcaccgg aggaggacgc    60
gatgctcaag gcctacattg aggagcgtgg caccggcaac aactggattg cactgccaca   120
caagattggg ctgaagagat gcggcaagag ctgcaggctg aggtggctca actacctgag   180
gcccaacata aagcactggg acttcacccc agaggaggac agcaccatct gcaagctcta   240
cattagcatc gggagcaggt ggtcaatcat cgccgcacag ctgccaggaa ggaccgacaa   300
cgacgtcaag aactactgga acaccaagct caagaagcgg ctccttggcg gccgccgcaa   360
ggaccgcggc gccggcacgc agcagcaccg ccagggagag ctggacggcg gcaacaacga   420
aggggagcag cagccgctga gcgcgtccgc gatggagagg atccagctct gcatgcagct   480
gcaggaaatg cagaacccc tgagcagcat cggcaaccac aacaacccct tgcacctgtg    540
gcagcctgga agccatcatc aggtggccgc cactcacagt aacaacaggc acaacaacag   600
caacagcagc cgcagcagca gc                                           622
```

<210> SEQ ID NO 38
<211> LENGTH: 693
<212> TYPE: DNA
<213> ORGANISM: Antirrhinum majus

<400> SEQUENCE: 38

```
atgggaagag ctccatgttg tgataaggca aatgtaaaaa aagggccatg gtcacctgaa    60
gaagatgcaa agcttaaaga gtacatagag caacaaggca gtgttggaaa ttggattgct   120
cttccacaaa aagctggttt gagaagatgt ggaaagagct gcagattgag atggttgaac   180
tatcttagac caaacattaa gcatggagag ttttcagatg atgaagatag aatcatttgc   240
agcctctttg ctaacattgg aagcaggtgg tcaataatag cagctcaatt accaggaaga   300
actgataatg acatcaagaa ctattggaac acaaaactca gaaaaaaact catgggagca   360
atgtcccctt catatcagaa aaaacctcat caagctacaa cttttccttt accatctact   420
cataattttc tctcacaaga ctctccatat tcatctcttc tctcacaaat ctcatcagca   480
tatgaaggta acaacaacaa ctattacaac acctcaatta aggccttctc aagagcctat   540
gaacccataa tttctccaaa tcctaatgcc cctaattcag tcctacaaac acaagattca   600
tatgtgggtc ccatgcatgg cgattacaat aataataatc tcctaatctt tggaggggaa   660
ccaagctgca gttcatctga tgggagtcaa att                                693
```

<210> SEQ ID NO 39
<211> LENGTH: 231
<212> TYPE: PRT
<213> ORGANISM: Antirrhinum majus

<400> SEQUENCE: 39

Met Gly Arg Ala Pro Cys Cys Asp Lys Ala Asn Val Lys Lys Gly Pro
1               5                   10                  15

Trp Ser Pro Glu Glu Asp Ala Lys Leu Lys Glu Tyr Ile Glu Gln Gln
            20                  25                  30

Gly Ser Val Gly Asn Trp Ile Ala Leu Pro Gln Lys Ala Gly Leu Arg
        35                  40                  45

```
Arg Cys Gly Lys Ser Cys Arg Leu Arg Trp Leu Asn Tyr Leu Arg Pro
 50                  55                  60

Asn Ile Lys His Gly Glu Phe Ser Asp Asp Glu Asp Arg Ile Ile Cys
 65                  70                  75                  80

Ser Leu Phe Ala Asn Ile Gly Ser Arg Trp Ser Ile Ile Ala Ala Gln
                 85                  90                  95

Leu Pro Gly Arg Thr Asp Asn Asp Ile Lys Asn Tyr Trp Asn Thr Lys
            100                 105                 110

Leu Lys Lys Lys Leu Met Gly Ala Met Ser Pro Ser Tyr Gln Lys Lys
        115                 120                 125

Pro His Gln Ala Thr Thr Phe Pro Leu Pro Ser Thr His Asn Phe Leu
    130                 135                 140

Ser Gln Asp Ser Pro Tyr Ser Ser Leu Leu Ser Gln Ile Ser Ser Ala
145                 150                 155                 160

Tyr Glu Gly Asn Asn Asn Asn Tyr Tyr Asn Thr Ser Ile Lys Ala Phe
                165                 170                 175

Ser Arg Ala Tyr Glu Pro Ile Ile Ser Pro Asn Pro Asn Ala Pro Asn
            180                 185                 190

Ser Val Leu Gln Thr Gln Asp Ser Tyr Val Gly Pro Met His Gly Asp
        195                 200                 205

Tyr Asn Asn Asn Asn Leu Leu Ile Phe Gly Gly Glu Pro Ser Cys Ser
    210                 215                 220

Ser Ser Asp Gly Ser Gln Ile
225                 230

<210> SEQ ID NO 40
<211> LENGTH: 1050
<212> TYPE: DNA
<213> ORGANISM: Aquilegia

<400> SEQUENCE: 40
```

| | | | | | |
|---|---|---|---|---|---|
| atgggaagag | ctccttgttg | tgacaaagcc | aatgttaaga | aaggtccatg | gtcacctgaa | 60 |
| gaagatgcaa | aactcaaaga | atacattgaa | caacatggta | caggagggaa | ttggatcgcc | 120 |
| ttgccacaaa | agattggcct | taagagatgt | gggaagagct | gtcgtctcag | atggttgaat | 180 |
| tatctccgtc | caaatcttaa | gcatggaggt | ttctctgaag | aagaagatca | catgatttgc | 240 |
| agcctctata | tgagtattgg | aagccgatgg | tccatcattg | cagcacaatt | acctggtcgg | 300 |
| actgacaacg | acataaaaaa | ctattggaac | actaagctga | agaagaagct | cttgggaaaa | 360 |
| caaaggaagg | aacaccaagc | tcgtagagct | agctacctaa | gcaagacag | catgaagaaa | 420 |
| agcaattcta | ttccactggt | aattgcagat | catgggatgc | aaacgccgta | ctggccacca | 480 |
| gagccactga | tgcctatatc | aacaccgtat | ccaaaccaag | gcaatcggca | taatgatcat | 540 |
| gcatctctta | gaaaattact | gatcaaactt | gggggaagt | tttctgatga | ttatcaacaa | 600 |
| gaacccaaca | acgatgcaaa | gaataatctt | cacctcccca | ttgaatgttc | ctcaacatat | 660 |
| caacaattca | atgatcagaa | atccattaat | ctattctctt | cttcgtcttc | cataagttcc | 720 |
| ttggatattc | cctattctaa | attgttgacc | aacgagtaca | atatcgaggg | agcaagcatg | 780 |
| cacatgttgc | aaggccttaa | cggatttccg | gttgagtttg | atgagatgat | atgtagcaat | 840 |
| ccagagagtt | tagatgaatt | ggaatgccat | tatggagttg | gtatggacaa | tggagtaagc | 900 |
| agtagtggtc | caatatcaac | agaaagcact | acctgggatg | acatgggatc | tttcatcaac | 960 |
| cctcctaata | tcaccaacta | tgaagcttta | caacaagaag | tgatacaaga | atgtgcatta | 1020 |
| ttcgaccagt | cgaggtacct | tggatttcag | | | | 1050 |

<210> SEQ ID NO 41
<211> LENGTH: 350
<212> TYPE: PRT
<213> ORGANISM: Aquilegia

<400> SEQUENCE: 41

```
Met Gly Arg Ala Pro Cys Cys Asp Lys Ala Asn Val Lys Lys Gly Pro
1               5                   10                  15

Trp Ser Pro Glu Glu Asp Ala Lys Leu Lys Glu Tyr Ile Glu Gln His
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Leu Lys His Gly Gly Phe Ser Glu Glu Glu Asp His Met Ile Cys
65                  70                  75                  80

Ser Leu Tyr Met Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Leu Gly Lys Gln Arg Lys Glu His Gln Ala Arg
        115                 120                 125

Arg Ala Ser Tyr Leu Lys Gln Asp Ser Met Lys Lys Ser Asn Ser Ile
    130                 135                 140

Pro Leu Val Ile Ala Asp His Gly Met Gln Thr Pro Tyr Trp Pro Pro
145                 150                 155                 160

Glu Pro Leu Met Pro Ile Ser Thr Pro Tyr Pro Asn Gln Gly Asn Arg
                165                 170                 175

His Asn Asp His Ala Ser Leu Arg Lys Leu Leu Ile Lys Leu Gly Gly
            180                 185                 190

Lys Phe Ser Asp Asp Tyr Gln Gln Glu Pro Asn Asn Asp Ala Lys Asn
        195                 200                 205

Asn Leu His Leu Pro Ile Glu Cys Ser Ser Thr Tyr Gln Gln Phe Asn
    210                 215                 220

Asp Gln Lys Ser Ile Asn Leu Phe Ser Ser Ser Ser Ile Ser Ser
225                 230                 235                 240

Leu Asp Ile Pro Tyr Ser Lys Leu Leu Thr Asn Glu Tyr Asn Ile Glu
                245                 250                 255

Gly Ala Ser Met His Met Leu Gln Gly Leu Asn Gly Phe Pro Val Glu
            260                 265                 270

Phe Asp Glu Met Ile Cys Ser Asn Pro Glu Ser Leu Asp Glu Leu Glu
        275                 280                 285

Cys His Tyr Gly Val Gly Met Asp Asn Gly Val Ser Ser Ser Gly Pro
    290                 295                 300

Ile Ser Thr Glu Ser Thr Thr Trp Asp Asp Met Gly Ser Phe Ile Asn
305                 310                 315                 320

Pro Pro Asn Ile Thr Asn Tyr Glu Ala Leu Gln Gln Glu Val Ile Gln
                325                 330                 335

Glu Cys Ala Leu Phe Asp Gln Ser Arg Tyr Leu Gly Phe Gln
            340                 345                 350
```

<210> SEQ ID NO 42
<211> LENGTH: 1005
<212> TYPE: DNA

<213> ORGANISM: Aquilegia

<400> SEQUENCE: 42

```
atgggaaggg caccttgttg tgacaaagca aatgtcaaga aaggaccatg gtctcctgaa      60
gaagacacaa ggcttaagga gtacatagag aaatttggga ctggtgggaa ctggattgct     120
cttccacaaa aagctggtct aaagagatgt gggaagagtt gtagattgag atggcttaat     180
tatcttaggc caaacataaa acatggccaa ttctccgatg atgaagataa agtgatctgc     240
agcctctttg ctagcatagg tagcaggtgg tcaataatag ctgcacagtt gccaggcagg     300
actgacaatg atatcaaaaa ctattggaac accaagctca agaaaaaatt tatggggttt     360
gttccttcat cacagattaa agcacttcca ccaatctttc catctccatt ccacactgga     420
tcaacatatg attactaccc tttatcaaaa tctcttccag accttgaatc tctttcaatc     480
ccatcaaatt ttttgaacaa cactaacact acaaccagta ttattagtac atctcttcat     540
gaatcccaac aaaatttgga aggtttcatg caccattatc aagagaaaga caactttctt     600
atctttggag gtgaacctag ttgcagttct tctgatggaa gctgtactaa tcaaataagc     660
tacaacaaag atattgagta tgactatagt ggcaatggca atggtggtgg tggtggtgga     720
aatggtccta atggtgtaag attaggccaa gagagttatt tttgcaatgg agttcaagat     780
aatcagaaat tcatgcttgg taatggttcc attggtagta atggatggtc tgatcagagg     840
ctaaatagtg gattaatgtg gggtgatgat cagacatcat taccattaga tcatcatcat     900
tatgatggtc ttgaggatat taaactagtc aaaaacagta gtggttcttg tagtaatatt     960
ttcaatggtg atgaaactaa agcacagagt agaatcatgt acttc                   1005
```

<210> SEQ ID NO 43
<211> LENGTH: 335
<212> TYPE: PRT
<213> ORGANISM: Aquilegia

<400> SEQUENCE: 43

```
Met Gly Arg Ala Pro Cys Cys Asp Lys Ala Asn Val Lys Lys Gly Pro
1               5                   10                  15

Trp Ser Pro Glu Glu Asp Thr Arg Leu Lys Glu Tyr Ile Glu Lys Phe
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Gln Phe Ser Asp Asp Glu Asp Lys Val Ile Cys
65                  70                  75                  80

Ser Leu Phe Ala Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Phe Met Gly Phe Val Pro Ser Ser Gln Ile Lys Ala
        115                 120                 125

Leu Pro Pro Ile Phe Pro Ser Pro Phe His Thr Gly Ser Thr Tyr Asp
    130                 135                 140

Tyr Tyr Pro Leu Ser Lys Ser Leu Pro Asp Leu Glu Ser Leu Ser Ile
145                 150                 155                 160

Pro Ser Asn Phe Leu Asn Asn Thr Asn Thr Thr Thr Ser Ile Ile Ser
                165                 170                 175
```

```
Thr Ser Leu His Glu Ser Gln Gln Asn Leu Glu Gly Phe Met His His
            180                 185                 190
Tyr Gln Glu Lys Asp Asn Phe Leu Ile Phe Gly Glu Pro Ser Cys
        195                 200                 205
Ser Ser Ser Asp Gly Ser Cys Thr Asn Gln Ile Ser Tyr Asn Lys Asp
210                 215                 220
Ile Glu Tyr Asp Tyr Ser Gly Asn Gly Asn Gly Gly Gly Gly Gly
225                 230                 235                 240
Asn Gly Pro Asn Gly Val Arg Leu Gly Gln Glu Ser Tyr Phe Cys Asn
                245                 250                 255
Gly Val Gln Asp Asn Gln Lys Phe Met Leu Gly Asn Gly Ser Ile Gly
            260                 265                 270
Ser Asn Gly Trp Ser Asp Gln Arg Leu Asn Ser Gly Leu Met Trp Gly
        275                 280                 285
Asp Asp Gln Thr Ser Leu Pro Leu Asp His His His Tyr Asp Gly Leu
290                 295                 300
Glu Asp Ile Lys Leu Val Lys Asn Ser Ser Gly Ser Cys Ser Asn Ile
305                 310                 315                 320
Phe Asn Gly Asp Glu Thr Lys Ala Gln Ser Arg Ile Met Tyr Phe
                325                 330                 335
```

<210> SEQ ID NO 44
<211> LENGTH: 435
<212> TYPE: DNA
<213> ORGANISM: Arachis hypogaea
<220> FEATURE:
<221> NAME/KEY: misc_feature
<222> LOCATION: (335)..(335)
<223> OTHER INFORMATION: n can be any nucleotide
<220> FEATURE:
<221> NAME/KEY: misc_feature
<222> LOCATION: (340)..(340)
<223> OTHER INFORMATION: n can be any nucleotide
<220> FEATURE:
<221> NAME/KEY: misc_feature
<222> LOCATION: (377)..(377)
<223> OTHER INFORMATION: n can be any nucleotide
<220> FEATURE:
<221> NAME/KEY: misc_feature
<222> LOCATION: (389)..(389)
<223> OTHER INFORMATION: n can be any nucleotide
<220> FEATURE:
<221> NAME/KEY: misc_feature
<222> LOCATION: (414)..(414)
<223> OTHER INFORMATION: n can be any nucleotide
<220> FEATURE:
<221> NAME/KEY: misc_feature
<222> LOCATION: (424)..(424)
<223> OTHER INFORMATION: n can be any nucleotide
<220> FEATURE:
<221> NAME/KEY: misc_feature
<222> LOCATION: (433)..(433)
<223> OTHER INFORMATION: n can be any nucleotide

<400> SEQUENCE: 44

```
atgggaagag ctccttgttg tgacaaagca aatgtgaaga gaggaccatg gtctcctgat      60
gaggatgcaa cactcaagaa ctatcttcac actcatggca ctggaggaaa ttggattgca     120
ttgccaagaa aagctggttt aaggaggtgt gggaagagtt gccgtctaag gtggctgaat     180
tatctaaggc cagatataaa acatggagga tttaccgaac aagaggatca aatcatttgc     240
actctctata ctcaaatggg aagcagatgg tctgcaatag catctcaact tcctggcaga     300
acagacaatg atgtcaaaaa ctattggaac accangctcn agaagaagct aatggcagga     360
aaagtaattt cccctantaa taataatant aataaaacat tattgactac tcancgaaac     420
```
tcangatttt canga          435

<210> SEQ ID NO 45
<211> LENGTH: 145
<212> TYPE: PRT
<213> ORGANISM: Arachis hypogaea
<220> FEATURE:
<221> NAME/KEY: MISC_FEATURE
<222> LOCATION: (112)..(112)
<223> OTHER INFORMATION: X can be any amino acid
<220> FEATURE:
<221> NAME/KEY: MISC_FEATURE
<222> LOCATION: (114)..(114)
<223> OTHER INFORMATION: X can be any amino acid
<220> FEATURE:
<221> NAME/KEY: MISC_FEATURE
<222> LOCATION: (126)..(126)
<223> OTHER INFORMATION: X can be any amino acid
<220> FEATURE:
<221> NAME/KEY: MISC_FEATURE
<222> LOCATION: (130)..(130)
<223> OTHER INFORMATION: X can be any amino acid
<220> FEATURE:
<221> NAME/KEY: MISC_FEATURE
<222> LOCATION: (138)..(138)
<223> OTHER INFORMATION: X can be any amino acid
<220> FEATURE:
<221> NAME/KEY: MISC_FEATURE
<222> LOCATION: (142)..(142)
<223> OTHER INFORMATION: X can be any amino acid
<220> FEATURE:
<221> NAME/KEY: MISC_FEATURE
<222> LOCATION: (145)..(145)
<223> OTHER INFORMATION: X can be any amino acid

<400> SEQUENCE: 45

Met Gly Arg Ala Pro Cys Cys Asp Lys Ala Asn Val Lys Arg Gly Pro
1               5                   10                  15

Trp Ser Pro Asp Glu Asp Ala Thr Leu Lys Asn Tyr Leu His Thr His
            20                  25                  30

Gly Thr Gly Gly Asn Trp Ile Ala Leu Pro Arg Lys Ala Gly Leu Arg
        35                  40                  45

Arg Cys Gly Lys Ser Cys Arg Leu Arg Trp Leu Asn Tyr Leu Arg Pro
    50                  55                  60

Asp Ile Lys His Gly Gly Phe Thr Glu Gln Glu Asp Gln Ile Ile Cys
65                  70                  75                  80

Thr Leu Tyr Thr Gln Met Gly Ser Arg Trp Ser Ala Ile Ala Ser Gln
                85                  90                  95

Leu Pro Gly Arg Thr Asp Asn Asp Val Lys Asn Tyr Trp Asn Thr Xaa
            100                 105                 110

Leu Xaa Lys Lys Leu Met Ala Gly Lys Val Ile Ser Pro Xaa Asn Asn
        115                 120                 125

Asn Xaa Asn Lys Thr Leu Leu Thr Thr Xaa Arg Asn Ser Xaa Phe Ser
    130                 135                 140

Xaa
145

<210> SEQ ID NO 46
<211> LENGTH: 476
<212> TYPE: DNA
<213> ORGANISM: Arachis hypogaea

<400> SEQUENCE: 46
atgggaagag ctccttgttg tgacaaagca aatgtgaaga gaggaccatg gtctcctgat          60

```
gaggatgcaa cactcaagaa ctatcttcac actcatggca ctggaggaaa ttggattgca      120
ttgccaagaa aagctggttt aaggaggtgt gggaagagtt gccgtctaag gtggctgaat      180
tatctaaggc cagatataaa acatggagga tttaccgaac aagaggatca aatcatttgc      240
actctctata ctcaaatggg aagcagatgg tctgcaatag catctcaact tcctggcaga      300
acagacaatg atgtcaaaaa ctattggaac accaagctca agaagaagct aatggcagga      360
aaagtaattt cccctaataa taataataat aataaaacat tattgactac tcaacaaaac      420
tcagattttc aagataataa aaattgttca ccaccctcat catcatcatc attagt         476
```

```
<210> SEQ ID NO 47
<211> LENGTH: 159
<212> TYPE: PRT
<213> ORGANISM: Arachis hypogaea

<400> SEQUENCE: 47
```

Met Gly Arg Ala Pro Cys Cys Asp Lys Ala Asn Val Lys Arg Gly Pro
1               5                   10                  15

Trp Ser Pro Asp Glu Asp Ala Thr Leu Lys Asn Tyr Leu His Thr His
            20                  25                  30

Gly Thr Gly Gly Asn Trp Ile Ala Leu Pro Arg Lys Ala Gly Leu Arg
        35                  40                  45

Arg Cys Gly Lys Ser Cys Arg Leu Arg Trp Leu Asn Tyr Leu Arg Pro
    50                  55                  60

Asp Ile Lys His Gly Gly Phe Thr Glu Gln Glu Asp Gln Ile Ile Cys
65                  70                  75                  80

Thr Leu Tyr Thr Gln Met Gly Ser Arg Trp Ser Ala Ile Ala Ser Gln
                85                  90                  95

Leu Pro Gly Arg Thr Asp Asn Asp Val Lys Asn Tyr Trp Asn Thr Lys
            100                 105                 110

Leu Lys Lys Lys Leu Met Ala Gly Lys Val Ile Ser Pro Asn Asn Asn
        115                 120                 125

Asn Asn Asn Lys Thr Leu Leu Thr Thr Gln Gln Asn Ser Asp Phe Gln
130                 135                 140

Asp Asn Lys Asn Cys Ser Pro Pro Ser Ser Ser Ser Leu Val
145                 150                 155

```
<210> SEQ ID NO 48
<211> LENGTH: 744
<212> TYPE: DNA
<213> ORGANISM: Arachis stenosperma

<400> SEQUENCE: 48
```

```
atgggaagag ctccatgttg tgacaaggca aatgtgaaga gaggaccatg gtcacctgaa       60
gaagacttaa agctcaaaga atacatacac aagcatggca ctggtggcaa ttggattgct      120
cttcctcaaa aagctggtct aagagatgt gggaagagtt gcagactgag atggcttaac      180
tatctgaggc caaacattaa gcatggagaa ttttctgaag aggaagacag aatcatttgc      240
agcctctatg ttaacattgg aagcagatgg tcaattatag cagctcagtt gccaggaagg      300
actgacaatg atataaagaa ttattggaac actaagctca agaaaaaact catctctggt      360
ttcattccca attcttcttc tattcgacaa agaaacatc atcatcatca acaacaacaa       420
caacctccat ttccatcatc atcaataatg tacatggatc aatgttatgg atcttatgtc      480
acaggccttg ttgatcctat ttcacttcct tcaactgaat actatgcaaa cacaacaaca      540
acaacctcag ttccatttta ccagcaccaa gtagattcca tagttagccc cagcagcatg      600
```

```
caacaaaatt atcacatgtt tggaagtgaa ggtagttgca gtttctctga taatggaagc    660
agtatcaagc aagaggaaat tgggtatcat catcaaggat catacaacaa cattattgca    720
tttgatgagt tcaacaacac acaa                                           744
```

<210> SEQ ID NO 49
<211> LENGTH: 248
<212> TYPE: PRT
<213> ORGANISM: Arachis stenosperma

<400> SEQUENCE: 49

```
Met Gly Arg Ala Pro Cys Cys Asp Lys Ala Asn Val Lys Arg Gly Pro
1               5                   10                  15

Trp Ser Pro Glu Glu Asp Leu Lys Leu Lys Glu Tyr Ile His Lys His
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Glu Phe Ser Glu Glu Asp Arg Ile Ile Cys
65                  70                  75                  80

Ser Leu Tyr Val Asn Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Ile Ser Gly Phe Ile Pro Asn Ser Ser Ser Ile
        115                 120                 125

Arg Gln Arg Lys His His His Gln Gln Gln Gln Pro Pro Phe
    130                 135                 140

Pro Ser Ser Ser Ile Met Tyr Met Asp Gln Cys Tyr Gly Ser Tyr Val
145                 150                 155                 160

Thr Gly Leu Val Asp Pro Ile Ser Leu Pro Ser Thr Glu Tyr Tyr Ala
                165                 170                 175

Asn Thr Thr Thr Thr Thr Ser Val Pro Phe Tyr Gln His Gln Val Asp
            180                 185                 190

Ser Ile Val Ser Pro Ser Ser Met Gln Gln Asn Tyr His Met Phe Gly
        195                 200                 205

Ser Glu Gly Ser Cys Ser Phe Ser Asp Asn Gly Ser Ser Ile Lys Gln
    210                 215                 220

Glu Glu Ile Gly Tyr His His Gln Gly Ser Tyr Asn Asn Ile Ile Ala
225                 230                 235                 240

Phe Asp Glu Phe Asn Asn Thr Gln
                245
```

<210> SEQ ID NO 50
<211> LENGTH: 477
<212> TYPE: DNA
<213> ORGANISM: Brachypodium distachyon

<400> SEQUENCE: 50

```
atggggcgcg cgccgtgctg cgacaaggcg agcgtgaagc gcgggccgtg gtcgccggag    60
gaggacgagc agctccggcg ctacgtccgc gcccatggca tcggcggcaa ctggatcgcc   120
ctgccgcaca agccgggct gaagcggtgc ggcaagagct gccggctgcg gtggctgaac   180
tacctgcggc cggacatcag gcacggcggg tacacggccg aggaggaccg ggtcatctgc   240
```

-continued

| | | | | |
|---|---|---|---|---|
| tccctatacg | ggtcaatcgg | cagccggtgg | tcgattatcg | cgtccaagct | ccccggccgc | 300 |
| acggacaacg | acgtcaagaa | ctactggaac | accaagctca | agaagaaggc | cgtcgccatg | 360 |
| gggatgcagc | atgccaccgg | aggatcagcc | ttctccgctc | cccatagcca | gtgcgcgctc | 420 |
| tcgccggcgg | cctcgggctc | ctcctcgtcg | accgtcgaca | ccactagctc | cagcgcc | 477 |

<210> SEQ ID NO 51
<211> LENGTH: 159
<212> TYPE: PRT
<213> ORGANISM: Brachypodium distachyon

<400> SEQUENCE: 51

Met Gly Arg Ala Pro Cys Cys Asp Lys Ala Ser Val Lys Arg Gly Pro
1               5                   10                  15

Trp Ser Pro Glu Glu Asp Glu Gln Leu Arg Arg Tyr Val Arg Ala His
            20                  25                  30

Gly Ile Gly Gly Asn Trp Ile Ala Leu Pro His Lys Ala Gly Leu Lys
        35                  40                  45

Arg Cys Gly Lys Ser Cys Arg Leu Arg Trp Leu Asn Tyr Leu Arg Pro
    50                  55                  60

Asp Ile Arg His Gly Gly Tyr Thr Ala Glu Glu Asp Arg Val Ile Cys
65                  70                  75                  80

Ser Leu Tyr Gly Ser Ile Gly Ser Arg Trp Ser Ile Ile Ala Ser Lys
                85                  90                  95

Leu Pro Gly Arg Thr Asp Asn Asp Val Lys Asn Tyr Trp Asn Thr Lys
            100                 105                 110

Leu Lys Lys Lys Ala Val Ala Met Gly Met Gln His Ala Thr Gly Gly
        115                 120                 125

Ser Ala Phe Ser Ala Pro His Ser Gln Cys Ala Leu Ser Pro Ala Ala
    130                 135                 140

Ser Gly Ser Ser Ser Ser Thr Val Asp Thr Thr Ser Ser Ser Ala
145                 150                 155

<210> SEQ ID NO 52
<211> LENGTH: 717
<212> TYPE: DNA
<213> ORGANISM: Brachypodium distachyon

<400> SEQUENCE: 52

| | | | | |
|---|---|---|---|---|
| atggggaggg | cgccgtgctg | cgacagggcg | gcggtgaagc | gtgggccgtg | gtcgccggag | 60 |
| gaggacgaca | gctgcgcga | ctacatccag | cgccacggca | ccggcggcag | ctggatcacc | 120 |
| ttccccaaga | agccgggct | gaggaggtgt | ggcaagagct | gcaggctgcg | gtggctcaac | 180 |
| tacctccgcc | cggacatccg | cacggcggc | ttcaccgacg | aggaggacgc | gctcatcttc | 240 |
| tccctctaca | gcaagctcgg | cagcaagtgg | tcgctgatcg | cgtcgcagct | ggagaggagg | 300 |
| acggacaacg | acgtcaagaa | ccactggaac | accaagctca | agaagcgcct | cgcagccttc | 360 |
| tcctctcccc | cgtcgtcttc | ctcctccttc | ctgccggcgc | ctgcgcccat | ggccgtggcc | 420 |
| gtcgcgcacc | cgctcgccct | ggccgtgccg | accgtcaagg | ccgagacgta | cgcctacgac | 480 |
| gacttcatgg | cgccgccggc | cgcgctccac | gtcttcgacc | accgttcgg | caacggcgcc | 540 |
| gatcagcccg | gctccacgac | gtccgcctcc | gcagcgtcgt | ccatgtccaa | ctggtcgtcc | 600 |
| gcggcggaca | cgcggggc | cgccgacggg | ttcttcgcgg | acttctgcaa | cgccggcgcg | 660 |
| gcggaccagt | tcctcggcgg | cttctactac | cctctcgatc | ccaccttgtc | gctagtc | 717 |

<210> SEQ ID NO 53
<211> LENGTH: 239
<212> TYPE: PRT
<213> ORGANISM: Brachypodium distachyon

<400> SEQUENCE: 53

Met Gly Arg Ala Pro Cys Cys Asp Arg Ala Ala Val Lys Arg Gly Pro
1               5                   10                  15

Trp Ser Pro Glu Glu Asp Asp Lys Leu Arg Asp Tyr Ile Gln Arg His
            20                  25                  30

Gly Thr Gly Gly Ser Trp Ile Thr Phe Pro Lys Lys Ala Gly Leu Arg
        35                  40                  45

Arg Cys Gly Lys Ser Cys Arg Leu Arg Trp Leu Asn Tyr Leu Arg Pro
    50                  55                  60

Asp Ile Arg His Gly Gly Phe Thr Asp Glu Glu Asp Ala Leu Ile Phe
65                  70                  75                  80

Ser Leu Tyr Ser Lys Leu Gly Ser Lys Trp Ser Leu Ile Ala Ser Gln
                85                  90                  95

Leu Glu Arg Arg Thr Asp Asn Asp Val Lys Asn His Trp Asn Thr Lys
            100                 105                 110

Leu Lys Lys Arg Leu Ala Ala Phe Ser Ser Pro Ser Ser Ser Ser
        115                 120                 125

Ser Phe Leu Pro Ala Pro Ala Pro Met Ala Val Ala Val Ala His Pro
    130                 135                 140

Leu Ala Leu Ala Val Pro Thr Val Lys Ala Glu Thr Tyr Ala Tyr Asp
145                 150                 155                 160

Asp Phe Met Ala Pro Pro Ala Ala Leu His Val Phe Asp His Pro Phe
                165                 170                 175

Gly Asn Gly Ala Asp Gln Pro Gly Ser Thr Thr Ser Ala Ser Ala Ala
            180                 185                 190

Ser Ser Met Ser Asn Trp Ser Ser Ala Ala Asp Asn Ala Gly Ala Ala
        195                 200                 205

Asp Gly Phe Phe Ala Asp Phe Cys Asn Ala Gly Ala Ala Asp Gln Phe
210                 215                 220

Leu Gly Gly Phe Tyr Tyr Pro Leu Asp Pro Thr Leu Ser Leu Val
225                 230                 235

<210> SEQ ID NO 54
<211> LENGTH: 1092
<212> TYPE: DNA
<213> ORGANISM: Brassica napus

<400> SEQUENCE: 54
atgggaaggg caccgtgttg tgacaaagcc aacgtgaaga aagggccttg gtctcctgag      60
gaagatgcca aactcaaaga ttacatcgag aatagtggta caggaggcaa ctggatcgct     120
ttgcctcaga agattggtct aaggagatgt gggaagagtt gcagactaag gtggctcaac     180
tatttgagac caaacatcaa acatggtggc ttctctgagg aggaagacac catcatttgt     240
aacctttatg ttactattgg tagcaggtgg tctataattg ctgcacaact gccgggaaga     300
acggacaacg atatcaagaa ctattggaac acgaggctaa agaagaagct tctaaacaaa     360
caaaggacag agttccaaga agctcggatg aagcaagaga tggtgatgat gaagagacaa     420
caacaaggac atgaccacat caatggtagt acggatcttt atctgaaaaa catgtttgga     480
tcatcaccat ggccattact acaacagctt cctcatcatc aagtacctct tgtgatgatg     540
gaaccaacaa gttgtaacta ctaccaaacg tcaccctctt gtaacctaga acaaaagcca     600

-continued

```
cttatcactt tcaataacat ggtcaagatt gaagaagaac cggagaaaac aaaccctgat    660
catcctcagc atcaaaattc tatcacaaac cctttttgatg tctccgtctc ccagctcttg   720
ttagatcctg attactactt aggatcagga ggaggagaag gggattttgc tatcatgagt    780
agcagcacaa attctccatt accaaacaca agtggtgatc aaaatgaaca tcagcagcaa    840
gagattcttc aatggtttgg gagtagtaat cttcagacag aagcaagcag tgatatgttc    900
ttaaacaaca tagggaatct tgagaccaac gaggacacaa gattctactc atcattagcc    960
ggtgctggag cggctccggc aggaggaacg acgagcacat cggcagatca aagcacaata    1020
agttgggagg acataacctc tcttgttaat tccgaagatg caagttactt caatgggca     1080 aatcatttgt aa                                                        1092
```

<210> SEQ ID NO 55
<211> LENGTH: 363
<212> TYPE: PRT
<213> ORGANISM: Brassica napus

<400> SEQUENCE: 55

```
Met Gly Arg Ala Pro Cys Cys Asp Lys Ala Asn Val Lys Lys Gly Pro
1               5                  10                  15

Trp Ser Pro Glu Glu Asp Ala Lys Leu Lys Asp Tyr Ile Glu Asn Ser
            20                  25                  30

Gly Thr Gly Gly Asn Trp Ile Ala Leu Pro Gln Lys Ile Gly Leu Arg
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Asp Thr Ile Ile Cys
65                  70                  75                  80

Asn Leu Tyr Val Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Asn Lys Gln Arg Thr Glu Phe Gln Glu Ala
        115                 120                 125

Arg Met Lys Gln Glu Met Val Met Met Lys Arg Gln Gln Gln Gly His
    130                 135                 140

Asp His Ile Asn Gly Ser Thr Asp Leu Tyr Leu Lys Asn Met Phe Gly
145                 150                 155                 160

Ser Ser Pro Trp Pro Leu Leu Gln Gln Leu Pro His His Gln Val Pro
                165                 170                 175

Leu Val Met Met Glu Pro Thr Ser Cys Asn Tyr Tyr Gln Thr Ser Pro
            180                 185                 190

Ser Cys Asn Leu Glu Gln Lys Pro Leu Ile Thr Phe Asn Asn Met Val
        195                 200                 205

Lys Ile Glu Glu Glu Pro Glu Lys Thr Asn Pro Asp His Pro Gln His
    210                 215                 220

Gln Asn Ser Ile Thr Asn Pro Phe Asp Val Ser Val Ser Gln Leu Leu
225                 230                 235                 240

Leu Asp Pro Asp Tyr Tyr Leu Gly Ser Gly Gly Glu Gly Asp Phe
                245                 250                 255

Ala Ile Met Ser Ser Ser Thr Asn Ser Pro Leu Pro Asn Thr Ser Gly
            260                 265                 270

Asp Gln Asn Glu His Gln Gln Gln Glu Ile Leu Gln Trp Phe Gly Ser
```

```
            275                 280                 285
Ser Asn Leu Gln Thr Glu Ala Ser Ser Asp Met Phe Leu Asn Asn Ile
        290                 295                 300

Gly Asn Leu Glu Thr Asn Glu Asp Thr Arg Phe Tyr Ser Ser Leu Ala
305                 310                 315                 320

Gly Ala Gly Ala Ala Pro Ala Gly Gly Thr Thr Ser Thr Ser Ala Asp
                325                 330                 335

Gln Ser Thr Ile Ser Trp Glu Asp Ile Thr Ser Leu Val Asn Ser Glu
        340                 345                 350

Asp Ala Ser Tyr Phe Asn Gly Ala Asn His Leu
        355                 360

<210> SEQ ID NO 56
<211> LENGTH: 1116
<212> TYPE: DNA
<213> ORGANISM: Brassica napus

<400> SEQUENCE: 56
atgggaagag caccgtgttg tgataaggct aacgtgaaga aagggccttg gtctcctgaa      60
gaagatgcaa agctcaaaga ttacatcgag agtagtggca caggaggcaa ctggatcgct     120
ttgcctcaga gattggtct aaggagatgt gggaagagtt gcagactaag gtggcttaac     180
tatttgagac ctaacatcaa acatggtggc ttctctgagg aagaggacaa catcatttgt     240
aacctctatg ttactattgg tagcaggtgg tctataattg ctgcacaatt gcctggaaga     300
acagacaacg atatcaagaa ctattggaac acgaggctga agaagaagct tcttaacaaa     360
caaagaaaag agttccaaga agctcggatg aagcaagaga tggtgatgat gaaacgacag     420
caacaaggac aaggacaatg ccaaagtaat ggtagtacgg atctttatct gaacaacatg     480
tttagatcat caccatggcc attactgcct catcttcctc ctcctcatag tcaagtacct     540
cttgtgatga tggaaccaac aagctgcaat tactaccaac cgacaccgtc ttgcgcatta     600
gaacaaaagc cattgatccc actcaagaac atggtcaaga ttgaagcaga accggagaga     660
tcaaaccctg atcatcatta tccggaagac tcaatgacaa actcttttga tctttccttc     720
tctcagcttt tgttagatcc taattactac ctggaatcag gaggaggaga aggagagttt     780
gctctcatga gtagaagtac gaactctcca ttaccaaaca caagtagtga tcaccatcaa     840
catcaaaaag agattactca atggtttggg agtagtaatt ttcagacaga agctatcaat     900
gatgtgttct taaacaacaa caacttagcg aattttgaga ccaacgacga gaacgcaaaa     960
ctatatgcaa actcatcagt agccggagct ggagcagcgt tgccggagg aacgacgagt    1020 acatcggctg atcaaagcac aataagttgg gaggacataa cctctcttgt taactccgat    1080
gatgcaagat acttcaatgg gccaaataat gtgtaa                             1116

<210> SEQ ID NO 57
<211> LENGTH: 371
<212> TYPE: PRT
<213> ORGANISM: Brassica napus

<400> SEQUENCE: 57

Met Gly Arg Ala Pro Cys Cys Asp Lys Ala Asn Val Lys Lys Gly Pro
1               5                   10                  15

Trp Ser Pro Glu Glu Asp Ala Lys Leu Lys Asp Tyr Ile Glu Ser Ser
            20                  25                  30

Gly Thr Gly Gly Asn Trp Ile Ala Leu Pro Gln Lys Ile Gly Leu Arg
        35                  40                  45
```

```
Arg Cys Gly Lys Ser Cys Arg Leu Arg Trp Leu Asn Tyr Leu Arg Pro
 50                  55                  60
Asn Ile Lys His Gly Phe Ser Glu Glu Asp Asn Ile Ile Cys
 65                  70                  75                  80
Asn Leu Tyr Val Thr Ile Gly Ser Arg Trp Ser Ile Ile Ala Ala Gln
                     85                  90                  95
Leu Pro Gly Arg Thr Asp Asn Asp Ile Lys Asn Tyr Trp Asn Thr Arg
                100                 105                 110
Leu Lys Lys Lys Leu Leu Asn Lys Gln Arg Lys Glu Phe Gln Glu Ala
                115                 120                 125
Arg Met Lys Gln Glu Met Val Met Met Lys Arg Gln Gln Gln Gly Gln
130                 135                 140
Gly Gln Cys Gln Ser Asn Gly Ser Thr Asp Leu Tyr Leu Asn Asn Met
145                 150                 155                 160
Phe Arg Ser Ser Pro Trp Pro Leu Leu Pro His Leu Pro Pro Pro His
                165                 170                 175
Ser Gln Val Pro Leu Val Met Met Glu Pro Thr Ser Cys Asn Tyr Tyr
                180                 185                 190
Gln Pro Thr Pro Ser Cys Ala Leu Glu Gln Lys Pro Leu Ile Pro Leu
                195                 200                 205
Lys Asn Met Val Lys Ile Glu Ala Glu Pro Glu Arg Ser Asn Pro Asp
210                 215                 220
His His Tyr Pro Glu Asp Ser Met Thr Asn Ser Phe Asp Leu Ser Phe
225                 230                 235                 240
Ser Gln Leu Leu Leu Asp Pro Asn Tyr Tyr Leu Glu Ser Gly Gly Gly
                245                 250                 255
Glu Gly Glu Phe Ala Leu Met Ser Arg Ser Thr Asn Ser Pro Leu Pro
                260                 265                 270
Asn Thr Ser Ser Asp His His Gln His Gln Lys Glu Ile Thr Gln Trp
                275                 280                 285
Phe Gly Ser Ser Asn Phe Gln Thr Glu Ala Ile Asn Asp Val Phe Leu
290                 295                 300
Asn Asn Asn Asn Leu Ala Asn Phe Glu Thr Asn Asp Glu Asn Ala Lys
305                 310                 315                 320
Leu Tyr Ala Asn Ser Ser Val Ala Gly Ala Gly Ala Ala Phe Ala Gly
                325                 330                 335
Gly Thr Thr Ser Thr Ser Ala Asp Gln Ser Thr Ile Ser Trp Glu Asp
                340                 345                 350
Ile Thr Ser Leu Val Asn Ser Asp Asp Ala Arg Tyr Phe Asn Gly Pro
                355                 360                 365
Asn Asn Val
    370

<210> SEQ ID NO 58
<211> LENGTH: 1454
<212> TYPE: DNA
<213> ORGANISM: Brassica napus

<400> SEQUENCE: 58
ctcctcttca tcatcaacat agttgagaaa gataaaaaat aaagagggag agaaagagaa      60
agaaacacat caagaacaag aataacgaat caagaagatg ggaagagcac cgtgttgtga     120
caaggctaac gtgaagaaag ggccgtggtc tcctgaagaa gacgcaaaac tcaaagatta     180
catcgagaat aatggcacag gaggcaactg gatcgcgttg cctcagaaga ttggtctaag     240
```

```
aagatgtggg aagagttgca gactaaggtg gctcaactat ttgagaccaa acatcaaaca      300
tggtggcttc tctgaggaag aggacaacat catttgtaac ctctatgtta ccattggtag      360
caggtggtct ataattgctg cacaattgcc tggaagaaca gacaacgata tcaagaacta      420
ttggaacacg aggctgaaga agaagcttct taacaaacaa agaaaagagt accaagaagc      480
tcggatgaag caagagatgg tgatgatgaa agcgacaagc aacaagggac aatgccaaag      540
taatgctagt acggatcttt attctgaaca acatgtttgg atcatcacca tggccattac      600
tgcctcagct tcctcctcct cattgtcaag tacctcttgt gatgatggaa ccaacaagct      660
gcaattacta ccaaccgaca ccgtcttgcg cattagaaca aaagccattg atcccactca      720
agaacatggt caagattgaa gaagaaccgg agagatcaaa ccctgatcat cattatccgg      780
aagactcaat gacaaactct tttgatcttt ccttttctca gcttttgtta gatcctaatt      840
actacctgga atcaggagga ggagaaggag agtttgctct catgagtagc agtacgaact      900
ctccattacc aaacacaagt gatgatcacc atcaacatca aaaagagatt actcaatggt      960
ttgggagtgg taattttcaa acagaagcta tcaatgatgt gttcttaaac aacaacaact     1020
tagcgaattt tgagaccaac gatgagaacg caaaactata tgcaaactca tcagtaaccg     1080
gagctggagc agcgtttgcc ggaggaacga cgagtacatc ggctgatcaa agcacaataa     1140
gttgggagga cataacctct cttcttaaat ccgatgatgc aagttacttc aatgggccaa     1200
atcatgtgta attttttctg caaaatttta tttttactta tatatataaa gaggttttg      1260 tataagtata tatgacataa gagagtggta aaaaaaatac atggattgag attaatattc     1320
tcatatttgt gtattttagc ttcaacttag ctttattcac gaagagcaat atatatgatc     1380
ttttgagttt ttcttttga ttaatgcttt tataaatttg aagagaaaa aaaaaaaaaa     1440 aaaaaaaaaa aaaa                                                        1454

<210> SEQ ID NO 59
<211> LENGTH: 753
<212> TYPE: DNA
<213> ORGANISM: Brassica napus

<400> SEQUENCE: 59
atgggaaggg caccgtgttg tgacaaagcc aacgtgaaga agggccttg gtctcctgag        60 gaagatgcca aactcaaaga ttacatcgag aatagtggta caggaggcaa ctggatcgct      120
ttgcctcaga agattggtct aaggagatgt gggaagagtt gcagactaag gtggctcaac      180
tatttgagac caaacatcaa acatggtggc ttctctgagg aggaagacac catcatttgt      240
aacctttatg ttactattgg tagcaggtgg tctataattg ctgcacaact gccgggaaga      300
acggacaacg atatcaagaa ctattggaac acgaggctaa agaagaagct tctaaacaaa      360
caaaggacag agttccaaga agctcggatg aagcaagaga tggtgatgat gaagagacaa      420
caacaaggac atgaccacat caatggtagt acggatcttt atctgaaaaa catgtttgga      480
tcatcaccat ggccattact acaacagctt cctcatcatc aagtacctct tgtgatgatg      540
gaaccaacaa gttgtaacta ctaccaaacg tcaccctctt gtaacctaga acaaagccca      600
cttatcactt tcaataacat ggtcaagatt gaagaagaac cggagaaaac aaaccctgat      660
catcctcagc atcaaaattc tatcacaaac ccttttgatg tctccgtctc ccagctcttg      720
ttagatcctg attactactt aggatcagga gga                                    753

<210> SEQ ID NO 60
```

<211> LENGTH: 251
<212> TYPE: PRT
<213> ORGANISM: Brassica napus

<400> SEQUENCE: 60

Met Gly Arg Ala Pro Cys Cys Asp Lys Ala Asn Val Lys Lys Gly Pro
1               5                   10                  15
Trp Ser Pro Glu Glu Asp Ala Lys Leu Lys Asp Tyr Ile Glu Asn Ser
                20                  25                  30
Gly Thr Gly Gly Asn Trp Ile Ala Leu Pro Gln Lys Ile Gly Leu Arg
            35                  40                  45
Arg Cys Gly Lys Ser Cys Arg Leu Arg Trp Leu Asn Tyr Leu Arg Pro
        50                  55                  60
Asn Ile Lys His Gly Gly Phe Ser Glu Glu Glu Asp Thr Ile Ile Cys
65                  70                  75                  80
Asn Leu Tyr Val Thr Ile Gly Ser Arg Trp Ser Ile Ala Ala Gln
                85                  90                  95
Leu Pro Gly Arg Thr Asp Asn Asp Ile Lys Asn Tyr Trp Asn Thr Arg
            100                 105                 110
Leu Lys Lys Lys Leu Leu Asn Lys Gln Arg Thr Glu Phe Gln Glu Ala
        115                 120                 125
Arg Met Lys Gln Glu Met Val Met Met Lys Arg Gln Gln Gln Gly His
    130                 135                 140
Asp His Ile Asn Gly Ser Thr Asp Leu Tyr Leu Lys Asn Met Phe Gly
145                 150                 155                 160
Ser Ser Pro Trp Pro Leu Leu Gln Gln Leu Pro His His Gln Val Pro
                165                 170                 175
Leu Val Met Met Glu Pro Thr Ser Cys Asn Tyr Tyr Gln Thr Ser Pro
            180                 185                 190
Ser Cys Asn Leu Glu Gln Lys Pro Leu Ile Thr Phe Asn Asn Met Val
        195                 200                 205
Lys Ile Glu Glu Glu Pro Glu Lys Thr Asn Pro Asp His Pro Gln His
    210                 215                 220
Gln Asn Ser Ile Thr Asn Pro Phe Asp Val Ser Val Ser Gln Leu Leu
225                 230                 235                 240
Leu Asp Pro Asp Tyr Tyr Leu Gly Ser Gly Gly
                245                 250

<210> SEQ ID NO 61
<211> LENGTH: 864
<212> TYPE: DNA
<213> ORGANISM: Brassica napus

<400> SEQUENCE: 61
atgggaaggg ctccatgttg tgacaaagca acgtcaaga gaggtccatg gtctcctgaa        60
gaagatgcaa agcttaaaga ttacatagag aaacaaggca ctggtggcaa ctggattgct       120
ctccctcaca agctggtttt aagaagatgt gggaagagtt gtagactgag gtggttaaac       180
tatttgaggc caaacataag acatggagat ttctctgagg aagaagacaa gattatcttc       240
agcctctttt cctccattgg aagcaggtgg tcagtaattg cagctcacct gcatggtaga       300
actgataacg acatcaagaa ctattggagc actaagctca agaagaagct cattgccact       360
atggctcctc caccacctca tcatctctta gccattgcct catcatcatc atcaccatca       420
tcatcacact acaacatgac caatagtctt cctccgtata acccatcaat atctacaaat       480
gagctgttaa cacctcatca ggagatgatg atgacaatga tggaccaaca acaacaacaa       540

```
ctattatacc aagaagccgt ggacagtttg gtaaattctc caaatagcaa caagcttata      600
atgagccatc aagaagacag ccgggagcaa agtacaaaca aaggaataat gttgttgagt      660
gatgtaagaa gtgggtcaag tacaacaagt acagtaacaa gagtgaagat ggaacaacat      720
gatcatcatc atgaagagag atcaatggaa gattatggaa tggaggagat caatcactta      780
ataaatagta gttgtacgag tagtagtagc aacagcttgt ggtttgatga aacaagacc       840 gatgatacgt tcatgttgta ctat                                              864
```

<210> SEQ ID NO 62
<211> LENGTH: 288
<212> TYPE: PRT
<213> ORGANISM: Brassica napus

<400> SEQUENCE: 62

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Asp Tyr Ile Glu Lys Gln
            20                  25                  30

Gly Thr Gly Gly Asn Trp Ile Ala Leu Pro His Lys Ala Gly Leu Arg
        35                  40                  45

Arg Cys Gly Lys Ser Cys Arg Leu Arg Trp Leu Asn Tyr Leu Arg Pro
    50                  55                  60

Asn Ile Arg His Gly Asp Phe Ser Glu Glu Asp Lys Ile Ile Phe
65                  70                  75                  80

Ser Leu Phe Ser Ser Ile Gly Ser Arg Trp Ser Val Ile Ala Ala His
                85                  90                  95

Leu His Gly Arg Thr Asp Asn Asp Ile Lys Asn Tyr Trp Ser Thr Lys
            100                 105                 110

Leu Lys Lys Lys Leu Ile Ala Thr Met Ala Pro Pro Pro His His
        115                 120                 125

Leu Leu Ala Ile Ala Ser Ser Ser Ser Pro Ser Ser Ser His Tyr
    130                 135                 140

Asn Met Thr Asn Ser Leu Pro Pro Tyr Asn Pro Ser Ile Ser Thr Asn
145                 150                 155                 160

Glu Leu Leu Thr Pro His Gln Glu Met Met Met Thr Met Met Asp Gln
                165                 170                 175

Gln Gln Gln Gln Leu Leu Tyr Gln Glu Ala Val Asp Ser Leu Val Asn
            180                 185                 190

Ser Pro Asn Ser Asn Lys Leu Ile Met Ser His Gln Glu Asp Ser Arg
        195                 200                 205

Glu Gln Ser Thr Asn Lys Gly Ile Met Leu Leu Ser Asp Val Arg Ser
    210                 215                 220

Gly Ser Ser Thr Thr Ser Thr Val Thr Arg Val Lys Met Glu Gln His
225                 230                 235                 240

Asp His His His Glu Glu Arg Ser Met Glu Asp Tyr Gly Met Glu Glu
                245                 250                 255

Ile Asn His Leu Ile Asn Ser Ser Cys Thr Ser Ser Ser Asn Ser
            260                 265                 270

Leu Trp Phe Asp Glu Asn Lys Thr Asp Asp Thr Phe Met Leu Tyr Tyr
        275                 280                 285
```

<210> SEQ ID NO 63
<211> LENGTH: 792
<212> TYPE: DNA

```
<213> ORGANISM: Brassica rapa
<220> FEATURE:
<221> NAME/KEY: misc_feature
<222> LOCATION: (760)..(760)
<223> OTHER INFORMATION: n can be any nucleotide

<400> SEQUENCE: 63
atgggaagag caccgtgttg tgacaaggct aacgtgaaga aagggccttg gtctcctgaa      60
gaagatgcaa agctcaaaga ttacatcgag agtagtggca caggaggcaa ctggatcgct     120
ttgcctcaga agattggtct aaggagatgt gggaagagtt gcagactaag gtggcttaac     180
tatttgagac ctaacatcaa acatggtggc ttctctgagg aagaggacaa catcatttgt     240
aacctctatg ttactattgg tagcaggtgg tctataattg ctgcacaatt gcctggaaga     300
acagacaacg atatcaagaa ctattggaac acgaggctga agaagaagct tcttaacaaa     360
caaagaaaag agttccaaga agctcggatg aagcaagaga tggtgatgat gaaacgacag     420
caacaaggac aaggacaatg ccaaagtaat ggtagtacgg atctttatct gaacaacatg     480
tttagatcat caccatggcc attactgcct catcttcctc ctcctcatag tcaagtacct     540
cttgtgatga tggaaccaac aagctgcaat tactaccaac cgacaccgtc ttgcgcatta     600
gaacaaaagc cattgatccc actcaagaac atggtcaaga ttgaagcaga accggagaga     660
tcaaaccctg atcatcatta tccggaagac tcaatgacaa actcttttga tctttccttc     720
tctcagcttt tgttagatcc taattactac ctggaatcan gaggaggaga aaggagagtt     780
tgctctcatg ag                                                         792

<210> SEQ ID NO 64
<211> LENGTH: 264
<212> TYPE: PRT
<213> ORGANISM: Brassica rapa
<220> FEATURE:
<221> NAME/KEY: MISC_FEATURE
<222> LOCATION: (254)..(254)
<223> OTHER INFORMATION: X can be any amino acid

<400> SEQUENCE: 64

Met Gly Arg Ala Pro Cys Cys Asp Lys Ala Asn Val Lys Lys Gly Pro
1               5                   10                  15

Trp Ser Pro Glu Glu Asp Ala Lys Leu Lys Asp Tyr Ile Glu Ser Ser
            20                  25                  30

Gly Thr Gly Gly Asn Trp Ile Ala Leu Pro Gln Lys Ile Gly Leu Arg
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Glu Asp Asn Ile Ile Cys
65                  70                  75                  80

Asn Leu Tyr Val Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Asn Lys Gln Arg Lys Glu Phe Gln Glu Ala
        115                 120                 125

Arg Met Lys Gln Glu Met Val Met Met Lys Arg Gln Gln Gly Gln
    130                 135                 140

Gly Gln Cys Gln Ser Asn Gly Ser Thr Asp Leu Tyr Leu Asn Asn Met
145                 150                 155                 160

Phe Arg Ser Ser Pro Trp Pro Leu Leu Pro His Leu Pro Pro Pro His
```

```
                     165                 170                 175
Ser Gln Val Pro Leu Val Met Met Glu Pro Thr Ser Cys Asn Tyr Tyr
            180                 185                 190

Gln Pro Thr Pro Ser Cys Ala Leu Glu Gln Lys Pro Leu Ile Pro Leu
        195                 200                 205

Lys Asn Met Val Lys Ile Glu Ala Glu Pro Glu Arg Ser Asn Pro Asp
    210                 215                 220

His His Tyr Pro Glu Asp Ser Met Thr Asn Ser Phe Asp Leu Ser Phe
225                 230                 235                 240

Ser Gln Leu Leu Leu Asp Pro Asn Tyr Tyr Leu Glu Ser Xaa Gly Gly
                245                 250                 255

Glu Arg Arg Val Cys Ser His Glu
            260
```

<210> SEQ ID NO 65
<211> LENGTH: 558
<212> TYPE: DNA
<213> ORGANISM: Brassica rapa

<400> SEQUENCE: 65

```
atgggaaggg caccgtgttg tgacaaagcc aacgtgaaga aagggccttg gtctcctgag      60
gaagatgcca aactcaaaga ttacatcgag aatagtggta caggaggcaa ctggatcgct     120
ttgcctcaaa agattggtct aaggagatgt gggaagagtt gcagactaag gtggctcaac     180
tatttgagac caaacatcaa acatggtggc ttctctgagg aagaagacaa catcatttgt     240
aacctctatg ttactattgg tagcaggtgg tctataattg ctgcacaact gtcgggaaga     300
acggacaacg atatcaagaa ctattggaac acgaggctaa agaagaagct tctaaacaaa     360
caaaggaaag agtttcaaga agctcggatg aagcaagaga tggtgatgat gaagagacaa     420
caagaaggac atgaccacat caatggtagt acggatcttt atctgaaaaa tatgtttgga     480
tcatcaccat ggccattact acaacagctt cctctgttgg gattgcgaaa tcccgtgtcc     540
aactctatct tatcttat                                                   558
```

<210> SEQ ID NO 66
<211> LENGTH: 186
<212> TYPE: PRT
<213> ORGANISM: Brassica rapa

<400> SEQUENCE: 66

```
Met Gly Arg Ala Pro Cys Cys Asp Lys Ala Asn Val Lys Lys Gly Pro
1               5                  10                  15

Trp Ser Pro Glu Glu Asp Ala Lys Leu Lys Asp Tyr Ile Glu Asn Ser
            20                  25                  30

Gly Thr Gly Gly Asn Trp Ile Ala Leu Pro Gln Lys Ile Gly Leu Arg
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Glu Asp Asn Ile Ile Cys
65                  70                  75                  80

Asn Leu Tyr Val Thr Ile Gly Ser Arg Trp Ser Ile Ile Ala Ala Gln
                85                  90                  95

Leu Ser Gly Arg Thr Asp Asn Asp Ile Lys Asn Tyr Trp Asn Thr Arg
            100                 105                 110

Leu Lys Lys Lys Leu Leu Asn Lys Gln Arg Lys Glu Phe Gln Glu Ala
        115                 120                 125
```

Arg Met Lys Gln Glu Met Val Met Met Lys Arg Gln Gln Glu Gly His
        130                 135                 140

Asp His Ile Asn Gly Ser Thr Asp Leu Tyr Leu Lys Asn Met Phe Gly
145                 150                 155                 160

Ser Ser Pro Trp Pro Leu Leu Gln Gln Leu Pro Leu Leu Gly Leu Arg
                165                 170                 175

Asn Pro Val Ser Asn Ser Ile Leu Ser Tyr
            180                 185

<210> SEQ ID NO 67
<211> LENGTH: 501
<212> TYPE: DNA
<213> ORGANISM: Carthamus tinctorius

<400> SEQUENCE: 67
atgataaggg caccctgctg cgacaaaacc aatgtgaaaa agggaccatg gtcttctgaa      60
gaagatgcta agctcaaaga ttacatcgga agtatggta ccggcggtaa ctggatcgct      120
cttccacaaa aaatcgagct caagatctgt gggacaaggt gcagattgag atggttgaat      180
tacctgagac ccaacatcaa gcatggggga ttctctgaag aagaagacaa catcatctgc     240
agcctctata ttagcatagg cagcaggtgg tccataattg cggctcaatt gccaggcaga     300
accgataacg acgtcaagaa ctattgcaac accgagctga agaagatatt actcggaggg     360
cgcaaacaat cccaggccaa taataagctc tcgggtgatc cgaaagacag caggcggata     420
gaaacgctaa gcaacttcgg gatcaaaagg ctccaactgc acaggcgact cggaagcctt     480
gaagacccta atttctgtca c                                                501

<210> SEQ ID NO 68
<211> LENGTH: 167
<212> TYPE: PRT
<213> ORGANISM: Carthamus tinctorius

<400> SEQUENCE: 68

Met Ile Arg Ala Pro Cys Cys Asp Lys Thr Asn Val Lys Lys Gly Pro
1               5                   10                  15

Trp Ser Ser Glu Glu Asp Ala Lys Leu Lys Asp Tyr Ile Gly Lys Tyr
                20                  25                  30

Gly Thr Gly Gly Asn Trp Ile Ala Leu Pro Gln Lys Ile Glu Leu Lys
            35                  40                  45

Ile Cys Gly Thr Arg Cys Arg Leu Arg Trp Leu Asn Tyr Leu Arg Pro
    50                  55                  60

Asn Ile Lys His Gly Gly Phe Ser Glu Glu Glu Asp Asn Ile Ile Cys
65                  70                  75                  80

Ser Leu Tyr Ile Ser Ile Gly Ser Arg Trp Ser Ile Ile Ala Ala Gln
                85                  90                  95

Leu Pro Gly Arg Thr Asp Asn Asp Val Lys Asn Tyr Cys Asn Thr Glu
            100                 105                 110

Leu Lys Lys Ile Leu Leu Gly Gly Arg Lys Gln Ser Gln Ala Asn Asn
        115                 120                 125

Lys Leu Ser Gly Asp Pro Lys Asp Ser Arg Arg Ile Glu Thr Leu Ser
    130                 135                 140

Asn Phe Gly Ile Lys Arg Leu Gln Leu His Arg Arg Leu Gly Ser Leu
145                 150                 155                 160

Glu Asp Pro Asn Phe Cys His
                165

<210> SEQ ID NO 69
<211> LENGTH: 749
<212> TYPE: DNA
<213> ORGANISM: Carthamus tinctorius

<400> SEQUENCE: 69

```
atggggagag cccttgttg tgataaagca atgtgaaga aaggtccatg gtctcaagaa      60
gaagatacaa aactcaaaga gtttattgaa aaatttggta ctggtggtaa ctggattgtt    120
ctccctcaaa aagctggtct gaaaagatgt gggaagagtt gcaggttgag atggcttaac    180
tatctaagac ccaatatcag gcatggtgaa ttctctgatg atgaagacag gatcatctgc    240
agcttgtatg ctacatttgg tagcagatgg tcagtaatag cagctcagct accaggaagg    300
actgacaatg atatcaagaa ctattggaac accaaactca agaagaagct cttcactatg    360
cttccttccc ttcaagaaaa acaaactttc tttccatctt tgcccttcca accaccacca    420
ccatatgatc accaccacca tcatcatcac ccatcagacc cattcttcac cacttcatca    480
tcatcatcat catcattcta caccagttac aaccctaact ttatgaatct taacaccact    540
tccaattctc tcattgttca agatcatgat gttaatgttg ttcaacacaa tctctcacca    600
ccaccgccac caccaccacc tgtgaaccat ttgatcaatt tgctgagcaa caacaccatt    660
gatgttaatg tgattgatga tcataactcc tacagttatc atctagggtt tcaagatgac    720
caccatgatc agagcatgtg caacagttc                                      749
```

<210> SEQ ID NO 70
<211> LENGTH: 250
<212> TYPE: PRT
<213> ORGANISM: Carthamus tinctorius

<400> SEQUENCE: 70

```
Met Gly Arg Ala Pro Cys Cys Asp Lys Ala Asn Val Lys Lys Gly Pro
1               5                   10                  15

Trp Ser Gln Glu Glu Asp Thr Lys Leu Lys Glu Phe Ile Glu Lys Phe
                20                  25                  30

Gly Thr Gly Gly Asn Trp Ile Val Leu Pro Gln Lys Ala Gly Leu Lys
            35                  40                  45

Arg Cys Gly Lys Ser Cys Arg Leu Arg Trp Leu Asn Tyr Leu Arg Pro
        50                  55                  60

Asn Ile Arg His Gly Glu Phe Ser Asp Asp Glu Asp Arg Ile Ile Cys
65                  70                  75                  80

Ser Leu Tyr Ala Thr Phe Gly Ser Arg Trp Ser Val Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Phe Thr Met Leu Pro Ser Leu Gln Glu Lys Gln
        115                 120                 125

Thr Phe Phe Pro Ser Leu Pro Phe Gln Pro Pro Pro Tyr Asp His
    130                 135                 140

His His His His His Pro Ser Asp Pro Phe Phe Thr Thr Ser Ser
145                 150                 155                 160

Ser Ser Ser Ser Ser Phe Tyr Thr Ser Tyr Asn Pro Asn Phe Met Asn
                165                 170                 175

Leu Asn Thr Thr Ser Asn Ser Leu Ile Val Gln Asp His Asp Val Asn
            180                 185                 190
```

Val Val Gln His Asn Leu Ser Pro Pro Pro Pro Pro Pro Val
            195                 200                 205

Asn His Leu Ile Asn Leu Leu Ser Asn Asn Thr Ile Asp Val Asn Val
    210                 215                 220

Ile Asp Asp His Asn Ser Tyr Ser Tyr His Leu Gly Phe Gln Asp Asp
225                 230                 235                 240

His His Asp Gln Ser Met Cys Asn Ser Ser
            245                 250

<210> SEQ ID NO 71
<211> LENGTH: 648
<212> TYPE: DNA
<213> ORGANISM: Centaurea maculosa

<400> SEQUENCE: 71

| | | | | | |
|---|---|---|---|---|---|
| atgggaaggg | caccttgttg | tgacaaagca | aacgttaaga | aagggccatg | gtctcccgaa | 60 |
| gaagatgcta | aactcaaaga | ttatatcgaa | aaatatggta | ccgggggtaa | ctggatcgct | 120 |
| cttccgcaga | agattggcat | aaagagatgt | ggaaaaagtt | gtagactaag | gtggttgaat | 180 |
| tacctaagac | ctaatatcaa | gcatggagga | ttctctgaag | aagaagacaa | catcatctgc | 240 |
| agcctctata | ttagtatcgg | cagcaggtgg | tccataattg | ctgcccaact | gcctggaaga | 300 |
| actgataatg | atatcaagaa | ctattggaac | actaggctaa | agaagaaatt | gcttggaagg | 360 |
| cgaaaacagt | ctcatgctag | taggctcggc | accggttcaa | accaggatcc | caaagatggg | 420 |
| aacgggctag | aaacgttaag | caattcggcc | atcgaaaggc | ttcaacttca | catgcaactt | 480 |
| caaagccttg | aaaaccctaa | tatcgctaat | catggtgtta | atctcgcgac | gtggccttgt | 540 |
| aagctgaacc | cgattcaaga | gaagatgatg | cagagtcttc | aacttctaaa | tgagtcgcca | 600 |
| aaccctctaa | tgatgcaacc | tcattcccct | caaaaggttg | aactttat | | 648 |

<210> SEQ ID NO 72
<211> LENGTH: 216
<212> TYPE: PRT
<213> ORGANISM: Centaurea maculosa

<400> SEQUENCE: 72

Met Gly Arg Ala Pro Cys Cys Asp Lys Ala Asn Val Lys Lys Gly Pro
1               5                   10                  15

Trp Ser Pro Glu Glu Asp Ala Lys Leu Lys Asp Tyr Ile Glu Lys Tyr
            20                  25                  30

Gly Thr Gly Gly Asn Trp Ile Ala Leu Pro Gln Lys Ile Gly Ile Lys
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Asp Asn Ile Ile Cys
65                  70                  75                  80

Ser Leu Tyr Ile Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Gly Arg Arg Lys Gln Ser His Ala Ser Arg
        115                 120                 125

Leu Gly Thr Gly Ser Asn Gln Asp Pro Lys Asp Gly Asn Gly Leu Glu
    130                 135                 140

Thr Leu Ser Asn Ser Ala Ile Glu Arg Leu Gln Leu His Met Gln Leu
145                 150                 155                 160

```
Gln Ser Leu Glu Asn Pro Asn Ile Ala Asn His Gly Val Asn Leu Ala
            165                 170                 175

Thr Trp Pro Cys Lys Leu Asn Pro Ile Gln Glu Lys Met Met Gln Ser
        180                 185                 190

Leu Gln Leu Leu Asn Glu Ser Pro Asn Pro Leu Met Met Gln Pro His
    195                 200                 205

Ser Pro Gln Lys Val Glu Leu Tyr
    210                 215

<210> SEQ ID NO 73
<211> LENGTH: 693
<212> TYPE: DNA
<213> ORGANISM: Centaurea maculosa

<400> SEQUENCE: 73
atgggaaggg caccttgttg tgacaaagca aacgttaaga aagggccatg gtctcccgaa      60
gaagatgcta aactcaaaga ttatatcgaa aaatatggta ccgggggtaa ctggatcgct     120
cttccgcaga agattggcat aaagagatgt ggaaaaagtt gtagactaag gtggttgaat     180
tacctaagac ctaatatcaa gcatggagga ttctctgaag aagaagacaa catcatctgc     240
agcctctata ttagtatcgg cagcaggtgg tccataattg ctgcccaact gcctggaaga     300
actgataatg atatcaagaa ctattggaac actaggctaa agaggaaatt gcttggaagg     360
cgaaaacagt ctcatgctag taggctcggc accggttcaa accaggatcc caaagatggg     420
aacgggctag aaacgttaag caattcggcc atcgaaaggc ttcaacttca catgcaactt     480
caaagccttg aaaaccctaa tatcgctaat catggtgtta atctcgcgac gtggccttgt     540
aagctgaacc cgattcaaga gaagatgatg cagagtcttc aacttctaaa tgagtcgcca     600
aaccctctaa tgatgcaacc tcattcccct caaaaggttg aactttatgc acaatcaaat     660
aactttcttc aacaagtgta ctctccatcg agc                                  693

<210> SEQ ID NO 74
<211> LENGTH: 231
<212> TYPE: PRT
<213> ORGANISM: Centaurea maculosa

<400> SEQUENCE: 74

Met Gly Arg Ala Pro Cys Cys Asp Lys Ala Asn Val Lys Lys Gly Pro
1               5                   10                  15

Trp Ser Pro Glu Glu Asp Ala

```
Thr Leu Ser Asn Ser Ala Ile Glu Arg Leu Gln Leu His Met Gln Leu
145                 150                 155                 160

Gln Ser Leu Glu Asn Pro Asn Ile Ala Asn His Gly Val Asn Leu Ala
            165                 170                 175

Thr Trp Pro Cys Lys Leu Asn Pro Ile Gln Glu Lys Met Met Gln Ser
        180                 185                 190

Leu Gln Leu Leu Asn Glu Ser Pro Asn Pro Leu Met Met Gln Pro His
            195                 200                 205

Ser Pro Gln Lys Val Glu Leu Tyr Ala Gln Ser Asn Asn Phe Leu Gln
        210                 215                 220

Gln Val Tyr Ser Pro Ser Ser
225                 230

<210> SEQ ID NO 75
<211> LENGTH: 651
<212> TYPE: DNA
<213> ORGANISM: Centaurea maculosa

<400> SEQUENCE: 75
atgggaagag ctccatgttg tgataaggca aatgtgaaga aagggccatg gtcacctgaa        60
gaagatagaa agctaaaaga gtacatagaa actcatggta ctggtggcaa ctggattgct       120
ctcccacaaa aagcaggcct tagaagatgt ggaaaaagct gcagattaag atggttgaac       180
tatctaagac caaacatcaa acatggtgaa ttttctgatg atgaagataa agttatctgt       240
gcactctttg ctagcattgg cagcaggtgg tcaataatgg cagcacagtt accaggaagg       300
acagacaatg atataaagaa ctactggaac acaaagctga agaagaagat gatgagcagc       360
ttaatctcca ttcctgaaat cagaaaacca tttcatcatc aacatcttga atctttcaaa       420
tcttcatcca actacatgag ctacccatca tcactctcta tttttcaaaa cagtaataat       480
atcagtgctc cattatcttc atcatcacca ccttcatcat atctctataa tagtacaaca       540
acaactactt ctactcatca tcatcatgat catcatcatc aaaccctatc tatcccatca       600
agccctactc ctgctcatgg atataatctg ggtttgggtc ccatggtggt a                651

<210> SEQ ID NO 76
<211> LENGTH: 217
<212> TYPE: PRT
<213> ORGANISM: Centaurea maculosa

<400> SEQUENCE: 76

Met Gly Arg Ala Pro Cys Cys Asp Lys Ala Asn Val Lys Lys Gly Pro
1               5                   10                  15

Trp Ser Pro Glu Glu Asp Arg Lys Leu Lys Glu Tyr Ile Glu Thr His
            20                  25                  30

Gly Thr Gly Gly Asn Trp Ile Ala Leu Pro Gln Lys Ala Gly Leu Arg
        35                  40                  45

Arg Cys Gly Lys Ser Cys Arg Leu Arg Trp Leu Asn Tyr Leu Arg Pro
    50                  55                  60

Asn Ile Lys His Gly Glu Phe Ser Asp Asp Glu Asp Lys Val Ile Cys
65                  70                  75                  80

Ala Leu Phe Ala Ser Ile Gly Ser Arg Trp Ser Ile Met Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Met Met Ser Ser Leu Ile Ser Ile Pro Glu Ile Arg
```

```
            115                 120                 125
Lys Pro Phe His His Gln His Leu Glu Ser Phe Lys Ser Ser Ser Asn
    130                 135                 140

Tyr Met Ser Tyr Pro Ser Ser Leu Ser Ile Phe Gln Asn Ser Asn Asn
145                 150                 155                 160

Ile Ser Ala Pro Leu Ser Ser Ser Pro Pro Ser Ser Tyr Leu Tyr
            165                 170                 175

Asn Ser Thr Thr Thr Thr Thr Ser Thr His His His Asp His His
            180                 185                 190

His Gln Thr Leu Ser Ile Pro Ser Ser Pro Thr Pro Ala His Gly Tyr
            195                 200                 205

Asn Leu Gly Leu Gly Pro Met Val Val
    210                 215
```

<210> SEQ ID NO 77
<211> LENGTH: 732
<212> TYPE: DNA
<213> ORGANISM: Centaurea solstitialis

<400> SEQUENCE: 77

```
atggggagag caccttgctg tgataaagcc aatgtgaaga aaggtccatg ggctcctgaa      60
gaagatgcta ctcttaaagc ttatattgaa gaacatggta ctggtggtaa ctggattgct     120
ttgcctcaga aaatagggct aaaagatgc gggaagagtt gtcgcctgcg gtggctaaat      180
tatctccgtc cgaatatcaa gcatggaggt ttttcggaag aagaagatcg cataatttgc     240
agcctctatg ttagcatagg gagcaggtgg tctataatcg cagcacaatt acctggacga     300
actgataacg atataaagaa ctactggaat acaaggctga agaagaaact cttgggtaag     360
caacgaaaag aacaaatttc tcgtagaaag ggggagatgc taatgaagaa agggagatcg     420
ccatcggaaa ttccaccttc cgtaatcgtt agtggtaacg ataccaataa caattgcccg     480
gatccttatt ggccagagtt gccggttttg ccacctgcgc cctattcgat ccaagaacca     540
tgctttgcca acggtcatgc ctctatacga aaactactca tgaagcttgg aggaaggttt     600
tcttgtgatg acaatggaaa ccagtccatc aacatggtct cacactttcc cattgatcat     660
cttccaacat cattaatgca tgatgatcac aactttattg ctagtagtac tactccggct     720
tcttcttcag ct                                                         732
```

<210> SEQ ID NO 78
<211> LENGTH: 244
<212> TYPE: PRT
<213> ORGANISM: Centaurea solstitialis

<400> SEQUENCE: 78

```
Met Gly Arg Ala Pro Cys Cys Asp Lys Ala Asn Val Lys Lys Gly Pro
1               5                   10                  15

Trp Ala Pro Glu Glu Asp Ala Thr Leu Lys Ala Tyr Ile Glu Glu His
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Glu Asp Arg Ile Ile Cys
65                  70                  75                  80

Ser Leu Tyr Val Ser Ile Gly Ser Arg Trp Ser Ile Ile Ala Ala Gln
                85                  90                  95
```

```
Leu Pro Gly Arg Thr Asp Asn Asp Ile Lys Asn Tyr Trp Asn Thr Arg
                100                 105                 110
Leu Lys Lys Lys Leu Leu Gly Lys Gln Arg Lys Glu Gln Ile Ser Arg
            115                 120                 125
Arg Lys Gly Glu Met Leu Met Lys Lys Gly Arg Ser Pro Ser Glu Ile
        130                 135                 140
Pro Pro Ser Val Ile Val Ser Gly Asn Asp Thr Asn Asn Asn Cys Pro
145                 150                 155                 160
Asp Pro Tyr Trp Pro Glu Leu Pro Val Leu Pro Ala Pro Tyr Ser
                165                 170                 175
Ile Gln Glu Pro Cys Phe Ala Asn Gly His Ala Ser Ile Arg Lys Leu
                180                 185                 190
Leu Met Lys Leu Gly Gly Arg Phe Ser Cys Asp Asp Asn Gly Asn Gln
            195                 200                 205
Ser Ile Asn Met Val Ser His Phe Pro Ile Asp His Leu Pro Thr Ser
        210                 215                 220
Leu Met His Asp Asp His Asn Phe Ile Ala Ser Ser Thr Thr Pro Ala
225                 230                 235                 240
Ser Ser Ser Ala
```

```
<210> SEQ ID NO 79
<211> LENGTH: 675
<212> TYPE: DNA
<213> ORGANISM: Centaurea solstitialis

<400> SEQUENCE: 79
atggggagag caccttgctg tgataaagcc aatgtgaaga aggtccatg ggctcctgaa    60
gaagatgcta ctcttaaagc ttatattgaa gaacatggta ctggtggtaa ctggattgct   120
ttgcctcaga aaatagggct taaaagatgc gggaagagtt gtcgcctgcg gtggctaaat   180
tatctccgtc cgaatatcaa gcatggaggt ttttcggaag aagaagatcg cataatttgc   240
agcctctatg ttagcatagg gagcaggtgg tctataatcg caccacaatt acctggacga   300
actgataacg atataaagaa ctactggaat acaaggctga agaagaaact cttgggtaag   360
caacgaaaag aacaaatttc tcgtaaaaag ggggagatgc taatgaagaa agggagatcg   420
ccatcggaaa ttccatcttc cgtaatcgtt agtggtaacg ataccaataa caattgcccg   480
gatccttatt ggccagagtt gccggttttg ccacctgcgc cctattcgat ccaagaacca   540
tgctttgcca acggtcatgc ctctatacga aaactactca tgaagcttgc aggaaggttt   600
tcttgtgatg acaatggaaa ccagtccatc aacatggtct cacacttacc cattgatcat   660
cttacgacat catta                                                    675

<210> SEQ ID NO 80
<211> LENGTH: 225
<212> TYPE: PRT
<213> ORGANISM: Centaurea solstitialis

<400> SEQUENCE: 80

Met Gly Arg Ala Pro Cys Cys Asp Lys Ala Asn Val Lys Lys Gly Pro
1               5                   10                  15
Trp Ala Pro Glu Glu Asp Ala Thr Leu Lys Ala Tyr Ile Glu Glu His
                20                  25                  30
Gly Thr Gly Gly Asn Trp Ile Ala Leu Pro Gln Lys Ile Gly Leu Lys
            35                  40                  45
```

```
Arg Cys Gly Lys Ser Cys Arg Leu Arg Trp Leu Asn Tyr Leu Arg Pro
 50                  55                  60
Asn Ile Lys His Gly Gly Phe Ser Glu Glu Asp Arg Ile Ile Cys
 65                  70                  75                  80
Ser Leu Tyr Val Ser Ile Gly Ser Arg Trp Ser Ile Ile Ala Pro Gln
                 85                  90                  95
Leu Pro Gly Arg Thr Asp Asn Asp Ile Lys Asn Tyr Trp Asn Thr Arg
                100                 105                 110
Leu Lys Lys Lys Leu Leu Gly Lys Gln Arg Lys Glu Gln Ile Ser Arg
                115                 120                 125
Lys Lys Gly Glu Met Leu Met Lys Lys Gly Arg Ser Pro Ser Glu Ile
130                 135                 140
Pro Ser Ser Val Ile Val Ser Gly Asn Asp Thr Asn Asn Cys Pro
145                 150                 155                 160
Asp Pro Tyr Trp Pro Glu Leu Pro Val Leu Pro Ala Pro Tyr Ser
                165                 170                 175
Ile Gln Glu Pro Cys Phe Ala Asn Gly His Ala Ser Ile Arg Lys Leu
                180                 185                 190
Leu Met Lys Leu Ala Gly Arg Phe Ser Cys Asp Asp Asn Gly Asn Gln
                195                 200                 205
Ser Ile Asn Met Val Ser His Leu Pro Ile Asp His Leu Thr Thr Ser
210                 215                 220
Leu
225

<210> SEQ ID NO 81
<211> LENGTH: 783
<212> TYPE: DNA
<213> ORGANISM: Centaurea solstitialis

<400> SEQUENCE: 81
atgggaagag caccttgctg tgacaaagcc aacgtcaaaa gaggaccatg gtcacctgaa      60
gaagatgcca aactcaaatc gtatatcgaa gaacatggaa ccggaggcaa ctggatcgct     120
ctacctcata agattggtct taagaggtgt ggcaagagtt gtcgccttcg atggttgaat     180
tatctacgcc caaatatcaa gcatggatct ttctccgaag aagaagatca catcatttgc     240
acccttatc tcagtattgg cagccgatgg tcaattatag ctgcacaact acctgggcga     300
accgataatg acatcaagaa ctactggaac acgaggctaa agaaaaagct tttgggaaaa     360
cagcgtaaag atcaacaatc ttcgaagaaa agtggtttga tcaagcaaga atgaagaga      420
gaagttcttg aagatttcaa ggcaccatct ttatgcatga gcatgaacct ctatcaatct     480
tactggccta cagatttccc taatttgatc cttacaaacc ctgatcatga tcatcatcaa     540
gagcaaccac ttcatgccaa aaaccaagat cccatcacaa gttttgatga tcaatacccct    600
tttgataccct ccccaaatca agcccaattg ttcgatcaaa accacgagaa acctatttca    660
accattaatt atcatcccca attgcaaaac acaccatata atcttgtgat caatggagat     720
caaggtgtga atctttttca agaattcaac aactacccat ttgggatcaa tgaattggtc     780
tac                                                                   783

<210> SEQ ID NO 82
<211> LENGTH: 261
<212> TYPE: PRT
<213> ORGANISM: Centaurea solstitialis

<400> SEQUENCE: 82
```

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Ser Tyr Ile Glu His
            20                  25                  30

Gly Thr Gly Gly Asn Trp Ile Ala Leu Pro His Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Ser Phe Ser Glu Glu Glu Asp His Ile Ile Cys
65                  70                  75                  80

Thr Leu Tyr Leu Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Gly Lys Gln Arg Lys Asp Gln Gln Ser Ser
            115                 120                 125

Lys Lys Ser Gly Leu Ile Lys Gln Glu Met Lys Arg Glu Val Leu Glu
        130                 135                 140

Asp Phe Lys Ala Pro Ser Leu Cys Met Ser Met Asn Leu Tyr Gln Ser
145                 150                 155                 160

Tyr Trp Pro Thr Asp Phe Pro Asn Leu Ile Leu Thr Asn Pro Asp His
                165                 170                 175

Asp His His Gln Glu Gln Pro Leu His Ala Lys Asn Gln Asp Pro Ile
            180                 185                 190

Thr Ser Phe Asp Asp Gln Tyr Pro Phe Asp Thr Ser Pro Asn Gln Ala
            195                 200                 205

Gln Leu Phe Asp Gln Asn His Glu Lys Pro Ile Ser Thr Ile Asn Tyr
        210                 215                 220

His Pro Gln Leu Gln Asn Thr Pro Tyr Asn Leu Val Ile Asn Gly Asp
225                 230                 235                 240

Gln Gly Val Asn Leu Phe Gln Glu Phe Asn Asn Tyr Pro Phe Gly Ile
                245                 250                 255

Asn Glu Leu Val Tyr
            260

<210> SEQ ID NO 83
<211> LENGTH: 768
<212> TYPE: DNA
<213> ORGANISM: Cichorium endivia

<400> SEQUENCE: 83
atgggaagag caccttgctg tgacaaagcc aacgtcaaaa gaggaccttg gtcacctgaa      60
gaagatgcca aactcaagtc ttacattgaa gaacatggaa cgggaggcaa ctggatcgct     120
ctacctcata aaatcggact caagaggtgt ggaaagagtt gtcgccttcg atggttaaat     180
tatcttcgcc caaacatcaa gcacggatct ttttccgaag aagaagatca cataatttgt     240
accctatatc ttagtattgg cagccggtgg tcaattatcg ctgcacaatt acccgggaga     300
actgataatg atatcaagaa ctactggaac acaaggctaa agaaaaagct tttgggaaag     360
cagcgtaaag atcaacaatt gtcaaagaga agtgcccaaa taaagcatga atgaaggag      420 agagtggttc ttgaggattt aaaggcacca tctttatgca tgagcatgaa tctttatcaa     480
tcatactggc ctgctgaatt cccttcgact ctcacggacc atgatcagca tcatcaagaa     540
catcatgtca aaacccaaga accgttttc aatgaatacc cttttgacat aatttcaaac      600
```

```
caagcacaat tgttctacca gaacagcgag aaacctatct cgactactgt ttaccatccc    660
cagttggcaa acatacccta ttttggaatt ggggatggca taaacttgtt tcaagaattc    720
aacaattacc catttgaaat caatgaattg gtttacaaca ccacacaa                 768
```

<210> SEQ ID NO 84
<211> LENGTH: 256
<212> TYPE: PRT
<213> ORGANISM: Cichorium endivia

<400> SEQUENCE: 84

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Ser Tyr Ile Glu Glu His
            20                  25                  30

Gly Thr Gly Gly Asn Trp Ile Ala Leu Pro His Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Ser Phe Ser Glu Glu Asp His Ile Ile Cys
65                  70                  75                  80

Thr Leu Tyr Leu Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Gly Lys Gln Arg Lys Asp Gln Gln Leu Ser
        115                 120                 125

Lys Arg Ser Ala Gln Ile Lys His Glu Met Lys Glu Arg Val Val Leu
    130                 135                 140

Glu Asp Leu Lys Ala Pro Ser Leu Cys Met Ser Met Asn Leu Tyr Gln
145                 150                 155                 160

Ser Tyr Trp Pro Ala Glu Phe Pro Ser Thr Leu Thr Asp His Asp Gln
                165                 170                 175

His His Gln Glu His His Val Lys Thr Gln Glu Pro Val Phe Asn Glu
            180                 185                 190

Tyr Pro Phe Asp Ile Ile Ser Asn Gln Ala Gln Leu Phe Tyr Gln Asn
        195                 200                 205

Ser Glu Lys Pro Ile Ser Thr Thr Val Tyr His Pro Gln Leu Ala Asn
    210                 215                 220

Ile Pro Tyr Phe Gly Ile Gly Asp Gly Ile Asn Leu Phe Gln Glu Phe
225                 230                 235                 240

Asn Asn Tyr Pro Phe Glu Ile Asn Glu Leu Val Tyr Asn Thr Thr Gln
                245                 250                 255
```

<210> SEQ ID NO 85
<211> LENGTH: 639
<212> TYPE: DNA
<213> ORGANISM: Cichorium intybus

<400> SEQUENCE: 85

```
atgggaaggg ctccatgttg tgacaaagaa aatgtaaaga gagggccatg gtctcctgaa     60
gaagatgcaa aactcaaaag cttcattgac aaaaacggca ctggtggtaa ctggattgct    120
ctccctcaca agctggtct aaaaagatgt ggcaagagct gcagattgag atggctaaac    180
tatctgaggc ccaatattaa gcatggtgaa ttcactgatg atgaagacaa gatcatctgc    240
```

```
agcttgtatg ctagcattgg tagcagatgg tcaataatag cagctcagct accaggaagg      300
actgataatg atatcaagaa ttactggaac accaagctca agaagaagct cttggctatg      360
cttccttcct ttcaaaagaa gtcatcttta tttccatcta catccctcca atcaccatca      420
ccatacagat caaatcagtt catgaccaat aattcgtcac cttttacgg ttataccact       480 accctaact tcatgaacat gaacaacaat atgatcagtt ctctgccgag acctaccagc       540
accaccacct gtgttcaaga tcatatcact catctctcac caccaccacc gctagatcca      600
aactctttga tcagtttaat gaccagcaac gttgacaac                              639
```

<210> SEQ ID NO 86
<211> LENGTH: 213
<212> TYPE: PRT
<213> ORGANISM: Cichorium intybus

<400> SEQUENCE: 86

```
Met Gly Arg Ala Pro Cys Cys Asp Lys Glu Asn Val Lys Arg Gly Pro
1               5                   10                  15

Trp Ser Pro Glu Glu Asp Ala Lys Leu Lys Ser Phe Ile Asp Lys Asn
            20                  25                  30

Gly Thr Gly Gly Asn Trp Ile Ala Leu Pro His Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Glu Phe Thr Asp Asp Glu Asp Lys Ile Ile Cys
65                  70                  75                  80

Ser Leu Tyr Ala Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Leu Ala Met Leu Pro Ser Phe Gln Lys Lys Ser
        115                 120                 125

Ser Leu Phe Pro Ser Thr Ser Leu Gln Ser Pro Ser Pro Tyr Arg Ser
    130                 135                 140

Asn Gln Phe Met Thr Asn Asn Ser Ser Pro Phe Tyr Gly Tyr Thr Thr
145                 150                 155                 160

Thr Pro Asn Phe Met Asn Met Asn Asn Met Ile Ser Ser Leu Pro
                165                 170                 175

Arg Pro Thr Ser Thr Thr Thr Cys Val Gln Asp His Ile Thr His Leu
            180                 185                 190

Ser Pro Pro Pro Leu Asp Pro Asn Ser Leu Ile Ser Leu Met Thr
        195                 200                 205

Ser Asn Val Asp Asn
    210
```

<210> SEQ ID NO 87
<211> LENGTH: 832
<212> TYPE: DNA
<213> ORGANISM: Cichorium intybus

<400> SEQUENCE: 87

```
tgggaagagc tccatgttgt gacaagtcaa aggtgaagaa agggccatgg tcgcctgagg      60
aagatacgaa gttgaaagac tatatacaca aaaatggtac tggaggcaac tggattgctc     120
ttccacataa agcaggcctt aaaagatgtg gaaaaagctg cagattgcga tggttgaact     180
accttagacc agacatcaaa cacggtgaat tctccgatca tgaagataga ctcatctgta     240
```

```
ctctctttc tagcatcggt agcaggtggt cagttatagc agcacagttg cctggaagaa        300
cggataatga tatcaagaac tactggaaca cgaagctcaa aaagaagctt atgaatttca        360
tctccaccaa tcgtcaaatt gggaaaccgc ttcgtcatct tgatcaatct atcaattgta        420
cttcttcaaa ttggagctac ccaacaagct cttctgctat aactgttgat aatcatccag        480
ttctaccatc agatgatcat ggatacatta atgtagaccc actggagacc tatcaagtaa        540
aagacgattc taccettatg tttgaaggcg gtgatcaagc tgctggttgt acttctactt        600
cggattggcg gtaccatcat gtgtatggtg gtggtgtgtt tgatgctcat aataacatgg        660
gagtcttgaa gaccggtgat tcttacaaga gagatgatgg gaattgtgaa aaggcaagtg        720
ggtattatgg ggattctaca ttggagtttg gtcttgagga gttcaagaag ctcattagca        780
ctaatctgtg cagcggtaac actaacaata atctcaatgt ctttgttgat ga             832
```

<210> SEQ ID NO 88
<211> LENGTH: 435
<212> TYPE: DNA
<213> ORGANISM: Citrus sinensis

<400> SEQUENCE: 88

```
atgggaagag ctccatgttg tgacaaagct aacgttaaaa gaggaccttg gtctgctgaa         60
gaagactcga ttctcaaaaa ttaccttgag caatttggaa atggcggcaa ctggattgct        120
ttacccaaga aagcaggcct taatagatgt ggcaagagtt gtcggctcag atggctaaat        180
tatctaaggc cagatattaa gcatggagga tttactaagg aagaagatac catcatatgc        240
aatctttatt gtaccatggg aagtaggtgg tctgttatag cttctcagct gccaggaaga        300
actgacaatg atgtaaagaa ttattggaac accaagttga agaaaaatgt tttggcagga        360
aagctgtcgg acaacactca agtttcagtt tcaacaattc ctgaagaatt tggaaattca        420
tcttactact tgagt                                                         435
```

<210> SEQ ID NO 89
<211> LENGTH: 145
<212> TYPE: PRT
<213> ORGANISM: Citrus sinensis

<400> SEQUENCE: 89

```
Met Gly Arg Ala Pro Cys Cys Asp Lys Ala Asn Val Lys Arg Gly Pro
1               5                   10                  15

Trp Ser Ala Glu Glu Asp Ser Ile Leu Lys Asn Tyr Leu Glu Gln Phe
            20                  25                  30

Gly Asn Gly Gly Asn Trp Ile Ala Leu Pro Lys Lys Ala Gly Leu Asn
        35                  40                  45

Arg Cys Gly Lys Ser Cys Arg Leu Arg Trp Leu Asn Tyr Leu Arg Pro
    50                  55                  60

Asp Ile Lys His Gly Gly Phe Thr Lys Glu Glu Asp Thr Ile Ile Cys
65                  70                  75                  80

Asn Leu Tyr Cys Thr Met Gly Ser Arg Trp Ser Val Ile Ala Ser Gln
                85                  90                  95

Leu Pro Gly Arg Thr Asp Asn Asp Val Lys Asn Tyr Trp Asn Thr Lys
            100                 105                 110

Leu Lys Lys Asn Val Leu Ala Gly Lys Leu Ser Asp Asn Thr Gln Val
        115                 120                 125

Ser Val Ser Thr Ile Pro Glu Glu Phe Gly Asn Ser Tyr Tyr Leu
    130                 135                 140
```

Ser
145

<210> SEQ ID NO 90
<211> LENGTH: 685
<212> TYPE: DNA
<213> ORGANISM: Coffea canephora

<400> SEQUENCE: 90

```
gcacgcaggg aaattaatcc acacacacac acacactcaa gcatttcaaa agcactcgaa      60
agaagcctgg atagagagaa gcagaaacag gcacagagtg taacaaccag agagagatgg     120
gaagagctcc ttgctgtgac aaggcgaatg tgaagaaagg accttggtcc cctgaagaag     180
atgcaaagct gaaggagtac atagaaaagt cagggactgg agggaattgg atagctcttc     240
cacacaaggc tggtaagccc acttatgaat ttccgtgtaa ttacaacact agtatttgtt     300
atggtttgcc agcagttggt tggcataatt atgatcaggg cttagaagat gcggaaagag     360
ttgcagattg agatggctta actacctcag gcccaacatt aaacatggag acttcacaga     420
tgatgaggat aggataattt gcagcctctt tgcgagcatt ggtagcaggt ggtcaataat     480
agcagctcaa ttaccaggca ggacggacaa tgacatcaag aactactgga acaccaagct     540
gaaaagaaa ataatgggat ctcacaaaaa atgccatcaa cccagcccct acgcatcacc     600
atattcgggg tttgagcctg catctttaac atcatcacca ttttcagctc catcaccatc     660
aatatcatcg gcgtatcaca attat                                          685
```

<210> SEQ ID NO 91
<211> LENGTH: 731
<212> TYPE: DNA
<213> ORGANISM: Coffea canephora

<400> SEQUENCE: 91

```
acacacactc aagcatttca aaagcactcg aaccctgcct ggatagagag aagcagaaac      60
aggcacagag tgtaacaacc agagagagat gggaagagct ccttgctgtg acaaggcgaa     120
tgtgaagaaa ggaccttggt cccctgaaga agatgcaaag ctgaaggagt acatagaaaa     180
gtcagggact ggagggaatt ggatagctct tccacacaag gctggtaagc ccacttatga     240
atttccgtgt aattacaaca ctagtatttg ttatggtttg ccagcagttg gttggcataa     300
ttatgatcag ggcttagaag atgcggaaag agttgcagat tgagatggct taactacctc     360
aggcccaaca ttaaacatgg agacttcaca gatgatgagg ataggataat ttgcagcctc     420
tttgcgagca ttggtagcag gtggtcaata atagcagctc aattaccagg caggacggac     480
aatgacatca agaactactg gaacaccaag ctgaaaaaga aaataatggg atctcacaaa     540
aaatgccatc aacccagccc ctacgcatca ccatattcgg ggtttgagcc tgcatctttaa    600
acatcatcac catttttcagc tccatcacca tcaatatcat cggcgtatca caattatcac    660
accaccaccc aatttaggtc cctctcacgc tatgaaactt tttcatcaac cccgccaagt    720
ctgttgaacg c                                                          731
```

<210> SEQ ID NO 92
<211> LENGTH: 711
<212> TYPE: DNA
<213> ORGANISM: Cucumis melo

<400> SEQUENCE: 92

```
atggggagag ctccttgctg tgacaaagca aacgtgaaga agggtccgtg gtcgccggag      60
```

-continued

```
gaagacatga aactcaaatc ctatatcgag cagcacggta caggtgggaa ctggattgca    120
ctgccccaga aaattggtct gaagagatgt gggaaaagct gccgactccg gtggttgaac    180
taccttcggc ctaatattaa gcatggggat ttttctgaag aagaagataa aataatttgc    240
agcctttatg tcagcattgg aagcaggtgg tcgattattg cagctcaatt accgggacga    300
acagacaacg atataaagaa ttattggaac acaagattga agaagaaatt atttggaaaa    360
cattatgaga acaacaaca acaattggtg agaagaggaa gaaaaattaa atccggaata    420
ggaaattcca tggctattgt ttttgataat caaggtattt acaataataa taataacaac    480
caatcgcctt tcttgccgaa attatcaccg gcgctcaatt caccgccacc accgccgtac    540
gctaattatc agccgcttca gttccattca aattcgttca gcaacaccgc cggcgttatt    600
gatgatctga ggagaaccga cagtgtactc cagtttggaa tggatggggc ttcgtgtcag    660
ccagtaacga gcacccacgt cggtgagttg ggagaaaggt tgtttacagc a            711
```

<210> SEQ ID NO 93
<211> LENGTH: 237
<212> TYPE: PRT
<213> ORGANISM: Cucumis melo

<400> SEQUENCE: 93

```
Met Gly Arg Ala Pro Cys Cys Asp Lys Ala Asn Val Lys Lys Gly Pro
1               5                   10                  15

Trp Ser Pro Glu Glu Asp Met Lys Leu Lys Ser Tyr Ile Glu Gln His
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Asp Lys Ile Ile Cys
65                  70                  75                  80

Ser Leu Tyr Val Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Phe Gly Lys His Tyr Glu Lys Gln Gln Gln Gln
        115                 120                 125

Leu Val Arg Arg Gly Arg Lys Ile Lys Ser Gly Ile Gly Asn Ser Met
    130                 135                 140

Ala Ile Val Phe Asp Asn Gln Gly Ile Tyr Asn Asn Asn Asn Asn Asn
145                 150                 155                 160

Gln Ser Pro Phe Leu Pro Lys Leu Ser Pro Ala Leu Asn Ser Pro Pro
                165                 170                 175

Pro Pro Pro Tyr Ala Asn Tyr Gln Pro Leu Gln Phe His Ser Asn Ser
            180                 185                 190

Phe Ser Asn Thr Ala Gly Val Ile Asp Asp Leu Arg Arg Thr Asp Ser
        195                 200                 205

Val Leu Gln Phe Gly Met Asp Gly Ala Ser Cys Gln Pro Val Thr Ser
    210                 215                 220

Thr His Val Gly Glu Leu Gly Glu Arg Leu Phe Thr Ala
225                 230                 235
```

<210> SEQ ID NO 94
<211> LENGTH: 831

```
<212> TYPE: DNA
<213> ORGANISM: Cucumis melo

<400> SEQUENCE: 94
atggggagag ctccttgctg tgacaaagca aacgtgaaga agggtccgtg gtcgccggag      60
gaagacatga aactcaaatc ctacatcgag cagcacggta caggtgggaa ctggattgca     120
ctgccccaga aaattggtct gaagagatgt gggaaaagct gccgactccg gtggttgaac     180
taccttcggc ctaatattaa gcatggggat ttttctgaag aagaagataa aataatttgc     240
agcctttatg tcagcattgg aagcaggtgg tcgattattg cagctcaatt accgggacga     300
acagacaacg atataaagaa ttattggaac acaagattga agaagaaatt atttggaaaa     360
cattatgaga acaacaaca caattggtg agaagaggaa gaaaaattaa atccggaata      420
ggaaattcca tggctattgt ttttgataat caaggtattt acaataataa taataacaac     480
caatcgcctt tcttgccgaa attatcaccg gcgctcaatt caccgccacc accgccgtac     540
gctaattatc agccgcttca gttccattca aattcgttca gcaacaccgc cggcgttatt     600
gatgatctga ggagaaccga cagtgtactc cagtttggaa tggatggggc ttcgtgtcag     660
ccagtaacga gcacccacgt cggtgagttg gagaaggttg tttacagcaa tactccgtcg     720
tttgacgatg ggctgcagtt ttcatgtgat aacaatgggt tgaatttgat gaacgatttg     780
gattgggggg aaatgagttc tttgatttct gctcctttat atccttcgat g              831

<210> SEQ ID NO 95
<211> LENGTH: 277
<212> TYPE: PRT
<213> ORGANISM: Cucumis melo

<400> SEQUENCE: 95

Met Gly Arg Ala Pro Cys Cys Asp Lys Ala Asn Val Lys Lys Gly Pro
1               5                   10                  15

Trp Ser Pro Glu Glu Asp Met Lys Leu Lys Ser Tyr Ile Glu Gln His
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Glu Glu Asp Lys Ile Ile Cys
65                  70                  75                  80

Ser Leu Tyr Val Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Phe Gly Lys His Tyr Glu Lys Gln Gln Gln Gln
        115                 120                 125

Leu Val Arg Arg Gly Arg Lys Ile Lys Ser Gly Ile Gly Asn Ser Met
    130                 135                 140

Ala Ile Val Phe Asp Asn Gln Gly Ile Tyr Asn Asn Asn Asn Asn
145                 150                 155                 160

Gln Ser Pro Phe Leu Pro Lys Leu Ser Pro Ala Leu Asn Ser Pro Pro
                165                 170                 175

Pro Pro Pro Tyr Ala Asn Tyr Gln Pro Leu Gln Phe His Ser Asn Ser
            180                 185                 190

Phe Ser Asn Thr Ala Gly Val Ile Asp Asp Leu Arg Arg Thr Asp Ser
        195                 200                 205
```

Val Leu Gln Phe Gly Met Asp Gly Ala Ser Cys Gln Pro Val Thr Ser
            210                 215                 220

Thr His Val Gly Glu Leu Glu Lys Val Val Tyr Ser Asn Thr Pro Ser
225                 230                 235                 240

Phe Asp Asp Gly Leu Gln Phe Ser Cys Asp Asn Asn Gly Leu Asn Leu
            245                 250                 255

Met Asn Asp Leu Asp Trp Gly Glu Met Ser Ser Leu Ile Ser Ala Pro
            260                 265                 270

Leu Tyr Pro Ser Met
        275

<210> SEQ ID NO 96
<211> LENGTH: 939
<212> TYPE: DNA
<213> ORGANISM: Daucus carota

<400> SEQUENCE: 96

```
atggggagag ctccttgctg tgacaaggca agtgtaaaga gagggccatg gtcacctgaa       60
gaagatcaga agctaaaaga ctatatagag aagcatggga ctggaggaaa ctggattgct      120
ctaccacaaa aggctggtct tagaagatgt gggaaaagct gcagattaag atggctcaac      180
tatctcaggc ctaacattaa acatggagaa ttttcagatg atgaagatag gatcatatgc      240
accctctttg ccaatattgg gagcaggtgg tcaataatag caggtcagtt accagggagg      300
actgacaatg atatcaagaa ctactggaac accaagctca agaagaaact cctcatgtct      360
tcattaatgc tccctaatcc ttttgttagg cctcctaata atattaataa ctaccaacaa      420
tacctattat catcaccatc tccttcttca tattcctccc cattgcctcc aacattgaga      480
ctttgtgaca acaattaccc aaccctaggt gcttctaggt cattcacaag tgagggcttc      540
tcaaatattt caacaaacct ctttaatatc cagcctcaag atcagggttt gggtcccatg      600
caaaattatc aagagaaaga atcacctctc attatgtttg gaggggcagg tgatgatcag      660
caagctgcta gctctagttc ttatgatgaa catttcatga tgttctccaa ctgtgggatg      720
aataatattt ctgatcaaca gaagcaagta aatcttggtg tgtctagtgg tgatcatgag      780
attgttagca atgtactgga tcagtataac atgagctgtg ttgaggagat taagcaactg      840
attagcacta ctaatctgtc atgtaattct aatctgagtt tctttgttga tgaaaacaag      900
acagtgagaa gtgaggagga gaaagtgttg atgtactac                             939
```

<210> SEQ ID NO 97
<211> LENGTH: 313
<212> TYPE: PRT
<213> ORGANISM: Daucus carota

<400> SEQUENCE: 97

Met Gly Arg Ala Pro Cys Cys Asp Lys Ala Ser Val Lys Arg Gly Pro
1               5                   10                  15

Trp Ser Pro Glu Glu Asp Gln Lys Leu Lys Asp Tyr Ile Glu Lys His
            20                  25                  30

Gly Thr Gly Gly Asn Trp Ile Ala Leu Pro Gln Lys Ala Gly Leu Arg
        35                  40                  45

Arg Cys Gly Lys Ser Cys Arg Leu Arg Trp Leu Asn Tyr Leu Arg Pro
    50                  55                  60

Asn Ile Lys His Gly Glu Phe Ser Asp Asp Glu Asp Arg Ile Ile Cys
65                  70                  75                  80

```
Thr Leu Phe Ala Asn Ile Gly Ser Arg Trp Ser Ile Ile Ala Gly Gln
                 85                  90                  95

Leu Pro Gly Arg Thr Asp Asn Asp Ile Lys Asn Tyr Trp Asn Thr Lys
            100                 105                 110

Leu Lys Lys Lys Leu Leu Met Ser Ser Leu Met Leu Pro Asn Pro Phe
        115                 120                 125

Val Arg Pro Pro Asn Asn Ile Asn Asn Tyr Gln Gln Tyr Leu Leu Ser
    130                 135                 140

Ser Pro Ser Pro Ser Ser Tyr Ser Ser Pro Leu Pro Pro Thr Leu Arg
145                 150                 155                 160

Leu Cys Asp Asn Asn Tyr Pro Thr Leu Gly Ala Ser Arg Ser Phe Thr
                165                 170                 175

Ser Glu Gly Phe Ser Asn Ile Ser Thr Asn Leu Phe Asn Ile Gln Pro
            180                 185                 190

Gln Asp Gln Gly Leu Gly Pro Met Gln Asn Tyr Gln Glu Lys Glu Ser
        195                 200                 205

Pro Leu Ile Met Phe Gly Gly Ala Gly Asp Gln Gln Ala Ala Ser
    210                 215                 220

Ser Ser Ser Tyr Asp Glu His Phe Met Met Phe Ser Asn Cys Gly Met
225                 230                 235                 240

Asn Asn Ile Ser Asp Gln Gln Lys Gln Val Asn Leu Gly Val Ser Ser
                245                 250                 255

Gly Asp His Glu Ile Val Ser Asn Val Leu Asp Gln Tyr Asn Met Ser
            260                 265                 270

Cys Val Glu Glu Ile Lys Gln Leu Ile Ser Thr Thr Asn Leu Ser Cys
        275                 280                 285

Asn Ser Asn Leu Ser Phe Phe Val Asp Glu Asn Lys Thr Val Arg Ser
    290                 295                 300

Glu Glu Glu Lys Val Leu Met Tyr Tyr
305                 310
```

<210> SEQ ID NO 98
<211> LENGTH: 744
<212> TYPE: DNA
<213> ORGANISM: Elaeis guineensis

<400> SEQUENCE: 98

```
atgggaagag cccttgttg cgacaaagcc aacgtgaaga aaggcccatg gtccccgag     60
gaggacgcca agctaaaggc ctacatcgag cagtatggca ctggaggcaa ctggatcgcc    120
ctccctcaaa agattggcct taagcgatgc ggtaagagct gccgcctccg atggctaaac    180
tatcttcgac cgaatattaa gcatggagga ttctctgaag aagaagatca catcatttgt    240
agcctgtaca tcagcatcgg tagcagatgg tctataattg ccgcccaatt gccgggaagg    300
accgataacg acatcaagaa ctactggaac acaaggctga gaaaaagct tttaggcaag     360
caacgcaagg atcaccagca acaggcgcgt cgaggtgggg ggccaaagca agaagatagg    420
agtgatgaga gcggaaatcc ggcagttgcc ggcgagggtg gcagccggag cacgtattgg    480
cctgagccag ccatgcctgt ttactcgacc ggccagcccg atcatcatct caacaacaac    540
catgcttcga cgacagatag actgctgatg atgctcgggg gaaggtcctc aacgacagt     600
aatgcaagcc atcagagccc tttcattcca cagtactcat cagttccact gccacagatc    660
tataataatt cagctagctt aattaacccct tcggtcaaca ccacttcctt caaagaagcc    720
atgcaagttc ctcatcggtt tgca                                            744
```

<210> SEQ ID NO 99
<211> LENGTH: 248
<212> TYPE: PRT
<213> ORGANISM: Elaeis guineensis

<400> SEQUENCE: 99

Met Gly Arg Ala Pro Cys Cys Asp Lys Ala Asn Val Lys Lys Gly Pro
1               5                   10                  15

Trp Ser Pro Glu Glu Asp Ala Lys Leu Lys Ala Tyr Ile Glu Gln Tyr
                20                  25                  30

Gly Thr Gly Gly Asn Trp Ile Ala Leu Pro Gln Lys Ile Gly Leu Lys
            35                  40                  45

Arg Cys Gly Lys Ser Cys Arg Leu Arg Trp Leu Asn Tyr Leu Arg Pro
        50                  55                  60

Asn Ile Lys His Gly Gly Phe Ser Glu Glu Asp His Ile Ile Cys
65                  70                  75                  80

Ser Leu Tyr Ile Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Gly Lys Gln Arg Lys Asp His Gln Gln Gln
        115                 120                 125

Ala Arg Arg Gly Gly Pro Lys Gln Glu Asp Arg Ser Asp Glu Ser
    130                 135                 140

Gly Asn Pro Ala Val Ala Gly Glu Gly Gly Ser Arg Ser Thr Tyr Trp
145                 150                 155                 160

Pro Glu Pro Ala Met Pro Val Tyr Ser Thr Gly Gln Pro Asp His His
                165                 170                 175

Leu Asn Asn Asn His Ala Ser Thr Thr Asp Arg Leu Leu Met Met Leu
            180                 185                 190

Gly Gly Arg Ser Ser Asn Asp Ser Asn Ala Ser His Gln Ser Pro Phe
        195                 200                 205

Ile Pro Gln Tyr Ser Ser Val Pro Leu Pro Gln Ile Tyr Asn Asn Ser
    210                 215                 220

Ala Ser Leu Ile Asn Pro Ser Val Asn Thr Thr Ser Phe Lys Glu Ala
225                 230                 235                 240

Met Gln Val Pro His Arg Phe Ala
                245

<210> SEQ ID NO 100
<211> LENGTH: 369
<212> TYPE: DNA
<213> ORGANISM: Elaeis oleifera

<400> SEQUENCE: 100
atgggaagag caccgtgctg tgacaaggct aatgtgaaga gaggaccatg gtctccagag      60
gaagatgcag tccttaaaaa ctatattgag aagcatggga gtgttggtaa ctggattgct     120
ttgccccaaa agcagggct caaacgttgc ggcaaaagct gccgcctccg atggctcaat     180
tacctccggc cagacatcaa gcacggcggc ttcacggagg aagaagacat cgccatctgc     240
actctctaca caaaaattgg aagcaggtgg tctgttattg cttccaagct gcgaggaaga     300
actgacaatg atgtcaagaa ttattggaac actaagctca agaaaaagat gataaacgga     360
caaattagt                                                             369

```
<210> SEQ ID NO 101
<211> LENGTH: 123
<212> TYPE: PRT
<213> ORGANISM: Elaeis oleifera

<400> SEQUENCE: 101
```

Met Gly Arg Ala Pro Cys Cys Asp Lys Ala Asn Val Lys Arg Gly Pro
1               5                   10                  15

Trp Ser Pro Glu Glu Asp Ala Val Leu Lys Asn Tyr Ile Glu Lys His
            20                  25                  30

Gly Ser Val Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asp Ile Lys His Gly Gly Phe Thr Glu Glu Asp Ile Ala Ile Cys
65                  70                  75                  80

Thr Leu Tyr Asn Lys Ile Gly Ser Arg Trp Ser Val Ile Ala Ser Lys
                85                  90                  95

Leu Arg Gly Arg Thr Asp Asn Asp Val Lys Asn Tyr Trp Asn Thr Lys
            100                 105                 110

Leu Lys Lys Lys Met Ile Asn Gly Gln Ile Ser
        115                 120

```
<210> SEQ ID NO 102
<211> LENGTH: 303
<212> TYPE: DNA
<213> ORGANISM: Eschscholzia californica

<400> SEQUENCE: 102
```

| atgggaagag | ctccatgttg | tgataaagca | aatgtaaaga | gaggtccatg | gtcacctgaa | 60 |
| gaagatggaa | agctcaaatc | ctatattgaa | gaacatggta | ctggtggtaa | ttggatagcc | 120 |
| ttgcctcaaa | aaataggtct | aaagagatgt | gggaagagtt | gtcgtctccg | gtggttgaac | 180 |
| tatcttcgac | caaacatcaa | gcatggtggt | ttctccgaag | aagaagataa | cattatatgc | 240 |
| aatctttata | ttagtatcgg | aagcaggtgg | tctataatag | cagcacaact | acctggaaga | 300 |
| act | | | | | | 303 |

```
<210> SEQ ID NO 103
<211> LENGTH: 101
<212> TYPE: PRT
<213> ORGANISM: Eschscholzia californica

<400> SEQUENCE: 103
```

Met Gly Arg Ala Pro Cys Cys Asp Lys Ala Asn Val Lys Arg Gly Pro
1               5                   10                  15

Trp Ser Pro Glu Glu Asp Gly Lys Leu Lys Ser Tyr Ile Glu Glu His
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Glu Asp Asn Ile Ile Cys
65                  70                  75                  80

Asn Leu Tyr Ile Ser Ile Gly Ser Arg Trp Ser Ile Ile Ala Ala Gln
                85                  90                  95

Leu Pro Gly Arg Thr
            100

<210> SEQ ID NO 104
<211> LENGTH: 332
<212> TYPE: DNA
<213> ORGANISM: Euphorbia esula

<400> SEQUENCE: 104

```
atggggagag ctccatgctg tgataaagct aatgtgaaga aaggtccatg gtcacctgag      60
gaagatgcta ctctcaaatc ttatattgaa gaaaatggca ccggcggcaa ctggattgcc     120
ttgcctcaaa aaattgggct aagagatgt gggaagagtt gtagacttag atggttgaat      180
tatctccggc caaatattaa acatggaggc ttttctgagg aggaagataa cattatttgc     240
agcctctata taaatattgg aagcaggtgg tctataattg ctgcacaatt acctggaagg     300
actgataatg atataaagaa ctactggaac ac                                   332
```

<210> SEQ ID NO 105
<211> LENGTH: 111
<212> TYPE: PRT
<213> ORGANISM: Euphorbia esula

<400> SEQUENCE: 105

```
Met

-continued

```
acagacaatg atataaaaaa ttattggaac acaaagttga agaagaagct aatgatgagc    360
ataatcaaca ctaatcctac tcttaatcct caaccaaaat tactatctac tgctggattt    420
tcttctcttc ttcaatttag tccttcttcc ccaatttctt ccaccacatc accatcatct    480
tcttcttctt cttcatcaat attaaacact aattacaata atttgtcatt agtagaaccc    540
acaattcagc cattttcaaa caacccgtta atgggttctc tccaaaatta tcctcatcaa    600
gcaaattatc atatgggttt tgaagggtat aatggtaatt actataatgg agagattaat    660
aatcacagtg agtatggatt agaggagatt aaggaaatga ttagcacaac taatacaatt    720
agtagcaact ttttgtttga agaaaannng acagagagta ttatgtactt t             771
```

<210> SEQ ID NO 107
<211> LENGTH: 257
<212> TYPE: PRT
<213> ORGANISM: Euphorbia esula
<220> FEATURE:
<221> NAME/KEY: MISC_FEATURE
<222> LOCATION: (249)..(249)
<223> OTHER INFORMATION: X can be any amino acid
<220> FEATURE:
<221> NAME/KEY: MISC_FEATURE
<222> LOCATION: (250)..(250)
<223> OTHER INFORMATION: X can be any amino acid

<400> SEQUENCE: 107

```
Met Gly Arg Ala Pro Cys Cys Asp Lys Ala Asn Val Lys Lys Gly Pro
1               5                   10                  15

Trp Ser Pro Glu Glu Asp Ala Ala Leu Lys Asp Tyr Ile Glu Lys Asn
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Asp His Glu Asp Arg Ile Ile Trp
65                  70                  75                  80

Thr Leu Tyr Ser Asn Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Met Met Ser Ile Ile Asn Thr Asn Pro Thr Leu
        115                 120                 125

Asn Pro Gln Pro Lys Leu Leu Ser Thr Ala Gly Phe Ser Ser Leu Leu
    130                 135                 140

Gln Phe Ser Pro Ser Ser Pro Ile Ser Ser Thr Thr Ser Pro Ser Ser
145                 150                 155                 160

Ser Ser Ser Ser Ser Ser Ile Leu Asn Thr Asn Tyr Asn Asn Leu Ser
                165                 170                 175

Leu Val Glu Pro Thr Ile Gln Pro Phe Ser Asn Asn Pro Leu Met Gly
            180                 185                 190

Ser Leu Gln Asn Tyr Pro His Gln Ala Asn Tyr His Met Gly Phe Glu
        195                 200                 205

Gly Tyr Asn Gly Asn Tyr Asn Gly Glu Ile Asn Asn His Ser Glu
    210                 215                 220

Tyr Gly Leu Glu Glu Ile Lys Glu Met Ile Ser Thr Thr Asn Thr Ile
225                 230                 235                 240

Ser Ser Asn Phe Leu Phe Glu Glu Xaa Xaa Thr Glu Ser Ile Met Tyr
```

Phe

<210> SEQ ID NO 108
<211> LENGTH: 649
<212> TYPE: DNA
<213> ORGANISM: Euphorbia tirucalli

<400> SEQUENCE: 108

```
aattattagt tcagcaagat caatacaagt atgggaagag ctccttgctg cgacaaagcc      60
aacgtcaaaa aaggcccttg gtcccctgaa gaagatagct aagcttaaat cttatattga     120
gaaacatggc accggtggta actggattgc tttgcctcaa aaaattggcc ttaaaagatg     180
tggaaagagt tgccgtctta gatagttgaa ctatcttcgc ccaaacatca acatggcgg      240
cttctctgag gaagaagata acatcatttg cagcctttat attagtattg ggagcagata     300
gtctataatt gcagcccaat tgccaggaag aactgataat gacataaaaa attactggaa     360
cacaaggctg aaaagaagc ttcttggaaa gcaaagaaaa gagcaacatt ctagcagaag      420
aggaaatggc ctcaagcaag atattatcaa gagagcaaat cggaccaata atattaattc     480
atctgatcaa aattactctc attggcctga gctgcctttg cttgctccta caccattcat     540
ctccacccaa aatcaagcct tcaatgatca tgcttctatc aggaaattgc ttgtgaagct     600
tggagggaaa ttttctgatg atcatcaaga taatcccatt tttaattct                 649
```

<210> SEQ ID NO 109
<211> LENGTH: 671
<212> TYPE: DNA
<213> ORGANISM: Ginkgo biloba

<400> SEQUENCE: 109

```
gattggattg ccttacccca taaagcaggt ctgaagcgat gcggtaagag ctgcagacta      60
agatggttga actatttgag gcctgatatc aagcatggag gcttctctga agaagaagac     120
actatcattt gtagcctcta cggcagcatt ggaagcaggt ggtctatcat tgctgcgcag     180
ttaccgggta gaacagacaa cgatatcaag aattactgga acacaagact gaagaaaaaa     240
ttgcttggga aatgcaagga tcatcagcaa actcgtcgtc tgtcaagaga agcagagaag     300
gaagtgagag cctttgcttc agaagccgtg tccgtggcca ccactccaac ctcgtctaca     360
tctcttgcaa atccagtatc ttatcacatg actactgatc cctctaatta tgccagtttg     420
gatgccggaa tggtctctca ggcgttggaa cactcgagtt ctcccataag aaccatattg     480
gctcatgatc agtctccatt atctccaagt acagctcatg ggtttgggaa tattcatgat     540
gatcacgaag ctttcagaga aatgtcgat tatgcctgcc ttacaagcct gctcatgcgg      600
cttaatgaag gcagcgattc tttcacaaac atttcttgcg gaatatcaag tacctctcaa     660
gttatatccc c                                                          671
```

<210> SEQ ID NO 110
<211> LENGTH: 1068
<212> TYPE: DNA
<213> ORGANISM: Glycine max

<400> SEQUENCE: 110

```
atggggaggg caccttgctg tgacaaagca aacgtgaaga aggtccttg gtcgccagaa        60
gaagatacca aactcaaatc ctacatcgaa cagcacggaa ccggaggaaa ctggatcgct     120
ttgccacaaa agattggcct taaacgatgt ggcaagagtt gccgtctcag gtggctaaac     180
```

```
tacctccgcc ctaacatcag acacggtggt ttctccgaag aagaagacaa catcatttgc    240
agcctctacg ttagcattgg aagcaggtgg tcggtcattg cagcacaatt gccgggaaga    300
actgataatg acataaagaa ctattggaac acgaggctga agaagaagct tctagggaaa    360
caccgtaagg aactacaggc acgcaacaaa ggaaacggtg gtatccttaa acaggagaac    420
agttcctcgc tcttgcttca gcaaaacagt gctcaacaat tacatccatg ttggccacag    480
attccagtgc tgccactttc atcaccgtac acaaaccaaa gtccaagttt caacgaccaa    540
gattccatta gaaagcttct aatcaagctt ggagggagat tctccgatga ttatcaaccc    600
atcctagatg ggttgaatct tcagttccca catggttcaa attctctctc atcaacacaa    660
caaattcaag aggagcaagt ccatgttggt tcttctgcac tagggtgcat gaactctatt    720
ggccacaatc aagtacaatt tggtcagagt aatgagtact gtgctgagtt ggtgcaagga    780
caagggagtt tcattaccac agcaattggg gaaatggttt cttctaatga ttattctcga    840
aggttattag gtgggtcgtt ggagttcttc tatggggagg aaatgattac tgataataag    900
ataatgggtg cttgtgcttc ttcaagttgt gggcaaagta ctaattgggg tgaaaccagt    960
agttctctga tgtatccttc tcttgttgct tcgaattacg agggtgtgcg gcaagagatg   1020
ccacgagaat gtgcttttca agagttgagc tacccggggg cgcaatag                1068

<210> SEQ ID NO 111
<211> LENGTH: 355
<212> TYPE: PRT
<213> ORGANISM: Glycine max

<400> SEQUENCE: 111

Met Gly Arg Ala Pro Cys Cys Asp Lys Ala Asn Val Lys Lys Gly Pro
1               5                   10                  15

Trp Ser Pro Glu Glu Asp Thr Lys Leu Lys Ser Tyr Ile Glu Gln His
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Arg His Gly Gly Phe Ser Glu Glu Asp Asn Ile Ile Cys
65                  70                  75                  80

Ser Leu Tyr Val Ser Ile Gly Ser Arg Trp Ser Val Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Gly Lys His Arg Lys Glu Leu Gln Ala Arg
        115                 120                 125

Asn Lys Gly Asn Gly Gly Ile Leu Lys Gln Glu Asn Ser Ser Ser Leu
    130                 135                 140

Leu Leu Gln Gln Asn Ser Ala Gln Gln Leu His Pro Cys Trp Pro Gln
145                 150                 155                 160

Ile Pro Val Leu Pro Leu Ser Ser Pro Tyr Thr Asn Gln Ser Pro Ser
                165                 170                 175

Phe Asn Asp Gln Asp Ser Ile Arg Lys Leu Leu Ile Lys Leu Gly Gly
            180                 185                 190

Arg Phe Ser Asp Asp Tyr Gln Pro Ile Leu Asp Gly Leu Asn Leu Gln
        195                 200                 205

Phe Pro His Gly Ser Asn Ser Leu Ser Ser Thr Gln Gln Ile Gln Glu
```

Glu Gln Val His Val Gly Ser Ser Ala Leu Gly Cys Met Asn Ser Ile
225                 230                 235                 240

Gly His Asn Gln Val Gln Phe Gly Gln Ser Asn Glu Tyr Cys Ala Glu
            245                 250                 255

Leu Val Gln Gly Gln Gly Ser Phe Ile Thr Thr Ala Ile Gly Glu Met
            260                 265                 270

Val Ser Ser Asn Asp Tyr Ser Arg Arg Leu Leu Gly Gly Ser Leu Glu
            275                 280                 285

Phe Phe Tyr Gly Glu Glu Met Ile Thr Asp Asn Lys Ile Met Gly Ala
        290                 295                 300

Cys Ala Ser Ser Ser Cys Gly Gln Ser Thr Asn Trp Gly Glu Thr Ser
305                 310                 315                 320

Ser Ser Leu Met Tyr Pro Ser Leu Val Ala Ser Asn Tyr Glu Gly Val
            325                 330                 335

Arg Gln Glu Met Pro Arg Glu Cys Ala Phe Gln Glu Leu Ser Tyr Pro
            340                 345                 350

Gly Ala Gln
        355

<210> SEQ ID NO 112
<211> LENGTH: 444
<212> TYPE: DNA
<213> ORGANISM: Glycine max

<400> SEQUENCE: 112
atggggaggg caccttgctg tgacaaagca acgtgaaga aggtccttg gtcgccagaa      60 gaagatacca aactcaaatc ctacatcgaa cagcacggaa ccggaggaaa ctggatcgct     120
ttgccacaaa agattggcct taaacgatgt ggcaagagtt gccgtctcag gtggctaaac     180
tacctccgcc ctaacatcag acacggtggt ttctccgaag aagaagacaa catcatttgc     240
agcctctacg ttagcattgg aagcaggtgg tcggtcattg cagcacaatt gccgggaaga     300
actgataatg acataaagaa ctattggaac acgaggctga agaagaagct tctagggaaa     360
caccgtaagg aactacaggc acgcaacaaa ggaaacggtg tatccttaa acaggagaac      420 agttcctcgc tcttgcttca gcaa                                            444

<210> SEQ ID NO 113
<211> LENGTH: 148
<212> TYPE: PRT
<213> ORGANISM: Glycine max

<400> SEQUENCE: 113

Met Gly Arg Ala Pro Cys Cys Asp Lys Ala Asn Val Lys Lys Gly Pro
1               5                   10                  15

Trp Ser Pro Glu Glu Asp Thr Lys Leu Lys Ser Tyr Ile Glu Gln His
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Arg His Gly Gly Phe Ser Glu Glu Glu Asp Asn Ile Ile Cys
65                  70                  75                  80

Ser Leu Tyr Val Ser Ile Gly Ser Arg Trp Ser Val Ile Ala Ala Gln
            85                  90                  95

```
Leu Pro Gly Arg Thr Asp Asn Asp Ile Lys Asn Tyr Trp Asn Thr Arg
            100                 105                 110

Leu Lys Lys Lys Leu Leu Gly Lys His Arg Lys Glu Leu Gln Ala Arg
        115                 120                 125

Asn Lys Gly Asn Gly Gly Ile Leu Lys Gln Glu Asn Ser Ser Ser Leu
    130                 135                 140

Leu Leu Gln Gln
145

<210> SEQ ID NO 114
<211> LENGTH: 627
<212> TYPE: DNA
<213> ORGANISM: Glycine max

<400> SEQUENCE: 114
atgggtagag ctccatgctg tgacaaggcc aacgtgaaga aaggaccatg gtctcctgaa      60
gaggatgctg cactcaaagc ctacattgaa agaatggaa ctggtggcaa ttggattgct     120
cttcctcaga aaattggttt ggaaaggtgt ggaaagagtt gcagactag gtggttaaat     180 tacttgaggc ctaatatcaa acatggtgga tttactgaag aagaagacaa catcatctgc     240
agcctgtaca ttagcattgg aagcaggtgg tccataattg ctgctcagtt acctggaagg     300
acagataacg acatcaagaa ctattggaac actagattga agaagaaact gctcgggagg     360
cgcaaacaat ctaacttaag cgcaaaagac acaaacaatg gaatagagga gaattcttat     420
tcaaatgccc taagctcttc agctcttgaa agactccaac tgcacatgca acttcaaagc     480
cttcaaaacc ctttctcttt ctacaacaac ccggcgctgt ggcccaagtt gcatcctttc     540
caagaaaaga tgatccagag cctgcagtct ttgaatgatg gctctagccc tgtgatgcaa     600
aatgctttgc ctaattccca catgtcg                                        627

<210> SEQ ID NO 115
<211> LENGTH: 209
<212> TYPE: PRT
<213> ORGANISM: Glycine max

<400> SEQUENCE: 115

Met Gly Arg Ala Pro Cys Cys Asp Lys Ala Asn Val Lys Lys Gly Pro
1               5                   10                  15

Trp Ser Pro Glu Glu Asp Ala Ala Leu Lys Ala Tyr Ile Glu Lys Asn
            20                  25                  30

Gly Thr Gly Gly Asn Trp Ile Ala Leu Pro Gln Lys Ile Gly Leu Glu
        35                  40                  45

Arg Cys Gly Lys Ser Cys Arg Leu Arg Trp Leu Asn Tyr Leu Arg Pro
    50                  55                  60

Asn Ile Lys His Gly Gly Phe Thr Glu Glu Asp Asn Ile Ile Cys
65                  70                  75                  80

Ser Leu Tyr Ile Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Gly Arg Arg Lys Gln Ser Asn Leu Ser Ala
        115                 120                 125

Lys Asp Thr Asn Asn Gly Ile Glu Glu Asn Ser Tyr Ser Asn Ala Leu
    130                 135                 140

Ser Ser Ser Ala Leu Glu Arg Leu Gln Leu His Met Gln Leu Gln Ser
145                 150                 155                 160
```

```
Leu Gln Asn Pro Phe Ser Phe Tyr Asn Asn Pro Ala Leu Trp Pro Lys
            165                 170                 175

Leu His Pro Phe Gln Glu Lys Met Ile Gln Ser Leu Gln Ser Leu Asn
            180                 185                 190

Asp Gly Ser Ser Pro Val Met Gln Asn Ala Leu Pro Asn Ser His Met
            195                 200                 205

Ser

<210> SEQ ID NO 116
<211> LENGTH: 684
<212> TYPE: DNA
<213> ORGANISM: Glycine max

<400> SEQUENCE: 116
atgggtagag ctccttgttg tgacaaggca aatgtaaaga aagggccatg gtcaccagaa        60
gaagatgcaa agctaaagga ctacatagag caacatggca ctggaggcaa ttggattgcg       120
cttccacaaa aagttggttt gaaaagatgt ggaaagagtt gtagactaag gtggcttaat       180
tatcttagac ccaacattaa gcatggtcaa ttctctgaag cagaagataa aataatctgt       240
agcctctttg ctagcattgg aagcaggtgg tccataatag catctcagtt gccggggagg       300
actgacaatg atatcaagaa ctattggaac accaagctta agaagaaaat gatggccatg       360
aatccttcac tccaaaggaa gcctcaacaa attacccttt atccatcct tcaaagttca        420 gcatattcat caccatcgtc attcagagac agtaacaaca tctcatacta ccaccctcac       480
ggttcctttt cctactcgtc aaatcttctg agtggtaaca cacttctgc ttctgctaat        540 tccttctttc aagcacaaga gagtttcatt gaccccactc agaagtgcca attcaaagat       600
agcagcaaca atagcatgtt tttgtttggt ggtgaagcca cagccacagc cactagttgc       660
agctcttctg atgggagctg caac                                              684

<210> SEQ ID NO 117
<211> LENGTH: 228
<212> TYPE: PRT
<213> ORGANISM: Glycine max

<400> SEQUENCE: 117

Met Gly Arg Ala Pro Cys Cys Asp Lys Ala Asn Val Lys Lys Gly Pro
1               5                   10                  15

Trp Ser Pro Glu Glu Asp Ala Lys Leu Lys Asp Tyr Ile Glu Gln His
            20                  25                  30

Gly Thr Gly Gly Asn Trp Ile Ala Leu Pro Gln Lys Val Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Gln Phe Ser Glu Ala Glu Asp Lys Ile Ile Cys
65                  70                  75                  80

Ser Leu Phe Ala Ser Ile Gly Ser Arg Trp Ser Ile Ile Ala Ser Gln
                85                  90                  95

Leu Pro Gly Arg Thr Asp Asn Asp Ile Lys Asn Tyr Trp Asn Thr Lys
            100                 105                 110

Leu Lys Lys Lys Met Met Ala Met Asn Pro Ser Leu Gln Arg Lys Pro
        115                 120                 125

Gln Gln Ile Thr Leu Leu Ser Ile Leu Gln Ser Ser Ala Tyr Ser Ser
    130                 135                 140
```

```
Pro Ser Ser Phe Arg Asp Ser Asn Asn Ile Ser Tyr Tyr His Pro His
145                 150                 155                 160

Gly Ser Phe Ser Tyr Ser Ser Asn Leu Leu Ser Gly Asn Asn Thr Ser
            165                 170                 175

Ala Ser Ala Asn Ser Phe Phe Gln Ala Gln Glu Ser Phe Ile Asp Pro
        180                 185                 190

Thr Gln Lys Cys Gln Phe Lys Asp Ser Ser Asn Asn Ser Met Phe Leu
    195                 200                 205

Phe Gly Gly Glu Ala Thr Ala Thr Ala Thr Ser Cys Ser Ser Ser Asp
210                 215                 220

Gly Ser Cys Asn
225

<210> SEQ ID NO 118
<211> LENGTH: 1068
<212> TYPE: DNA
<213> ORGANISM: Gossypium

<400> SEQUENCE: 118
atggggagag ctccttgttg tgacaaagct aacgtcaaga aaggcccatg gtcacctgaa      60
gaagacacca agctcaaggc atacatcgag cagcatggca ctggcggaaa ctggatcgct     120
ttgcctcaca aaattggcct taagagatgt gggaagagct gccgcctcag atggttaaac     180
tatctccgcc caaatattaa gcatggagga ttctccgaag aagaagataa aattatttgc     240
agcctctata tcagtattgg gagcaggtgg tctattattg ctgcacaatt accggggagg     300
actgataacg atataaagaa ctattggaac acaaggctta agaagaagct tctgggcaag     360
caacgcaaag agcatcagtc tcgaagaggc aacagcctaa agcaagatat gaagagatca     420
tcagctagtg tgggggattc catggttcct gcagataaca tcaatcaaat cccttactgg     480
ccagagctgc ctgtgctggc tgcggcggcg gctcccatac cgcactcaag tcaagaacat     540
cgcattgaca gccaagcctc gatgagaaga ttactaatca gcttggggg aagattttct     600 gaggatgatc atgtggttaa tgatgggaca actcttcatc agtttcctaa tgatttatcc     660
actactgatc aggatcttta cgagcagact gtctatgtgc cctcttcttc ttcttcttct     720
cccatggatg ccttgagctt aagcaataac atcggttctc agtttgtgaa ctctcagttc     780
gccatagatg gagggaatct gcccattctg caaggacaaa gcactacttt ttcatcagag     840
ctccaggaaa tgggatatag cagcaaccca cagagattag atggaatgga gttcttatat     900
ggggaaggca tggtcgataa tagaggcgtg aatccttgtg aaagcattgg ctggggtgac     960
actagctctc tggttggccc tccttgtgct tcggaatatg gagtcatgca acaaggaatg    1020
cttcaagaat atggttttag tgagatgagg tacccaggag gagcgcaa                 1068

<210> SEQ ID NO 119
<211> LENGTH: 356
<212> TYPE: PRT
<213> ORGANISM: Gossypium

<400> SEQUENCE: 119

Met Gly Arg Ala Pro Cys Cys Asp Lys Ala Asn Val Lys Lys Gly Pro
1               5                   10                  15

Trp Ser Pro Glu Glu Asp Thr Lys Leu Lys Ala Tyr Ile Glu Gln His
            20                  25                  30

Gly Thr Gly Gly Asn Trp Ile Ala Leu Pro His Lys Ile Gly Leu Lys
        35                  40                  45
```

```
            Arg Cys Gly Lys Ser Cys Arg Leu Arg Trp Leu Asn Tyr Leu Arg Pro
                 50                  55                  60

Asn Ile Lys His Gly Gly Phe Ser Glu Glu Asp Lys Ile Ile Cys
             65                  70                  75                  80

Ser Leu Tyr Ile Ser Ile Gly Ser Arg Trp Ser Ile Ile Ala Ala Gln
                             85                  90                  95

Leu Pro Gly Arg Thr Asp Asn Asp Ile Lys Asn Tyr Trp Asn Thr Arg
                        100                 105                 110

Leu Lys Lys Lys Leu Leu Gly Lys Gln Arg Lys Glu His Gln Ser Arg
                    115                 120                 125

Arg Gly Asn Ser Leu Lys Gln Asp Met Lys Arg Ser Ser Ala Ser Val
                130                 135                 140

Gly Asp Ser Met Val Pro Ala Asp Asn Ile Asn Gln Ile Pro Tyr Trp
            145                 150                 155                 160

Pro Glu Leu Pro Val Leu Ala Ala Ala Ala Pro Ile Pro His Ser
                            165                 170                 175

Ser Gln Glu His Arg Ile Asp Ser Gln Ala Ser Met Arg Leu Leu
                        180                 185                 190

Ile Lys Leu Gly Gly Arg Phe Ser Glu Asp Asp His Val Val Asn Asp
                    195                 200                 205

Gly Thr Thr Leu His Gln Phe Pro Asn Asp Leu Ser Thr Thr Asp Gln
                210                 215                 220

Asp Leu Tyr Glu Gln Thr Val Tyr Val Pro Ser Ser Ser Ser Ser Ser
            225                 230                 235                 240

Pro Met Asp Ala Leu Ser Leu Ser Asn Asn Ile Gly Ser Gln Phe Val
                            245                 250                 255

Asn Ser Gln Phe Ala Ile Asp Gly Gly Asn Leu Pro Ile Leu Gln Gly
                        260                 265                 270

Gln Ser Thr Thr Phe Ser Ser Glu Leu Gln Glu Met Gly Tyr Ser Ser
                    275                 280                 285

Asn Pro Gln Arg Leu Asp Gly Met Glu Phe Leu Tyr Gly Glu Gly Met
                290                 295                 300

Val Asp Asn Arg Gly Val Asn Pro Cys Glu Ser Ile Gly Trp Gly Asp
            305                 310                 315                 320

Thr Ser Ser Leu Val Gly Pro Pro Cys Ala Ser Glu Tyr Gly Val Met
                            325                 330                 335

Gln Gln Gly Met Leu Gln Glu Tyr Gly Phe Ser Glu Met Arg Tyr Pro
                        340                 345                 350

Gly Gly Ala Gln
                    355

<210> SEQ ID NO 120
<211> LENGTH: 633
<212> TYPE: DNA
<213> ORGANISM: Gossypium

<400> SEQUENCE: 120
atgggtcgag ctccttgctg tgacaaagcc aacgtgaaga aaggaccatg gtcacctgaa      60
gaagatgcta agcttaaggc ttatatcgaa cagtatggca ctggtggcaa ctggattgct     120
cttcctcaga aaattggtct taagcgatgt gggaagagtt gcaggttgag atggctgaat     180
tatttgaggc caaacattaa gcatggtgga ttctctgagg aagaagacaa catcatatgc     240
agtctctata agtataggg aagcaggtgg tccataattg ctgcacaact gcctggaaga     300
actgataatg atatcaaaaa ctactggaac accaaattaa agaagaaact acttggagg     360
```

```
cgcaaacaac ctagtaacat ccataggtta tcgaatcaag accctaatga tcctcatcaa      420
cctactggtt cagatgataa tcaattctct cagggtttga gtaacttagc catggaacgt      480
cttcagcttc atatgcagct ccaaactctt cagaacccct tctctttcta taataaccct      540
gctttatggc ctaagattca ccccttgcaa gaaaagatga tccaaaacat gcaggcttct      600
aatggaaacc cttgtctcgt cctctgcctg atg                                   633
```

<210> SEQ ID NO 121
<211> LENGTH: 211
<212> TYPE: PRT
<213> ORGANISM: Gossypium

<400> SEQUENCE: 121

Met Gly Arg Ala Pro Cys Cys Asp Lys Ala Asn Val Lys Lys Gly Pro
1               5                   10                  15

Trp Ser Pro Glu Glu Asp Ala Lys Leu Lys Ala Tyr Ile Glu Gln Tyr
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Asp Asn Ile Ile Cys
65                  70                  75                  80

Ser Leu Tyr Ile Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Leu Gly Arg Arg Lys Gln Pro Ser Asn Ile His
        115                 120                 125

Arg Leu Ser Asn Gln Asp Pro Asn Asp Pro His Gln Pro Thr Gly Ser
    130                 135                 140

Asp Asp Asn Gln Phe Ser Gln Gly Leu Ser Asn Leu Ala Met Glu Arg
145                 150                 155                 160

Leu Gln Leu His Met Gln Leu Gln Thr Leu Gln Asn Pro Phe Ser Phe
                165                 170                 175

Tyr Asn Asn Pro Ala Leu Trp Pro Lys Ile His Pro Leu Gln Glu Lys
            180                 185                 190

Met Ile Gln Asn Met Gln Ala Ser Asn Gly Asn Pro Cys Leu Val Leu
        195                 200                 205

Cys Leu Met
    210

<210> SEQ ID NO 122
<211> LENGTH: 542
<212> TYPE: DNA
<213> ORGANISM: Hedyotis terminalis

<400> SEQUENCE: 122

```
atgggaagag caccttgctg cgacaaagcc aatgtgaagc gaggtccatg gtcacctgaa      60
gaagatgcta aactcaaatc ctacattgag gaatttggca ccggaggaaa ttggatttcc      120
ttaccccaga aaataggtct caagagatgc ggaaaaagtt gtcggctgag atggttgaat      180
tatctgcggc ctaacatcaa gcatggcgga ttttcagaag aagaagatac cataatctgc      240
agcctctata tgagcatagg aagcaggtgg tctattatag cgggacagct gcccggaaga      300
```

```
actgataatg acataaagaa ctactggaat acgaagctga agaagaagtt actagggaaa    360
caacgaaagg atccaaagcc acgttcatca agctcagtct tgactaaaag aaaacagaat    420
tcagtaattt ctgaagacat aagtttatac aacaccataa cacatccaca gatggcttta    480
ccagcagttc atgttccaaa gcttgaacaa caagtccatt tccagtatca gccatctttt    540
gc                                                                  542
```

<210> SEQ ID NO 123
<211> LENGTH: 181
<212> TYPE: PRT
<213> ORGANISM: Hedyotis terminalis

<400> SEQUENCE: 123

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Ser Tyr Ile Glu Glu Phe
            20                  25                  30

Gly Thr Gly Gly Asn Trp Ile Ser Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Glu Asp Thr Ile Ile Cys
65                  70                  75                  80

Ser Leu Tyr Met Ser Ile Gly Ser Arg Trp Ser Ile Ile Ala Gly Gln
                85                  90                  95

Leu Pro Gly Arg Thr Asp Asn Asp Ile Lys Asn Tyr Trp Asn Thr Lys
            100                 105                 110

Leu Lys Lys Lys Leu Leu Gly Lys Gln Arg Lys Asp Pro Lys Pro Arg
        115                 120                 125

Ser Ser Ser Ser Val Leu Thr Lys Arg Lys Gln Asn Ser Val Ile Ser
    130                 135                 140

Glu Asp Ile Ser Leu Tyr Asn Thr Ile Thr His Pro Gln Met Ala Leu
145                 150                 155                 160

Pro Ala Val His Val Pro Lys Leu Glu Gln Gln Val His Phe Gln Tyr
                165                 170                 175

Gln Pro Ser Phe Ala
            180
```

<210> SEQ ID NO 124
<211> LENGTH: 616
<212> TYPE: DNA
<213> ORGANISM: Helianthus annuus

<400> SEQUENCE: 124

```
gatgcaaaac ttaagaatt tattgagaaa tacggaactg gtggtaactg gattgctctc     60
cctcaaaaag ctggtcttaa agatgtgga aagagttgca ggttaagatg gctaaactat    120
ctgagaccaa atataagaca tggtgaattc tctgaagagg aagataggat cattttcagc    180
ttgtatgcta gcattggtag cagatggtcg gtaatagcag ctcagctacc aggaaggact    240
gacaatgaca tcaagaatta ctggaacact aaactgaaga agaagctttt aactatgctt    300
cctatttttc aagaaaaatc atcttttttt ccacctatac cctttcaacc acaaccacca    360
tcaaaggatc atcttacatc tcaccagttc ttgaacaatt catcatcatt ctacactttt    420 agtacccta acttcatgaa tgttgacaac acttctaact ctctcttgt tcatgaagag    480 catactaatg ttactgatct tcagtcatca gtaccacccc caccccaccc actacaactt    540
```

```
catgcaaaca gtttgatgtg caacaacaat actgatgtta atgataactg ttatagtagt      600
tatagcatgt gcaaca                                                      616

<210> SEQ ID NO 125
<211> LENGTH: 645
<212> TYPE: DNA
<213> ORGANISM: Helianthus argophyllus

<400> SEQUENCE: 125
atgggtagag caccatgttg tgacaaaaca aatgtgaaaa agggaccttg gtcttctgaa       60
gaagatgcta agctcaaaga ttacatcgaa aagtatggta ctggtggtaa ctggattgca      120
cttccccaga agatcgggct aaagaggtgt ggaaaaagtt gcagattgag atggttaaat      180
taccttcgac ccaacatcaa gcatggagga ttctctgaag aagaagacaa catcatctgc      240
agcctctata ttagtatagg cagcaggtgg tctataatag cggctcaact tcctggaaga      300
acagataacg acatcaagaa ctactggaac acaaggctga agaagaagtt actcggaagg      360
cgcaaacaat cgcaggcgaa taagctctcg ggttcaagcc agtacccgaa agacggcagc      420
ggaatagaaa ccctaagcaa ctcagctatt gaaaggcttc aactccacat gcaactccaa      480
agccttgaaa accctaattt ccctcactat gataatcccc ccatgtggcc ttgcaaattg      540
aatcctatac aagaaaaaat gatgcaaact ctccaacttg caaatgaatc ctctaatcct      600
ctcatgatgc aaaatttctc acctgctact cctcaaaagg ttgaa                      645

<210> SEQ ID NO 126
<211> LENGTH: 215
<212> TYPE: PRT
<213> ORGANISM: Helianthus argophyllus

<400> SEQUENCE: 126

Met Gly Arg Ala Pro Cys Cys Asp Lys Thr Asn Val Lys Lys Gly Pro
1               5                   10                  15

Trp Ser Ser Glu Glu Asp Ala Lys Leu Lys Asp Tyr Ile Glu Lys Tyr
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Asp Asn Ile Ile Cys
65                  70                  75                  80

Ser Leu Tyr Ile Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Gly Arg Arg Lys Gln Ser Gln Ala Asn Lys
        115                 120                 125

Leu Ser Gly Ser Ser Gln Tyr Pro Lys Asp Gly Ser Gly Ile Glu Thr
    130                 135                 140

Leu Ser Asn Ser Ala Ile Glu Arg Leu Gln Leu His Met Gln Leu Gln
145                 150                 155                 160

Ser Leu Glu Asn Pro Asn Phe Pro His Tyr Asp Asn Pro Pro Met Trp
                165                 170                 175

Pro Cys Lys Leu Asn Pro Ile Gln Glu Lys Met Met Gln Thr Leu Gln
            180                 185                 190
```

```
Leu Ala Asn Glu Ser Ser Asn Pro Leu Met Met Gln Asn Phe Ser Pro
        195                 200                 205

Ala Thr Pro Gln Lys Val Glu
        210             215

<210> SEQ ID NO 127
<211> LENGTH: 716
<212> TYPE: DNA
<213> ORGANISM: Helianthus argophyllus

<400> SEQUENCE: 127
atggggagag cccttgttg tgacaaagca aatgtgaaga aggggccatg gtcttctgaa      60
gaagatgcaa aactcaaaga atttattggg aaatatggaa ctggtgggaa ctggattgct     120
ctccctcaaa aagctggcct taaaagatgt ggaaagagtt gcagattaag gtggctaaac     180
tatctaagac ccaacattag acatggtgaa tactctgatg aagaagacag gatcatatgc     240
aacttgtatg ctagcattgg tagcagatgg tctgttatag ctgctcaact accaggaagg     300
actgataatg atatcaagaa ctactggaac accaaactga agaagaaact tttaactatg     360
ccttcttacc ttcaagaaaa acaaacattt ttttcatcta tgtcctttca accaccacca     420
ccatcatata atattacatc acaccaattg ttaaacaatt catcatcatg ttactctttt     480
agtaccccta acttcatgaa tgttgacaac atgtccaact ctctctttgt taatgatgat     540
attcataaca atcttactaa tcttcaatca ccaacacctc ttgcaaacaa tttggtgagt     600
aacaacagtg ttgatgttgt taatgataac tgtttgagtt atctagggtt tcaagatggg     660
cattatggca tgtgcaatag tccaatgctc atgtatggag gtacatgttc ttcttc        716

<210> SEQ ID NO 128
<211> LENGTH: 239
<212> TYPE: PRT
<213> ORGANISM: Helianthus argophyllus

<400> SEQUENCE: 128

Met Gly Arg Ala Pro Cys Cys Asp Lys Ala Asn Val Lys Lys Gly Pro
1               5                  10                  15

Trp Ser Ser Glu Glu Asp Ala Lys Leu Lys Glu Phe Ile Gly Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Arg His Gly Glu Tyr Ser Asp Glu Glu Asp Arg Ile Ile Cys
65                  70                  75                  80

Asn Leu Tyr Ala Ser Ile Gly Ser Arg Trp Ser Val Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Leu Thr Met Pro Ser Tyr Leu Gln Glu Lys Gln
        115                 120                 125

Thr Phe Phe Ser Ser Met Ser Phe Gln Pro Pro Pro Ser Tyr Asn
    130                 135                 140

Ile Thr Ser His Gln Leu Leu Asn Asn Ser Ser Cys Tyr Ser Phe
145                 150                 155                 160

Ser Thr Pro Asn Phe Met Asn Val Asp Asn Met Ser Asn Ser Leu Phe
                165                 170                 175
```

Val Asn Asp Asp Ile His Asn Asn Leu Thr Asn Leu Gln Ser Pro Thr
                180                 185                 190

Pro Leu Ala Asn Asn Leu Val Ser Asn Ser Val Asp Val Val Asn
        195                 200                 205

Asp Asn Cys Leu Ser Tyr Leu Gly Phe Gln Asp Gly His Tyr Gly Met
210                 215                 220

Cys Asn Ser Pro Met Leu Met Tyr Gly Gly Thr Cys Ser Ser Ser
225                 230                 235

<210> SEQ ID NO 129
<211> LENGTH: 803
<212> TYPE: DNA
<213> ORGANISM: Helianthus ciliaris

<400> SEQUENCE: 129

```
agactacata caaactcatg gtactggtgg caactggatt actctcccac aaaaagcagg      60
ccttagaaga tgtggtaaga gttgcaggtt gagatggctc aactatctca gaccaaacat     120
caaacatggt gaattttctg atgatgaaga caaacttatt tgtacccttt atgctagcat     180
tggtagcagg tggtcaataa tggcagcaca gttaccagga agaacagata atgatatcaa     240
gaactactgg aacacaaaac tgaagaagaa gaagatgatg agcaacttaa ttaccatgcc     300
tgaaattcaa aaacctcttc atcatcttca ttctttcatt tcctcgacaa actacaacta     360
cccatcactg tcaaatttcc atcctagtga tatcaatatt aatgctccat tatcatcacc     420
accaccacca cagtcatcat atatctatag ctcacacact gctagatatc atgatcaaac     480
cctatctatc ccatcaagtc ctacaataac aacaactgct tctgctgatg ctgctgctgt     540
tgtttctgat catcatcacc atccagttct acaaccacaa gatcatggga atcttggtta     600
ccaaagggta aaagacagtt ctacccttgt gatgtttgga ggtgatcaag ctagttccag     660
tacttctaac tctgagggga gttgtcatta tgagtatggt actggtatag gtgtgtatga     720
tcacaacaag tacaacatgg acatatgag gagcaatcct ttcaaggaat gtgggatgat     780
gacacatgat aaggattttg ggt                                              803
```

<210> SEQ ID NO 130
<211> LENGTH: 684
<212> TYPE: DNA
<213> ORGANISM: Helianthus exilis
<220> FEATURE:
<221> NAME/KEY: misc_feature
<222> LOCATION: (631)..(631)
<223> OTHER INFORMATION: n is any nucleotide

<400> SEQUENCE: 130

```
atgggaagag cactttgttg tgacaaagct aatgtcaaaa gaggaccatg gtcacctgaa      60
gaagatgcca aactcaagtc atatatcgat gaatatggca ccggcggcaa ctggattgcg     120
ctaccgcata aaataggact caggagatgt ggcaagagtt gtcgccttcg atggttaaac     180
tatcttcgtc cgaatatcaa gcatggatct ttctcggaag aagaagacca tatcatttcc     240
accctctatc tcaatatcgg tagccggtgg tccattatag cttcacaatt acccgggaga     300
actgataatg atatcaagaa ctactggaac acaagactaa agaaaaaact catgggaatg     360
cagcgaaaag atcaacaatt gtcaaagaga ggtgggataa tcaagcaaga aatgaagaga     420
gaggttcttg aagatttaaa ggtaccatct ttatccacaa gcatgaatct ttatcaatct     480
ttctggccta cagaattccc tttgatagtc acaaacccta accatcatgg tcaagaactt     540
catgtgaaac cacaagatcc caccttttaat cactacccctt ttgacacaac ttcaatccaa     600
```
ccagaattgt tggatcaaaa caacaagagt ncattgccaa acacaccta ttttgctaat    660 ggggatgttg taaacctatt tcaa                                          684

<210> SEQ ID NO 131
<211> LENGTH: 228
<212> TYPE: PRT
<213> ORGANISM: Helianthus exilis
<220> FEATURE:
<221> NAME/KEY: MISC_FEATURE
<222> LOCATION: (211)..(211)
<223> OTHER INFORMATION: X is any amino acid

<400> SEQUENCE: 131

Met Gly Arg Ala Leu Cys Cys Asp Lys Ala Asn Val Lys Arg Gly Pro
1               5                   10                  15

Trp Ser Pro Glu Glu Asp Ala Lys Leu Lys Ser Tyr Ile Asp Glu Tyr
            20                  25                  30

Gly Thr Gly Gly Asn Trp Ile Ala Leu Pro His Lys Ile Gly Leu Arg
        35                  40                  45

Arg Cys Gly Lys Ser Cys Arg Leu Arg Trp Leu Asn Tyr Leu Arg Pro
    50                  55                  60

Asn Ile Lys His Gly Ser Phe Ser Glu Glu Glu Asp His Ile Ile Ser
65                  70                  75                  80

Thr Leu Tyr Leu Asn Ile Gly Ser Arg Trp Ser Ile Ile Ala Ser Gln
                85                  90                  95

Leu Pro Gly Arg Thr Asp Asn Asp Ile Lys Asn Tyr Trp Asn Thr Arg
            100                 105                 110

Leu Lys Lys Lys Leu Met Gly Met Gln Arg Lys Asp Gln Gln Leu Ser
        115                 120                 125

Lys Arg Gly Gly Ile Ile Lys Gln Glu Met Lys Arg Glu Val Leu Glu
    130                 135                 140

Asp Leu Lys Val Pro Ser Leu Ser Thr Ser Met Asn Leu Tyr Gln Ser
145                 150                 155                 160

Phe Trp Pro Thr Glu Phe Pro Leu Ile Val Thr Asn Pro Asn His His
                165                 170                 175

Gly Gln Glu Leu His Val Lys Pro Gln Asp Pro Thr Phe Asn His Tyr
            180                 185                 190

Pro Phe Asp Thr Thr Ser Ile Gln Pro Glu Leu Leu Asp Gln Asn Asn
        195                 200                 205

Lys Ser Xaa Leu Pro Asn Thr Pro Tyr Phe Ala Asn Gly Asp Val Val
    210                 215                 220

Asn Leu Phe Gln
225

<210> SEQ ID NO 132
<211> LENGTH: 654
<212> TYPE: DNA
<213> ORGANISM: Helianthus exilis

<400> SEQUENCE: 132
atggggagag cccttgttg tgacaaagca aatgtgaaga aagggccatg gtcttctgaa    60
gaagatgcaa aactcaaaga atttattggg aaatatggaa ctggtgggaa ctggattgct   120
ctccctcaaa aagctggcct taaaagatgt ggaaagagtt gcagattaag gtggctaaac   180
tatctaagac ccaacattag acatggtgaa tactctgatg aagaagacag gatcatatgc   240
aacttgtatg ctagcattgg tagcagatgg tctgttatag ctgctcaact accaggaagg   300

```
actgataatg atatcaagaa ttactggaac actaaactga agaagaaact tttaactatg      360
ccttcttacc ttcaagaaaa gcaaacattt ttttcatcca tgcccttcca accaccacca      420
ccatcatata atattacatc acaccagatc ttgaacaatt catcatcatg ttactctttt      480
agtaccccta acttcatgaa tgttgacaac atgtccaact cactctttgt tcatgatgat      540
attcataaca atcttactaa tcttcaatca ccaacacctc ttgcagacaa tttgatgagt      600
aacaacagtg ttgatgttgt taatgataag tgtttgagtt atctagggtt tcaa            654
```

<210> SEQ ID NO 133
<211> LENGTH: 218
<212> TYPE: PRT
<213> ORGANISM: Helianthus exilis

<400> SEQUENCE: 133

```
Met Gly Arg Ala Pro Cys Cys Asp Lys Ala Asn Val Lys Lys Gly Pro
1               5                   10                  15

Trp Ser Ser Glu Glu Asp Ala Lys Leu Lys Glu Phe Ile Gly Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Arg His Gly Glu Tyr Ser Asp Glu Glu Asp Arg Ile Ile Cys
65                  70                  75                  80

Asn Leu Tyr Ala Ser Ile Gly Ser Arg Trp Ser Val Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Leu Thr Met Pro Ser Tyr Leu Gln Glu Lys Gln
        115                 120                 125

Thr Phe Phe Ser Ser Met Pro Phe Gln Pro Pro Pro Ser Tyr Asn
    130                 135                 140

Ile Thr Ser His Gln Ile Leu Asn Asn Ser Ser Ser Cys Tyr Ser Phe
145                 150                 155                 160

Ser Thr Pro Asn Phe Met Asn Val Asp Asn Met Ser Asn Ser Leu Phe
                165                 170                 175

Val His Asp Asp Ile His Asn Asn Leu Thr Asn Leu Gln Ser Pro Thr
            180                 185                 190

Pro Leu Ala Asp Asn Leu Met Ser Asn Asn Ser Val Asp Val Val Asn
        195                 200                 205

Asp Lys Cys Leu Ser Tyr Leu Gly Phe Gln
    210                 215
```

<210> SEQ ID NO 134
<211> LENGTH: 840
<212> TYPE: DNA
<213> ORGANISM: Helianthus paradoxus

<400> SEQUENCE: 134

```
tgccaactaa ggcttatatc gaagaacatg gcaccggagg caactggatt gctctacctc       60
ataaaattgg cctcaagaga tgtggcaaga gttgtcgcct tcgatggcta aactatcttc      120
gcccaaacat caagcatgga tctttctccg aggaagaaga tcacatcatt tgcaccctct      180
atctcagtat tggcagccgg tggtctatca tagcggcaca attgcctggg cgaacggata      240
```

```
atgatatcaa gaactactgg aacacgagac taaagaaaaa actaatggga aaacaacgga      300
aagatcaaca atcgtcgaaa cgaggttgct taatcaagca agaaatgaag agagaggttc      360
ttgaagattt aaaggcacca tctttatgca tgagcatgaa tctttatcaa tcttactggc      420
caacagaatt ccctttgatt ctcacaaacc ctaatcagca tcatcatcaa gaacttgcca      480
aaacccaaga tcccactttt gagccatacc aatttgacac aatctcaaat caacccgaat      540
tgttcaatca aaacaacgat aaaccgatat caactgcttc ttaccatcct cagttgccaa      600
acacacccta ttttctaaat ggagatggta taaatctgtt tcaagaattc aacaattacc      660
catttgggat cgatgaattt ggctgcaaca caacacagtt agagcagttt gatgggttgg      720
ttggggtttt ggataacctt gtcaatggaa gcaattgcac aagctcatcg gcagaaagta      780
caactagttg gggtgatcct ctagcatgcc ctcctccccc tccgatggcg tatgatgatt      840
```

<210> SEQ ID NO 135
<211> LENGTH: 429
<212> TYPE: DNA
<213> ORGANISM: Helianthus petiolaris

<400> SEQUENCE: 135

```
atgggaagag caccttgctg tgacaaagcc aacgtcaaaa gaggaccatg gtcacctgaa       60
gaagatgcca aactaaaggc ttatatcgaa gaacatggca ccggaggcaa ctggattgct      120
ctacctcata aaattggcct caagagatgt ggcaagagtt gtcgccttcg atggctaaac      180
tatcttcgcc caaacatcaa gcatggatct ttctccgagg aagaagatca catcatttgc      240
accctctatc tcagtattgg cagccggtgg tctatcatag cggcacaatt gcctgggcga      300
acggataatg atatcaagaa ctactggaac acgagactaa agaaaaaaac taatgggaaa      360
acaacggaaa gatcaacaat cgtcgaaacg aggtggctta atcaagcaag aaatgaagag      420
agaggttct                                                             429
```

<210> SEQ ID NO 136
<211> LENGTH: 143
<212> TYPE: PRT
<213> ORGANISM: Helianthus petiolaris

<400> SEQUENCE: 136

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Ala Tyr Ile Glu Glu His
            20                  25                  30

Gly Thr Gly Gly Asn Trp Ile Ala Leu Pro His Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Ser Phe Ser Glu Glu Asp His Ile Ile Cys
65                  70                  75                  80

Thr Leu Tyr Leu Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Thr Asn Gly Lys Thr Thr Glu Arg Ser Thr Ile Val
        115                 120                 125

Glu Thr Arg Trp Leu Asn Gln Ala Arg Asn Glu Glu Arg Gly Ser
    130                 135                 140
```

<210> SEQ ID NO 137
<211> LENGTH: 723
<212> TYPE: DNA
<213> ORGANISM: Helianthus petiolaris

<400> SEQUENCE: 137

| | | |
|---|---|---|
| atgggaagag caccttgttg tgacaaagct aatgtaaaaa gaggaccatg gtcacctgaa | 60 |
| gaagatgcca aactcaagtc atatattgat gaatatggca ccggcggcaa ctggatcgcg | 120 |
| ctaccgcata aaataggact caggagatgt ggcaagagtt gccgccttcg atggttaaac | 180 |
| tatcttcgtc cgaatatcaa gcatggatct ttctcggaag aagaagatca tatcattccc | 240 |
| actctctatc tcaatatcgg tagccggtgg tcaattatag cttcacattt acccggccgg | 300 |
| actgataatg atatcaagaa ctactggaac acaagactaa agaaaaaact catgggaatg | 360 |
| cagcgaaaag atcaacaatt gtcaaagaga ggggggatag tcaagcaaga aatgaagaga | 420 |
| gaggttcttg aagaattaaa gggaccatct ttagctacaa gcatgaatct ttatcaatct | 480 |
| ttttggccta cagaatccgc tttgatagtc acaaacccta atcatcatgg tcaagaactt | 540 |
| catgtgaaac cacaagatcc cacctttaat cactacccct ttgacacaac ctcaatccaa | 600 |
| ccagaattgt tggatcaaaa caacaagaat cagttgctaa acacacccta ttttgctaat | 660 |
| ggggatgttg taaacctatt tcaagaattc acaattaccc atttgagatc aatgagttta | 720 |
| act | 723 |

<210> SEQ ID NO 138
<211> LENGTH: 241
<212> TYPE: PRT
<213> ORGANISM: Helianthus petiolaris

<400> SEQUENCE: 138

Met Gly Arg Ala Pro Cys Cys Asp Lys Ala Asn Val Lys Arg Gly Pro
1               5                   10                  15

Trp Ser Pro Glu Glu Asp Ala Lys Leu Lys Ser Tyr Ile Asp Glu Tyr
            20                  25                  30

Gly Thr Gly Gly Asn Trp Ile Ala Leu Pro His Lys Ile Gly Leu Arg
        35                  40                  45

Arg Cys Gly Lys Ser Cys Arg Leu Arg Trp Leu Asn Tyr Leu Arg Pro
    50                  55                  60

Asn Ile Lys His Gly Ser Phe Ser Glu Glu Asp His Ile Ile Ser
65                  70                  75                  80

Thr Leu Tyr Leu Asn Ile Gly Ser Arg Trp Ser Ile Ile Ala Ser His
                85                  90                  95

Leu Pro Gly Arg Thr Asp Asn Asp Ile Lys Asn Tyr Trp Asn Thr Arg
            100                 105                 110

Leu Lys Lys Lys Leu Met Gly Met Gln Arg Lys Asp Gln Gln Leu Ser
        115                 120                 125

Lys Arg Gly Gly Ile Val Lys Gln Glu Met Lys Arg Glu Val Leu Glu
    130                 135                 140

Glu Leu Lys Gly Pro Ser Leu Ala Thr Ser Met Asn Leu Tyr Gln Ser
145                 150                 155                 160

Phe Trp Pro Thr Glu Ser Ala Leu Ile Val Thr Asn Pro Asn His His
                165                 170                 175

Gly Gln Glu Leu His Val Lys Pro Gln Asp Pro Thr Phe Asn His Tyr
            180                 185                 190

Pro Phe Asp Thr Thr Ser Ile Gln Pro Glu Leu Leu Asp Gln Asn Asn

-continued

```
                195                 200                 205

Lys Asn Gln Leu Leu Asn Thr Pro Tyr Phe Ala Asn Gly Asp Val Val
    210                 215                 220

Asn Leu Phe Gln Glu Phe Thr Ile Thr His Leu Arg Ser Met Ser Leu
225                 230                 235                 240

Thr
```

```
<210> SEQ ID NO 139
<211> LENGTH: 758
<212> TYPE: DNA
<213> ORGANISM: Helianthus tuberosus
<220> FEATURE:
<221> NAME/KEY: misc_feature
<222> LOCATION: (612)..(612)
<223> OTHER INFORMATION: n is any nucleotide

<400> SEQUENCE: 139
atgggtagag caccatgttg tgacaaaaca aatgtgaaaa agggaccttg gtcttctgaa      60
gaagatgcta agctcaaaga ttatatcgaa agtatggta ctggtggtaa ctggattgca     120
cttccccaga agatcgggct aaagaggtgc ggaaaaagtt gcagattgag atggttaaat    180
taccttcgac ccaacatcaa gcatggagga ttctctgaag aagaagacaa catcatctgc    240
agcctctata ttagtatagg cagcaggtgg tctataatag cggctcaact tcctggaaga    300
acagataacg acatcaagaa ctactggaac acaaggttga agaagaagtt actcggaagg    360
cgcaaacaat cacaggcgaa taagctttcg ggttcaagcc aggacccgaa agacggcagc    420
ggaatagaaa ccctaagcaa ctcagccatt gaaaggcttc aacttcacat gcaactccaa    480
agccttgaaa accctaattt ccctcactat gataatcccc ccatgtggcc ttgcaagttg    540
aatcctatac aagaaaaaat gatgcaaact ctccaacttg caaatgaagc ctctaaccct    600
ctcatgatgc anaatttctc acctgctact cctcaaaaag ttgaatacta tgcacaatcc    660
aataaccctc tttctctaca agaaaactgg gtcgtttccg gcaatatgat gattaacgga    720
atggagaatt ccatgggaat caacattcct gagtcatc                            758
```

```
<210> SEQ ID NO 140
<211> LENGTH: 253
<212> TYPE: PRT
<213> ORGANISM: Helianthus tuberosus
<220> FEATURE:
<221> NAME/KEY: MISC_FEATURE
<222> LOCATION: (204)..(204)
<223> OTHER INFORMATION: X is any amino acid

<400> SEQUENCE: 140

Met Gly Arg Ala Pro Cys Cys Asp Lys Thr Asn Val Lys Lys Gly Pro
1               5                   10                  15

Trp Ser Ser Glu Glu Asp Ala Lys Leu Lys Asp Tyr Ile Glu Lys Tyr
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Asp Asn Ile Ile Cys
65                  70                  75                  80

Ser Leu Tyr Ile Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
```

```
            100             105              110
Leu Lys Lys Lys Leu Leu Gly Arg Arg Lys Gln Ser Gln Ala Asn Lys
        115                 120                 125

Leu Ser Gly Ser Ser Gln Asp Pro Lys Asp Gly Ser Gly Ile Glu Thr
130                 135                 140

Leu Ser Asn Ser Ala Ile Glu Arg Leu Gln Leu His Met Gln Leu Gln
145                 150                 155                 160

Ser Leu Glu Asn Pro Asn Phe Pro His Tyr Asp Asn Pro Pro Met Trp
                165                 170                 175

Pro Cys Lys Leu Asn Pro Ile Gln Glu Lys Met Met Gln Thr Leu Gln
                180                 185                 190

Leu Ala Asn Glu Ala Ser Asn Pro Leu Met Met Xaa Asn Phe Ser Pro
                195                 200                 205

Ala Thr Pro Gln Lys Val Glu Tyr Tyr Ala Gln Ser Asn Asn Pro Leu
                210                 215                 220

Ser Leu Gln Glu Asn Trp Val Val Ser Gly Asn Met Met Ile Asn Gly
225                 230                 235                 240

Met Glu Asn Ser Met Gly Ile Asn Ile Pro Glu Ser Ser
                245                 250
```

<210> SEQ ID NO 141
<211> LENGTH: 473
<212> TYPE: DNA
<213> ORGANISM: Hordeum vulgare

<400> SEQUENCE: 141

```
atggggaggg cgccgtgctg cgacagggcg gcggtgaacc ggggcccgtg gtcgccggag    60
gaggacgacg cgctgcgcga ctacatgcag cgccatggca acaccggcag ctggatcacc   120
ctccccgcca agccgggct caagaggtgc ggcaagagct gcaggctgcg gtggctcaac   180
tacctgcgcc cggacatccg ccacggcggc ttcaccgacg aggaggacgc catcatctac   240
tccctctaca gccagctcgg cagcaagtgg tcgctgatag cgtcgcagct ggagaggagg   300
acggacaacg acgtcaagaa ccactggaac accaagctca gaagcgcct cgtcgccgcg   360
ccgccgcct tccggccgc ccctcctcc cgccgccccc cgtccttcac tccggccgca   420
gcgcacgcgc acgcgcaccc gtcgccgctg ctcccgctcc ccgcgccgac cgt          473
```

<210> SEQ ID NO 142
<211> LENGTH: 158
<212> TYPE: PRT
<213> ORGANISM: Hordeum vulgare

<400> SEQUENCE: 142

```
Met Gly Arg Ala Pro Cys Cys Asp Arg Ala Ala Val Asn Arg Gly Pro
1               5                   10                  15

Trp Ser Pro Glu Glu Asp Asp Ala Leu Arg Asp Tyr Met Gln Arg His
                20                  25                  30

Gly Asn Thr Gly Ser Trp Ile Thr Leu Pro Ala Lys Ala Gly Leu Lys
            35                  40                  45

Arg Cys Gly Lys Ser Cys Arg Leu Arg Trp Leu Asn Tyr Leu Arg Pro
        50                  55                  60

Asp Ile Arg His Gly Gly Phe Thr Asp Glu Glu Asp Ala Ile Ile Tyr
65                  70                  75                  80

Ser Leu Tyr Ser Gln Leu Gly Ser Lys Trp Ser Leu Ile Ala Ser Gln
                85                  90                  95
```

Leu Glu Arg Arg Thr Asp Asn Asp Val Lys Asn His Trp Asn Thr Lys
            100                 105                 110

Leu Lys Lys Arg Leu Val Ala Ala Ala Ala Phe Pro Ala Ala Pro
    115                 120                 125

Ser Ser Arg Arg Pro Pro Ser Phe Thr Pro Ala Ala His Ala His
    130                 135                 140

Ala His Pro Ser Pro Leu Leu Pro Leu Pro Ala Pro Thr Val
145                 150                 155

<210> SEQ ID NO 143
<211> LENGTH: 792
<212> TYPE: DNA
<213> ORGANISM: Humulus lupulus

<400> SEQUENCE: 143

```
atgggaagag cccttgttg cgacaaaacc aaagtgaaaa gaggaccttg gtctcctgaa      60
gaagacgccg ccctcaagca ctacatgcac aacaatggaa ctgggggtaa ttggattgct    120
ctacctcaca aagcaggtct taaccggtgc ggcaaaagtt gtcgtttgag atggctgaat    180
tatctcagac cagatatcaa gcacgggggt tttaccgagg aagaagacaa tgttgtttgg    240
accctttaca gtaacatcgg aagtaggtgg tctgtcatag catcccaact acctggaaga    300
acagacaacg atgtgaaaaa ccactggaac accaagttga agaaaaaact attggcaaga    360
agcaccaact gcaatgagac tactaacact accgatcacc tcaacttggc tcggttctca    420
ccattgattc cgaaaactga gaattctgat caagggaact cagcttattg ttatactaat    480
tcagatacat taccatatct gatgaatggg aactgtgtgc aaaactttga tctcaagaag    540
ccaagtaaac cttcttactc atcaaaccct gttcaagttt ctgattttgg aacaaatggg    600
aacaccagtt ctagcatttc atcaactaga gaggcttcga gtctttcaac ttcatcatct    660
actttggcta tggagaacta tactaatttt gcttcatggt ctggcactgg cattgaaagt    720
actgaagatg ggattcttgt ggacttggga tttgactctt ctaatgatgt tttcctgagt    780
ggctttggat tt                                                         792
```

<210> SEQ ID NO 144
<211> LENGTH: 264
<212> TYPE: PRT
<213> ORGANISM: Humulus lupulus

<400> SEQUENCE: 144

Met Gly Arg Ala Pro Cys Cys Asp Lys Thr Lys Val Lys Arg Gly Pro
1               5                   10                  15

Trp Ser Pro Glu Glu Asp Ala Ala Leu Lys His Tyr Met His Asn Asn
            20                  25                  30

Gly Thr Gly Gly Asn Trp Ile Ala Leu Pro His Lys Ala Gly Leu Asn
        35                  40                  45

Arg Cys Gly Lys Ser Cys Arg Leu Arg Trp Leu Asn Tyr Leu Arg Pro
    50                  55                  60

Asp Ile Lys His Gly Gly Phe Thr Glu Glu Glu Asp Asn Val Val Trp
65                  70                  75                  80

Thr Leu Tyr Ser Asn Ile Gly Ser Arg Trp Ser Val Ile Ala Ser Gln
                85                  90                  95

Leu Pro Gly Arg Thr Asp Asn Asp Val Lys Asn His Trp Asn Thr Lys
            100                 105                 110

Leu Lys Lys Lys Leu Leu Ala Arg Ser Thr Asn Cys Asn Glu Thr Thr
        115                 120                 125

```
Asn Thr Thr Asp His Leu Asn Leu Ala Arg Phe Ser Pro Leu Ile Pro
        130                 135                 140

Lys Thr Glu Asn Ser Asp Gln Gly Asn Ser Ala Tyr Cys Tyr Thr Asn
145                 150                 155                 160

Ser Asp Thr Leu Pro Tyr Leu Met Asn Gly Asn Cys Val Gln Asn Phe
                165                 170                 175

Asp Leu Lys Lys Pro Ser Lys Pro Ser Tyr Ser Ser Asn Pro Val Gln
            180                 185                 190

Val Ser Asp Phe Gly Thr Asn Gly Asn Thr Ser Ser Ile Ser Ser
        195                 200                 205

Thr Arg Glu Ala Ser Ser Leu Ser Thr Ser Ser Thr Leu Ala Met
    210                 215                 220

Glu Asn Tyr Thr Asn Phe Ala Ser Trp Ser Gly Thr Gly Ile Glu Ser
225                 230                 235                 240

Thr Glu Asp Gly Ile Leu Val Asp Leu Gly Phe Asp Ser Ser Asn Asp
                245                 250                 255

Val Phe Leu Ser Gly Phe Gly Phe
            260
```

```
<210> SEQ ID NO 145
<211> LENGTH: 783
<212> TYPE: DNA
<213> ORGANISM: Lactuca perennis
<220> FEATURE:
<221> NAME/KEY: misc_feature
<222> LOCATION: (709)..(709)
<223> OTHER INFORMATION: n is any nucleotide

<400> SEQUENCE: 145
atgggaagag caccttgctg tgacaaagcc aacgtcaaaa gaggaccttg gtcacctgaa      60
gaagatgcca aactcaagtc ttacattgaa gaacatggca ccggaggcaa ctggatcgct     120
ctacctcata aaatcggact caaaaggtgt ggcaagagtt gtcgccttag atggttaaat     180
tatcttcgcc caaacataaa gcatggatct ttctccgaag aagaagatca catcatttgt     240
accctatatc ttagtattgg cagcaggtgg tctatcatcg cagcacaatt acctggaaga     300
actgataatg atataaaaaa ctactggaac acgaggctaa agaaaaagct tttgggaaag     360
cagcgtaaag atcaacaatc gtcaaagaga ggtgggcaag tcaagcaaga aatgaagaca     420
gaggtgtttg aggacttaaa ggcaccatct ttatgcatga ccatgaatct ttatcaatca     480
tactggcctt cagaattccc tttgattctc acaaaccctg atcaacatca tcaggaactt     540
cacgtcaaaa accaagatcc caatttcaac ccatacccat ttgacataac ctcaaaccaa     600
gcccaaatgt tccatcagaa ctgtgaaaaa cctatctcta ctacctctta ccatccccag     660
ttggcaacca caccctatta tccaaatggg gatggagtaa acctgtttnc agaatttaaa     720
cattacccat ttgagatcaa tgaattggtt tacaacacca cacaattaga ccagtttgat     780
ggg                                                                    783
```

```
<210> SEQ ID NO 146
<211> LENGTH: 261
<212> TYPE: PRT
<213> ORGANISM: Lactuca perennis
<220> FEATURE:
<221> NAME/KEY: MISC_FEATURE
<222> LOCATION: (237)..(237)
<223> OTHER INFORMATION: X is any amino acid
<220> FEATURE:
<221> NAME/KEY: MISC_FEATURE
```

<222> LOCATION: (247)..(247)

<400> SEQUENCE: 146

| Met | Gly | Arg | Ala | Pro | Cys | Cys | Asp | Lys | Ala | Asn | Val | Lys | Arg | Gly | Pro |
|---|---|---|---|---|---|---|---|---|---|---|---|---|---|---|---|
| 1 | | | | 5 | | | | | 10 | | | | | 15 | |
| Trp | Ser | Pro | Glu | Glu | Asp | Ala | Lys | Leu | Lys | Ser | Tyr | Ile | Glu | His | |
| | | | 20 | | | | | 25 | | | | | 30 | | |
| Gly | Thr | Gly | Gly | Asn | Trp | Ile | Ala | Leu | Pro | His | Lys | Ile | Gly | Leu | Lys |
| | | 35 | | | | | 40 | | | | | 45 | | | |
| Arg | Cys | Gly | Lys | Ser | Cys | Arg | Leu | Arg | Trp | Leu | Asn | Tyr | Leu | Arg | Pro |
| | 50 | | | | 55 | | | | | 60 | | | | | |
| Asn | Ile | Lys | His | Gly | Ser | Phe | Ser | Glu | Glu | Asp | His | Ile | Ile | Cys | |
| 65 | | | | 70 | | | | 75 | | | | | 80 | | |
| Thr | Leu | Tyr | Leu | Ser | Ile | Gly | Ser | Arg | Trp | Ser | Ile | Ile | Ala | Ala | Gln |
| | | | 85 | | | | | 90 | | | | | 95 | | |
| Leu | Pro | Gly | Arg | Thr | Asp | Asn | Asp | Ile | Lys | Asn | Tyr | Trp | Asn | Thr | Arg |
| | | | 100 | | | | | 105 | | | | | 110 | | |
| Leu | Lys | Lys | Lys | Leu | Leu | Gly | Lys | Gln | Arg | Lys | Asp | Gln | Gln | Ser | Ser |
| | | | 115 | | | | 120 | | | | | 125 | | | |
| Lys | Arg | Gly | Gly | Gln | Val | Lys | Gln | Glu | Met | Lys | Thr | Glu | Val | Phe | Glu |
| | 130 | | | | | 135 | | | | | 140 | | | | |
| Asp | Leu | Lys | Ala | Pro | Ser | Leu | Cys | Met | Thr | Met | Asn | Leu | Tyr | Gln | Ser |
| 145 | | | | | 150 | | | | | 155 | | | | | 160 |
| Tyr | Trp | Pro | Ser | Glu | Phe | Pro | Leu | Ile | Leu | Thr | Asn | Pro | Asp | Gln | His |
| | | | | 165 | | | | | 170 | | | | | 175 | |
| His | Gln | Glu | Leu | His | Val | Lys | Asn | Gln | Asp | Pro | Asn | Phe | Asn | Pro | Tyr |
| | | | 180 | | | | | 185 | | | | | 190 | | |
| Pro | Phe | Asp | Ile | Thr | Ser | Asn | Gln | Ala | Gln | Met | Phe | His | Gln | Asn | Cys |
| | | 195 | | | | | 200 | | | | | 205 | | | |
| Glu | Lys | Pro | Ile | Ser | Thr | Thr | Ser | Tyr | His | Pro | Gln | Leu | Ala | Thr | Thr |
| | 210 | | | | | 215 | | | | | 220 | | | | |
| Pro | Tyr | Tyr | Pro | Asn | Gly | Asp | Gly | Val | Asn | Leu | Phe | Xaa | Glu | Phe | Lys |
| 225 | | | | | 230 | | | | | 235 | | | | | 240 |
| His | Tyr | Pro | Phe | Glu | Ile | Asn | Glu | Leu | Val | Tyr | Asn | Thr | Thr | Gln | Leu |
| | | | | 245 | | | | | 250 | | | | | 255 | |
| Asp | Gln | Phe | Asp | Gly | | | | | | | | | | | |
| | | | | 260 | | | | | | | | | | | |

<210> SEQ ID NO 147
<211> LENGTH: 756
<212> TYPE: DNA
<213> ORGANISM: Lactuca saligna

<400> SEQUENCE: 147

```
atgggaaggg ctccatgttg tgacaaggca aacgtgaaga agggccatg  gtcacctgaa    60
gaagatagaa agcttaaaga ctacatagaa acgcatggca ctggtggcaa ctggatcgct   120
ctcccacaaa aagcaggcct tagacgatgt ggaaagagct gcagattgag atggttgaac   180
tatctgagac caaacattaa acatggcgaa ttttctgatg atgaagataa agttatctgt   240
gccctctatg ctagcattgg tagcaggtgg tcaataatgg cagcacagtt accaggaaga   300
acagacaatg atatcaagaa ctactggaac acaaagctga agaagaagat gatgaacagc   360
ttaatcaccc tacccgaact tagaaaacct cttcaacatc ttcaatcttt cagttcttca   420
acaaactaca gctacccatc aaaatcgatt tttcaaaatt gtaatatcaa tgttaatgct   480
```

```
ccattatcat catcaatatc atcgtctcca tcatatttgt acagtacaaa tacttctagc      540
taccatgatc aaaccttatc tatcccatct agccctagaa ttaatgctgc taatcgtcaa      600
catccagctc tccaatcaca agatcatgga tttctcggtt tggtttccgc ggagacttac      660
cagcaggggg taaaagacag ttctacccctt gtcttctttg gaggtgatca agctagttgc      720
agttctaatt ccgatgggag ctgccattat gagtat                                756
```

<210> SEQ ID NO 148
<211> LENGTH: 252
<212> TYPE: PRT
<213> ORGANISM: Lactuca saligna

<400> SEQUENCE: 148

```
Met Gly Arg Ala Pro Cys Cys Asp Lys Ala Asn Val Lys Lys Gly Pro
1               5                   10                  15

Trp Ser Pro Glu Glu Asp Arg Lys Leu Lys Asp Tyr Ile Glu Thr His
                20                  25                  30

Gly Thr Gly Gly Asn Trp Ile Ala Leu Pro Gln Lys Ala Gly Leu Arg
            35                  40                  45

Arg Cys Gly Lys Ser Cys Arg Leu Arg Trp Leu Asn Tyr Leu Arg Pro
        50                  55                  60

Asn Ile Lys His Gly Glu Phe Ser Asp Asp Glu Asp Lys Val Ile Cys
65                  70                  75                  80

Ala Leu Tyr Ala Ser Ile Gly Ser Arg Trp Ser Ile Met Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Met Met Asn Ser Leu Ile Thr Leu Pro Glu Leu Arg
        115                 120                 125

Lys Pro Leu Gln His Leu Gln Ser Phe Ser Ser Thr Asn Tyr Ser
    130                 135                 140

Tyr Pro Ser Lys Ser Ile Phe Gln Asn Cys Asn Ile Asn Val Asn Ala
145                 150                 155                 160

Pro Leu Ser Ser Ser Ile Ser Ser Ser Pro Ser Tyr Leu Tyr Ser Thr
                165                 170                 175

Asn Thr Ser Ser Tyr His Asp Gln Thr Leu Ser Ile Pro Ser Ser Pro
            180                 185                 190

Arg Ile Asn Ala Ala Asn Arg Gln His Pro Ala Leu Gln Ser Gln Asp
        195                 200                 205

His Gly Phe Leu Gly Leu Val Ser Ala Glu Thr Tyr Gln Gln Gly Val
    210                 215                 220

Lys Asp Ser Ser Thr Leu Val Phe Phe Gly Gly Asp Gln Ala Ser Cys
225                 230                 235                 240

Ser Ser Asn Ser Asp Gly Ser Cys His Tyr Glu Tyr
                245                 250
```

<210> SEQ ID NO 149
<211> LENGTH: 774
<212> TYPE: DNA
<213> ORGANISM: Lactuca sativa

<400> SEQUENCE: 149

```
atgggaaggg ctccgtgttg tgacaaagaa aatgtaaaga gaggcccatg gtctcctgaa       60
gaagacgcaa aactcaaaag cttcatcgac aaatatggca ctggtggtaa ctggattgct      120
ctccctcaca agctggtct aaagaggtgt ggaaagagct gcagattgcg atggttaaac      180
```

```
tatctgaggc caatattaa gcatggtgaa ttcactgatg atgaagacaa gatcatctgc      240
agcttgtatg ctagcattgg tagcagatgg tcaataatag cagctcagct accaggaagg      300
actgataatg atataaagaa ttactggaac accaaactca agaagaagct cttggctatg      360
cttccttcct ttcaaaagaa ggcatctttt tttccatcta tatcccttca atcaccatca      420
ccatacagat catcagatca gttcatgacc gataattctt ccctttttcta cggttacact      480 aatttcatga acatgaacaa caatatcaac tctctgctga cacctaccac caacaccacc      540
accggtgttc aagatcatct gatctcacca tcaccaccac caccaccagg agccgatcta      600
aactctttaa tcggtttgat gaccaacaac attgatcaca atgagaattc tttctattta      660
gggtatcagg agaatcatca gagcatgtac aacacccca tggaatacca ctaccttaca      720
tcagatgtga agaaccgat gctcattttt ggagtggtgg tgagggtcat gaag          774
```

<210> SEQ ID NO 150
<211> LENGTH: 258
<212> TYPE: PRT
<213> ORGANISM: Lactuca sativa

<400> SEQUENCE: 150

```
Met Gly Arg Ala Pro Cys Cys Asp Lys Glu Asn Val Lys Arg Gly Pro
1               5                   10                  15

Trp Ser Pro Glu Glu Asp Ala Lys Leu Lys Ser Phe Ile Asp Lys Tyr
            20                  25                  30

Gly Thr Gly Gly Asn Trp Ile Ala Leu Pro His Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Glu Phe Thr Asp Asp Glu Asp Lys Ile Ile Cys
65                  70                  75                  80

Ser Leu Tyr Ala Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Leu Ala Met Leu Pro Ser Phe Gln Lys Lys Ala
        115                 120                 125

Ser Phe Phe Pro Ser Ile Ser Leu Gln Ser Pro Ser Pro Tyr Arg Ser
    130                 135                 140

Ser Asp Gln Phe Met Thr Asp Asn Ser Ser Leu Phe Tyr Gly Tyr Thr
145                 150                 155                 160

Asn Phe Met Asn Met Asn Asn Asn Ile Asn Ser Leu Leu Thr Pro Thr
                165                 170                 175

Thr Asn Thr Thr Thr Gly Val Gln Asp His Leu Ile Ser Pro Ser Pro
            180                 185                 190

Pro Pro Pro Pro Gly Ala Asp Leu Asn Ser Leu Ile Gly Leu Met Thr
        195                 200                 205

Asn Asn Ile Asp His Asn Glu Asn Ser Phe Tyr Leu Gly Tyr Gln Glu
    210                 215                 220

Asn His Gln Ser Met Tyr Asn Thr Pro Met Glu Tyr His Tyr Leu Thr
225                 230                 235                 240

Ser Asp Val Lys Glu Pro Met Leu Ile Phe Gly Val Val Val Arg Val
                245                 250                 255

Met Lys
```

<210> SEQ ID NO 151
<211> LENGTH: 816
<212> TYPE: DNA
<213> ORGANISM: Lactuca sativa

<400> SEQUENCE: 151

| | | | | | |
|---|---|---|---|---|---|
| atgggaaggg | ctccgtgttg | tgacaaagaa | aatgtaaaga | gaggcccatg | gtctcctgaa | 60 |
| gaagacgcaa | aactcaaaag | cttcatcgac | aaatatggca | ctggtggtaa | ctggattgct | 120 |
| ctccctcaca | agctggtctc | aaaaaggtgt | ggaaagagct | gcagattgcg | atggttaaac | 180 |
| tatctgaggc | ccaatattaa | gcatggtgaa | ttcactgatg | atgaagacaa | gatcatctgc | 240 |
| agcttgtatg | ctagcattgg | tagcagatgg | tcaataatag | cagctcagct | accaggaagg | 300 |
| actgataatg | atataaagaa | ttactggaac | accaaactca | agaagaagct | cttggctatg | 360 |
| cttccttcct | ttcaaaagaa | ggcatctttt | tttccatcta | tatcccttca | atcaccatca | 420 |
| ccatacagat | catcagatca | gttcatgacc | gataattctt | ccctttttcta | cggttacact | 480 |
| aatttcatga | acatgaacaa | caatatcaac | tctctgctga | cacctaccac | caacaccacc | 540 |
| accggtgttc | aagatcatct | gatctcacca | tcaccaccac | caccaccagg | agccgatcta | 600 |
| aactctttaa | tcggtttgat | gaccaacaac | attgacaaca | atgagaattc | tttctattta | 660 |
| gggtatcagg | agaatcatca | gagcatgtac | aacaccccca | tggaatacca | ctaccttaca | 720 |
| tcagatgtga | agaaccgat | gctcattttt | ggaagtggtg | gtgagggtca | tgaagtgagc | 780 |
| accactggtt | cttcctctga | agctgggagt | tctttg | | | 816 |

<210> SEQ ID NO 152
<211> LENGTH: 272
<212> TYPE: PRT
<213> ORGANISM: Lactuca sativa

<400> SEQUENCE: 152

Met Gly Arg Ala Pro Cys Cys Asp Lys Glu Asn Val Lys Arg Gly Pro
1               5                   10                  15

Trp Ser Pro Glu Glu Asp Ala Lys Leu Lys Ser Phe Ile Asp Lys Tyr
            20                  25                  30

Gly Thr Gly Gly Asn Trp Ile Ala Leu Pro His Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Glu Phe Thr Asp Asp Glu Asp Lys Ile Ile Cys
65                  70                  75                  80

Ser Leu Tyr Ala Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Leu Ala Met Leu Pro Ser Phe Gln Lys Lys Ala
        115                 120                 125

Ser Phe Phe Pro Ser Ile Ser Leu Gln Ser Pro Ser Pro Tyr Arg Ser
    130                 135                 140

Ser Asp Gln Phe Met Thr Asp Asn Ser Ser Leu Phe Tyr Gly Tyr Thr
145                 150                 155                 160

Asn Phe Met Asn Met Asn Asn Asn Ile Asn Ser Leu Leu Thr Pro Thr
                165                 170                 175

Thr Asn Thr Thr Thr Gly Val Gln Asp His Leu Ile Ser Pro Ser Pro
            180                 185                 190

```
Pro Pro Pro Gly Ala Asp Leu Asn Ser Leu Ile Gly Leu Met Thr
        195                 200                 205

Asn Asn Ile Asp Asn Asn Glu Asn Ser Phe Tyr Leu Gly Tyr Gln Glu
        210                 215                 220

Asn His Gln Ser Met Tyr Asn Thr Pro Met Glu Tyr His Tyr Leu Thr
225                 230                 235                 240

Ser Asp Val Lys Glu Pro Met Leu Ile Phe Gly Ser Gly Glu Gly
                245                 250                 255

His Glu Val Ser Thr Thr Gly Ser Ser Ser Glu Ala Gly Ser Ser Leu
            260                 265                 270

<210> SEQ ID NO 153
<211> LENGTH: 750
<212> TYPE: DNA
<213> ORGANISM: Lactuca sativa

<400> SEQUENCE: 153
atgggaagag ctccatgttg tgacaagtca aggtgaaga aagggccatg gtcacctcaa      60
gaagatacaa agttgaaaga ctacatacac aaaaatggta ctggaggcaa ctggattgct    120
cttccacata aagcaggcct taaagatgt gggaaaagct gccgattaag atggttgaac     180
taccttagac cagacatcaa acatggtgaa ttctccgacc atgaagatag actcatctat    240
actctctttt ctagcatcgg tagcaggtgg tcagtaatag cagcacagtt accaggaaga    300
acagataatg atatcaagaa ctactggaac acgaagctca agaagaagat tatgaatttc    360
atctccacca atcatcaaac tgagaaacca cttcatcatc ttgagtttgt caattgtcct    420
tcttcaaact atagctaccc gacaagctct tcggttacaa ctgttgataa tcatccagtt    480
ctaccatcag atgatcatgg atacataaat gtggacatgg aaacctaccg agtaaaagac    540
aattctaccc tttttatgct tgaaggtgat gctcaagctg ctgattgcag ttctaattct    600
gatggaaggt ggcatcatgt gtatggtagt ggtgcgtttg atgcgcgtaa taacatggga    660
ggcttgaaga caagtaattc ctacatggga gttgatggga attattgtga aaaggcaaga    720
gggtgttatg gggattctac catggagttt                                    750

<210> SEQ ID NO 154
<211> LENGTH: 250
<212> TYPE: PRT
<213> ORGANISM: Lactuca sativa

<400> SEQUENCE: 154

Met Gly Arg Ala Pro Cys Cys Asp Lys Ser Lys Val Lys Lys Gly Pro
1               5                   10                  15

Trp Ser Pro Gln Glu Asp Thr Lys Leu Lys Asp Tyr Ile His Lys Asn
            20                  25                  30

Gly Thr Gly Gly Asn Trp Ile Ala Leu Pro His Lys Ala Gly Leu Lys
        35                  40                  45

Arg Cys Gly Lys Ser Cys Arg Leu Arg Trp Leu Asn Tyr Leu Arg Pro
    50                  55                  60

Asp Ile Lys His Gly Glu Phe Ser Asp His Glu Asp Arg Leu Ile Tyr
65                  70                  75                  80

Thr Leu Phe Ser Ser Ile Gly Ser Arg Trp Ser Val Ile Ala Ala Gln
                85                  90                  95

Leu Pro Gly Arg Thr Asp Asn Asp Ile Lys Asn Tyr Trp Asn Thr Lys
            100                 105                 110
```

```
Leu Lys Lys Lys Ile Met Asn Phe Ile Ser Thr Asn His Gln Thr Glu
            115                 120                 125

Lys Pro Leu His His Leu Glu Phe Val Asn Cys Pro Ser Ser Asn Tyr
        130                 135                 140

Ser Tyr Pro Thr Ser Ser Ser Val Thr Thr Val Asp Asn His Pro Val
145                 150                 155                 160

Leu Pro Ser Asp Asp His Gly Tyr Ile Asn Val Asp Met Glu Thr Tyr
                165                 170                 175

Arg Val Lys Asp Asn Ser Thr Leu Phe Met Leu Glu Gly Asp Ala Gln
                180                 185                 190

Ala Ala Asp Cys Ser Ser Asn Ser Asp Gly Arg Trp His His Val Tyr
            195                 200                 205

Gly Ser Gly Ala Phe Asp Ala Arg Asn Asn Met Gly Gly Leu Lys Thr
        210                 215                 220

Ser Asn Ser Tyr Met Gly Val Asp Gly Asn Tyr Cys Glu Lys Ala Arg
225                 230                 235                 240

Gly Cys Tyr Gly Asp Ser Thr Met Glu Phe
                245                 250

<210> SEQ ID NO 155
<211> LENGTH: 893
<212> TYPE: DNA
<213> ORGANISM: Lactuca serriola

<400> SEQUENCE: 155
ggaagagctc catgttgtga ccagtcaaag gtgaagaaag gccatggtc acctcaagaa      60 gatacaaagt tgaaagacta catacacaaa atggtactg gaggcaactg gattgctctt    120
ccacataaag caggccttaa agatgtggg aaaagctgcc gattaagatg gttgaactac    180
cttagaccag acatcaaaca tggtgaattc tccgaccatg aagatagact catctatact    240
ctcttttcta gcatcggtag caggtggtca gtaatagcag cacagttacc aggaagaaca    300
gataatgata tcaagaacta ctggaacacg aagctcaaga agaagattat gaatttcatc    360
tccaccaatc atcaaactga gaaccactt catcatcttg agtttgtcaa ttgtccttct    420
tcaaactata gctacccgac aagctcttcg gttacaactg ttgataatca tccagttcta    480
ccatcagatg atcatggata cataaatgtg gacatggaaa cctaccgagt aaaagacaat    540
tctacccttt ttatgcttga aggtgatgct caagctgctg attgcagttc taattctgat    600
ggaaggtggc atcatgtgta tggtagtggt gcgtttgatg cgcgtaataa catgggaggc    660
ttgaagacaa gtaattccta catgggagtt gatgggaatt attgtgaaaa ggcaagaggg    720
tgttatgggg attctactat ggagtttagt cttgaggagt tcaagaagct cattagcact    780
aatctttgca acagtaacac taacaataat ctcaatgtct tgttgatga actcaaggca    840 gaagagaaca ttatgtacta ctaaactatt ttgatttatt ttggtgtaaa aaa           893

<210> SEQ ID NO 156
<211> LENGTH: 702
<212> TYPE: DNA
<213> ORGANISM: Lactuca virosa
<220> FEATURE:
<221> NAME/KEY: misc_feature
<222> LOCATION: (566)..(566)
<223> OTHER INFORMATION: n is any nucleotide

<400> SEQUENCE: 156
atgggaagag caccttgctg tgacaaagcc aacgtcaaaa gaggaccttg gtcacctgaa      60
```

```
gaagatgcca aactcaagtc ttacattgaa aacatggca ccggaggcaa ctggattgct    120
ctacctcaca aaatcggact tagatggtta aattatcttc gcccaaacat aaagcatgga    180
tctttctccg aagaagaaga tcacatcatt tgcaccccat atcttagtat tggaagccgg    240
tggtctatca tcgcagcaca attacctgga agaactgata atgatataaa aaactactgg    300
aacacgaggc taagaaaaa gcttttggga agcagcgta aagatcaaca atcgtcaaag    360
agaggtgcgc aagtcaagca agaaatgaag agagaggtgt ttgaggagtt aaaggcacca    420
tctttatgca tgagcatgaa tctttatcaa tcatactggc cttcagaatt cccttttgatt    480 ctcacaaacc ctgatcaact tcatcaagaa cttcatgtca aaaccaagt tcccaatttc    540 aaccaatacc cttttgacac aacctncaac caagccgaaa tgttccacca gaactgtgaa    600
aaacctatct ctactaccgc ttatcatccc cagttggcaa acacacacta ttatccaaat    660
ggggatggaa taaacctgtt tcaagaatta acattacccg ta                       702
```

<210> SEQ ID NO 157
<211> LENGTH: 234
<212> TYPE: PRT
<213> ORGANISM: Lactuca virosa
<220> FEATURE:
<221> NAME/KEY: MISC_FEATURE
<222> LOCATION: (189)..(189)
<223> OTHER INFORMATION: X is any amino acid

<400> SEQUENCE: 157

```
Met Gly Arg Ala Pro Cys Cys Asp Lys Ala Asn Val Lys Arg Gly Pro
1               5                   10                  15

Trp Ser Pro Glu Glu Asp Ala Lys Leu Lys Ser Tyr Ile Glu Glu His
            20                  25                  30

Gly Thr Gly Gly Asn Trp Ile Ala Leu Pro His Lys Ile Gly Leu Arg
        35                  40                  45

Trp Leu Asn Tyr Leu Arg Pro Asn Ile Lys His Gly Ser Phe Ser Glu
    50                  55                  60

Glu Glu Asp His Ile Ile Cys Thr Pro Tyr Leu Ser Ile Gly Ser Arg
65                  70                  75                  80

Trp Ser Ile Ile Ala Ala Gln Leu Pro Gly Arg Thr Asp Asn Asp Ile
                85                  90                  95

Lys Asn Tyr Trp Asn Thr Arg Leu Lys Lys Lys Leu Leu Gly Lys Gln
            100                 105                 110

Arg Lys Asp Gln Gln Ser Ser Lys Arg Gly Ala Gln Val Lys Gln Glu
        115                 120                 125

Met Lys Arg Glu Val Phe Glu Glu Leu Lys Ala Pro Ser Leu Cys Met
    130                 135                 140

Ser Met Asn Leu Tyr Gln Ser Tyr Trp Pro Ser Glu Phe Pro Leu Ile
145                 150                 155                 160

Leu Thr Asn Pro Asp Gln Leu His Gln Glu Leu His Val Lys Asn Gln
                165                 170                 175

Val Pro Asn Phe Asn Gln Tyr Pro Phe Asp Thr Xaa Asn Gln Ala
            180                 185                 190

Glu Met Phe His Gln Asn Cys Glu Lys Pro Ile Ser Thr Thr Ala Tyr
        195                 200                 205

His Pro Gln Leu Ala Asn Thr His Tyr Tyr Pro Asn Gly Asp Gly Ile
    210                 215                 220

Asn Leu Phe Gln Glu Leu Thr Leu Pro Val
225                 230
```

<210> SEQ ID NO 158
<211> LENGTH: 867
<212> TYPE: DNA
<213> ORGANISM: Lactuca virosa

<400> SEQUENCE: 158

```
atgggaagag ctccatgttg tgacaagtca aaggtgaaga aagggccatg gtcacctcaa      60
gaagatacaa agttgaaaga ctacatacac aaaaatggta ccggaggcaa ctggattgct     120
cttccacata aagcaggtct taaaagatgt gggaaaagct gccgattaag atggttgaac     180
tacctaagac cagacatcaa acatggtgaa ttctccgacc atgaagatag actcatctat     240
actctctttt ctagcatcgg tagcaggtgg tcagtaatag cagcacagtt accaggaaga     300
acagataatg atatcaagaa ctactggaac acgaagctca agaagaagat tatgaatttc     360
atctccacca atcatcaaac tgagaaaccg cttcatcatc ttgagtctgt caattgtcct     420
tcttcaaact atagctaccc aacaagctct tcggttacaa ctgttgataa tcatccagtt     480
ctaccatcag atgatcatgg atacataaat gtggacatgg aaacctaccg agtaaaagac     540
aattctaccc tttttatgct tgaaggtgat gctcaagctg ctgatgattg cagttctaat     600
tctgatggaa ggtggcatca tgtgtatggt agtggtgcgt ttgatgctca taataacatg     660
ggaggcttga agacaagtaa ttcctacatg ggagttgatg ggaattattg tgaaaaagca     720
agagggtgtt atggggattc tactatggag tttagtcttg aggagttcaa gaagctcatt     780
agcactaatc tttgcagcag taacactaac aataaatctc atgtctttgt tgatgaaact     840
caggcagaag agaacattat gtactac                                         867
```

<210> SEQ ID NO 159
<211> LENGTH: 289
<212> TYPE: PRT
<213> ORGANISM: Lactuca virosa

<400> SEQUENCE: 159

```
Met Gly Arg Ala Pro Cys Cys Asp Lys Ser Lys Val Lys Lys Gly Pro
1               5                   10                  15

Trp Ser Pro Gln Glu Asp Thr Lys Leu Lys Asp Tyr Ile His Lys Asn
            20                  25                  30

Gly Thr Gly Gly Asn Trp Ile Ala Leu Pro His Lys Ala Gly Leu Lys
        35                  40                  45

Arg Cys Gly Lys Ser Cys Arg Leu Arg Trp Leu Asn Tyr Leu Arg Pro
    50                  55                  60

Asp Ile Lys His Gly Glu Phe Ser Asp His Glu Asp Arg Leu Ile Tyr
65                  70                  75                  80

Thr Leu Phe Ser Ser Ile Gly Ser Arg Trp Ser Val Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Ile Met Asn Phe Ile Ser Thr Asn His Gln Thr Glu
        115                 120                 125

Lys Pro Leu His His Leu Glu Ser Val Asn Cys Pro Ser Ser Asn Tyr
    130                 135                 140

Ser Tyr Pro Thr Ser Ser Ser Val Thr Thr Val Asp Asn His Pro Val
145                 150                 155                 160

Leu Pro Ser Asp Asp His Gly Tyr Ile Asn Val Asp Met Glu Thr Tyr
                165                 170                 175
```

```
Arg Val Lys Asp Asn Ser Thr Leu Phe Met Leu Glu Gly Asp Ala Gln
            180                 185                 190

Ala Ala Asp Asp Cys Ser Ser Asn Ser Asp Gly Arg Trp His His Val
            195                 200                 205

Tyr Gly Ser Gly Ala Phe Asp Ala His Asn Asn Met Gly Gly Leu Lys
            210                 215                 220

Thr Ser Asn Ser Tyr Met Gly Val Asp Gly Asn Tyr Cys Glu Lys Ala
225                 230                 235                 240

Arg Gly Cys Tyr Gly Asp Ser Thr Met Glu Phe Ser Leu Glu Glu Phe
                245                 250                 255

Lys Lys Leu Ile Ser Thr Asn Leu Cys Ser Ser Asn Thr Asn Asn Lys
            260                 265                 270

Ser His Val Phe Val Asp Glu Thr Gln Ala Glu Glu Asn Ile Met Tyr
            275                 280                 285

Tyr

<210> SEQ ID NO 160
<211> LENGTH: 392
<212> TYPE: DNA
<213> ORGANISM: Liriodendron tulipifera

<400> SEQUENCE: 160
atggggagag ctccttgctg cgacaaggcc aacgtgaaaa gagggccttg gtctcccgaa        60
gaagacacag ccctcaaaaa ctacgtcgag aaacatggaa gtggtgggaa ttggattgct       120
ttaccccaca agcaggcct caaacgttgc ggcaagagtt gccgcctgcg gtggcttaat       180
tatcttagac cagacatcaa acatggaggt tttaccgacg aagaagataa catcatatgc       240
gctctctaca aaacattgg gagcaaatgg tctatcatag cttctcatct gccagggaga       300
acagacaatg atgtgaagaa ctactggaat actaagctga aaagaagct attggcagga       360 aatacaaatc tcacaaggga tgcttctatt ac                                     392

<210> SEQ ID NO 161
<211> LENGTH: 131
<212> TYPE: PRT
<213> ORGANISM: Liriodendron tulipifera

<400> SEQUENCE: 161

Met Gly Arg Ala Pro Cys Cys Asp Lys Ala Asn Val Lys Arg Gly Pro
1               5                   10                  15

Trp Ser Pro Glu Glu Asp Thr Ala Leu Lys Asn Tyr Val Glu Lys His
            20                  25                  30

Gly Ser Gly Gly Asn Trp Ile Ala Leu Pro His Lys Ala Gly Leu Lys
        35                  40                  45

Arg Cys Gly Lys Ser Cys Arg Leu Arg Trp Leu Asn Tyr Leu Arg Pro
    50                  55                  60

Asp Ile Lys His Gly Gly Phe Thr Asp Glu Glu Asp Asn Ile Ile Cys
65                  70                  75                  80

Ala Leu Tyr Lys Asn Ile Gly Ser Lys Trp Ser Ile Ile Ala Ser His
                85                  90                  95

Leu Pro Gly Arg Thr Asp Asn Asp Val Lys Asn Tyr Trp Asn Thr Lys
            100                 105                 110

Leu Lys Lys Lys Leu Leu Ala Gly Asn Thr Asn Leu Thr Arg Asp Ala
            115                 120                 125

Ser Ile Thr
        130
```

<210> SEQ ID NO 162
<211> LENGTH: 563
<212> TYPE: DNA
<213> ORGANISM: Malus domestica

<400> SEQUENCE: 162

```
atggggagag ctccttgctg tgacaaggca atgtaaaga aaggaccatg gtcacctgaa      60
gaagatgcaa agctgaaaga gtacatagaa aaatatggga ctggagggaa ttggattgct     120
cttccacaga agctggtct taggagatgt gggaagagct gcagactaag atggcttaac     180
tatctgaggc ccaacattaa acatggtgaa ttttctgatg aagaagatag aattatctgc     240
aacctctta ctaacattgg aagcaggtgg tcaataatag cagctcagtt gccaggcagg     300
actgacaatg atatcaaaaa ctactggaac accaagcaaa aaagaagct catgggcata      360
agcattctcc catcccagct gctaaaatct cacccatctc ttctccttca aacttcatcc     420
acatcctctt cgccgttatc ataccgagga agcaacacca gcactacatt ttacacacaa     480
accaggtctt tcaccggcac tttggagccc atttcttttt cacaaagtct aatgagcagc     540
agttccatta attctgctcc ttc                                              563
```

<210> SEQ ID NO 163
<211> LENGTH: 188
<212> TYPE: PRT
<213> ORGANISM: Malus domestica

<400> SEQUENCE: 163

```
Met Gly Arg Ala Pro Cys Cys Asp Lys Ala Asn Val Lys Lys Gly Pro
1               5                   10                  15

Trp Ser Pro Glu Glu Asp Ala Lys Leu Lys Glu Tyr Ile Glu Lys Tyr
            20                  25                  30

Gly Thr Gly Gly Asn Trp Ile Ala Leu Pro Gln Lys Ala Gly Leu Arg
        35                  40                  45

Arg Cys Gly Lys Ser Cys Arg Leu Arg Trp Leu Asn Tyr Leu Arg Pro
    50                  55                  60

Asn Ile Lys His Gly Glu Phe Ser Asp Glu Asp Arg Ile Ile Cys
65                  70                  75                  80

Asn Leu Phe Thr Asn Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Gln Lys Lys Lys Leu Met Gly Ile Ser Ile Leu Pro Ser Gln Leu Leu
        115                 120                 125

Lys Ser His Pro Ser Leu Leu Leu Gln Thr Ser Thr Ser Ser Ser
    130                 135                 140

Pro Leu Ser Tyr Arg Gly Ser Asn Thr Ser Thr Phe Tyr Thr Gln
145                 150                 155                 160

Thr Arg Ser Phe Thr Gly Thr Leu Glu Pro Ile Ser Phe Ser Gln Ser
                165                 170                 175

Leu Met Ser Ser Ser Ser Ile Asn Ser Ala Pro Ser
            180                 185
```

<210> SEQ ID NO 164
<211> LENGTH: 1044
<212> TYPE: DNA
<213> ORGANISM: Malus domestica

<400> SEQUENCE: 164

```
atggggaggg ctccttgttg tgacaaagca aacgtgaaga agggaccatg gtcaccagaa      60
gaagattcaa agctaaaaga gtacatagag aagtatggga ctggtgggaa ttggattgct     120
ctcccacaga aagctggtct gaagagatgt gggaaaagct gcagattgag atggcttaac     180
tatctgaggc caaacatcaa acatggagaa ttctctgatg aggaagacag gataatatgc     240
agcctctttg ctagtattgg aagcaggtgg tcagttatag ctgctcagct gccaggcagg     300
actgacaacg atatcaagaa ctactggaac accaagctca agaagaagct catggggatg     360
catatgggtc ctcctcgacc tcacaaccac cataaaaatt tactaaagcc tcccccattt     420
ccttcttcct ctcatcacaa ttaccaaaac caaccattaa ttccatctga acctctatcg     480
tcgctgtaca aagacctaag caattacaac agatctttct tagggtttga agcgccagtg     540
ccattgccac acaagttttc gctgacgtcc aataatttct caaacatttc caccaactct     600
tctattttc aaaccctaaa ttacccagct ggagtgaagg aaaataacaa taataatacc       660
ctcctcgtgt ttggaagtga agggagttgc agtacttcgt ctgatggaag ctgtaataat     720
cagatcagct atgactactg cagcagatca gagattaata acatcaacca agaagaaatg     780
ggttttgatc atcagggctt catgatgctt aactatggca accaatggac cgaaaggcca     840
aatgggtttt attttggatc agaaaacaac acattagaat ttactgatct ggacgaagat     900
gttaagcagc agctgattag tactagaagt aaaaataatt ataataataa tactattata     960
aatgagtcct ctaagtctaa cagctttta ttcaatgtta atgaaagcaa gacagaagat    1020
gatgagaagg tcatgtattt ctac                                          1044
```

<210> SEQ ID NO 165
<211> LENGTH: 348
<212> TYPE: PRT
<213> ORGANISM: Malus domestica

<400> SEQUENCE: 165

```
Met Gly Arg Ala Pro Cys Cys Asp Lys Ala Asn Val Lys Lys Gly Pro
1               5                   10                  15

Trp Ser Pro Glu Glu Asp Ser Lys Leu Lys Glu Tyr Ile Glu Lys Tyr
                20                  25                  30

Gly Thr Gly Gly Asn Trp Ile Ala Leu Pro Gln Lys Ala Gly Leu Lys
            35                  40                  45

Arg Cys Gly Lys Ser Cys Arg Leu Arg Trp Leu Asn Tyr Leu Arg Pro
        50                  55                  60

Asn Ile Lys His Gly Glu Phe Ser Asp Glu Glu Asp Arg Ile Ile Cys
65                  70                  75                  80

Ser Leu Phe Ala Ser Ile Gly Ser Arg Trp Ser Val Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Met Gly Met His Met Gly Pro Pro Arg Pro His
        115                 120                 125

Asn His His Lys Asn Leu Leu Lys Pro Pro Phe Pro Ser Ser Ser
    130                 135                 140

His His Asn Tyr Gln Asn Gln Pro Leu Ile Pro Ser Glu Pro Leu Ser
145                 150                 155                 160

Ser Leu Tyr Lys Asp Leu Ser Asn Tyr Asn Arg Ser Phe Leu Gly Phe
                165                 170                 175
```

```
Glu Ala Pro Val Pro Leu Pro Pro Gln Val Ser Leu Thr Ser Asn Asn
                180                 185                 190

Phe Ser Asn Ile Ser Thr Asn Ser Ser Ile Phe Gln Thr Leu Asn Tyr
            195                 200                 205

Pro Ala Gly Val Lys Glu Asn Asn Asn Asn Thr Leu Leu Val Phe
        210                 215                 220

Gly Ser Glu Gly Ser Cys Ser Thr Ser Ser Asp Gly Ser Cys Asn Asn
225                 230                 235                 240

Gln Ile Ser Tyr Asp Tyr Cys Ser Arg Ser Glu Ile Asn Asn Ile Asn
                245                 250                 255

Gln Glu Glu Met Gly Phe Asp His Gln Gly Phe Met Met Leu Asn Tyr
                260                 265                 270

Gly Asn Gln Trp Thr Glu Arg Pro Asn Gly Phe Tyr Phe Gly Ser Glu
            275                 280                 285

Asn Asn Thr Leu Glu Phe Thr Asp Leu Asp Glu Asp Val Lys Gln Gln
        290                 295                 300

Leu Ile Ser Thr Arg Ser Lys Asn Asn Tyr Asn Asn Thr Ile Ile
305                 310                 315                 320

Asn Glu Ser Ser Lys Ser Asn Ser Phe Leu Phe Asn Val Asn Glu Ser
                325                 330                 335

Lys Thr Glu Asp Asp Glu Lys Val Met Tyr Phe Tyr
            340                 345

<210> SEQ ID NO 166
<211> LENGTH: 596
<212> TYPE: DNA
<213> ORGANISM: Manihot esculenta

<400> SEQUENCE: 166
atgggaaggg ctccttgctg tgataaagct aatgtgaaga aaggcccatg gtcaccagaa      60
gaagatgcaa agcttaaaga ctatatagag aaacaaggga ctgtaggaaa ttggattgct     120
ctccctcaaa aggctggtct caaaagatgt gggaaaagct gcagattaag atggctaaat     180
tatctgagac ccaacatcaa gcatggagat ttttctgatg atgaagataa aataatctgt     240
aaactctatt ccaacattgg gagcaggtgg tcaataatag cagctcagtt gccaggcagg     300
actgataatg atatcaaaaa ctattggaac acaaaactca gaagaagct tatggggatg      360 atgatgattc atccttctca aacaaaatta ccccaccaat taactacaaa gtttgcttct     420
cttctttgtc aggcttcatc atcatcatca tcaataccat catcaccatc tactgcaata     480
tcttcaccat catcttcata tgccctagct aggtctttca ctgaacctat tccattttca     540
agtaacaatt ccttcactgc tgctaataaa tccatcctcc catcccaaga aagctc        596

<210> SEQ ID NO 167
<211> LENGTH: 199
<212> TYPE: PRT
<213> ORGANISM: Manihot esculenta

<400> SEQUENCE: 167

Met Gly Arg Ala Pro Cys Cys Asp Lys Ala Asn Val Lys Lys Gly Pro
1               5                   10                  15

Trp Ser Pro Glu Glu Asp Ala Lys Leu Lys Asp Tyr Ile Glu Lys Gln
                20                  25                  30

Gly Thr Val Gly Asn Trp Ile Ala Leu Pro Gln Lys Ala Gly Leu Lys
            35                  40                  45

Arg Cys Gly Lys Ser Cys Arg Leu Arg Trp Leu Asn Tyr Leu Arg Pro
```

|    |    |    |    | 50 |    |    |    |    | 55 |    |    |    |    | 60 |    |

Asn Ile Lys His Gly Asp Phe Ser Asp Glu Asp Lys Ile Ile Cys
65                  70                  75                  80

Lys Leu Tyr Ser Asn Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Met Gly Met Met Met Ile His Pro Ser Gln Thr
        115                 120                 125

Lys Leu Pro His Gln Leu Thr Thr Lys Phe Ala Ser Leu Leu Cys Gln
    130                 135                 140

Ala Ser Ser Ser Ser Ser Ser Ile Pro Ser Ser Pro Ser Thr Ala Ile
145                 150                 155                 160

Ser Ser Pro Ser Ser Ser Tyr Ala Leu Ala Arg Ser Phe Thr Glu Pro
                165                 170                 175

Ile Pro Phe Ser Ser Asn Asn Ser Phe Thr Ala Ala Asn Lys Ser Ile
            180                 185                 190

Leu Pro Ser Gln Glu Ser Ser
        195

<210> SEQ ID NO 168
<211> LENGTH: 543
<212> TYPE: DNA
<213> ORGANISM: Marchantia polymorpha
<220> FEATURE:
<221> NAME/KEY: misc_feature
<222> LOCATION: (421)..(421)
<223> OTHER INFORMATION: n is any nucleotide
<220> FEATURE:
<221> NAME/KEY: misc_feature
<222> LOCATION: (436)..(436)
<223> OTHER INFORMATION: n is any nucleotide
<220> FEATURE:
<221> NAME/KEY: misc_feature
<222> LOCATION: (478)..(478)
<223> OTHER INFORMATION: n is any nucleotide
<220> FEATURE:
<221> NAME/KEY: misc_feature
<222> LOCATION: (493)..(493)
<223> OTHER INFORMATION: n is any nucleotide
<220> FEATURE:
<221> NAME/KEY: misc_feature
<222> LOCATION: (505)..(505)
<223> OTHER INFORMATION: n is any nucleotide
<220> FEATURE:
<221> NAME/KEY: misc_feature
<222> LOCATION: (509)..(509)
<223> OTHER INFORMATION: n is any nucleotide
<220> FEATURE:
<221> NAME/KEY: misc_feature
<222> LOCATION: (514)..(514)
<223> OTHER INFORMATION: n is any nucleotide
<220> FEATURE:
<221> NAME/KEY: misc_feature
<222> LOCATION: (522)..(522)
<223> OTHER INFORMATION: n is any nucleotide
<220> FEATURE:
<221> NAME/KEY: misc_feature
<222> LOCATION: (523)..(523)
<223> OTHER INFORMATION: n is any nucleotide
<220> FEATURE:
<221> NAME/KEY: misc_feature
<222> LOCATION: (529)..(529)
<223> OTHER INFORMATION: n is any nucleotide
<220> FEATURE:
<221> NAME/KEY: misc_feature
<222> LOCATION: (529)..(529)
<223> OTHER INFORMATION: n is any nucleotide
<220> FEATURE:

```
<221> NAME/KEY: misc_feature
<222> LOCATION: (541)..(541)
<223> OTHER INFORMATION: n is any nucleotide

<400> SEQUENCE: 168
atgggtcgag ctccatgttg tgacaaggcc aatgtgaaaa agggtccttg gtcgcccgaa      60
gaggatgcca agctcaagtc tttcatcgaa cacaatggca caggtggcaa ttggatcacg     120
ctgccgagca aagcaggtct gaagcgctgc ggaaagagct gcagactccg ctggatcaat     180
tatttgcgtc ccgacatcaa acatggaagc ttcactgaag aagaagaaaa gacaatttat     240
cgcctccacg ctcaaattgg cagcagatgg tccttgatcg ctgctcagct gcctgggaga     300
accgataacg atatcaagaa ttactggaac actcggctga agaagaagct cctggagaga     360
gctataatat ggtgggtgcg gacgtccgca ccactctttc cagatttatc ccatgaatca     420
nccggccaac gatcanatgt caaatgccgt ggggagagaa ggccttctga attctcantt     480
tctgcatgct cangcttatt atcantacnt tcancaacaa cnnccgcant attatcttcc     540 nca                                                                 543

<210> SEQ ID NO 169
<211> LENGTH: 181
<212> TYPE: PRT
<213> ORGANISM: Marchantia polymorpha
<220> FEATURE:
<221> NAME/KEY: MISC_FEATURE
<222> LOCATION: (141)..(141)
<223> OTHER INFORMATION: X is any amino acid
<220> FEATURE:
<221> NAME/KEY: MISC_FEATURE
<222> LOCATION: (146)..(146)
<223> OTHER INFORMATION: X is any amino acid
<220> FEATURE:
<221> NAME/KEY: MISC_FEATURE
<222> LOCATION: (160)..(160)
<223> OTHER INFORMATION: X is any amino acid
<220> FEATURE:
<221> NAME/KEY: MISC_FEATURE
<222> LOCATION: (165)..(165)
<223> OTHER INFORMATION: X is any amino acid
<220> FEATURE:
<221> NAME/KEY: MISC_FEATURE
<222> LOCATION: (169)..(169)
<223> OTHER INFORMATION: X is any amino acid
<220> FEATURE:
<221> NAME/KEY: MISC_FEATURE
<222> LOCATION: (170)..(170)
<223> OTHER INFORMATION: X is any amino acid
<220> FEATURE:
<221> NAME/KEY: MISC_FEATURE
<222> LOCATION: (172)..(172)
<223> OTHER INFORMATION: X is any amino acid
<220> FEATURE:
<221> NAME/KEY: MISC_FEATURE
<222> LOCATION: (175)..(175)
<223> OTHER INFORMATION: X is any amino acid
<220> FEATURE:
<221> NAME/KEY: MISC_FEATURE
<222> LOCATION: (177)..(177)
<223> OTHER INFORMATION: X is any amino acid
<220> FEATURE:
<221> NAME/KEY: MISC_FEATURE
<222> LOCATION: (181)..(181)
<223> OTHER INFORMATION: X is any amino acid

<400> SEQUENCE: 169

Met Gly Arg Ala Pro Cys Cys Asp Lys Ala Asn Val Lys Lys Gly Pro
1               5                   10                  15

Trp Ser Pro Glu Glu Asp Ala Lys Leu Lys Ser Phe Ile Glu His Asn
            20                  25                  30
```

```
Gly Thr Gly Gly Asn Trp Ile Thr Leu Pro Ser Lys Ala Gly Leu Lys
            35                  40                  45

Arg Cys Gly Lys Ser Cys Arg Leu Arg Trp Ile Asn Tyr Leu Arg Pro
 50                  55                  60

Asp Ile Lys His Gly Ser Phe Thr Glu Glu Glu Lys Thr Ile Tyr
 65                  70                  75                  80

Arg Leu His Ala Gln Ile Gly Ser Arg Trp Ser Leu Ile Ala Ala Gln
                85                  90                  95

Leu Pro Gly Arg Thr Asp Asn Asp Ile Lys Asn Tyr Trp Asn Thr Arg
                100                 105                 110

Leu Lys Lys Lys Leu Leu Glu Arg Ala Ile Ile Trp Trp Val Arg Thr
                115                 120                 125

Ser Ala Pro Leu Phe Pro Asp Leu Ser His Glu Ser Xaa Gly Gln Arg
                130                 135                 140

Ser Xaa Val Lys Cys Arg Gly Glu Arg Arg Pro Ser Glu Phe Ser Xaa
145                 150                 155                 160

Ser Ala Cys Ser Xaa Leu Leu Ser Xaa Xaa Ser Xaa Thr Thr Xaa Ala
                165                 170                 175

Xaa Leu Ser Ser Xaa
            180

<210> SEQ ID NO 170
<211> LENGTH: 1050
<212> TYPE: DNA
<213> ORGANISM: Medicago truncatula

<400> SEQUENCE: 170
atgggtagag ctccatgctg tgacaaggct aacgtgaaga aaggaccttg gtctcctgaa      60
gaagatgcta cactcaaatc ttacattgaa acaaatggaa ctggaggaaa ttggattgct     120
cttcctcaaa aaattgggct caagagatgt ggaaagagtt gcagactag gtggttaaat      180 tacttgagac ctaatatcaa acatggtgga tttactgaag aagaagacaa catcatttgc     240
agcctttaca taagcattgg aagcaggtgg tccattattg ctgctcagtt acctggaaga     300
acagacaatg acataaaaaa ctattggaac acaagattga agaagaaatt actcggaaag     360
cgaaaacagt cgaatataaa caactgcttg atgaaccaaa aggacacaaa tggaatagat     420
gagaattctt attcaaattc attaagtagc tcagctcttg agacttca acttcatatg       480 caacttcaaa gccttcaaaa cccttgtct ttttacaata taaccctgc tgcactagtt        540 tggccaaagt tgcatccttc tcaagaaaaa atgatccaaa ttagccttca aaactctaat     600
aacaacccta tgatgcaaaa tgctttctct tcaccacagg ttgatctttt ggagaatatt     660
attcctttgg agaataataa taacaattca gttaccttca atgcttctgg aaatagtagt     720
aataataata attcaatcat gcattcaagt gttgcaccaa gaggagaagc tgttgagaag     780
agtactaaca atgaaggaat tcaggaactg gaaagtgaac tagatgaaat ctctcaacaac    840 agaaatataa ttactatgga agatgaatat cgtgtggctg aatttgattg tttcagagat     900
atgaataata atggttcaaa ggatcaaaac ttgatatggt ggtcaaatga ttcaggtgat     960
actaaatcag atcctcaaa ctcatgggat tcaacaacta atcttatgca agaagggatg     1020
ttccaagatt atgaactagg ttatggtctg                                     1050

<210> SEQ ID NO 171
<211> LENGTH: 350
<212> TYPE: PRT
```

<213> ORGANISM: Medicago truncatula

<400> SEQUENCE: 171

```
Met Gly Arg Ala Pro Cys Cys Asp Lys Ala Asn Val Lys Lys Gly Pro
1               5                   10                  15

Trp Ser Pro Glu Glu Asp Ala Thr Leu Lys Ser Tyr Ile Glu Thr Asn
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Gly Phe Thr Glu Glu Asp Asn Ile Ile Cys
65                  70                  75                  80

Ser Leu Tyr Ile Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Gly Lys Arg Lys Gln Ser Asn Ile Asn Asn
        115                 120                 125

Cys Leu Met Asn Gln Lys Asp Thr Asn Gly Ile Asp Glu Asn Ser Tyr
130                 135                 140

Ser Asn Ser Leu Ser Ser Ala Leu Glu Arg Leu Gln Leu His Met
145                 150                 155                 160

Gln Leu Gln Ser Leu Gln Asn Pro Leu Ser Phe Tyr Asn Asn Pro
                165                 170                 175

Ala Ala Leu Val Trp Pro Lys Leu His Pro Ser Gln Glu Lys Met Ile
            180                 185                 190

Gln Ile Ser Leu Gln Asn Ser Asn Asn Pro Met Met Gln Asn Ala
        195                 200                 205

Phe Ser Ser Pro Gln Val Asp Leu Leu Glu Asn Ile Ile Pro Leu Glu
210                 215                 220

Asn Asn Asn Asn Asn Ser Val Thr Phe Asn Ala Ser Gly Asn Ser Ser
225                 230                 235                 240

Asn Asn Asn Asn Ser Ile Met His Ser Ser Val Ala Pro Arg Gly Glu
                245                 250                 255

Ala Val Glu Lys Ser Thr Asn Asn Glu Gly Ile Gln Glu Leu Glu Ser
            260                 265                 270

Glu Leu Asp Glu Ile Leu Asn Asn Arg Asn Ile Ile Thr Met Glu Asp
        275                 280                 285

Glu Tyr Arg Val Ala Glu Phe Asp Cys Phe Arg Asp Met Asn Asn Asn
    290                 295                 300

Gly Ser Lys Asp Gln Asn Leu Ile Trp Trp Ser Asn Asp Ser Gly Asp
305                 310                 315                 320

Thr Lys Ser Gly Ser Ser Asn Ser Trp Asp Ser Thr Thr Asn Leu Met
                325                 330                 335

Gln Glu Gly Met Phe Gln Asp Tyr Glu Leu Gly Tyr Gly Leu
            340                 345                 350
```

<210> SEQ ID NO 172
<211> LENGTH: 576
<212> TYPE: DNA
<213> ORGANISM: Medicago truncatula

<400> SEQUENCE: 172
atgggtagag ctccttgttg tgacaaagca aacgtgaaga aaggtccatg gtctccagaa      60

```
gaagattcta aactcaaatc ttacatagaa caacatggta ctggtggtaa ctggattgct      120
ctcccacaaa aaattggctt gaagcgttgt ggaaagagct gtcgtctccg gtggctaaac      180
tatcttcgcc ctaatctcaa acatggtggt ttctccgaag aagaagataa cattatttgc      240
agcctttaca ttagtattgg aagcaggtgg tcgataattg cagctcaatt gccaggaaga      300
actgataatg acataaagaa ctattggaat acaaggttga aaagaagct tttggggaaa       360 caccgtaaag atcaacaaca acaagcacgt aatagaggaa ataatggtgc tattgttaag      420
caagaaagca ataataatag agtgatgagt agtaatgaat tttccttatc aaatttggtt      480
caagaacaac catatttacc acatgtcatg caacctttgc tatcaacacc ccaacctcca      540
ccaccatcaa tgttgtcata cacaaaccaa caaggc                                576
```

```
<210> SEQ ID NO 173
<211> LENGTH: 192
<212> TYPE: PRT
<213> ORGANISM: Medicago truncatula

<400> SEQUENCE: 173
```

```
Met Gly Arg Ala Pro Cys Cys Asp Lys Ala Asn Val Lys Lys Gly Pro
1               5                   10                  15

Trp Ser Pro Glu Glu Asp Ser Lys Leu Lys Ser Tyr Ile Glu Gln His
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Leu Lys His Gly Gly Phe Ser Glu Glu Asp Asn Ile Ile Cys
65                  70                  75                  80

Ser Leu Tyr Ile Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Gly Lys His Arg Lys Asp Gln Gln Gln Gln
        115                 120                 125

Ala Arg Asn Arg Gly Asn Asn Gly Ala Ile Val Lys Gln Glu Ser Asn
    130                 135                 140

Asn Asn Arg Val Met Ser Ser Asn Glu Phe Ser Leu Ser Asn Leu Val
145                 150                 155                 160

Gln Glu Gln Pro Tyr Leu Pro His Val Met Gln Pro Leu Leu Ser Thr
                165                 170                 175

Pro Gln Pro Pro Pro Ser Met Leu Ser Tyr Thr Asn Gln Gln Gly
            180                 185                 190
```

```
<210> SEQ ID NO 174
<211> LENGTH: 596
<212> TYPE: DNA
<213> ORGANISM: Nuphar advena

<400> SEQUENCE: 174
```

```
atgggaaggt ctccgtgctg tgacaaggcc aacgttaaga gagggccatg gtcgcctgag      60
gaggacgcca ccctcaagaa ctacgttgag aggtttggca ccggaggcaa ttggattgca     120
ttgcctcaga aagcagggct caagcgttgt ggaaagagct gccgtttgcg ttggcttaac     180
taccttagac ctgatattag gcacggtggt tttactgagg aagaggatac catcattttc     240
```

```
tctctctatg agagcatggg cagcaggtgg tctgtcatag catcacagtt accaggaaga    300
accgacaatg atgtgaagaa ttactggaac accaagttga agaagaaaat gcttgcagca    360
aaagccaatc ttgacagtga tgcccatatt cacatgaatt cagtttcaat ctcatcatca    420
tcttcacctt caccttcacc ttcctcttca tcaccatcca cttccactcc tacccattta    480
accattgcat caaaaagtgt gggccctgcc tattacttct ccaaactcag ctgcaccaaa    540
tcccaagatg aaggcatggt gatgcctcca atggaagttg ctttcagta cactct         596
```

<210> SEQ ID NO 175
<211> LENGTH: 199
<212> TYPE: PRT
<213> ORGANISM: Nuphar advena

<400> SEQUENCE: 175

```
Met Gly Arg Ser Pro Cys Cys Asp Lys Ala Asn Val Lys Arg Gly Pro
1               5                   10                  15

Trp Ser Pro Glu Glu Asp Ala Thr Leu Lys Asn Tyr Val Glu Arg Phe
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asp Ile Arg His Gly Gly Phe Thr Glu Glu Asp Thr Ile Ile Phe
65                  70                  75                  80

Ser Leu Tyr Glu Ser Met Gly Ser Arg Trp Ser Val Ile Ala Ser Gln
                85                  90                  95

Leu Pro Gly Arg Thr Asp Asn Asp Val Lys Asn Tyr Trp Asn Thr Lys
            100                 105                 110

Leu Lys Lys Lys Met Leu Ala Ala Lys Ala Asn Leu Asp Ser Asp Ala
        115                 120                 125

His Ile His Met Asn Ser Val Ser Ile Ser Ser Ser Ser Pro Ser
    130                 135                 140

Pro Ser Pro Ser Ser Ser Ser Pro Ser Thr Ser Thr Pro Thr His Leu
145                 150                 155                 160

Thr Ile Ala Ser Lys Ser Val Gly Pro Ala Tyr Tyr Phe Ser Lys Leu
                165                 170                 175

Ser Cys Thr Lys Ser Gln Asp Glu Gly Met Val Met Pro Pro Met Glu
            180                 185                 190

Val Gly Phe Gln Tyr Thr Leu
        195
```

<210> SEQ ID NO 176
<211> LENGTH: 795
<212> TYPE: DNA
<213> ORGANISM: Oryza sativa

<400> SEQUENCE: 176

```
atggggagga cgccgtgctg cgacagggag gcggtgaaga ggggcccgtg gtcgccggag    60
gaggacgacg cgctgcgcga ctacatcaac cgccacggca ccgccggcaa ctggatctcc    120
ctccccaaca aggccgggtt gaggaggtgc ggcaagagct gcaggctgcg gtggctcaac    180
tacctccgcc ccgacatccg ccatggcgcc ttcaccgacg aggaggacgc catcatcacc    240
tccctctact ccaagctcgg cagcaagtgg tcgaccatcg cggcgcagct ggagaggagg    300
acggacaacg acgtcaagaa ccactggaac accaagctca agcgccgcct cgccgccgcc    360
```

```
gccgcctgca cgcccttact gccgctcccg gcgccgccgc ccctcgccgc cacgcacacg      420
tcgccgtcgt cgtcgctgct gctcctcccg ccgctcgccg taccgaccgt caagaccgag      480
gcgtacacct gcgacgactt cctgcagcag ctgctgccga ccgccaccgc cgccacggcg      540
ctccgggatc ccttcgccga cggcgccgcc acggacggcg gctcgacgtc cgcctccgcc      600
gcgtcgtcgg ggtccaactg gtcggcggac accggcgtcg tcgtcgtcgg tggcggcggc      660
ggcggcgggc tgttcccgga attctgcatg agctccgacg acctcgccgg cgccgccacg      720
gcggaggacg accacttcat cggcggcggc tactactacc ctctcgatcc gagcttgtca      780
tcatcactag tgtag                                                      795
```

<210> SEQ ID NO 177
<211> LENGTH: 264
<212> TYPE: PRT
<213> ORGANISM: Oryza sativa

<400> SEQUENCE: 177

```
Met Gly Arg Thr Pro Cys Cys Asp Arg Glu Ala Val Lys Arg Gly Pro
1               5                   10                  15

Trp Ser Pro Glu Glu Asp Asp Ala Leu Arg Asp Tyr Ile Asn Arg His
            20                  25                  30

Gly Thr Ala Gly Asn Trp Ile Ser Leu Pro Asn Lys Ala Gly Leu Arg
        35                  40                  45

Arg Cys Gly Lys Ser Cys Arg Leu Arg Trp Leu Asn Tyr Leu Arg Pro
    50                  55                  60

Asp Ile Arg His Gly Ala Phe Thr Asp Glu Glu Asp Ala Ile Ile Thr
65                  70                  75                  80

Ser Leu Tyr Ser Lys Leu Gly Ser Lys Trp Ser Thr Ile Ala Ala Gln
                85                  90                  95

Leu Glu Arg Arg Thr Asp Asn Asp Val Lys Asn His Trp Asn Thr Lys
            100                 105                 110

Leu Lys Arg Arg Leu Ala Ala Ala Ala Cys Thr Pro Leu Leu Pro
        115                 120                 125

Leu Pro Ala Pro Pro Leu Ala Ala Thr His Thr Ser Pro Ser Ser
    130                 135                 140

Ser Leu Leu Leu Pro Pro Leu Ala Val Pro Thr Val Lys Thr Glu
145                 150                 155                 160

Ala Tyr Thr Cys Asp Asp Phe Leu Gln Gln Leu Leu Pro Thr Ala Thr
                165                 170                 175

Ala Ala Thr Ala Leu Arg Asp Pro Phe Ala Asp Gly Ala Ala Thr Asp
            180                 185                 190

Gly Gly Ser Thr Ser Ala Ser Ala Ala Ser Gly Ser Asn Trp Ser
        195                 200                 205

Ala Asp Thr Gly Val Val Val Gly Gly Gly Gly Gly Leu
    210                 215                 220

Phe Pro Glu Phe Cys Met Ser Asp Asp Leu Ala Gly Ala Ala Thr
225                 230                 235                 240

Ala Glu Asp Asp His Phe Ile Gly Gly Gly Tyr Tyr Tyr Pro Leu Asp
                245                 250                 255

Pro Ser Leu Ser Ser Ser Leu Val
            260
```

<210> SEQ ID NO 178
<211> LENGTH: 957
<212> TYPE: DNA

<213> ORGANISM: Oryza sativa

<400> SEQUENCE: 178

```
atggggaggg cgccgtgctg cgacaaggcg agcgtgaaga gggggccgtg gtcgccggag    60
gaggacgagc tgctgcggag ctacgtccgc agccacggca ccggtggcaa ctggatcgcg   120
ctcccgcaga aagcagggct gaaccggtgc gggaagagct gtaggctgcg gtggctcaac   180
tacctccgcc cggacatcaa gcacggcggc tacaccgacc aggaggaccg gatcatctgt   240
tccctctaca actccatcgg aagcaggtgg tccatcatcg cgtcgaagct gcccggccgg   300
acggacaacg acgtcaagaa ttactggaat accaagctca agaagaaggc catggccatg   360
catcatcatc atcagccgcc gccgccgcag cagcaacact accaccacca ccaccaccac   420
cgtgtcgccg gcggtggcgc gcgcgtcacg ctcgtgtcgc ctccgcccgc cccgcagagc   480
caatgcgcgt ccatgcagcc gtcgccggcg tccgcctcct cgtccggcgg cgacgcgtgc   540
agcttcggcg ccgccgccat gtactccccc tcccgtcaa cccagcaggc gccacaggcg   600
gcgacgctcg cggtcgcggg gtacacctcc gtggcgacgg cggcggcggc ggcggcggtg   660
gcggcgcagc gctcgccgct cgacgagctg atctgccagg tgccaccacc tcccactact   720
accgccgcca ctgctgggc cagcggcgtg accctcgacg acgtgttctt gcccgagctc   780
gtcggagccg gcgagttccc caacggcgac ctcttcggcg ggttcggccc gctgctccag   840
gacaggtcgt ccatggagct ctccgcgtgc tacttcccca cgccgcggc ggcggagatg   900
tggccggcgg ccacggacat cgtcaagccg gccgggctgt gccacagcct gacatga     957
```

<210> SEQ ID NO 179
<211> LENGTH: 318
<212> TYPE: PRT
<213> ORGANISM: Oryza sativa

<400> SEQUENCE: 179

```
Met Gly Arg Ala Pro Cys Cys Asp Lys Ala Ser Val Lys Arg Gly Pro
1               5                   10                  15

Trp Ser Pro Glu Glu Asp Glu Leu Leu Arg Ser Tyr Val Arg Ser His
            20                  25                  30

Gly Thr Gly Gly Asn Trp Ile Ala Leu Pro Gln Lys Ala Gly Leu Asn
        35                  40                  45

Arg Cys Gly Lys Ser Cys Arg Leu Arg Trp Leu Asn Tyr Leu Arg Pro
    50                  55                  60

Asp Ile Lys His Gly Gly Tyr Thr Asp Gln Glu Asp Arg Ile Ile Cys
65                  70                  75                  80

Ser Leu Tyr Asn Ser Ile Gly Ser Arg Trp Ser Ile Ile Ala Ser Lys
                85                  90                  95

Leu Pro Gly Arg Thr Asp Asn Asp Val Lys Asn Tyr Trp Asn Thr Lys
            100                 105                 110

Leu Lys Lys Lys Ala Met Ala Met His His His His Gln Pro Pro
        115                 120                 125

Pro Gln Gln Gln His Tyr His His His His His Arg Val Ala Gly
    130                 135                 140

Gly Gly Ala Arg Val Thr Leu Val Ser Pro Pro Ala Pro Gln Ser
145                 150                 155                 160

Gln Cys Ala Ser Met Gln Pro Ser Pro Ala Ser Ala Ser Ser Ser Gly
                165                 170                 175

Gly Asp Ala Cys Ser Phe Gly Ala Ala Ala Met Tyr Ser Pro Ser Pro
            180                 185                 190
```

Ser Thr Gln Gln Ala Pro Gln Ala Ala Thr Leu Ala Val Ala Gly Tyr
        195                 200                 205

Thr Ser Val Ala Thr Ala Ala Ala Ala Val Ala Ala Ala Ala Gln Arg
        210                 215                 220

Ser Pro Leu Asp Glu Leu Ile Cys Gln Val Pro Pro Pro Thr Thr
225                 230                 235                 240

Thr Ala Ala Asp Cys Trp Ala Ser Gly Val Thr Leu Asp Asp Val Phe
                245                 250                 255

Leu Pro Glu Leu Val Gly Ala Gly Glu Phe Pro Asn Gly Asp Leu Phe
                260                 265                 270

Gly Gly Phe Gly Pro Leu Leu Gln Asp Arg Ser Ser Met Glu Leu Ser
                275                 280                 285

Ala Cys Tyr Phe Pro Asn Ala Ala Ala Glu Met Trp Pro Ala Ala
        290                 295                 300

Thr Asp Ile Val Lys Pro Ala Gly Leu Cys His Ser Leu Thr
305                 310                 315

<210> SEQ ID NO 180
<211> LENGTH: 897
<212> TYPE: DNA
<213> ORGANISM: Oryza sativa

<400> SEQUENCE: 180
atggggaggt cgccgtgctg cgacaaggcg agcgtgaagc gggggccgtg gtcggaggag      60
gaggacgcca tactcaggag cttcgtcgag aggttcggca atgccggcaa ctggatcgcg     120
ctgccccaca agcagggct taaacggtgc ggcaagagct gccgcctccg gtggctcaac     180
tacctccgcc ggcgatccg gcacggcggc ttcaccgacg aggaggacaa cctcatcctg     240
tcgctctacg gcgaaatggg aagcaagtgg tcggtgatcg cgtccaagct ccccggccgg     300
acggacaacg acgtcaagaa ctactggaac accaagctca agaagaggta cttggccgcg     360
gccgcaacag aagcaaccac tcctcctcct cctgccgccg cgacgatga caacaaccca     420 acgacacaag cctccagcca acccgctcct cctactcctc cggcgcccct cgtcaacctc     480
gacgcggccg cctcgacgg cgccgtgggc gacaacgacg agctcctgct gcacaagtcg     540
gagcagctgt acgccgagct gatgggcctc atcgagcagc agcagtactc cacgatcacc     600
gccgccgccg tcgacgcggc gacgacgacg acgtcgtggt cgtcgccgtc gacgggaacg     660
acaagtccga ccgctagcag cagtactgac ggcagcagca gcagcagcaa cctgccgtgg     720
ccggccgtgg acgtgcacga cagtacgatg atgccgccgt tgtcggagtc cagcggcagc     780
agcagcggct tgttcttcgg ctctcacgcg ttcggtagtg gctcgttcca agacctgctc     840
ggctctgcag cttccttcga cgatgtcatg ctgtcgcaag atgctgta ctactag     897

<210> SEQ ID NO 181
<211> LENGTH: 298
<212> TYPE: PRT
<213> ORGANISM: Oryza sativa

<400> SEQUENCE: 181

Met Gly Arg Ser Pro Cys Cys Asp Lys Ala Ser Val Lys Arg Gly Pro
1               5                   10                  15

Trp Ser Glu Glu Glu Asp Ala Ile Leu Arg Ser Phe Val Glu Arg Phe
                20                  25                  30

Gly Asn Ala Gly Asn Trp Ile Ala Leu Pro His Lys Ala Gly Leu Lys
        35                  40                  45

Arg Cys Gly Lys Ser Cys Arg Leu Arg Trp Leu Asn Tyr Leu Arg Pro
 50                  55                  60

Ala Ile Arg His Gly Gly Phe Thr Asp Glu Asp Asn Leu Ile Leu
 65              70                  75                  80

Ser Leu Tyr Gly Glu Met Gly Ser Lys Trp Ser Val Ile Ala Ser Lys
                 85                  90                  95

Leu Pro Gly Arg Thr Asp Asn Asp Val Lys Asn Tyr Trp Asn Thr Lys
                100                 105                 110

Leu Lys Lys Arg Tyr Leu Ala Ala Ala Thr Glu Ala Thr Thr Pro
            115                 120                 125

Pro Pro Pro Ala Ala Gly Asp Asp Asn Asn Pro Thr Thr Gln Ala
            130                 135                 140

Ser Ser Gln Pro Ala Pro Pro Thr Pro Pro Ala Pro Leu Val Asn Leu
145                 150                 155                 160

Asp Ala Ala Gly Leu Asp Gly Ala Val Gly Asp Asn Asp Glu Leu Leu
                165                 170                 175

Leu His Lys Ser Glu Gln Leu Tyr Ala Glu Leu Met Gly Leu Ile Glu
            180                 185                 190

Gln Gln Gln Tyr Ser Thr Ile Thr Ala Ala Ala Val Asp Ala Ala Thr
            195                 200                 205

Thr Thr Thr Ser Trp Ser Ser Pro Ser Thr Gly Thr Thr Ser Pro Thr
210                 215                 220

Ala Ser Ser Ser Thr Asp Gly Ser Ser Ser Ser Asn Leu Pro Trp
225                 230                 235                 240

Pro Ala Val Asp Val His Asp Ser Thr Met Met Pro Pro Leu Ser Glu
                245                 250                 255

Ser Ser Gly Ser Ser Ser Gly Leu Phe Phe Gly Ser His Ala Phe Gly
            260                 265                 270

Ser Gly Ser Phe Gln Asp Leu Leu Gly Ser Ala Ala Ser Phe Asp Asp
            275                 280                 285

Val Met Leu Ser Gln Glu Met Leu Tyr Tyr
290                 295

<210> SEQ ID NO 182
<211> LENGTH: 1692
<212> TYPE: DNA
<213> ORGANISM: Oryza sativa

<400> SEQUENCE: 182

```
atggcggcgg cggcggctcg cgatgacgac ctcggcaacg acgacctcga cgatgaccgg    60
tcaaatccac gccgccagtc tggaggtcgc acggccggcc caatccggca ggggttgcat   120
ggtgacatag gcctccaaat gacggcagcc atggctggtg acgacgcaaa tgacggcggc   180
catggctggc ggcggtggct gtcaacggcg gcggtcgcgg cggtgctcct cagcttaggg   240
gatggtggtg acgatgacaa ggcaaccgag gggatacggg ggagctcagc agggatgtat   300
actgataaaa gatcagtttc agaggacaca cacctctatc catctactaa acctactata   360
aagccagccc ggccacaacc ccagatgcac ccgctcaccg ctgctgccaa acacgccatc   420
accataccac caccaccacc accagccgca gcagctagct acacatcgtc gccgtcgtca   480
ggcactagcg atccatcggt tctagatctc tcttctgctg agatagacga cgacggcgac   540
ggcgacgacg atcgagctga gcagcaagaa atcaagaatt cgaaggagtt agtgatgggg   600
agggcgccgt gctgcgacaa ggcgagcgtg aagaagggc cgtggtcgcc ggaggaggac   660
```

-continued

```
gccaagctca aggcctacat cgaggagaac ggcaccggcg gcaactggat cgcgctgccg      720
cagaagatcg ggctgaagag atgtggcaag agttgcaggc tcagatggct caactacctg      780
cggccaaaca ttaagcatgg tgatttcaca gaagaagagg agcacatcat ttgtagcctc      840
tacattagca tcggtagcag gtggtcgatc atcgcggcgc agctgccggg gagaacggac      900
aacgacatca agaactactg gaacaccaag ctgaagaaga agctcctcgg caagcgcgcg      960
ccgtcgcgcc gcgcccgcgc aaaccaagac cactgcggtc tagcaggcag cgccgccgcc     1020
gccatgtgcg gtggcgtcgg caccgcggcg gcggcggcgc cgccgcatca agccctaagc     1080
tcgtcggccc tcgagcggat ccagctccac atgcgcctcc aaggcctcta caacagcgcg     1140
ttcggctgca ccaccaccag cagcaacggc ggcggcgtcg gcgtcgcgcc gccgcagtgg     1200
ccgaagctcg aggcgctgct gccgagcaga ccgctcccgg ccgtgcagcc gacggacgcc     1260
gtcgtcgcca ccgtgcaaca cccccatcat ttggtcgtcg gcggccatac cctcgccacc     1320
gccgccgccg ccgccgccac cacgtcggag gcgttccaag ccgccgagca cctcgaccct     1380
gcggcggcga ccggttcgaa ctacatgccg ggagtcgccg gtgtagagat gacctcgtcg     1440
tcgtcaatgg cgggtggtgg tgggttcgtc gccggctacg gtctccacga cgagctatac     1500
gacttcctct tcaagtgcga gtcgatcggc ggagcgcaag gcgggatcat cccttcgtcg     1560
ttgccggagc tgcagtgccc ggacggcagc gccatcatcg gcgccgacga gaagttctcg     1620
acgtggacgt cgtcgtcttg cgactacggt tcgggcggcg ccggcgatta cgttctaggg     1680
tatgatcaat aa                                                          1692
```

<210> SEQ ID NO 183
<211> LENGTH: 563
<212> TYPE: PRT
<213> ORGANISM: Oryza sativa

<400> SEQUENCE: 183

```
Met Ala Ala Ala Ala Arg Asp Asp Leu Gly Asn Asp Asp Leu
  1               5                  10                  15

Asp Asp Asp Arg Ser Asn Pro Arg Arg Gln Ser Gly Gly Arg Thr Ala
                 20                  25                  30

Gly Pro Ile Arg Gln Gly Leu His Gly Asp Ile Gly Leu Gln Met Thr
             35                  40                  45

Ala Ala Met Ala Gly Asp Ala Asn Asp Gly Gly His Gly Trp Arg
         50                  55                  60

Arg Trp Leu Ser Thr Ala Ala Val Ala Ala Val Leu Leu Ser Leu Gly
 65                  70                  75                  80

Asp Gly Gly Asp Asp Asp Lys Ala Thr Glu Gly Ile Arg Gly Ser Ser
                 85                  90                  95

Ala Gly Met Tyr Thr Asp Lys Arg Ser Val Ser Glu Asp Thr His Leu
            100                 105                 110

Tyr Pro Ser Thr Lys Pro Thr Ile Lys Pro Ala Arg Pro Gln Pro Gln
            115                 120                 125

Met His Pro Leu Thr Ala Ala Lys His Ala Ile Thr Ile Pro Pro
        130                 135                 140

Pro Pro Pro Pro Ala Ala Ala Ser Tyr Thr Ser Ser Pro Ser Ser
145                 150                 155                 160

Gly Thr Ser Asp Pro Ser Val Leu Asp Leu Ser Ser Ala Glu Ile Asp
                165                 170                 175

Asp Asp Gly Asp Gly Asp Asp Arg Ala Glu Gln Gln Glu Ile Lys
            180                 185                 190
```

```
Asn Ser Lys Glu Leu Val Met Gly Arg Ala Pro Cys Cys Asp Lys Ala
        195                 200                 205
Ser Val Lys Lys Gly Pro Trp Ser Pro Glu Glu Asp Ala Lys Leu Lys
210                 215                 220
Ala Tyr Ile Glu Glu Asn Gly Thr Gly Gly Asn Trp Ile Ala Leu Pro
225                 230                 235                 240
Gln Lys Ile Gly Leu Lys Arg Cys Gly Lys Ser Cys Arg Leu Arg Trp
            245                 250                 255
Leu Asn Tyr Leu Arg Pro Asn Ile Lys His Gly Asp Phe Thr Glu Glu
            260                 265                 270
Glu Glu His Ile Ile Cys Ser Leu Tyr Ile Ser Ile Gly Ser Arg Trp
        275                 280                 285
Ser Ile Ile Ala Ala Gln Leu Pro Gly Arg Thr Asp Asn Asp Ile Lys
290                 295                 300
Asn Tyr Trp Asn Thr Lys Leu Lys Lys Leu Leu Gly Lys Arg Ala
305                 310                 315                 320
Pro Ser Arg Arg Ala Arg Ala Asn Gln Asp His Cys Gly Leu Ala Gly
            325                 330                 335
Ser Ala Ala Ala Ala Met Cys Gly Gly Val Gly Thr Ala Ala Ala Ala
        340                 345                 350
Ala Pro Pro His Gln Ala Leu Ser Ser Ala Leu Glu Arg Ile Gln
        355                 360                 365
Leu His Met Arg Leu Gln Gly Leu Tyr Asn Ser Ala Phe Gly Cys Thr
        370                 375                 380
Thr Thr Ser Ser Asn Gly Gly Gly Val Gly Val Ala Pro Pro Gln Trp
385                 390                 395                 400
Pro Lys Leu Glu Ala Leu Leu Pro Ser Arg Pro Leu Pro Ala Val Gln
            405                 410                 415
Pro Thr Asp Ala Val Val Ala Thr Val Gln His Pro His His Leu Val
            420                 425                 430
Val Gly Gly His Thr Leu Ala Thr Ala Ala Ala Ala Ala Thr Thr
        435                 440                 445
Ser Glu Ala Phe Gln Ala Ala Glu His Leu Asp Pro Ala Ala Ala Thr
        450                 455                 460
Gly Ser Asn Tyr Met Pro Gly Val Ala Gly Val Glu Met Thr Ser Ser
465                 470                 475                 480
Ser Ser Met Ala Gly Gly Gly Phe Val Ala Gly Tyr Gly Leu His
            485                 490                 495
Asp Glu Leu Tyr Asp Phe Leu Phe Lys Cys Glu Ser Ile Gly Gly Ala
            500                 505                 510
Gln Gly Gly Ile Ile Pro Ser Ser Leu Pro Glu Leu Gln Cys Pro Asp
            515                 520                 525
Gly Ser Ala Ile Ile Gly Ala Asp Glu Lys Phe Ser Thr Trp Thr Ser
            530                 535                 540
Ser Ser Cys Asp Tyr Gly Ser Gly Gly Ala Gly Asp Tyr Val Leu Gly
545                 550                 555                 560
Tyr Asp Gln

<210> SEQ ID NO 184
<211> LENGTH: 870
<212> TYPE: DNA
<213> ORGANISM: Oryza sativa

<400> SEQUENCE: 184
```

```
atgggcgcg cgccgtgctg cgacaaggcg agcgtgaagc gggggccgtg gtcgccggag    60
gaggacgagc agctgcggag ctacgtccag agccacggca tcggcggcaa ctggatcgcg   120
ctcccgcaga aagcagggct caaccgctgc ggcaagagct gcaggctccg gtggctcaac   180
tacctgaggc cggacatcaa gcacggcggc tacaccgagc aggaggacca catcatctgc   240
tcgctctaca actcgattgg aagcaggtgg tccatcatcg cgtcgaagct ccccggccgg   300
actgacaacg acgtcaagaa ctactggaac accaagctca agaagaaagc catgggcgcc   360
gtgcagccgc gcgccgccgc ctcggcgccg agccaatgca cgtcgtcagc gatggcgccg   420
gcgctctcgc cggcctcctc gtccgtcacc agctcgagcg gcgacgcctg cttcgccgcc   480
gccgccacca ccaccaccac catgtacccg ccaccgacga cgccgccgca gcagcagttc   540
atccgcttcg acgcaccacc cgcggcggcg gcggcggcat ccccgaccga cctcgcgccc   600
gtgccaccac cggccaccgt cacggcggac ggcgacggcg gctgggcgtc cgacgccttg   660
tccctcgacg acgtgttcct cggcgagctc acggccggcg agccgctgtt cccttacgcc   720
gagctgttca gcggcttcgc cggcgcggcg ccggacagca aggccacctt ggagctctcg   780
gcgtgctact ccccgaacat ggcggagatg tgggcggcct ccgaccacgc ctacgccaag   840
ccacagggtc tctgcaacac cctgacatag                                    870
```

<210> SEQ ID NO 185
<211> LENGTH: 289
<212> TYPE: PRT
<213> ORGANISM: Oryza sativa

<400> SEQUENCE: 185

```
Met Gly Arg Ala Pro Cys Cys Asp Lys Ala Ser Val Lys Arg Gly Pro
1               5                   10                  15

Trp Ser Pro Glu Glu Asp Glu Gln Leu Arg Ser Tyr Val Gln Ser His
            20                  25                  30

Gly Ile Gly Gly Asn Trp Ile Ala Leu Pro Gln Lys Ala Gly Leu Asn
        35                  40                  45

Arg Cys Gly Lys Ser Cys Arg Leu Arg Trp Leu Asn Tyr Leu Arg Pro
    50                  55                  60

Asp Ile Lys His Gly Gly Tyr Thr Glu Gln Glu Asp His Ile Ile Cys
65                  70                  75                  80

Ser Leu Tyr Asn Ser Ile Gly Ser Arg Trp Ser Ile Ile Ala Ser Lys
                85                  90                  95

Leu Pro Gly Arg Thr Asp Asn Asp Val Lys Asn Tyr Trp Asn Thr Lys
            100                 105                 110

Leu Lys Lys Lys Ala Met Gly Ala Val Gln Pro Arg Ala Ala Ala Ser
        115                 120                 125

Ala Pro Ser Gln Cys Thr Ser Ser Ala Met Ala Pro Ala Leu Ser Pro
    130                 135                 140

Ala Ser Ser Ser Val Thr Ser Ser Gly Asp Ala Cys Phe Ala Ala
145                 150                 155                 160

Ala Ala Thr Thr Thr Thr Thr Met Tyr Pro Pro Pro Thr Pro Pro
                165                 170                 175

Gln Gln Gln Phe Ile Arg Phe Asp Ala Pro Pro Ala Ala Ala Ala
            180                 185                 190

Ala Ser Pro Thr Asp Leu Ala Pro Val Pro Pro Ala Thr Val Thr
        195                 200                 205

Ala Asp Gly Asp Gly Gly Trp Ala Ser Asp Ala Leu Ser Leu Asp Asp
```

Val Phe Leu Gly Glu Leu Thr Ala Gly Glu Pro Leu Phe Pro Tyr Ala
225                 230                 235                 240

Glu Leu Phe Ser Gly Phe Ala Gly Ala Ala Pro Asp Ser Lys Ala Thr
            245                 250                 255

Leu Glu Leu Ser Ala Cys Tyr Phe Pro Asn Met Ala Glu Met Trp Ala
            260                 265                 270

Ala Ser Asp His Ala Tyr Ala Lys Pro Gln Gly Leu Cys Asn Thr Leu
            275                 280                 285

Thr

<210> SEQ ID NO 186
<211> LENGTH: 951
<212> TYPE: DNA
<213> ORGANISM: Oryza sativa

<400> SEQUENCE: 186

```
atggggaggg caccttgctg tgacaaggca acagtgaaga aggggccatg gtcacctgag    60
gaggatgcaa tgctcaagaa ctacattgag gagcatggca ccggtggcaa ctggattgca   120
ctgcctcaca gattgggct gaagaggtgt ggcaagagct gcaggctaag gtggctgaat   180
tacctgaggc aaacataaa gcatgggac ttcaccccag aggaggacag catcatctgc   240
agcctctaca ttagcatagg gagcaggtgg tcaatcatag cagcacagct gccagggagg   300
acggacaacg atgtcaagaa ctactggaac acaaagctga agaagagact ccttggccgg   360
cgcaaggacc gcggcggcgg ccaccaccac cgcagccaga gcaccgccga cgatcttccg   420
gccggtggtg acggcggcat gaacgacggc ggcggcggcg gcggagagcg gtcgctgagc   480
gcgtcggcga tggagaggat ccagctctgc atgcagctgc aggagctgca gaacccactg   540
tccatccacc acaaccccctt gctctctcat cagtggccaa gcaaggccac cattgatgat   600
cagaatcaca caatgtcac tgtggctgaa catggaatgt caagctctgt gagcgaccac   660
caccgcctcg atgggcagca gctggagagc ggcgccggcg ccgccgccat gcagcaggcg   720
tcgccgtcga gcgcggcga gaactccaac gtcgtcgtcg ccatcgaggc cgagctccag   780
gagcttctct acgccggcgg cggcgcgatc gtcgacggcg gcgcgccgcc gcaggggat   840
gtggactggt ggagctatga tcagggaaag cagtcacctg tgacttgctg ggatttcacc   900
cctgaaacca gctccatctt ccaggattat gcaacagttt atgacatctg a           951
```

<210> SEQ ID NO 187
<211> LENGTH: 316
<212> TYPE: PRT
<213> ORGANISM: Oryza sativa

<400> SEQUENCE: 187

Met Gly Arg Ala Pro Cys Cys Asp Lys Ala Thr Val Lys Lys Gly Pro
1               5                   10                  15

Trp Ser Pro Glu Glu Asp Ala Met Leu Lys Asn Tyr Ile Glu Glu His
            20                  25                  30

Gly Thr Gly Gly Asn Trp Ile Ala Leu Pro His Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Thr Pro Glu Glu Asp Ser Ile Ile Cys
65                  70                  75                  80

```
Ser Leu Tyr Ile Ser Ile Gly Ser Arg Trp Ser Ile Ile Ala Ala Gln
                 85                  90                  95

Leu Pro Gly Arg Thr Asp Asn Asp Val Lys Asn Tyr Trp Asn Thr Lys
            100                 105                 110

Leu Lys Lys Arg Leu Leu Gly Arg Arg Lys Asp Arg Gly Gly Gly His
        115                 120                 125

His His Arg Ser Gln Ser Thr Ala Asp Asp Leu Pro Ala Gly Gly Asp
    130                 135                 140

Gly Gly Met Asn Asp Gly Gly Gly Gly Glu Arg Ser Leu Ser
145                 150                 155                 160

Ala Ser Ala Met Glu Arg Ile Gln Leu Cys Met Gln Leu Gln Glu Leu
                165                 170                 175

Gln Asn Pro Leu Ser Ile His His Asn Pro Leu Leu Ser His Gln Trp
            180                 185                 190

Pro Ser Lys Ala Thr Ile Asp Asp Gln Asn His Asn Asn Val Thr Val
        195                 200                 205

Ala Glu His Gly Met Ser Ser Val Ser Asp His His Arg Leu Asp
    210                 215                 220

Gly Gln Gln Leu Glu Ser Gly Ala Gly Ala Ala Met Gln Gln Ala
225                 230                 235                 240

Ser Pro Ser Ser Gly Gly Glu Asn Ser Asn Val Val Ala Ile Glu
                245                 250                 255

Ala Glu Leu Gln Glu Leu Leu Tyr Ala Gly Gly Ala Ile Val Asp
            260                 265                 270

Gly Gly Ala Pro Pro Gln Gly Asp Val Asp Trp Trp Ser Tyr Asp Gln
        275                 280                 285

Gly Lys Gln Ser Pro Val Thr Cys Trp Asp Phe Thr Pro Glu Thr Ser
    290                 295                 300

Ser Ile Phe Gln Asp Tyr Ala Thr Val Tyr Asp Ile
305                 310                 315

<210> SEQ ID NO 188
<211> LENGTH: 1134
<212> TYPE: DNA
<213> ORGANISM: Oryza sativa

<400> SEQUENCE: 188
atgggcaggg cgccgtgctg cgacaaggcg acggtgaaga agggcccgtg ggcgccggag    60
gaggacgccg cgctcaaggc ctacgtcgac gcccatggca ccggcggcaa ctggatcgcc   120
ctcccccaca agatcgggct gaacaggtgc ggcaagagct gccggctgcg gtggctcaac   180
tacctccggc cgaacatccg gcacggcggc ttcaccgagg acgaggaccg cctcatctgc   240
agcctctaca tcgccatcgg gagcaggtgg gcgaccatcg cggcgcagct gccggggagg   300
acggacaacg acatcaagaa ctactggaac agcaagctca gcgccgcct gctcggcggc   360 ggccgccggc cgcggggcgc gccaccgcg ctcgtgctcg ccggcccggg ccccgctgta   420
accgccgccg ccacgtcgcg caacgccatg gccgcgtcgg cgatcgagcg gatgcagctc   480
agcgtgcggc tgcgccgcct ggaggccgcg gcgccgccgc cgccgcagcc cttcaccttc   540
tacggcagca acaacctcgc cgcgccgccg tggcagcagc ctatctcccc ggccgcgggc   600
ggcagctcgg agatgccacg gcggctgcat caccaccacc cctccggcgc cgccgctacc   660
tcgagctact ccggcctgat cagcagctgg ccgtcgtctc gctcccacat catccacgac   720
gcctggctcg acgcctcctc cacccgccg ctgtcgacga cgagcatggg cgacgccgcc   780
```

-continued

```
acgacgacga cgacggccgg cggggagagc tcgagctcga cgccgacggt gagcacggcc    840
accacgccgt tcatcggcgg cagcatcgac atggacgacg agatcgacat gctgctccag    900
cagatcaggt gcttcgatga aacggcgac gacggcgacg acgacgccga ccagcggctg    960
atcgtcggcg acgaggccgc agccggagca gagaactacc tcagggcatt gatagacgag   1020
gcggcagcga acgtggcga tgtcggcgtt ggctcctgga gctcttgctc tactccagga   1080
gtggactccg tgttccatga gtatgctcag ctagactacg acagtataa ttaa          1134
```

<210> SEQ ID NO 189
<211> LENGTH: 377
<212> TYPE: PRT
<213> ORGANISM: Oryza sativa

<400> SEQUENCE: 189

```
Met Gly Arg Ala Pro Cys Cys Asp Lys Ala Thr Val Lys Lys Gly Pro
1               5                   10                  15

Trp Ala Pro Glu Glu Asp Ala Ala Leu Lys Ala Tyr Val Asp Ala His
            20                  25                  30

Gly Thr Gly Gly Asn Trp Ile Ala Leu Pro His Lys Ile Gly Leu Asn
        35                  40                  45

Arg Cys Gly Lys Ser Cys Arg Leu Arg Trp Leu Asn Tyr Leu Arg Pro
    50                  55                  60

Asn Ile Arg His Gly Gly Phe Thr Glu Asp Glu Asp Arg Leu Ile Cys
65                  70                  75                  80

Ser Leu Tyr Ile Ala Ile Gly Ser Arg Trp Ala Thr Ile Ala Ala Gln
                85                  90                  95

Leu Pro Gly Arg Thr Asp Asn Asp Ile Lys Asn Tyr Trp Asn Ser Lys
            100                 105                 110

Leu Lys Arg Arg Leu Leu Gly Gly Gly Arg Arg Pro Gly Ala Pro
            115                 120                 125

Pro Arg Leu Val Leu Ala Gly Pro Gly Pro Ala Val Thr Ala Ala Ala
        130                 135                 140

Thr Ser Arg Asn Ala Met Ala Ala Ser Ala Ile Glu Arg Met Gln Leu
145                 150                 155                 160

Ser Val Arg Leu Arg Arg Leu Glu Ala Ala Ala Pro Pro Pro Pro Gln
                165                 170                 175

Pro Phe Thr Phe Tyr Gly Ser Asn Asn Leu Ala Ala Pro Pro Trp Gln
            180                 185                 190

Gln Pro Ile Ser Pro Ala Ala Gly Gly Ser Ser Glu Met Pro Arg Arg
        195                 200                 205

Leu His His His Pro Ser Gly Ala Ala Ala Thr Ser Ser Tyr Ser
    210                 215                 220

Gly Leu Ile Ser Ser Trp Pro Ser Ser Arg Ser His Ile Ile His Asp
225                 230                 235                 240

Ala Trp Leu Asp Ala Ser Ser Thr Pro Pro Leu Ser Thr Thr Ser Met
                245                 250                 255

Gly Asp Ala Ala Thr Thr Thr Thr Ala Gly Gly Glu Ser Ser Ser
            260                 265                 270

Ser Thr Pro Thr Val Ser Thr Ala Thr Thr Pro Phe Ile Gly Gly Ser
        275                 280                 285

Ile Asp Met Asp Asp Glu Ile Asp Met Leu Leu Gln Gln Ile Arg Cys
    290                 295                 300

Phe Asp Glu Asn Gly Asp Asp Gly Asp Asp Ala Asp Gln Arg Leu
305                 310                 315                 320
```

Ile Val Gly Asp Glu Ala Ala Gly Ala Glu Asn Tyr Leu Arg Ala
                325                 330                 335

Leu Ile Asp Glu Ala Ala Ala Asn Gly Gly Asp Val Gly Val Gly Ser
            340                 345                 350

Trp Ser Ser Cys Ser Thr Pro Gly Val Asp Ser Val Phe His Glu Tyr
        355                 360                 365

Ala Gln Leu Asp Tyr Gly Gln Tyr Asn
    370                 375

<210> SEQ ID NO 190
<211> LENGTH: 885
<212> TYPE: DNA
<213> ORGANISM: Oryza sativa

<400> SEQUENCE: 190

| | |
|---|---|
| atgaagaagg gaaatggtc caaggaagag gacgatttga tcaaaaacca catggagaag | 60 |
| tatggcattg ccgtagctg caggcactg tctgatgctt tagggctgca gaggtgtggc | 120 |
| cggagctgcc gttcccggtg gctgaactac cttcggccgg ggctgaagca cggcgacttc | 180 |
| tcgccggcgg aggagaggat catctgcaag atgtacagca agaagggaag cagctggtcg | 240 |
| gccatcgccg cgcagctgcc ggggaggacg gacctcgccg tcaagaacta ctggaacagc | 300 |
| acgctcaaga agaggttccc ggcggcggcg cggcgaggag gcaccgccgc cgcgcgccgc | 360 |
| aggcaccgcc ccgccgccag cgccaccaca tcgtccgacg acgacgacga cgtcgacgtc | 420 |
| gacgacgcga ccccgcccgg cctcgcgctg gtcgtctaca gcgaggggag caccgccgcc | 480 |
| gcggcggcgg ccggcgagct cgctccgtac tccatctcat ccccggccgc cactgccgac | 540 |
| gcggcggaag aagaagagcc gatcgcggcc gttccgatca gcacctgcat cctggcactg | 600 |
| ccgccgccac caccaccgcc accgccgccg ccgagcgatg ccaccggcgg cgaggtgagc | 660 |
| atcccctgct tccccttctc gccgctgcca ttcatcgagc cggacttgcc ggagctgacc | 720 |
| tggacgaccg acctcgacga cattaccgcc accttcgatg ccgccgcctg ccgctacccg | 780 |
| aagcggccgc atccaatcac accggattcg cctcgccttc gaagcttcc cgccattgcc | 840 |
| ggcttcgacg acgtgcagag cttccttgtct tggttcgatg actga | 885 |

<210> SEQ ID NO 191
<211> LENGTH: 294
<212> TYPE: PRT
<213> ORGANISM: Oryza sativa

<400> SEQUENCE: 191

Met Lys Lys Gly Lys Trp Ser Lys Glu Glu Asp Asp Leu Ile Lys Asn
1               5                   10                  15

His Met Glu Lys Tyr Gly Ile Gly Arg Ser Trp Gln Ala Leu Ser Asp
            20                  25                  30

Ala Leu Gly Leu Gln Arg Cys Gly Arg Ser Cys Arg Ser Arg Trp Leu
        35                  40                  45

Asn Tyr Leu Arg Pro Gly Leu Lys His Gly Asp Phe Ser Pro Ala Glu
    50                  55                  60

Glu Arg Ile Ile Cys Lys Met Tyr Ser Lys Lys Gly Ser Ser Trp Ser
65                  70                  75                  80

Ala Ile Ala Ala Gln Leu Pro Gly Arg Thr Asp Leu Ala Val Lys Asn
                85                  90                  95

Tyr Trp Asn Ser Thr Leu Lys Lys Arg Phe Pro Ala Ala Ala Ala Ala
            100                 105                 110

Arg Ser Thr Ala Ala Ala Arg Arg Arg His Arg Pro Ala Ser Ala
            115                 120                 125

Thr Thr Ser Ser Asp Asp Asp Asp Val Asp Val Asp Asp Ala Thr
    130                 135                 140

Pro Pro Gly Leu Ala Leu Val Val Tyr Ser Glu Gly Ser Thr Ala Ala
145                 150                 155                 160

Ala Ala Ala Ala Gly Glu Leu Ala Pro Tyr Ser Ile Ser Ser Pro Ala
                165                 170                 175

Ala Thr Ala Asp Ala Ala Glu Glu Glu Pro Ile Ala Ala Val Pro
            180                 185                 190

Ile Ser Thr Cys Ile Leu Ala Leu Pro Pro Pro Pro Pro Pro Pro
            195                 200                 205

Pro Pro Pro Ser Asp Ala Thr Gly Gly Glu Val Ser Ile Pro Cys Phe
    210                 215                 220

Pro Phe Ser Pro Leu Pro Phe Ile Glu Pro Asp Leu Pro Glu Leu Thr
225                 230                 235                 240

Trp Thr Thr Asp Leu Asp Asp Ile Thr Ala Thr Phe Asp Ala Ala Ala
                245                 250                 255

Cys Arg Tyr Pro Lys Arg Pro His Pro Ile Thr Pro Asp Ser Pro Arg
            260                 265                 270

Leu Pro Lys Leu Pro Ala Ile Ala Gly Phe Asp Asp Val Gln Ser Phe
            275                 280                 285

Leu Ser Trp Phe Asp Asp
    290

<210> SEQ ID NO 192
<211> LENGTH: 807
<212> TYPE: DNA
<213> ORGANISM: Picea

<400> SEQUENCE: 192

```
atgggaagag cgccctgttg tgacaaggca aatgtcaaaa agggaccatg gtcgccagaa      60
gaagacgcaa aactcaaggc ctttatcgag caacatggca ctggtggcaa ttggattgct     120
cttccacaga aagctggtct gaaaaggtgt ggaaaaagct gcaggcttag atggttgaac     180
tatttgaggc cagatataag gcatggtggt ttctcagagg atgaagatag catcatttgt     240
ggcctctatg caagcattgg aagcaggtgg tccataattg cagcccagtt accgggaaga     300
acggacaatg acatcaaaaa ctactggaat acaagactga agaaaaaact gcctgggaag     360
cgtaaagagc agcaaacacg taggtttaaa gaagcaaaga gcatgggtaa tggggcaggg     420
ccttatgttt cagaaggtat gtctgctgca tcatccacca taaatgcaat tagatctctg     480
atgtcaaaca cagaggcact ttatctgtcc gatcgaatgc tcatatggaa tatggatcca     540
tcgttaggcc tacttaatcc tcagttcttg cagcatactg tatcaaatat tgctaattat     600
tgctcaagct cggagcatgt tagctttgga actggtcctc cccaggattg gatcaggagc     660
ttacatttga caatgcaagt cttagaaagc tgctcttcag gactgaatgc gccttcactg     720
cagacaataa caataatacc tctcaagcat ctcccgcaat cattagttct cagatatatt     780
ccccatctac tattttggat cccgggc                                         807
```

<210> SEQ ID NO 193
<211> LENGTH: 269
<212> TYPE: PRT
<213> ORGANISM: Picea

<400> SEQUENCE: 193

| | | | | | | | | | | | | | | |
|---|---|---|---|---|---|---|---|---|---|---|---|---|---|---|
|Met|Gly|Arg|Ala|Pro|Cys|Cys|Asp|Lys|Ala|Asn|Val|Lys|Lys|Gly|Pro
1| | | |5| | | | |10| | | | |15| 
Trp|Ser|Pro|Glu|Glu|Asp|Ala|Lys|Leu|Lys|Ala|Phe|Ile|Glu|Gln|His
| | | |20| | | | |25| | | | |30| |
Gly|Thr|Gly|Gly|Asn|Trp|Ile|Ala|Leu|Pro|Gln|Lys|Ala|Gly|Leu|Lys
| | |35| | | | |40| | | | |45| | |
Arg|Cys|Gly|Lys|Ser|Cys|Arg|Leu|Arg|Trp|Leu|Asn|Tyr|Leu|Arg|Pro
|50| | | | |55| | | | |60| | | | |
Asp|Ile|Arg|His|Gly|Gly|Phe|Ser|Glu|Asp|Glu|Asp|Ser|Ile|Ile|Cys
65| | | | |70| | | | |75| | | | |80
Gly|Leu|Tyr|Ala|Ser|Ile|Gly|Ser|Arg|Trp|Ser|Ile|Ile|Ala|Ala|Gln
| | | |85| | | | |90| | | | |95| |
Leu|Pro|Gly|Arg|Thr|Asp|Asn|Asp|Ile|Lys|Asn|Tyr|Trp|Asn|Thr|Arg
| | |100| | | | |105| | | | |110| | |
Leu|Lys|Lys|Lys|Leu|Pro|Gly|Lys|Arg|Lys|Glu|Gln|Gln|Thr|Arg|Arg
| |115| | | | |120| | | | |125| | | |
Phe|Lys|Glu|Ala|Lys|Ser|Met|Gly|Asn|Gly|Ala|Gly|Pro|Tyr|Val|Ser
|130| | | | |135| | | | |140| | | | |
Glu|Gly|Met|Ser|Ala|Ala|Ser|Ser|Thr|Ile|Asn|Ala|Ile|Arg|Ser|Leu
145| | | | |150| | | | |155| | | | |160
Met|Ser|Asn|Thr|Glu|Ala|Leu|Tyr|Leu|Ser|Asp|Arg|Met|Pro|His|Met
| | | |165| | | | |170| | | | |175| |
Asp|Met|Asp|Pro|Ser|Leu|Gly|Leu|Leu|Asn|Pro|Gln|Phe|Leu|Gln|His
| | |180| | | | |185| | | | |190| | |
Thr|Val|Ser|Asn|Ile|Ala|Asn|Tyr|Cys|Ser|Ser|Ser|Glu|His|Val|Ser
| |195| | | | |200| | | | |205| | | |
Phe|Gly|Thr|Gly|Pro|Pro|Gln|Asp|Trp|Ile|Arg|Ser|Leu|His|Leu|Thr
|210| | | | |215| | | | |220| | | | |
Met|Gln|Val|Leu|Glu|Ser|Cys|Ser|Ser|Gly|Leu|Asn|Ala|Pro|Ser|Leu
225| | | | |230| | | | |235| | | | |240
Gln|Thr|Ile|Thr|Ile|Ile|Pro|Leu|Lys|His|Leu|Pro|Gln|Ser|Leu|Val
| | | |245| | | | |250| | | | |255| |
Leu|Arg|Tyr|Ile|Pro|His|Leu|Leu|Phe|Trp|Ile|Pro|Gly| | | |
| | |260| | | | |265| | | | | | | |

<210> SEQ ID NO 194
<211> LENGTH: 495
<212> TYPE: DNA
<213> ORGANISM: Picea

<400> SEQUENCE: 194

```
atgggccgag caccctgctg cgacaaagca aatgtcaaga gagggccgtg gtctcctgaa      60
gaggacacca tactcaaaaa tttcgtagag aagcatggca ccggaggcaa ctggatcgct     120
ttgcctcgca aagcaggttt gaaaaggtgc ggcaagagct gtagactgag gtggttgaat     180
tatttgaggc ctgatatcaa gcacggtgac ttctcagaag aagaagacag catcatttgc     240
agcctctata ccagcattgg aagcagatgg tctatcattg cagcccagtt gcccgggaga     300
acagacaacg acataaagaa ctactggaac acgcggctga gaaaaaaatt gcttggcaaa     360
tgcaccaagg acaacgataa tcagcaaatc cggcgcttac tggcaaaaga agcagccaaa     420
ggtgcgggaa ttaggagacc ttacaacggt gatcatattt cttcagaaac ggccgccatg     480
tctgcgtcaa acact                                                      495
```

<210> SEQ ID NO 195
<211> LENGTH: 165
<212> TYPE: PRT
<213> ORGANISM: Picea

<400> SEQUENCE: 195

```
Met Gly Arg Ala Pro Cys Cys Asp Lys Ala Asn Val Lys Arg Gly Pro
1               5                   10                  15

Trp Ser Pro Glu Glu Asp Thr Ile Leu Lys Asn Phe Val Glu Lys His
            20                  25                  30

Gly Thr Gly Gly Asn Trp Ile Ala Leu Pro Arg Lys Ala Gly Leu Lys
        35                  40                  45

Arg Cys Gly Lys Ser Cys Arg Leu Arg Trp Leu Asn Tyr Leu Arg Pro
    50                  55                  60

Asp Ile Lys His Gly Asp Phe Ser Glu Glu Asp Ser Ile Ile Cys
65                  70                  75                  80

Ser Leu Tyr Thr Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Gly Lys Cys Thr Lys Asp Asn Asp Asn Gln
        115                 120                 125

Gln Ile Arg Arg Leu Leu Ala Lys Glu Ala Lys Gly Ala Gly Ile
130                 135                 140

Arg Arg Pro Tyr Asn Gly Asp His Ile Ser Ser Glu Thr Ala Ala Met
145                 150                 155                 160

Ser Ala Ser Asn Thr
                165
```

<210> SEQ ID NO 196
<211> LENGTH: 827
<212> TYPE: DNA
<213> ORGANISM: Pinus

<400> SEQUENCE: 196

```
atgggaagag caccctgttg tgacaaggca aatgtcaaaa aaggatcttg gtcaccagaa     60
gaagacgcaa aactcaaggc gtttattgaa cagcatggca ctggtggcaa ttggattgct    120
cttccacaga aagctggtct gaaaaggtgt ggaaagagct gcaggcttag atggttgaac    180
tatttgaggc cagatataag gcatggtggt ttctcagaag atgaagataa catcatttgt    240
agcctctatg caagcattgg aagcaggtgg tctataattg cagcccagtt acctggaaga    300
acagacaatg acataaaaaa ttactggaac acaaggctga gaaaaagtt gcttgggaaa    360
cgtaaagatc agcaaacacg taggtttaaa gaagcaaaga acatgagtaa tggcacaggg    420
ccttatgttt cagaaggtat gtctactaca tcatccacca tcaatgcaat tagatctctg    480
atgtcaaaca ccgaggcact ttatctgtca gatcgaatgc tcatatggaa tatcgatcca    540
tcatcattgg gcctgcttaa tcctcaggtc ttgcagcata ctgtatcaaa tattgctaat    600
tattgctcaa gctcagagca tattagcttt ggaactggtc ctccccaggg actggatcag    660
gagcttacat ttgacaatgc aagtctgaga aagctgctct taggactga gtgtggcttc    720
actgcagaaa ataacaataa cagtgtctct caagcatctc caccaatcat tagttctcag    780
atatattccc catctactat tttggatccc ggacttgtcc atgactc              827
```

<210> SEQ ID NO 197

```
<211> LENGTH: 276
<212> TYPE: PRT
<213> ORGANISM: Pinus

<400> SEQUENCE: 197
```

| | | | | | | | | | | | | | | |
|---|---|---|---|---|---|---|---|---|---|---|---|---|---|---|
|Met|Gly|Arg|Ala|Pro|Cys|Cys|Asp|Lys|Ala|Asn|Val|Lys|Lys|Gly|Ser|
|1| | | |5| | | | |10| | | | |15| |

Met Gly Arg Ala Pro Cys Cys Asp Lys Ala Asn Val Lys Lys Gly Ser
1               5                   10                  15

Trp Ser Pro Glu Glu Asp Ala Lys Leu Lys Ala Phe Ile Glu Gln His
                20                  25                  30

Gly Thr Gly Asn Trp Ile Ala Leu Pro Gln Lys Ala Gly Leu Lys
            35                  40                  45

Arg Cys Gly Lys Ser Cys Arg Leu Arg Trp Leu Asn Tyr Leu Arg Pro
        50                  55                  60

Asp Ile Arg His Gly Gly Phe Ser Glu Asp Glu Asp Asn Ile Ile Cys
65                  70                  75                  80

Ser Leu Tyr Ala Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Gly Lys Arg Lys Asp Gln Gln Thr Arg Arg
        115                 120                 125

Phe Lys Glu Ala Lys Asn Met Ser Asn Gly Thr Gly Pro Tyr Val Ser
130                 135                 140

Glu Gly Met Ser Thr Thr Ser Ser Thr Ile Asn Ala Ile Arg Ser Leu
145                 150                 155                 160

Met Ser Asn Thr Glu Ala Leu Tyr Leu Ser Asp Arg Met Pro His Met
                165                 170                 175

Asp Ile Asp Pro Ser Ser Leu Gly Leu Leu Asn Pro Gln Val Leu Gln
            180                 185                 190

His Thr Val Ser Asn Ile Ala Asn Tyr Cys Ser Ser Ser Glu His Ile
        195                 200                 205

Ser Phe Gly Thr Gly Pro Pro Gln Gly Leu Asp Gln Glu Leu Thr Phe
210                 215                 220

Asp Asn Ala Ser Leu Arg Lys Leu Leu Phe Arg Thr Glu Cys Gly Phe
225                 230                 235                 240

Thr Ala Glu Asn Asn Asn Asn Ser Val Ser Gln Ala Ser Pro Pro Ile
                245                 250                 255

Ile Ser Ser Gln Ile Tyr Ser Pro Ser Thr Ile Leu Asp Pro Gly Leu
            260                 265                 270

Val His Asp Ser
        275

```
<210> SEQ ID NO 198
<211> LENGTH: 1245
<212> TYPE: DNA
<213> ORGANISM: Pinus

<400> SEQUENCE: 198
atgggtcgag caccctgctg tgacaaagca aatgtcaaga gagggccatg gtctcctgaa     60
gaggacacca tactaaaaaa tttcgtggag aagcatggca ctggaggcaa ctggatcgct    120
ttgcctcgca aagcaggttt aaaaaggtgt ggcaagagtt gcaggctgag atggctgaat    180
tatttgaggc ctgatattaa gcatggtgac ttctcagaag aagaagacga catcatttgc    240
accctgtata ccagcattgg aagcagatgg tctatcattg cagcccagtt gccagggcga    300
acagacaacg acataaagaa ctactggaac acgcggctga agaaaaaatt gcttggcaaa    360
```

```
tgcagcaagg acaacgataa tcagcaaatc cgacgcctac tggcaaaaga agcagctaaa    420
ggcgcgggaa ttagaggact ttacaacggt gatcataata tttcttcaga aacggccgcc    480
atttctgcat caaacactca aagttcgtca gaatctctga cagaaacagc cactgccgca    540
aatgccatga atagcccttt taatgccctt gaaacgggta aagtcccggg atcgaattcg    600
tctgagtcaa aagcggccgg ttttaatgcc acccacagtc ctaatacccca ttattatgaa    660 caaggtttca gtcaaatcat gtctcaggca gatcagtatt cttccctgac acacatgctt    720
ctgagactcg agaataacga gagcgattgc tcaacagaca atattcaatc tctgggcatc    780
gatacaattc ccagtgaggt ccctttctac gcttccacgg ccatgaatgt aaaagctgaa    840
gccatggagc gcccatctag tgatccccag ctcaatcaag cccgcaattc agtgcctgca    900
ctctgggaaa cctgtaccag caattccaca tctgggggca acaattatca gttcagtacg    960
ttgataaacg atgatacggg caatttcagc tatgggctct cagcggacat ggatgagttc   1020
atagtgtatc gaaattatgg aggcaatggc tcaatatctc aggtgaaaga ggagcctgac   1080
tactccacag ctgaagccta ctgggcttct caactagctg aacctgcaaa gtcctcaggc   1140
ttaacaacaa catgtcccaa ttatgcatac attttgccat catctgaggg tggtatgggt   1200
tctggaacta ccccacaggg gctctttcag gagggaatta tctat              1245

<210> SEQ ID NO 199
<211> LENGTH: 415
<212> TYPE: PRT
<213> ORGANISM: Pinus

<400> SEQUENCE: 199

Met Gly Arg Ala Pro Cys Cys Asp Lys Ala Asn Val Lys Arg Gly Pro
1               5                   10                  15

Trp Ser Pro Glu Glu Asp Thr Ile Leu Lys Asn Phe Val Glu Lys His
            20                  25                  30

Gly Thr Gly Gly Asn Trp Ile Ala Leu Pro Arg Lys Ala Gly Leu Lys
        35                  40                  45

Arg Cys Gly Lys Ser Cys Arg Leu Arg Trp Leu Asn Tyr Leu Arg Pro
    50                  55                  60

Asp Ile Lys His Gly Asp Phe Ser Glu Glu Asp Ile Ile Cys
65                  70                  75                  80

Thr Leu Tyr Thr Ser Ile Gly Ser Arg Trp Ser Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Gly Lys Cys Ser Lys Asp Asn Asp Asn Gln
        115                 120                 125

Gln Ile Arg Arg Leu Leu Ala Lys Glu Ala Ala Lys Gly Ala Gly Ile
    130                 135                 140

Arg Gly Leu Tyr Asn Gly Asp His Asn Ile Ser Ser Glu Thr Ala Ala
145                 150                 155                 160

Ile Ser Ala Ser Asn Thr Gln Ser Ser Ser Glu Ser Leu Thr Glu Thr
                165                 170                 175

Ala Thr Ala Ala Asn Ala Met Asn Ser Pro Tyr Asn Ala Leu Glu Thr
            180                 185                 190

Gly Lys Val Pro Gly Ser Asn Ser Ser Glu Ser Lys Ala Ala Gly Phe
        195                 200                 205

Asn Ala Thr His Ser Pro Asn Thr His Tyr Tyr Glu Gln Gly Phe Ser
```

```
                  210                 215                 220
Gln Ile Met Ser Gln Ala Asp Gln Tyr Ser Ser Leu Thr His Met Leu
225                 230                 235                 240

Leu Arg Leu Glu Asn Asn Glu Ser Asp Cys Ser Thr Asp Asn Ile Gln
                245                 250                 255

Ser Leu Gly Ile Asp Thr Ile Pro Ser Glu Val Pro Phe Tyr Ala Ser
            260                 265                 270

Thr Ala Met Asn Val Lys Ala Glu Ala Met Glu Arg Pro Ser Ser Asp
        275                 280                 285

Pro Gln Leu Asn Gln Ala Arg Asn Ser Val Pro Ala Leu Trp Glu Thr
    290                 295                 300

Cys Thr Ser Asn Ser Thr Ser Gly Gly Asn Asn Tyr Gln Phe Ser Thr
305                 310                 315                 320

Leu Ile Asn Asp Asp Thr Gly Asn Phe Ser Tyr Gly Leu Ser Ala Asp
                325                 330                 335

Met Asp Glu Phe Ile Val Tyr Arg Asn Tyr Gly Gly Asn Gly Ser Ile
            340                 345                 350

Ser Gln Val Lys Glu Glu Pro Asp Tyr Ser Thr Ala Glu Ala Tyr Trp
        355                 360                 365

Ala Ser Gln Leu Ala Glu Pro Ala Lys Ser Ser Gly Leu Thr Thr Thr
    370                 375                 380

Cys Pro Asn Tyr Ala Tyr Ile Leu Pro Ser Ser Glu Gly Gly Met Gly
385                 390                 395                 400

Ser Gly Thr Thr Pro Gln Gly Leu Phe Gln Glu Gly Ile Ile Tyr
                405                 410                 415
```

<210> SEQ ID NO 200
<211> LENGTH: 681
<212> TYPE: DNA
<213> ORGANISM: Poncirus trifoliata

<400> SEQUENCE: 200

```
atgggtaggg ctccttgctg tgacaaggca atgtgaaga agggccatg gtcacctgaa      60
gaagactcaa agcttaagga gtacatagag aaatatggca ctggtggcaa ctggattgct     120
cttcctcaga agctggtct aaagagatgt gggaaaagtt gcagactgag atggctcaac     180
tatttgaggc aaatattaa acatggggaa tttactgatg aggaagatag ctgatctgt      240
agcctctttg ctagcattgg aagcagatgg tcaattatag ctgctcagct accgggtagg     300
actgataatg atatcaaaaa ctactggaac acaaagctca agaagaaact catggccatg     360
gctcctccat tatcatcaca aaagaagagc actgctccac cactgatccc atcatctcat     420
catcatcacc aagctttagt gtcactacta ccatctcaac cctattacac cccttctaat     480
aaatctctta tcagtaactc ttttgattct tttgaaccca tttcatcaaa caccccatta     540
catcttttg acaacaacaa cttgatccaa atccaagaaa accagctgtt tagtaataat     600
aattccatgc agggttacta tccaatgaaa gacaatttct tgacttttgg tagcgagcaa     660
agttgcagtt cttctgatgg t                                                681
```

<210> SEQ ID NO 201
<211> LENGTH: 227
<212> TYPE: PRT
<213> ORGANISM: Poncirus trifoliata

<400> SEQUENCE: 201

Met Gly Arg Ala Pro Cys Cys Asp Lys Ala Asn Val Lys Lys Gly Pro

```
            1               5                  10                 15
Trp Ser Pro Glu Glu Asp Ser Lys Leu Lys Glu Tyr Ile Glu Lys Tyr
                20                  25                 30

Gly Thr Gly Gly Asn Trp Ile Ala Leu Pro Gln Lys Ala Gly Leu Lys
         35                 40                  45

Arg Cys Gly Lys Ser Cys Arg Leu Arg Trp Leu Asn Tyr Leu Arg Pro
 50                 55                  60

Asn Ile Lys His Gly Glu Phe Thr Asp Glu Asp Arg Leu Ile Cys
 65                 70                  75                 80

Ser Leu Phe Ala Ser Ile Gly Ser Arg Trp Ser Ile Ile Ala Ala Gln
                 85                 90                  95

Leu Pro Gly Arg Thr Asp Asn Asp Ile Lys Asn Tyr Trp Asn Thr Lys
                100                105                 110

Leu Lys Lys Lys Leu Met Ala Met Ala Pro Pro Leu Ser Ser Gln Lys
                115                120                 125

Lys Ser Thr Ala Pro Pro Leu Ile Pro Ser Ser His His His Gln
130                 135                 140

Ala Leu Val Ser Leu Leu Pro Ser Gln Pro Tyr Tyr Thr Pro Ser Asn
145                 150                 155                 160

Lys Ser Leu Ile Ser Asn Ser Phe Asp Ser Phe Glu Pro Ile Ser Ser
                165                 170                 175

Asn Thr Pro Leu His Leu Phe Asn Asn Asn Leu Ile Gln Ile Gln
                180                 185                 190

Glu Asn Gln Leu Phe Ser Asn Asn Ser Met Gln Gly Tyr Tyr Pro
            195                 200                 205

Met Lys Asp Asn Phe Leu Thr Phe Gly Ser Glu Gln Ser Cys Ser Ser
210                 215                 220

Ser Asp Gly
225

<210> SEQ ID NO 202
<211> LENGTH: 423
<212> TYPE: DNA
<213> ORGANISM: Populus

<400> SEQUENCE: 202
atggggaggg ctccttgctg cgacaaagcc aacgtcaaga aaggcccatg gtcacctgaa     60
gaagatgcga agctcaagtc atatatagag cagcatggca ctggtggtaa ctggattgct    120
ttgcctcaaa aaattggtct taagagatgc ggcaagagct gccgccttag atggttaaat    180
tatcttcgcc cgaatattaa gcacggaggc ttctctgaag aagaagataa cataatttgc    240
agcctttaca ttagtatcgg aagcagatgg tccataattg cagcacaatt gccaggaaga    300
accgataatg atataaagaa ctactggaac acaaggctga agaagaagct tcttggcaag    360
cagcgaaaag agcaacaggc tcgcagaagt agtggcctaa gcaagaaat gaagagagga    420
aat                                                                  423

<210> SEQ ID NO 203
<211> LENGTH: 345
<212> TYPE: PRT
<213> ORGANISM: Populus

<400> SEQUENCE: 203

Met Gly Arg Ala Pro Cys Cys Asp Lys Ala Asn Val Lys Lys Gly Pro
 1               5                  10                 15
```

| | | | | | | | | | | | | |
|---|---|---|---|---|---|---|---|---|---|---|---|---|
|Trp|Ser|Pro|Glu 20|Glu|Asp|Ala|Lys|Leu 25|Lys|Ser|Tyr|Ile|Glu|Gln 30|His|

| | | | | | | | | | | | |
|---|---|---|---|---|---|---|---|---|---|---|---|
|Gly|Thr|Gly 35|Asn|Trp|Ile|Ala|Leu 40|Pro|Gln|Lys|Ile|Gly 45|Leu|Lys|

| | | | | | | | | | | | |
|---|---|---|---|---|---|---|---|---|---|---|---|
|Arg|Cys 50|Gly|Lys|Ser|Cys 55|Arg|Leu|Arg|Trp|Leu 60|Asn|Tyr|Leu|Arg|Pro|

| | | | | | | | | | | | |
|---|---|---|---|---|---|---|---|---|---|---|---|
|Asn 65|Ile|Lys|His|Gly 70|Phe|Ser|Glu|Glu|Glu 75|Asp|Asn|Ile|Ile|Cys 80|

| | | | | | | | | | | | |
|---|---|---|---|---|---|---|---|---|---|---|---|
|Ser|Leu|Tyr|Ile|Ser 85|Ile|Gly|Ser|Arg|Trp 90|Ser|Ile|Ile|Ala|Ala 95|Gln|

| | | | | | | | | | | | |
|---|---|---|---|---|---|---|---|---|---|---|---|
|Leu|Pro|Gly|Arg 100|Thr|Asp|Asn|Asp|Ile 105|Lys|Asn|Tyr|Trp|Asn 110|Thr|Arg|

| | | | | | | | | | | | |
|---|---|---|---|---|---|---|---|---|---|---|---|
|Leu|Lys|Lys 115|Lys|Leu|Leu|Gly 120|Lys|Gln|Arg|Lys|Glu 125|Gln|Gln|Ala|Arg|

| | | | | | | | | | | | |
|---|---|---|---|---|---|---|---|---|---|---|---|
|Arg|Ser 130|Gly|Leu|Lys|Gln 135|Glu|Met|Lys|Arg|Gly 140|Asn|Gly|Asn|Pro|

| | | | | | | | | | | | |
|---|---|---|---|---|---|---|---|---|---|---|---|
|Val 145|Val|Pro|Ala|Asp|Asn 150|Asn|Gln|Asn|Pro|Tyr 155|Trp|Pro|Glu|Leu 160|

| | | | | | | | | | | | |
|---|---|---|---|---|---|---|---|---|---|---|---|
|Pro|Ile|Leu|Ala|Pro 165|Ile|Pro|Tyr|Ser|Asn 170|His|Glu|Pro|His|Phe 175|Asn|

| | | | | | | | | | | | |
|---|---|---|---|---|---|---|---|---|---|---|---|
|Asp|His|Ala|Ser 180|Ile|Arg|Lys|Leu|Leu 185|Ile|Lys|Leu|Gly|Gly 190|Lys|Phe|

| | | | | | | | | | | | |
|---|---|---|---|---|---|---|---|---|---|---|---|
|Ser|Asp|Asp 195|Asp|Gln|Val|Asn|His 200|Asn|Ala|Met|Asn|Pro 205|Gln|Phe|Pro|

| | | | | | | | | | | | |
|---|---|---|---|---|---|---|---|---|---|---|---|
|Ala|Asp 210|Val|Ser|Tyr|Thr|Gln 215|Gln|Leu|Tyr|Asp|Gln 220|Ser|Ile|Asn|

| | | | | | | | | | | | |
|---|---|---|---|---|---|---|---|---|---|---|---|
|Val 225|Ser|Ser|Ser|Ala|Pro 230|Met|Glu|Glu|Thr|Leu 235|Asp|Asp|Thr|Asp 240|

| | | | | | | | | | | | |
|---|---|---|---|---|---|---|---|---|---|---|---|
|Gln|Phe|Ala|Gln|Thr 245|Gln|Tyr|Asp|Ile|Asp 250|Gly|Ala|Ala|Gly 255|Leu|Gln|

| | | | | | | | | | | | |
|---|---|---|---|---|---|---|---|---|---|---|---|
|Met|Leu|Gln|Gly 260|Gln|Ser|Ser|Phe|Pro 265|Ala|Gly|Leu|Glu|Gln 270|Met|Val|

| | | | | | | | | | | | |
|---|---|---|---|---|---|---|---|---|---|---|---|
|Ser|Ser|Asn 275|Pro|Pro|Arg|Leu|Asp 280|Gly|Leu|Glu|Phe|Leu 285|Leu|Gly|Asp|

| | | | | | | | | | | | |
|---|---|---|---|---|---|---|---|---|---|---|---|
|Asp|Met 290|Val|Asn|Asn|Arg|Ile 295|Arg|Thr|Ala|Tyr|Gly 300|Thr|Glu|Ser|Met|

| | | | | | | | | | | | |
|---|---|---|---|---|---|---|---|---|---|---|---|
|Ile 305|Asp|Cys|Gly|Glu|Met 310|Thr|Ser|Leu|Ile|Phe 315|Pro|Pro|Gly|Ala|Ser 320|

| | | | | | | | | | | | |
|---|---|---|---|---|---|---|---|---|---|---|---|
|Asn|Cys|Glu|Gly|Ile 325|Ile|Gln|Gln|Arg|Leu 330|Leu|Gln|Glu|Cys|Ala 335|Phe|

| | | | | | | |
|---|---|---|---|---|---|---|
|Asp|Glu|Pro|Arg 340|Tyr|Pro|Gly|Pro 345|Leu|

<210> SEQ ID NO 204
<211> LENGTH: 572
<212> TYPE: DNA
<213> ORGANISM: Populus

<400> SEQUENCE: 204

```
atggggagag ctccttgctg tgacaaagcc aacgtgaaga aaggtccatg gtctcccgag      60
gaagatgcca tactcaaggc ctatattgag cagcatggaa cgggtggcaa ttggattgcc     120
ttgccacaga agataggcct gaaaaggtgt ggcaagagtt gtcgacttag atggttgaat     180
tatctccgtc caaacattaa acatggaggg ttttcagagg aagaagataa cattatttgc     240
```

```
agtctctata taagtattgg aagcaggtgg tctatcattg ctgctcagtt acctggaaga      300
accgataatg atataaaaaa ctactggaac acaaggctta agaagaagct cttaggaaaa      360
cagcgcaagg aacaagcagc ccggcgagct agtctcaagc aagaaatcat gacaaagaga      420
gaaataaatg agagcttcat ggttcctggg gctatccctc atcaacaaag cccttactgg      480
ccagaggtac cagctctagt catgaatcaa aaccaagatt ctcatttgat ggatcaagaa      540
tccattagga acttgctgat caaacttggt gg                                    572
```

<210> SEQ ID NO 205
<211> LENGTH: 191
<212> TYPE: PRT
<213> ORGANISM: Populus

<400> SEQUENCE: 205

```
Met Gly Arg Ala Pro Cys Cys Asp Lys Ala Asn Val Lys Lys Gly Pro
1               5                   10                  15

Trp Ser Pro Glu Glu Asp Ala Ile Leu Lys Ala Tyr Ile Glu Gln His
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Asp Asn Ile Ile Cys
65                  70                  75                  80

Ser Leu Tyr Ile Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Gly Lys Gln Arg Lys Glu Gln Ala Ala Arg
        115                 120                 125

Arg Ala Ser Leu Lys Gln Glu Ile Met Thr Lys Arg Glu Ile Asn Glu
    130                 135                 140

Ser Phe Met Val Pro Gly Ala Ile Pro His Gln Gln Ser Pro Tyr Trp
145                 150                 155                 160

Pro Glu Val Pro Ala Leu Val Met Asn Gln Asn Gln Asp Ser His Leu
                165                 170                 175

Met Asp Gln Glu Ser Ile Arg Asn Leu Leu Ile Lys Leu Gly Gly
            180                 185                 190
```

<210> SEQ ID NO 206
<211> LENGTH: 999
<212> TYPE: DNA
<213> ORGANISM: Populus

<400> SEQUENCE: 206

```
atgggaaggg ctccttgttg tgacaaggct aatatgaaga aagggccctg gccgcctgaa       60
gaagatgcaa agctgaagga gtacttggaa aaacaaggga ctggagggaa ttggattgct      120
ctcccacaaa aggctggtca taaagatgt gggaaaagct gcagattaag atggctaaac      180
tatctcaggc ccaacattaa acatggagag ttctctgatg atgaagacag gataatctgc      240
agcctatatg ccaacattgg aagccggtgg tcaataatag cagctcagtt gccaggcagg      300
acggataatg acataaaaaa ctactggaac accaagctca agaagaaact aatgggtgtg      360
attaatccta ttgctcagag aaaacctcag caagctgctc tttttttcatc tctccttcaa      420 gctacatcat caccgtcttc accatccact ctcctgtcat caccatcatc atcattcaca      480
```

```
tgcagcaaca acagttatta cagtaaccta actaggtctt tcactgatcc aatctcattt      540
tcatcaagtc ctatgagcac tagctctttc gctactgctt ccatgctaca ccccaacaa      600 acctttgtgg ggcctatgca aaatgatcaa gttaaagata gtcttataat gtttggaggt      660
gaagccagct gcagctcgtc tgatgggagt tgcaacaacc agatgagcca tgtcaaagag      720
gagtatgaat atagtggtgg tacaaataac aacaatgaac agatggggtt acaaaattat      780
ccctacaatg gggttgaaga tggccaaaaa ttgatggttt caagtgaggc tgctgctcat      840
ggtgtactta atgggtggat tgagaagcaa aatgggttat ggccgggaga taactcacta      900
gactatggtc tagaggagat taagcaactt attagcacta gcagctgtaa tagcttttg       960 tttgatgaaa acaagacagg aggaaaagtc atgtactac                            999
```

<210> SEQ ID NO 207
<211> LENGTH: 333
<212> TYPE: PRT
<213> ORGANISM: Populus

<400> SEQUENCE: 207

```
Met Gly Arg Ala Pro Cys Cys Asp Lys Ala Asn Met Lys Lys Gly Pro
1               5                   10                  15

Trp Pro Pro Glu Glu Asp Ala Lys Leu Lys Glu Tyr Leu Glu Lys Gln
            20                  25                  30

Gly Thr Gly Gly Asn Trp Ile Ala Leu Pro Gln Lys Ala Gly His Lys
        35                  40                  45

Arg Cys Gly Lys Ser Cys Arg Leu Arg Trp Leu Asn Tyr Leu Arg Pro
    50                  55                  60

Asn Ile Lys His Gly Glu Phe Ser Asp Asp Glu Asp Arg Ile Ile Cys
65                  70                  75                  80

Ser Leu Tyr Ala Asn Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Met Gly Val Ile Asn Pro Ile Ala Gln Arg Lys
        115                 120                 125

Pro Gln Gln Ala Ala Leu Phe Ser Ser Leu Leu Gln Ala Thr Ser Ser
    130                 135                 140

Pro Ser Ser Pro Ser Thr Leu Leu Ser Ser Pro Ser Ser Ser Phe Thr
145                 150                 155                 160

Cys Ser Asn Asn Ser Tyr Tyr Ser Asn Leu Thr Arg Ser Phe Thr Asp
                165                 170                 175

Pro Ile Ser Phe Ser Ser Ser Pro Met Ser Thr Ser Ser Phe Ala Thr
            180                 185                 190

Ala Ser Met Leu His Pro Gln Gln Thr Phe Val Gly Pro Met Gln Asn
        195                 200                 205

Asp Gln Val Lys Asp Ser Leu Ile Met Phe Gly Gly Glu Ala Ser Cys
    210                 215                 220

Ser Ser Ser Asp Gly Ser Cys Asn Asn Gln Met Ser His Val Lys Glu
225                 230                 235                 240

Glu Tyr Glu Tyr Ser Gly Gly Thr Asn Asn Asn Glu Gln Met Gly
                245                 250                 255

Leu Gln Asn Tyr Pro Tyr Asn Gly Val Glu Asp Gly Gln Lys Leu Met
            260                 265                 270

Val Ser Ser Glu Ala Ala Ala His Gly Val Leu Asn Gly Trp Ile Glu
```

|   |   |   | 275 |   |   |   | 280 |   |   |   | 285 |   |
|---|---|---|---|---|---|---|---|---|---|---|---|---|

Lys Gln Asn Gly Leu Trp Pro Gly Asp Asn Ser Leu Asp Tyr Gly Leu
    290                      295                      300

Glu Glu Ile Lys Gln Leu Ile Ser Thr Ser Cys Asn Ser Phe Leu
305                      310                      315                320

Phe Asp Glu Asn Lys Thr Gly Gly Lys Val Met Tyr Tyr
            325                      330

<210> SEQ ID NO 208
<211> LENGTH: 387
<212> TYPE: DNA
<213> ORGANISM: Quercus petraea

<400> SEQUENCE: 208

```
atgggaagag ctccttgttg tgataaggcc aacgtgaaaa aagggccatg gtcacctgaa      60
gaagatgcaa agctgaaaga gtatatagat aaatatggga ctggagggaa ttggattgct     120
cttccacaga aagcaggtct caagagatgt ggaaaaagcc gcagattaag atggcttaac     180
tatctcagac ccaacattaa acatggtgaa ttcactgaaa atgaagatag gataatatgc     240
agcctctttg ctaacattgg aagcaggtgg tcaataatag cagctcagtt gccaggcagg     300
acagacaatg accttaagaa ctattgtaac accaagctta agaagaaact catgggtata     360
tttcctccat ctcagagaaa aggtcac                                         387
```

<210> SEQ ID NO 209
<211> LENGTH: 129
<212> TYPE: PRT
<213> ORGANISM: Quercus petraea

<400> SEQUENCE: 209

Met Gly Arg Ala Pro Cys Cys Asp Lys Ala Asn Val Lys Lys Gly Pro
1                  5                    10                  15

Trp Ser Pro Glu Glu Asp Ala Lys Leu Lys Glu Tyr Ile Asp Lys Tyr
           20                    25                    30

Gly Thr Gly Gly Asn Trp Ile Ala Leu Pro Gln Lys Ala Gly Leu Lys
              35                    40                    45

Arg Cys Gly Lys Ser Arg Arg Leu Arg Trp Leu Asn Tyr Leu Arg Pro
    50                    55                    60

Asn Ile Lys His Gly Glu Phe Thr Glu Asn Glu Asp Arg Ile Ile Cys
65                    70                    75                80

Ser Leu Phe Ala Asn Ile Gly Ser Arg Trp Ser Ile Ile Ala Ala Gln
              85                    90                    95

Leu Pro Gly Arg Thr Asp Asn Asp Leu Lys Asn Tyr Cys Asn Thr Lys
           100                    105                  110

Leu Lys Lys Lys Leu Met Gly Ile Phe Pro Pro Ser Gln Arg Lys Gly
              115                    120                  125

His

<210> SEQ ID NO 210
<211> LENGTH: 547
<212> TYPE: DNA
<213> ORGANISM: Quercus suber

<400> SEQUENCE: 210

```
accttgctct cctattctgg catgcttaat ttctggaatt ttctatacaa actttatgcc      60
acaccctcct taaatatta attattggct gtttccctaa taaccatgta tatcttcaag     120
```

```
ctttttataat cctctctctc tctctctctc tctctctctc tctctctcat attcttattt      180
gggtttcaga gggagaagct ataggctata gcatcaagct caaagcaaca ccatggggag      240
agctccatgt tgtgacaaag caaacgtcaa gaaaggccca tggtcacctg aagaagatgc      300
caagctcaag tcgtatatag agaagcatgg caccggtggt aactggatcg ctttaccaca      360
aaaaaattgg cctgaagaga tgcggcaaga gttgccgcct tagatggtta aactatctcc      420
gtccaaatat caagcatgga ggattttcag aagaggaaga taacataatt tgcagcctct      480
atattagtat tggaagcagg tggtctatta ttgcagcaca attgccagga agaacagata      540
atgatat                                                                547
```

```
<210> SEQ ID NO 211
<211> LENGTH: 648
<212> TYPE: DNA
<213> ORGANISM: Raphanus raphanistrum

<400> SEQUENCE: 211
atgggaaggg caccttgttg tgacaaagcc aacgtgaaga agggccttg gtctcctgag       60 gaagatgcca aactcaaaga ttacatcgag aatagtggta caggaggcaa ctggatcgct     120
ttgcctcaga agattggtct aaggagatgt gggaagagtt gcaggctaag gtggctcaac     180
tatttgagac caaacatcaa acatggtggc ttctctgagg aagaagacaa catcatttgt     240
aacctctatg ttactattgg tagcaggtgg tctataattg ctgcacaact gccgggaaga     300
acggacaacg atatcaagaa ctactggaac acgaggctga agaagaagct tctaaacaaa     360
caaaggaaag agttccaaga agctcgaatg aagcaagaga tggtgatgat gaagaggcaa     420
caacaagtac aaaatggtag tacggatctt tatctgaaaa acatgtttgg atcatcatca     480
tggccattac tacaacagct tcctcatcat caagtacctc ttgtgatgat ggaaccaaca     540
aactgtaact actaccaaat gtcaccgtct tgcaacctag aacaaaagca acttatcgct     600
ctcaataaca tggtcaagat tgaagaagaa ccggagagaa caaaccct                  648
```

```
<210> SEQ ID NO 212
<211> LENGTH: 216
<212> TYPE: PRT
<213> ORGANISM: Raphanus raphanistrum

<400> SEQUENCE: 212

Met Gly Arg Ala Pro Cys Cys Asp Lys Ala Asn Val Lys Lys Gly Pro
1               5                   10                  15

Trp Ser Pro Glu Glu Asp Ala Lys Leu Lys Asp Tyr Ile Glu Asn Ser
            20                  25                  30

Gly Thr Gly Gly Asn Trp Ile Ala Leu Pro Gln Lys Ile Gly Leu Arg
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Asp Asn Ile Ile Cys
65                  70                  75                  80

Asn Leu Tyr Val Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Asn Lys Gln Arg Lys Glu Phe Gln Glu Ala
        115                 120                 125

Arg Met Lys Gln Glu Met Val Met Met Lys Arg Gln Gln Gln Val Gln
```

```
            130                 135                 140
Asn Gly Ser Thr Asp Leu Tyr Leu Lys Asn Met Phe Gly Ser Ser
145                 150                 155                 160

Trp Pro Leu Leu Gln Gln Leu Pro His His Gln Val Pro Leu Val Met
                165                 170                 175

Met Glu Pro Thr Asn Cys Asn Tyr Tyr Gln Met Ser Pro Ser Cys Asn
            180                 185                 190

Leu Glu Gln Lys Gln Leu Ile Ala Leu Asn Asn Met Val Lys Ile Glu
        195                 200                 205

Glu Glu Pro Glu Arg Thr Asn Pro
    210                 215

<210> SEQ ID NO 213
<211> LENGTH: 846
<212> TYPE: DNA
<213> ORGANISM: Raphanus raphanistrum

<400> SEQUENCE: 213
ggatactttt ctccattata cacattttca tgtatgtata tataaatcat cacatacacg      60
caccataaca ctaacatcct cctcctcttc atcatcaaca tagttgagaa agatcgaaaa     120
aaagagagag aaagagggat acatcaagaa caagaatcgc gaatcaagag gatgggaagg     180
gcaccgtgtt gtgataaggc taacgtgaag aaagggcctt ggtctcctga agaagatgca     240
aaactcaaag attacataga gagtagtggc acaggaggca actggatcgc tttgcctcag     300
aagattggtc taaggagatg tgggaagagt tgcagactaa ggtggctcaa ctatttaaga     360
ccaaacatca acatggtgg cttctctgag gaagaggaca catcatttg taacctctat      420 gttactattg gtagcaggtg gtctataata gctgcacaat gcctggaag aacagacaat     480 gacatcaaga actattggaa cacgaggctg aagaagaagc ttcttaacaa acaaagaaaa     540
gagttccaag aagctcggat acagcagaga tggtgatgat gaaacgacaa caacaagaca     600
aggacaattc caaattaatg gtagtacgga tctttatctg aacaacatgt ttggatcatc     660
agcatggcca ttactacctc agcttcctcc tcctcatagt caagtacctc ttgtgatgat     720
ggaaccaaca agctgcaatt actaccaaac gacaccttct tgcacataga caaagcatga     780
tacactcaga cacgtcagat gagagacgag agaacaacct gatcatcatc accacgagac     840
tctatg                                                               846

<210> SEQ ID NO 214
<211> LENGTH: 522
<212> TYPE: DNA
<213> ORGANISM: Raphanus raphanistrum

<400> SEQUENCE: 214
atgggaaggg caccttgttg tgacaaagcc aacgtgaaga aagggccttg gtctcctgag      60
gaagatgcca aactcaaaga ttacatcgag aatagtggta caggaggcaa ctggatcgct     120
ttgcctcaga gattggtctc aaggagatgt gggaagagtt gcaggctaag gtggctcaac     180
tatttgagac caaacatcaa acatggtggc ttctctgagg aagaagacaa catcatttgt     240
aacctctatg ttactattgg tagcaggtgg tctataattg ctgcacaact gccgggaaga     300
acggacaacg atatcaagaa ctactggaac acgaggctga agaagaagct tctaaacaaa     360
caaaggaaag agttccaaga agctcgaatg aagcaagaga tggtgatgat gaagaggcaa     420
caacaagtac aaaatggtag tacggatctt tatctgaaaa acatgtttgg atcatcatca     480
```

```
tggccattac tacaacagct tcctcatcat caagtacctc tt                              522
```

<210> SEQ ID NO 215
<211> LENGTH: 174
<212> TYPE: PRT
<213> ORGANISM: Raphanus raphanistrum

<400> SEQUENCE: 215

```
Met Gly Arg Ala Pro Cys Cys Asp Lys Ala Asn Val Lys Lys Gly Pro
1               5                   10                  15

Trp Ser Pro Glu Glu Asp Ala Lys Leu Lys Asp Tyr Ile Glu Asn Ser
            20                  25                  30

Gly Thr Gly Asn Trp Ile Ala Leu Pro Gln Lys Ile Gly Leu Arg
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Glu Asp Asn Ile Ile Cys
65                  70                  75                  80

Asn Leu Tyr Val Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
            100                 105                 110

Leu Lys Lys Lys Leu Leu Asn Lys Gln Arg Lys Glu Phe Gln Glu Ala
        115                 120                 125

Arg Met Lys Gln Glu Met Val Met Met Lys Arg Gln Gln Gln Val Gln
    130                 135                 140

Asn Gly Ser Thr Asp Leu Tyr Leu Lys Asn Met Phe Gly Ser Ser Ser
145                 150                 155                 160

Trp Pro Leu Leu Gln Gln Leu Pro His His Gln Val Pro Leu
                165                 170
```

<210> SEQ ID NO 216
<211> LENGTH: 842
<212> TYPE: DNA
<213> ORGANISM: Raphanus raphanistrum

<400> SEQUENCE: 216

```
tcttcaaaaa cgaaaccaag attcctcaaa cagaacacac agagtagcta taaggaccga     60
gagagatcgt agagagatgg ggagggctcc atgttgtgac aaagcaaatg tgaagagagg    120
tccatggtct ccggaagaag atgcaaagct taaagattac atagagaaac aaggcactgg    180
tggcaactgg attgctctcc ctcacaaagc tggtttaagg agatgtggga agagttgtag    240
actgaggtgg ttaaactatt tgaggccaaa cataagacat ggagatttct ctgaggaaga    300
agacaatatt atctgcagcc tctttgcctc cattggaaca ctaagctcaa gaagaagctc    360
attgccacta tggctcctcc accacctcat caactcgtag ccattgcctc atcatcatca    420
tcaccatcat catcacacta caacatgacc aataatcttc ctccgtataa cccaacaata    480
tctacaaacc agctgatctc acctcatctc tcacctcatc aggagatgat gatgacaatg    540
atggaccaac aacaacaact attatacaaa gaagccatgg acagtttggt aaattctcca    600
aatagcaaca agcttataat gagccatcaa gaagacagcc atgcgcaaag tacaaacaaa    660
ggaataatgt tgttgagtga tgtaagaagt gggtcaagca caacaagtac agtaacaaga    720
gtgaagatgg aacaacatga tcatcatcat gaagagagat caatgcaaga ttatggaatg    780
gaggagatca atcacttaat aagtagtagt tgtacgagta gtagtagcac agcttgtggt    840
``` tt                                                                          842

<210> SEQ ID NO 217
<211> LENGTH: 788
<212> TYPE: DNA
<213> ORGANISM: Raphanus sativus

<400> SEQUENCE: 217
gctcctcatc aagtacctct tgtgatgatg gaaccgacaa actgtaacta ctaccaaacg    60
tcaccgtctt gcaacctaga acaaaagcaa ccgatcgctc tcaataacat ggtcaagatt   120
gaagaagaac cggagagaac aaaccctgat catcatcagc atcaagattc tatcacaaac   180
ccttttgatg tctccttctc tcagcttttg ttagatcctt attactactt aggatcagga   240
gaaggaggag gagaagggga ttttgctatc atgagtagca gcacaaattc tccattacca   300
aacacaagtg gtgatcaaaa tgaacatcag cagcaagaga tttttcaatg gtttgggagt   360
agtaatcttc agacagaagc aagcagcgat atgttcttaa acaacaacat agcgaatctt   420
gagaccaacg agggcacaaa attctactca tcattagctg gcgctggggc ggctttggcc   480
gaaggaacga cgagtacatc cgcagatcaa agcacaataa gttgggagga cataacttct   540
cttgttaatt cagaagatgc aagttacttc aatgggccaa attagttatg tgcattttc    600
aataaacatt tgacttttg aggtgtttca ttttgtataa ttatgtatca ttagcgggtc    660
ggccgattaa ttatatggat tgagattaat gttcatgcag agatttgttt agtttagttt   720
caacttagct ttatgtacga accttttttt taacaccatt cacgacatat atatgagtga   780
agagatct                                                            788

<210> SEQ ID NO 218
<211> LENGTH: 731
<212> TYPE: DNA
<213> ORGANISM: Rosa hybrida

<400> SEQUENCE: 218
atgggaagag ctccatgttg tgacaaagct agtgtcaaaa gggggcaatg gtctcctgag    60
gaagatgaag ctctcaagac ttaccttgag actcatggaa ctggtggcaa ttggattcat   120
ctgcctcaaa aagctgggct taggagatgt gggaagagct gccgtctgcg gtggttgaac   180
tatctgaggc cagacatcaa acatggaggc ttcactgaag aggaggacaa cattatctgt   240
aacctctaca ctcaaatggg aagccgatgg tcatacatag ctgctcaaat gcctggaaga   300
acagacaatg atgtgaagaa ctattggaac accaaattga agaagaggtt ttttagcaaa   360
aacccaaatg cctcctcact cacactgcct tgtgttccaa acttgaaac caatgatgag    420
tttcagaccc aaatacctcc cacattgatg ttatctgatt ataattctgg attgaatgcc   480
tatgatcaaa gtttgagctt aaagccaaat ccattacaca actccaagct cacgggctta   540
tcacaatttg gtgcaagttc tgtttcaatg tctcaagatg gttctagtgt ttcagattcg   600
tcttcaattg ctgcagttga aaatggttta ctacatggaa atagcttcat aaatgaggat   660
gctgctggga tacccatgga ttttggattt ggaggattgc cttatgatgt tgtcaatcag   720
atgtggtttg g                                                        731

<210> SEQ ID NO 219
<211> LENGTH: 244
<212> TYPE: PRT
<213> ORGANISM: Rosa hybrida

<400> SEQUENCE: 219

```
Met Gly Arg Ala Pro Cys Cys Asp Lys Ala Ser Val Lys Arg Gly Gln
1               5                   10                  15

Trp Ser Pro Glu Glu Asp Glu Ala Leu Lys Thr Tyr Leu Glu Thr His
            20                  25                  30

Gly Thr Gly Gly Asn Trp Ile His Leu Pro Gln Lys Ala Gly Leu Arg
        35                  40                  45

Arg Cys Gly Lys Ser Cys Arg Leu Arg Trp Leu Asn Tyr Leu Arg Pro
    50                  55                  60

Asp Ile Lys His Gly Gly Phe Thr Glu Glu Asp Asn Ile Ile Cys
65                  70                  75                  80

Asn Leu Tyr Thr Gln Met Gly Ser Arg Trp Ser Tyr Ile Ala Ala Gln
                85                  90                  95

Met Pro Gly Arg Thr Asp Asn Asp Val Lys Asn Tyr Trp Asn Thr Lys
            100                 105                 110

Leu Lys Lys Arg Phe Phe Ser Lys Asn Pro Asn Ala Ser Ser Leu Thr
        115                 120                 125

Leu Pro Cys Val Pro Lys Leu Glu Thr Asn Asp Glu Phe Gln Thr Gln
    130                 135                 140

Ile Pro Pro Thr Leu Met Leu Ser Asp Tyr Asn Ser Gly Leu Asn Ala
145                 150                 155                 160

Tyr Asp Gln Ser Leu Ser Leu Lys Pro Asn Pro Leu His Asn Ser Lys
                165                 170                 175

Leu Thr Gly Leu Ser Gln Phe Gly Ala Ser Ser Val Ser Met Ser Gln
            180                 185                 190

Asp Gly Ser Ser Val Ser Asp Ser Ser Ile Ala Ala Val Glu Asn
        195                 200                 205

Gly Leu Leu His Gly Asn Ser Phe Ile Asn Glu Asp Ala Ala Gly Ile
    210                 215                 220

Pro Met Asp Phe Gly Phe Gly Gly Leu Pro Tyr Asp Val Val Asn Gln
225                 230                 235                 240

Met Trp Phe Gly
```

<210> SEQ ID NO 220
<211> LENGTH: 362
<212> TYPE: DNA
<213> ORGANISM: Saccharum officinarum
<220> FEATURE:
<221> NAME/KEY: misc_feature
<222> LOCATION: (207)..(207)
<220> FEATURE:
<221> NAME/KEY: misc_feature
<222> LOCATION: (207)..(207)
<223> OTHER INFORMATION: n is any nucleotide

<400> SEQUENCE: 220

```
atggggcgcg cgccgtgctg cgacaaggcg agcgtgaagc gggggccctg gtcgcccgag      60
gaggacgagc agctgcggag ctacgtccag cgcaacggca tcggcggcaa ctggatcgcc     120
ctgccgcaga aagcagggct gaaccggtgc ggcaagagct gccggctgcg gtggctcaac     180
tacctgcggc cggacatcaa gcacggnggc tacaccgagc aggaggaccg gatcatctgg     240
tcactctaca gctccatcgg aagcaggtgg tcgatcatcg cgtccaagct ccccggccgg     300
accgacaacg acgtcaagaa ctactggaac accaagctca gaagaaggc catggcggcg     360
gt                                                                   362
```

<210> SEQ ID NO 221

-continued

```
<211> LENGTH: 121
<212> TYPE: PRT
<213> ORGANISM: Saccharum officinarum

<400> SEQUENCE: 221

Met Gly Arg Ala Pro Cys Cys Asp Lys Ala Ser Val Lys Arg Gly Pro
1               5                   10                  15

Trp Ser Pro Glu Glu Asp Glu Gln Leu Arg Ser Tyr Val Gln Arg Asn
            20                  25                  30

Gly Ile Gly Gly Asn Trp Ile Ala Leu Pro Gln Lys Ala Gly Leu Asn
        35                  40                  45

Arg Cys Gly Lys Ser Cys Arg Leu Arg Trp Leu Asn Tyr Leu Arg Pro
    50                  55                  60

Asp Ile Lys His Gly Gly Tyr Thr Glu Gln Glu Asp Arg Ile Ile Trp
65                  70                  75                  80

Ser Leu Tyr Ser Ser Ile Gly Ser Arg Trp Ser Ile Ile Ala Ser Lys
                85                  90                  95

Leu Pro Gly Arg Thr Asp Asn Asp Val Lys Asn Tyr Trp Asn Thr Lys
            100                 105                 110

Leu Lys Lys Lys Ala Met Ala Ala Val
        115                 120

<210> SEQ ID NO 222
<211> LENGTH: 393
<212> TYPE: DNA
<213> ORGANISM: Saccharum officinarum
<220> FEATURE:
<221> NAME/KEY: misc_feature
<222> LOCATION: (296)..(296)
<223> OTHER INFORMATION: n is any nucleotide
<220> FEATURE:
<221> NAME/KEY: misc_feature
<222> LOCATION: (351)..(351)
<223> OTHER INFORMATION: n is any nucleotide

<400> SEQUENCE: 222
atgggtcggg cgccgtgctg cgacaagacg agtgtgaagc gggggccgtg gtcgcccgag      60
gaggacgagc tgctgcggag ctacgtccac aaccacggca ccggcggcaa ctggatcgcg     120
ctcccgcaca aagcagggct gaaccggtgc ggcaagagct gccggctgcg gtggctcaac     180
tacctgcgcc cggacatcaa gcacggcggc tacacggagc aggaggaccg gatcatctgc     240
tccctctaca actccatcgg gagcaggtgg tccatcatcg cgtccaagct gccggngcgg     300
acggacaacg acgtcaagaa ctactgggac accaagctca agaagaaggc natcgccatg     360
caccaccacc agcagcagca gcagcaggag tac                                 393

<210> SEQ ID NO 223
<211> LENGTH: 131
<212> TYPE: PRT
<213> ORGANISM: Saccharum officinarum
<220> FEATURE:
<221> NAME/KEY: MISC_FEATURE
<222> LOCATION: (99)..(99)
<223> OTHER INFORMATION: X is any amino acid

<400> SEQUENCE: 223

Met Gly Arg Ala Pro Cys Cys Asp Lys Thr Ser Val Lys Arg Gly Pro
1               5                   10                  15

Trp Ser Pro Glu Glu Asp Glu Leu Leu Arg Ser Tyr Val His Asn His
            20                  25                  30

Gly Thr Gly Gly Asn Trp Ile Ala Leu Pro His Lys Ala Gly Leu Asn
```

```
            35                  40                  45
Arg Cys Gly Lys Ser Cys Arg Leu Arg Trp Leu Asn Tyr Leu Arg Pro
 50                  55                  60

Asp Ile Lys His Gly Gly Tyr Thr Glu Gln Glu Asp Arg Ile Ile Cys
 65                  70                  75                  80

Ser Leu Tyr Asn Ser Ile Gly Ser Arg Trp Ser Ile Ile Ala Ser Lys
                 85                  90                  95

Leu Pro Xaa Arg Thr Asp Asn Asp Val Lys Asn Tyr Trp Asp Thr Lys
            100                 105                 110

Leu Lys Lys Lys Ala Ile Ala Met His His Gln Gln Gln Gln Gln
        115                 120                 125

Gln Glu Tyr
130
```

<210> SEQ ID NO 224
<211> LENGTH: 726
<212> TYPE: DNA
<213> ORGANISM: Saccharum officinarum

<400> SEQUENCE: 224

```
atggggcgga cgccgtgctg cgacagggcg gccgtgaagc agggcccgtg gtcgccggag      60
gaggacgagg cgctgcggag ctacgtccag cgccacggca gcggcggcaa ctggatcgcc     120
atgcccaaga aagccgggct caagaggtgc ggcaagagct gcaggctgcg ctggctcaac     180
tacctccgcc cggacatccg ccacggcggc ttcaccgccg aggaggacgc cgtcatcatg     240
tccctccaca cccagctcgg gagcaagtgg tcgctgatag cctcgcagat ggaagggagg     300
acggacaacg acgtcaagaa ccactggaac accaagctca agaagcgcct cctcgccgcc     360
gccctgtccc cgttcccgcc acctcacgcc cggctgccgg cgcccgcgcc tgcttccagc     420
accgcgcacg cgtcgtcgct attcccttcg ctcgacatac cgaccgtgaa gacggaggcg     480
tacacctgcg acgacttcct ggcgccgggc ctccgcgacc cgttcgctgc cgccgccgac     540
ggctccacct cggtcgcctc cgcggcgtcg tcggcctcca actggtcgac ggcggacaac     600
ggcgccagcg aagcgtccct cttcctgctg gacttctgcg cgggccccga cctcggcgcc     660
gccgctgacc agctccagct ccccggcggc tactactacc ctctcgatcc aagcttgtcg     720
ccggta                                                               726
```

<210> SEQ ID NO 225
<211> LENGTH: 242
<212> TYPE: PRT
<213> ORGANISM: Saccharum officinarum

<400> SEQUENCE: 225

```
Met Gly Arg Thr Pro Cys Cys Asp Arg Ala Ala Val Lys Gln Gly Pro
 1               5                  10                  15

Trp Ser Pro Glu Glu Asp Glu Ala Leu Arg Ser Tyr Val Gln Arg His
                20                  25                  30

Gly Ser Gly Gly Asn Trp Ile Ala Met Pro Lys Lys Ala Gly Leu Lys
            35                  40                  45

Arg Cys Gly Lys Ser Cys Arg Leu Arg Trp Leu Asn Tyr Leu Arg Pro
 50                  55                  60

Asp Ile Arg His Gly Gly Phe Thr Ala Glu Glu Asp Ala Val Ile Met
 65                  70                  75                  80

Ser Leu His Thr Gln Leu Gly Ser Lys Trp Ser Leu Ile Ala Ser Gln
                 85                  90                  95
```

```
Met Glu Gly Arg Thr Asp Asn Asp Val Lys Asn His Trp Asn Thr Lys
            100                 105                 110

Leu Lys Lys Arg Leu Leu Ala Ala Ala Leu Ser Pro Phe Pro Pro Pro
        115                 120                 125

His Ala Arg Leu Pro Ala Pro Ala Pro Ala Ser Thr Ala His Ala
    130                 135                 140

Ser Ser Leu Phe Pro Ser Leu Asp Ile Pro Thr Val Lys Thr Glu Ala
145                 150                 155                 160

Tyr Thr Cys Asp Asp Phe Leu Ala Pro Ala Leu Arg Asp Pro Phe Ala
                165                 170                 175

Ala Ala Ala Asp Gly Ser Thr Ser Val Ala Ser Ala Ser Ser Ala
            180                 185                 190

Ser Asn Trp Ser Thr Ala Asp Asn Gly Ala Ser Glu Ala Ser Leu Phe
        195                 200                 205

Leu Leu Asp Phe Cys Ala Gly Pro Asp Leu Gly Ala Ala Asp Gln
        210                 215                 220

Leu Gln Leu Pro Gly Gly Tyr Tyr Tyr Pro Leu Asp Pro Ser Leu Ser
225                 230                 235                 240

Pro Val
```

```
<210> SEQ ID NO 226
<211> LENGTH: 413
<212> TYPE: DNA
<213> ORGANISM: Secale cereale

<400> SEQUENCE: 226
atggggaggg cgccgtgctg cgacagggcg gcggtgaaga ggggcccgtg gtcgccggag      60
gaggacgacg cgctgcgcga ctacatgcag cgctacggaa acaccggcag ctggatcacg     120
ctccccatga gaggtgggct caagaggtgc ggcaagagct gcaggctgcg gtggctcaac     180
tacctccgcc ccgacatccg ccacggcggc ttcaccgacg aggaggacac catcatctac     240
tccctctaca gccagctggg cagcaagtgg tcgctgatag cgtcgcagct ggagaggagg     300
acggacaacg acgtcaagaa ccactggaac accaagctca gaagcggct cgccgccgcg     360 gccgccgcct tctccacccg ccgttccccg tccttcatgc cgctaccggc gcc            413

<210> SEQ ID NO 227
<211> LENGTH: 138
<212> TYPE: PRT
<213> ORGANISM: Secale cereale

<400> SEQUENCE: 227

Met Gly Arg Ala Pro Cys Cys Asp Arg Ala Ala Val Lys Arg Gly Pro
1               5                   10                  15

Trp Ser Pro Glu Glu Asp Asp Ala Leu Arg Asp Tyr Met Gln Arg Tyr
            20                  25                  30

Gly Asn Thr Gly Ser Trp Ile Thr Leu Pro Met Arg Gly Gly Leu Lys
        35                  40                  45

Arg Cys Gly Lys Ser Cys Arg Leu Arg Trp Leu Asn Tyr Leu Arg Pro
    50                  55                  60

Asp Ile Arg His Gly Gly Phe Thr Asp Glu Asp Thr Ile Ile Tyr
65                  70                  75                  80

Ser Leu Tyr Ser Gln Leu Gly Ser Lys Trp Ser Leu Ile Ala Ser Gln
                85                  90                  95

Leu Glu Arg Arg Thr Asp Asn Asp Val Lys Asn His Trp Asn Thr Lys
```

```
              100                 105                 110
Leu Lys Lys Arg Leu Ala Ala Ala Ala Ala Phe Ser Thr Arg Arg
        115                 120                 125

Ser Pro Ser Phe Met Pro Leu Pro Ala Pro
130                 135

<210> SEQ ID NO 228
<211> LENGTH: 555
<212> TYPE: DNA
<213> ORGANISM: Solanum lycopersicum

<400> SEQUENCE: 228
atgggaagag ctccttgttg tgataagaat aatgttaaaa gagggccatg gtcaccagaa    60
gaagatgcta agcttaaaga attcattgaa aaatatggaa ctggtggtaa ttggattgct   120
cttcctctaa agctggatt aaagagatgt ggaaagagct gcagattaag atggctaaat    180
tatctaaggc caaatataaa gcatggtgat ttttctgatg aagaagatag gtaatatgc    240 agtttatatg ccagcattgg gagcaggtgg tcaattatag cagctcagtt accagggagg   300
accgacaatg atattaaaaa ctattggaac acaaagctta agaagaagct catgggtttt   360
attcagtcat catctaatat taaccagaga actaaatcac ctaatttatt attccctcct   420
acaagtactc ttcaaacaac ttttcaatcc caatctcaag catcaatttc aaatctttta   480
agagattcat atgtagagcc cattccacta gtccaaccaa atttcatgta caacaacaat   540
aacatgatga acttt                                                    555

<210> SEQ ID NO 229
<211> LENGTH: 185
<212> TYPE: PRT
<213> ORGANISM: Solanum lycopersicum

<400> SEQUENCE: 229

Met Gly Arg Ala Pro Cys Cys Asp Lys Asn Asn Val Lys Arg Gly Pro
1               5                   10                  15

Trp Ser Pro Glu Glu Asp Ala Lys Leu Lys Glu Phe Ile Glu Lys Tyr
            20                  25                  30

Gly Thr Gly Gly Asn Trp Ile Ala Leu Pro Leu Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Asp Glu Glu Asp Arg Val Ile Cys
65                  70                  75                  80

Ser Leu Tyr Ala Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Met Gly Phe Ile Gln Ser Ser Ser Asn Ile Asn
        115                 120                 125

Gln Arg Thr Lys Ser Pro Asn Leu Leu Phe Pro Pro Thr Ser Thr Leu
130                 135                 140

Gln Thr Thr Phe Gln Ser Gln Ser Gln Ala Ser Ile Ser Asn Leu Leu
145                 150                 155                 160

Arg Asp Ser Tyr Val Glu Pro Ile Pro Leu Val Gln Pro Asn Phe Met
                165                 170                 175

Tyr Asn Asn Asn Asn Met Met Asn Phe
            180                 185
```

<210> SEQ ID NO 230
<211> LENGTH: 476
<212> TYPE: DNA
<213> ORGANISM: Solanum tuberosum

<400> SEQUENCE: 230

```
atgggaagag ctccatgttg tgataaagca aatgtgaaga aagggccatg gtcacctgaa    60
gaagatgcaa aattaaaaga atatattaac aaatttggca ctggtggaaa ttggattgct   120
cttccacaaa aagctgggct aagaagatgt ggaaaaagct gcagattaag atggctaaat   180
tatcttaggc caaatattaa acacggagag ttttcagacg aagaagacag aatcatttgc   240
agcctttatg ctaacattgg aagcaggtgg tcaataatag cagctcaatt accaggcagg   300
acagataatg atatcaaaaa ctattggaac acaaagctca agaagaaatt aatgggattt   360
gtctcttcat ctcacaagat cattaggcct cttaatcatc atcattatca acaccaaatt   420
cccactaatt gttacaataa ttattcctca caaatttcac ttcttcaagc tccatc       476
```

<210> SEQ ID NO 231
<211> LENGTH: 159
<212> TYPE: PRT
<213> ORGANISM: Solanum tuberosum

<400> SEQUENCE: 231

```
Met Gly Arg Ala Pro Cys Cys Asp Lys Ala Asn Val Lys Lys Gly Pro
1               5                   10                  15
Trp Ser Pro Glu Glu Asp Ala Lys Leu Lys Glu Tyr Ile Asn Lys Phe
            20                  25                  30
Gly Thr Gly Gly Asn Trp Ile Ala Leu Pro Gln Lys Ala Gly Leu Arg
        35                  40                  45
Arg Cys Gly Lys Ser Cys Arg Leu Arg Trp Leu Asn Tyr Leu Arg Pro
    50                  55                  60
Asn Ile Lys His Gly Glu Phe Ser Asp Glu Glu Asp Arg Ile Ile Cys
65                  70                  75                  80
Ser Leu Tyr Ala Asn Ile Gly Ser Arg Trp Ser Ile Ile Ala Ala Gln
                85                  90                  95
Leu Pro Gly Arg Thr Asp Asn Asp Ile Lys Asn Tyr Trp Asn Thr Lys
            100                 105                 110
Leu Lys Lys Lys Leu Met Gly Phe Val Ser Ser His Lys Ile Ile
        115                 120                 125
Arg Pro Leu Asn His His His Tyr Gln His Ile Pro Thr Asn Cys
    130                 135                 140
Tyr Asn Asn Tyr Ser Ser Gln Ile Ser Leu Leu Gln Ala Pro Ser
145                 150                 155
```

<210> SEQ ID NO 232
<211> LENGTH: 471
<212> TYPE: DNA
<213> ORGANISM: Sorghum bicolor

<400> SEQUENCE: 232

```
atggggagag ctccgtgctg cgacaaggct actgtgaaga agggtccgtg gtcgccggag    60
gaggacgcca agctcaagtc ctacatcgag cagaacggca ccggcggtaa ctggatagcc   120
ctgcctcaga gataggtct gaagaggtgt ggcaagagct gccgcctccg gtggctcaac   180
tacctccggc caaacatcaa gcacggtggg ttctccgagg aggaagacag aataatcctt   240
```

| agcctctaca tcagcatagg cagcaggtgg tcgataatag cggcgcagct gccggggagg | 300 |
| acggacaatg acataaagaa ctactggaac acgaggctca agaagaagct cttcggcaag | 360 |
| caatcgcgca aggatcaacg gcagcatcag ttcatgcgcc agcaggcggc agcggcaaac | 420 |
| gatgggatga tgaagcaaga agcagcacaa cccgggatgc acccggaaca a | 471 |

<210> SEQ ID NO 233
<211> LENGTH: 157
<212> TYPE: PRT
<213> ORGANISM: Sorghum bicolor

<400> SEQUENCE: 233

```
Met Gly Arg Ala Pro Cys Cys Asp Lys Ala Thr Val Lys Lys Gly Pro
1               5                  10                  15
Trp Ser Pro Glu Glu Asp Ala Lys Leu Lys Ser Tyr Ile Glu Gln Asn
            20                  25                  30
Gly Thr Gly Gly Asn Trp Ile Ala Leu Pro Gln Lys Ile Gly Leu Lys
        35                  40                  45
Arg Cys Gly Lys Ser Cys Arg Leu Arg Trp Leu Asn Tyr Leu Arg Pro
    50                  55                  60
Asn Ile Lys His Gly Gly Phe Ser Glu Glu Asp Arg Ile Ile Leu
65                  70                  75                  80
Ser Leu Tyr Ile Ser Ile Gly Ser Arg Trp Ser Ile Ile Ala Ala Gln
                85                  90                  95
Leu Pro Gly Arg Thr Asp Asn Asp Ile Lys Asn Tyr Trp Asn Thr Arg
            100                 105                 110
Leu Lys Lys Lys Leu Phe Gly Lys Gln Ser Arg Lys Asp Gln Arg Gln
        115                 120                 125
His Gln Phe Met Arg Gln Ala Ala Ala Ala Asn Asp Gly Met Met
    130                 135                 140
Lys Gln Glu Ala Ala Gln Pro Gly Met His Pro Glu Gln
145                 150                 155
```

<210> SEQ ID NO 234
<211> LENGTH: 609
<212> TYPE: DNA
<213> ORGANISM: Sorghum bicolor

<400> SEQUENCE: 234

| atgggacgga cgccgtgctg cgacagggcg ccgtgaagc ggggcccgtg gtcgccggag | 60 |
| gaggacgagg cgctgcggag ctacgtccag cgccacggca cgcggcggcaa ctggatcgcc | 120 |
| atgcccaaga aagccgggct caagaggtgc ggcaagagct gcaggctgcg ctggctcaac | 180 |
| tacctccgcc ccgacatccg ccacggcggc ttcaccgccg aggaggacgc cgtcatcttg | 240 |
| tccctctaca cccagctcgg gagcaagtgg tcgctgatag cctcgcagat ggaggggagg | 300 |
| acggacaacg acgtcaagaa ccactggaac accaagctca gaagcgcct cctcgccgcc | 360 |
| gcgggcacct tctcgccggc accccacgcc cgggtgccgg cacccgcgcc tgctttccgt | 420 |
| accggacacg tttccccgtt gtcactggtc catcggttg gcataccgac cgtgaagaac | 480 |
| cgagcgtaca cctacgacga cttccttggc gccggcgctc gtgacccgtt cgccgccgcc | 540 |
| gacgggtcca cctcgggcgc cttccggggg tgtcggcctc aatggtccca ggggggacaa | 600 |
| cgggcccag | 609 |

<210> SEQ ID NO 235
<211> LENGTH: 203

```
<212> TYPE: PRT
<213> ORGANISM: Sorghum bicolor

<400> SEQUENCE: 235

Met Gly Arg Thr Pro Cys Cys Asp Arg Ala Ala Val Lys Arg Gly Pro
1               5                   10                  15

Trp Ser Pro Glu Glu Asp Glu Ala Leu Arg Ser Tyr Val Gln Arg His
            20                  25                  30

Gly Ser Gly Gly Asn Trp Ile Ala Met Pro Lys Lys Ala Gly Leu Lys
        35                  40                  45

Arg Cys Gly Lys Ser Cys Arg Leu Arg Trp Leu Asn Tyr Leu Arg Pro
    50                  55                  60

Asp Ile Arg His Gly Gly Phe Thr Ala Glu Glu Asp Ala Val Ile Leu
65                  70                  75                  80

Ser Leu Tyr Thr Gln Leu Gly Ser Lys Trp Ser Leu Ile Ala Ser Gln
                85                  90                  95

Met Glu Gly Arg Thr Asp Asn Asp Val Lys Asn His Trp Asn Thr Lys
            100                 105                 110

Leu Lys Lys Arg Leu Leu Ala Ala Gly Thr Phe Ser Pro Ala Pro
        115                 120                 125

His Ala Arg Val Pro Ala Pro Ala Pro Ala Phe Arg Thr Gly His Val
    130                 135                 140

Ser Pro Leu Ser Leu Val Pro Ser Val Gly Ile Pro Thr Val Lys Asn
145                 150                 155                 160

Arg Ala Tyr Thr Tyr Asp Asp Phe Leu Gly Ala Gly Ala Arg Asp Pro
                165                 170                 175

Phe Ala Ala Ala Asp Gly Ser Thr Ser Gly Ala Phe Arg Gly Cys Arg
            180                 185                 190

Pro Pro Met Val His Gly Gly Gln Arg Ala Gln
        195                 200

<210> SEQ ID NO 236
<211> LENGTH: 396
<212> TYPE: DNA
<213> ORGANISM: Sorghum propinquum

<400> SEQUENCE: 236
atggggcgcg cgccgtgctg cgacaaggcg agcgtgaagc gggggccctg gtcgcccgag     60
gaggacgagc agctgcggag ctacgtccag cgcaacggca tcggcggcaa ctggatcgcc    120
ctgccgcaga agcagggct gaaccggtgc ggcaagagct gccggctgcg gtggctcaac    180
tacctgcggc cggacatcaa gcacgggggc tacaccgagg aggaggaccg gatcatctgg    240
tcgctctaca gctccatcgg cagcaggtgg tccatcatcg cgtccaagct cccgggccgg    300
accgacaacg acgtcaagaa ctactggaac accaagctca agaagaaggc tatggccatg    360
gcggcggcgg ccggcctcag cgccagtagc agcgga                              396

<210> SEQ ID NO 237
<211> LENGTH: 132
<212> TYPE: PRT
<213> ORGANISM: Sorghum propinquum

<400> SEQUENCE: 237

Met Gly Arg Ala Pro Cys Cys Asp Lys Ala Ser Val Lys Arg Gly Pro
1               5                   10                  15

Trp Ser Pro Glu Glu Asp Glu Gln Leu Arg Ser Tyr Val Gln Arg Asn
            20                  25                  30
```

Gly Ile Gly Gly Asn Trp Ile Ala Leu Pro Gln Lys Ala Gly Leu Asn
          35                  40                  45

Arg Cys Gly Lys Ser Cys Arg Leu Arg Trp Leu Asn Tyr Leu Arg Pro
 50                  55                  60

Asp Ile Lys His Gly Gly Tyr Thr Glu Glu Asp Arg Ile Ile Trp
65                  70                  75                  80

Ser Leu Tyr Ser Ser Ile Gly Ser Arg Trp Ser Ile Ile Ala Ser Lys
                 85                  90                  95

Leu Pro Gly Arg Thr Asp Asn Asp Val Lys Asn Tyr Trp Asn Thr Lys
                100                 105                 110

Leu Lys Lys Lys Ala Met Ala Met Ala Ala Ala Gly Leu Ser Ala
                115                 120                 125

Ser Ser Ser Gly
      130

<210> SEQ ID NO 238
<211> LENGTH: 803
<212> TYPE: DNA
<213> ORGANISM: Taraxacum officinale

<400> SEQUENCE: 238

```
atggggagag caccttgctg tgataaagac aatgtaaaga aaggtccatg ggctcctgaa      60
gaagatgcta agcttaaagc atatattgaa gaacatggca ccgtggtaa ctggattgct     120
ttgcctcaga aaatcgggct caagagatgt ggaaagagtt gtcgcctccg gtggctaaat    180
tacctccggc caaatatcaa gcatggaggt ttctccgatg aagaagatcg cataatttgc    240
agcctctata ttagcatagg gagcaggtgg tctataattg cggcacaatt accggggcga    300
actgataacg atataaagaa ctactggaac acaaggctga agaagaagct cttgggtgca    360
ggtaaacaga gaaagaagaa aatatatgga agaaaacgag agttactaat gaaaaaagca    420
aggtcgacct catcggatat taatattcca tcatcgatag ttgtttccgg caaccaagac    480
ccagcttatt ggccggaaat gccgttgatg ccacctgtac cctactccaa taatcaagaa    540
ccgtgttttg ttaacgatca tgcttccata cgaaaaactac tcatcaagct tggaggacga    600
tttactaatt ccgatcatga taatggaagt caatccacca acacatcgt cgactctcac    660
tttccgatcg acactttcat tgatcttcag ggatcatcac aagaccatga tcagaagtta    720
attaatgcaa ttagtacgcc tctttcgtct tcttcatcat caatgttgct aaatagccca    780
tacaacatga tcatctttcc atc                                            803
```

<210> SEQ ID NO 239
<211> LENGTH: 268
<212> TYPE: PRT
<213> ORGANISM: Taraxacum officinale

<400> SEQUENCE: 239

Met Gly Arg Ala Pro Cys Cys Asp Lys Asp Asn Val Lys Lys Gly Pro
1               5                  10                  15

Trp Ala Pro Glu Glu Asp Ala Lys Leu Lys Ala Tyr Ile Glu Glu His
                20                  25                  30

Gly Thr Gly Gly Asn Trp Ile Ala Leu Pro Gln Lys Ile Gly Leu Lys
          35                  40                  45

Arg Cys Gly Lys Ser Cys Arg Leu Arg Trp Leu Asn Tyr Leu Arg Pro
 50                  55                  60

Asn Ile Lys His Gly Gly Phe Ser Asp Glu Glu Asp Arg Ile Ile Cys

```
              65                  70                  75                  80
Ser Leu Tyr Ile Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Arg
                100                 105                 110

Leu Lys Lys Lys Leu Leu Gly Ala Gly Lys Gln Arg Lys Glu Glu Ile
                115                 120                 125

Tyr Gly Arg Lys Arg Glu Leu Leu Met Lys Lys Ala Arg Ser Thr Ser
                130                 135                 140

Ser Asp Ile Asn Ile Pro Ser Ser Ile Val Ser Gly Asn Gln Asp
145                 150                 155                 160

Pro Ala Tyr Trp Pro Glu Met Pro Leu Met Pro Val Pro Tyr Ser
                165                 170                 175

Asn Asn Gln Glu Pro Cys Phe Val Asn Asp His Ala Ser Ile Arg Lys
                180                 185                 190

Leu Leu Ile Lys Leu Gly Gly Arg Phe Thr Asn Ser Asp His Asp Asn
                195                 200                 205

Gly Ser Gln Ser Thr Lys His Ile Val Asp Ser His Phe Pro Ile Asp
                210                 215                 220

Thr Phe Ile Asp Leu Gln Gly Ser Ser Gln Asp His Asp Gln Lys Leu
225                 230                 235                 240

Ile Asn Ala Ile Ser Thr Pro Leu Ser Ser Ser Ser Ser Met Leu
                245                 250                 255

Leu Asn Ser Pro Tyr Asn Met Ile Ile Phe Pro Ser
                260                 265

<210> SEQ ID NO 240
<211> LENGTH: 632
<212> TYPE: DNA
<213> ORGANISM: Triphysaria pusilla

<400> SEQUENCE: 240
atggggagag cgccttgttg tgacaaagcc aatgtaaaga gaggtccatg gtcacctgat      60
gaagacgatg ctcttaaatc ctacattcat aagcatggta ctggtggcaa ctggattgcc     120
ttgcctaaca aaattgggtt gaagagatgt ggaaagagtt gtcggctgag atggcttaat     180
tatctgcgcc caaacatcaa gcatggtggt tttactgaag aagaagataa ctttatttgc     240
aacctctata ttagtattgg aagcagatgg tctatcatcg cagctcaatt gcctggaaga     300
acagataacg atatcaaaaa ctactggaac actaggctaa ggaagaaact cttaggcagg     360
caacaaaggc gagaacaacg atccactaaa acaatatta ttagagtggc cagttctgat     420
caaaatcatc aaaattacac attagcccat gaatattatt cttcaaattt cagtttatac     480
cctcagccgc cgccgccacc accggcacat atggtggcgc cttcctttat ccaggcggca     540
tcgaatccac aaaccaatca catttccttc atttcaccat tagtcgaaga accaacgaca     600
tttgcagctt gttatgatga tcaatcacaa gt                                   632

<210> SEQ ID NO 241
<211> LENGTH: 211
<212> TYPE: PRT
<213> ORGANISM: Triphysaria pusilla

<400> SEQUENCE: 241

Met Gly Arg Ala Pro Cys Cys Asp Lys Ala Asn Val Lys Arg Gly Pro
1               5                   10                  15
```

```
Trp Ser Pro Asp Glu Asp Ala Leu Lys Ser Tyr Ile His Lys His
             20                  25                  30

Gly Thr Gly Gly Asn Trp Ile Ala Leu Pro Asn Lys Ile Gly Leu Lys
         35                  40                  45

Arg Cys Gly Lys Ser Cys Arg Leu Arg Trp Leu Asn Tyr Leu Arg Pro
     50                  55                  60

Asn Ile Lys His Gly Gly Phe Thr Glu Glu Asp Asn Phe Ile Cys
 65                  70                  75                  80

Asn Leu Tyr Ile Ser Ile Gly Ser Arg Trp Ser Ile Ile Ala Ala Gln
                 85                  90                  95

Leu Pro Gly Arg Thr Asp Asn Asp Ile Lys Asn Tyr Trp Asn Thr Arg
             100                 105                 110

Leu Arg Lys Lys Leu Leu Gly Arg Gln Gln Arg Glu Gln Arg Ser
         115                 120                 125

Thr Lys Asn Asn Ile Ile Arg Val Ala Ser Ser Asp Gln Asn His Gln
     130                 135                 140

Asn Tyr Thr Leu Ala His Glu Tyr Tyr Ser Ser Asn Phe Ser Leu Tyr
145                 150                 155                 160

Pro Gln Pro Pro Pro Pro Pro Ala His Met Val Ala Pro Ser Phe
                 165                 170                 175

Ile Gln Ala Ala Ser Asn Pro Gln Thr Asn His Ile Ser Phe Ile Ser
             180                 185                 190

Pro Leu Val Glu Glu Pro Thr Thr Phe Ala Ala Cys Tyr Asp Asp Gln
         195                 200                 205

Ser Gln Val
     210

<210> SEQ ID NO 242
<211> LENGTH: 651
<212> TYPE: DNA
<213> ORGANISM: Triphysaria pusilla

<400> SEQUENCE: 242
atgggaagag caccgtgctg tgacaaagcc gatgtgaaga agggaccctg gtcaactgaa      60
gaagatgcaa cattgaaagc ttatatcgag aaatatggaa ctggtggaaa ttggattgcc     120
cttcctcaga aaatcgggct aagagatgt gggaagagtt gcagactgag gtggttgaat     180
tacttgaggc ctaatctcaa gcatggtggt tttactgatg aagaagataa tgttatttgc     240
agcctctata tcagcattgg cagcaggtgg tctataatag ctgcccagtt accaggaaga     300
acagataatg acatcgagaa ttactggaac accaggctca agaaaaaatt actcggcagg     360
cgcaaacaag ctaattataa cactaaccga ctctcggctt taggcggcca ggatgagcca     420
aaagaagatg cctataactt gcaaaaccta agcagttcag ccctcgaaag actccaactc     480
cacatgcatc ttcaaaccct tcaaaaccat aattcctcat tttattccaa taatccggca     540
atttggccca agatgatcga aaccctaaac tccttaaacg ataaacaaaa catgaataat     600
ctgatgcagc aaattatccc ctccacccct catcaactct gtccgcctgt a              651

<210> SEQ ID NO 243
<211> LENGTH: 217
<212> TYPE: PRT
<213> ORGANISM: Triphysaria pusilla

<400> SEQUENCE: 243

Met Gly Arg Ala Pro Cys Cys Asp Lys Ala Asp Val Lys Lys Gly Pro
1               5                   10                  15
```

Trp Ser Thr Glu Glu Asp Ala Thr Leu Lys Ala Tyr Ile Glu Lys Tyr
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
 50                  55                  60

Asn Leu Lys His Gly Gly Phe Thr Asp Glu Glu Asp Asn Val Ile Cys
 65                  70                  75                  80

Ser Leu Tyr Ile Ser Ile Gly Ser Arg Trp Ser Ile Ala Ala Gln
                 85                  90                  95

Leu Pro Gly Arg Thr Asp Asn Asp Ile Glu Asn Tyr Trp Asn Thr Arg
                100                 105                 110

Leu Lys Lys Lys Leu Leu Gly Arg Arg Lys Gln Ala Asn Tyr Asn Thr
                115                 120                 125

Asn Arg Leu Ser Ala Leu Gly Gly Gln Asp Glu Pro Lys Glu Asp Ala
 130                 135                 140

Tyr Asn Leu Gln Asn Leu Ser Ser Ser Ala Leu Glu Arg Leu Gln Leu
145                 150                 155                 160

His Met His Leu Gln Thr Leu Gln Asn His Asn Ser Ser Phe Tyr Ser
                165                 170                 175

Asn Asn Pro Ala Ile Trp Pro Lys Met Ile Glu Thr Leu Asn Ser Leu
                180                 185                 190

Asn Asp Lys Gln Asn Met Asn Asn Leu Met Gln Gln Ile Ile Pro Ser
                195                 200                 205

Thr Pro His Gln Leu Cys Pro Pro Val
        210                 215

<210> SEQ ID NO 244
<211> LENGTH: 636
<212> TYPE: DNA
<213> ORGANISM: Triphysaria pusilla
<220> FEATURE:
<221> NAME/KEY: misc_feature
<222> LOCATION: (609)..(609)
<223> OTHER INFORMATION: n is any nucleotide

<400> SEQUENCE: 244
atgggaagag caccttgctg tgacaaggca aaagtgaaga aagggccatg gtctcctgat      60
gaagattcta aactaaaaga atatatacaa aaacatggga ctattggaaa ttggattgct     120
ctcccacaca aagttggtct aaaagatgt ggcaaaagct gcagattgag atggctcaat     180
tatctgagac caaatattaa gcatggagat ttttcagatg atgaggatac aattatttgc     240
acacttttta atagcattgg aagcaggtgg tcagtaatag cagcacaatt accaggcaga     300
acagacaatg atatcaagaa ctactggaac acaaagctca aaagaaaact catggccaat     360 aatatttta tgcctccaat ttctacccat taccaaatga ggcctcacca agctaccatg     420
taccctacaa caccaaataa ctcctaccca ataccatatg aatatgccat tagcaattgt     480
tatactaatt cgaccccaat taaaatttat cagcccatat cccctaactt caccacgcta     540
ttttcttcaa actcgatcgg cccgatgggt taatgggcc cggcccggcc tggatgggtt     600
acaaagatna tgaagaaatc ttccctgtgt tggtgg                              636

<210> SEQ ID NO 245
<211> LENGTH: 212
<212> TYPE: PRT
<213> ORGANISM: Triphysaria pusilla

```
<220> FEATURE:
<221> NAME/KEY: MISC_FEATURE
<222> LOCATION: (203)..(203)
<223> OTHER INFORMATION: X is any amino acid

<400> SEQUENCE: 245

Met Gly Arg Ala Pro Cys Cys Asp Lys Ala Lys Val Lys Lys Gly Pro
1               5                   10                  15

Trp Ser Pro Asp Glu Asp Ser Lys Leu Lys Glu Tyr Ile Gln Lys His
            20                  25                  30

Gly Thr Ile Gly Asn Trp Ile Ala Leu Pro His Lys Val Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Ser Asp Asp Glu Asp Thr Ile Ile Cys
65                  70                  75                  80

Thr Leu Phe Asn Ser Ile Gly Ser Arg Trp Ser Val Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Met Ala Asn Asn Ile Phe Met Pro Pro Ile Ser
        115                 120                 125

Thr His Tyr Gln Met Arg Pro His Gln Ala Thr Met Tyr Pro Thr Thr
    130                 135                 140

Pro Asn Asn Ser Tyr Pro Ile Pro Tyr Glu Tyr Ala Ile Ser Asn Cys
145                 150                 155                 160

Tyr Thr Asn Ser Thr Pro Ile Lys Ile Tyr Gln Pro Ile Ser Pro Asn
                165                 170                 175

Phe Thr Thr Leu Phe Ser Ser Asn Ser Ile Gly Pro Asp Gly Leu Met
            180                 185                 190

Gly Pro Ala Arg Pro Gly Trp Val Thr Lys Xaa Met Lys Lys Ser Ser
        195                 200                 205

Leu Cys Trp Trp
    210

<210> SEQ ID NO 246
<211> LENGTH: 419
<212> TYPE: DNA
<213> ORGANISM: Triphysaria versicolor

<400> SEQUENCE: 246
ggaagagcac cttgctgtga caaggcaaaa gtgaagaaag gccatggtc tcctgatgaa      60 gattctaaac taaaggaata tatacaaaaa catgggacta ttggaaattg gattgctctc    120
ccacacaaag ttggtcttaa aagatgtggc aaaagctgca gattgagatg gctcaattat    180
ctgagaccaa atattaagca tggagatttt tcagatgatg aggatacaat tatttgcaca    240 cttttttaata gcattggaag caggtggtca gtaatagcag cacaattacc aggcagaaca    300
gacaatgata tcaagaacta ctggaacaca aagctcaaaa agaaactcat ggccaataat    360 attttttatgc ctccaatttc tacccattac caaatgaggc ctcaccaagc taccatgta     419

<210> SEQ ID NO 247
<211> LENGTH: 606
<212> TYPE: DNA
<213> ORGANISM: Triphysaria versicolor

<400> SEQUENCE: 247
```

```
atgggaagag caccttgctg tgacaaggca aaagtgaaga aagggccatg gtctcctgat      60
gaagattcta aactaaaaga atatatacaa aaacatggga ctattggaaa ttggattgct     120
ctcccacaca aagttggtct taaaagatgt ggcaaaagct gcagattgag atggctcaat     180
tatctgagac caaatattaa gcatggagat ttttcagatg atgaggatac aattatttgc     240
acacttttta atagcattgg aagcaggtgg tcagtaatag cagcacaatt accaggcaga     300
acagacaatg atatcaagaa ctactggaac acaaagctca aaagaaaact catggccaat     360
aatatttta tgcctccaat ttctacccat taccaaatga ggcctcacca agctaccatg     420
taccatacaa caccaaataa ctcctaccca ataccatatg aatatgacat tagcaattgt     480
tatactaatt cgaccccaat taaaatttat cagcccatat ccctaacttt caccacgcta     540
ttttcttcaa actcgatcgg cccggatggg ttaatgggcc cggcccggcc tggatgggtt     600
aacaaa                                                                606
```

<210> SEQ ID NO 248
<211> LENGTH: 202
<212> TYPE: PRT
<213> ORGANISM: Triphysaria versicolor

<400> SEQUENCE: 248

```
Met Gly Arg Ala Pro Cys Cys Asp Lys Ala Lys Val Lys Lys Gly Pro
1               5                   10                  15
Trp Ser Pro Asp Glu Asp Ser Lys Leu Lys Glu Tyr Ile Gln Lys His
            20                  25                  30
Gly Thr Ile Gly Asn Trp Ile Ala Leu Pro His Lys Val Gly Leu Lys
        35                  40                  45
Arg Cys Gly Lys Ser Cys Arg Leu Arg Trp Leu Asn Tyr Leu Arg Pro
    50                  55                  60
Asn Ile Lys His Gly Asp Phe Ser Asp Asp Glu Asp Thr Ile Ile Cys
65                  70                  75                  80
Thr Leu Phe Asn Ser Ile Gly Ser Arg Trp Ser Val Ile Ala Ala Gln
                85                  90                  95
Leu Pro Gly Arg Thr Asp Asn Asp Ile Lys Asn Tyr Trp Asn Thr Lys
            100                 105                 110
Leu Lys Lys Lys Leu Met Ala Asn Asn Ile Phe Met Pro Pro Ile Ser
        115                 120                 125
Thr His Tyr Gln Met Arg Pro His Gln Ala Thr Met Tyr His Thr Thr
    130                 135                 140
Pro Asn Asn Ser Tyr Pro Ile Pro Tyr Glu Tyr Asp Ile Ser Asn Cys
145                 150                 155                 160
Tyr Thr Asn Ser Thr Pro Ile Lys Ile Tyr Gln Pro Ile Ser Pro Asn
                165                 170                 175
Phe Thr Thr Leu Phe Ser Ser Asn Ser Ile Gly Pro Asp Gly Leu Met
            180                 185                 190
Gly Pro Ala Arg Pro Gly Trp Val Asn Lys
        195                 200
```

<210> SEQ ID NO 249
<211> LENGTH: 903
<212> TYPE: DNA
<213> ORGANISM: Tricticum aestivum

<400> SEQUENCE: 249

```
atggggaggg cgccgtgctg cgacaaggcg acggtgaaga agggcccctg gtcgccggag      60
```

```
gaggacgcca agctcaaggc ctacatcgac gagaatggca ccggcggcaa ctggatcgcc    120
ctgccgcaga gatcgggct gaagaggtgc ggcaaaagct gtaggctcag atggctcaac    180
tatctgaggc caaacatcaa gcacggcgac ttcacagagg aagaggaaca catcatttgc    240
agcctctaca ttagcatcgg cagcaggtgg tcgatcatcg cggcgcagct gccgggcaga    300
acggacaacg acatcaagaa ctactggaac accaagctca agaagaagct cctcggcaag    360
cgcgcgccgt cccgccgcct gcagcgcgcc aaccaagacg cgccgatgcc ctactcctac    420
ctggcggcgg cggcggcag cgccagcagc agcgggaacg ctagcggacg tcgtggaagc    480
cgagcaacag ctaaaccctt ccgctggagc gagctacgac atgccggtgc cgggcggttt    540
cgaggagcga tccgcctcca agctagggtt tggctctgct gccggcgagg ccgctggagt    600
ggccagtacc gtcgagatga gctcggcgtc aatggtaggc ggtggcttcg gctacggcca    660
cgtcgacgag ctgtacgact tcctctacag caagcagctt gccgcggccg gagcctttca    720
aggcggagtt cctcccctgc cggagctgca gtgcccggat ggcggcgccg tcgttggtgc    780
cgacgagaag ttctccacgt ggatggcgtc ttgcgatcac tatgttccta cgaccggcgg    840
ccagcagctc cagctccaag gtggaaactc aatgaatctg caggatttcg ttttagggta    900
tga                                                                 903
```

<210> SEQ ID NO 250
<211> LENGTH: 300
<212> TYPE: PRT
<213> ORGANISM: Tricticum aestivum

<400> SEQUENCE: 250

```
Met Gly Arg Ala Pro Cys Cys Asp Lys Ala Thr Val Lys Lys Gly Pro
1               5                   10                  15

Trp Ser Pro Glu Glu Asp Ala Lys Leu Lys Ala Tyr Ile Asp Glu Asn
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Asp Phe Thr Glu Glu Glu His Ile Ile Cys
65                  70                  75                  80

Ser Leu Tyr Ile Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Leu Gly Lys Arg Ala Pro Ser Arg Arg Leu Gln
        115                 120                 125

Arg Ala Asn Gln Asp Ala Pro Met Pro Tyr Ser Tyr Leu Ala Ala Gly
    130                 135                 140

Gly Gly Ser Ala Ser Ser Ser Gly Asn Ala Ser Gly Arg Arg Gly Ser
145                 150                 155                 160

Arg Ala Thr Ala Lys Pro Phe Arg Trp Ser Glu Leu Arg His Ala Gly
                165                 170                 175

Ala Gly Arg Phe Arg Gly Ala Ile Arg Leu Gln Ala Arg Val Trp Leu
            180                 185                 190

Cys Cys Arg Arg Gly Arg Trp Ser Gly Gln Tyr Arg Arg Asp Glu Leu
        195                 200                 205

Gly Val Asn Gly Arg Arg Trp Leu Arg Leu Arg Pro Arg Arg Arg Ala
    210                 215                 220
```

```
Val Arg Leu Pro Leu Gln Gln Ala Ala Cys Arg Gly Arg Ser Leu Ser
225                 230                 235                 240

Arg Arg Ser Ser Ser Pro Ala Gly Ala Val Pro Gly Trp Arg Arg
            245                 250                 255

Arg Arg Trp Cys Arg Arg Glu Val Leu His Val Asp Gly Val Leu Arg
            260                 265                 270

Ser Leu Cys Ser Tyr Asp Arg Arg Pro Ala Ala Pro Ala Pro Arg Trp
            275                 280                 285

Lys Leu Asn Glu Ser Ala Gly Phe Arg Phe Arg Val
            290                 295                 300

<210> SEQ ID NO 251
<211> LENGTH: 648
<212> TYPE: DNA
<213> ORGANISM: Vaccinium corymbosum

<400> SEQUENCE: 251
atgggaagag ctccatgttg tgacaaggca aatgtgaaga aagggccatg gtccctgaa      60 gaagatgcaa agctaaaaga gtacatagat aagcatggga ctggagggaa ttggattgct    120
ctccctcaaa aagcagccct caaaagatgt ggaaaaagct gcagattgag atggctcaac    180
tatcttagac caaatatcaa acatggagag ttctctgatg atgaagatca taaaatctgc    240
agcctcttca ctactattgg aagcaggtgg tccataatag cagctcaatt gccaggaaga    300
acagataacg atatcaaaaa ctattggaac actaagctca agaagaaatt catgggaaaa    360
ttattccctc atccatctca aaatcagaga aaatcccacc aatccccaaa ttacccttca    420
tttttcccat tatattcacc acaatcccct acccaaacta gccatttcac aacctacgaa    480
aaccccattt cactcccacc aagttttttg aattccagtg ctaattttc tctctgatgcc    540 actccaacaa ctattctaca agcccaagag agttatgtgg gtcccatgtt tggaggtgaa    600
gcaagttcca gttctgatgg gagttgcagc aaccaggtga tcagaggg              648

<210> SEQ ID NO 252
<211> LENGTH: 216
<212> TYPE: PRT
<213> ORGANISM: Vaccinium corymbosum

<400> SEQUENCE: 252

Met Gly Arg Ala Pro Cys Cys Asp Lys Ala Asn Val Lys Lys Gly Pro
1               5                   10                  15

Trp Ser Pro Glu Glu Asp Ala Lys Leu Lys Glu Tyr Ile Asp Lys His
            20                  25                  30

Gly Thr Gly Gly Asn Trp Ile Ala Leu Pro Gln Lys Ala Ala Leu Lys
        35                  40                  45

Arg Cys Gly Lys Ser Cys Arg Leu Arg Trp Leu Asn Tyr Leu Arg Pro
    50                  55                  60

Asn Ile Lys His Gly Glu Phe Ser Asp Asp Glu Asp His Lys Ile Cys
65                  70                  75                  80

Ser Leu Phe Thr Thr Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Phe Met Gly Lys Leu Phe Pro His Pro Ser Gln Asn
        115                 120                 125

Gln Arg Lys Ser His Gln Ser Pro Asn Tyr Pro Ser Phe Phe Pro Leu
```

```
                130                 135                 140
Tyr Ser Pro Gln Ser Pro Thr Gln Thr Ser His Phe Thr Thr Tyr Glu
145                 150                 155                 160

Asn Pro Ile Ser Leu Pro Pro Ser Phe Leu Asn Ser Ser Ala Asn Phe
                165                 170                 175

Ser Ser Asp Ala Thr Pro Thr Thr Ile Leu Gln Ala Gln Glu Ser Tyr
            180                 185                 190

Val Gly Pro Met Phe Gly Gly Glu Ala Ser Ser Ser Asp Gly Ser
        195                 200                 205

Cys Ser Asn Gln Val Ile Arg Gly
    210                 215

<210> SEQ ID NO 253
<211> LENGTH: 1020
<212> TYPE: DNA
<213> ORGANISM: Vitis vinifera

<400> SEQUENCE: 253
atggggagag ctccttgctg tgacaaagcc aacgtcaaga aagggccatg gtcaccagag     60
gaagatgcca agctcaagac ttatattgag aaaaacggca ctgggggcaa ctggatagcc    120
ttacctcaaa agattggcct taagcgatgt gggaagagct gccgcctccg ctggttgaat    180
tatctcaggc ccaatatcaa acatggagga ttttcagagg aggaggataa catcatttgc    240
agcctctata agtattgg aagcaggtgg tccgtcatcg cgactcaatt accgggaaga     300
actgataatg atattaagaa ctactggaac acaaggttga agaaaaagct actcggcaag    360
cagcggaaag aacaacaggc tcgccgagct aactacgtca agcaagagat gaagagagaa    420
cctgggattt ttgtggttcc tgatcaggcc gttggcagaa acccttattg gcggagcta     480 cctgcagtat ctgtgcatcc gaaccaagat ccggatatca aggaccaagc atccattaag    540
aaattgctga tcaagctggg aggaagattt ggtgatgatg tcaacaacc aggcagtaac     600 agcataaact ttcagtaccc tcttgatatt ccaccgcac aagatggtcc atatgagaca     660
tccatgaaca tgtttgcctc atctacgtcg accatgaatt caatcaacag tacgggttcc    720
caattgccaa cacccacta tgacgtcaat ggatcagctt caaatgttct tcaagggtat    780
aacagcctcc taaatgaact ggtgtatggc aacccacaac aattagatgg ctctgggagc    840
ttttacggaa tagaagacat cgccaatggt agcactggga ctagctccgc agaaagcagc    900
agttggggag atataaactc tctggtttac ccctctatca tctccaatta tggagttggc    960
caacaagggc cattacaaga ttctggtttt gaagagttga ggtacctggg ctcccaatag   1020

<210> SEQ ID NO 254
<211> LENGTH: 339
<212> TYPE: PRT
<213> ORGANISM: Vitis vinifera

<400> SEQUENCE: 254

Met Gly Arg Ala Pro Cys Cys Asp Lys Ala Asn Val Lys Lys Gly Pro
1               5                   10                  15

Trp Ser Pro Glu Glu Asp Ala Lys Leu Lys Thr Tyr Ile Glu Lys Asn
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60
```

| | | | | | | | | | | | | | | |
|---|---|---|---|---|---|---|---|---|---|---|---|---|---|---|
|Asn|Ile|Lys|His|Gly|Gly|Phe|Ser|Glu|Glu|Glu|Asp|Asn|Ile|Ile|Cys|
|65| | | |70| | | |75| | | |80| | |

Ser Leu Tyr Ile Ser Ile Gly Ser Arg Trp Ser Val Ile Ala Thr Gln
            85                  90                  95

Leu Pro Gly Arg Thr Asp Asn Asp Ile Lys Asn Tyr Trp Asn Thr Arg
        100                 105                 110

Leu Lys Lys Lys Leu Leu Gly Lys Gln Arg Lys Glu Gln Gln Ala Arg
        115                 120                 125

Arg Ala Asn Tyr Val Lys Gln Glu Met Lys Arg Glu Pro Gly Ile Phe
        130                 135                 140

Val Val Pro Asp Gln Ala Val Gly Arg Asn Pro Tyr Trp Ala Glu Leu
145                 150                 155                 160

Pro Ala Val Ser Val His Pro Asn Gln Asp Pro Asp Ile Lys Asp Gln
                165                 170                 175

Ala Ser Ile Lys Lys Leu Leu Ile Lys Leu Gly Gly Arg Phe Gly Asp
            180                 185                 190

Asp Gly Gln Gln Pro Gly Ser Asn Ser Ile Asn Phe Gln Tyr Pro Leu
        195                 200                 205

Asp Ile Ser Thr Ala Gln Asp Gly Pro Tyr Glu Thr Ser Met Asn Met
210                 215                 220

Phe Ala Ser Ser Thr Ser Thr Met Asn Ser Ile Asn Ser Thr Gly Ser
225                 230                 235                 240

Gln Leu Pro Asn Thr His Tyr Asp Val Asn Gly Ser Ala Ser Asn Val
                245                 250                 255

Leu Gln Gly Tyr Asn Ser Leu Leu Asn Glu Leu Val Tyr Gly Asn Pro
            260                 265                 270

Gln Gln Leu Asp Gly Ser Gly Ser Phe Tyr Gly Ile Glu Asp Ile Ala
        275                 280                 285

Asn Gly Ser Thr Gly Thr Ser Ser Ala Glu Ser Ser Trp Gly Asp
        290                 295                 300

Ile Asn Ser Leu Val Tyr Pro Ser Ile Ile Ser Asn Tyr Gly Val Gly
305                 310                 315                 320

Gln Gln Gly Pro Leu Gln Asp Ser Gly Phe Glu Glu Leu Arg Tyr Leu
                325                 330                 335

Gly Ser Gln

<210> SEQ ID NO 255
<211> LENGTH: 1101
<212> TYPE: DNA
<213> ORGANISM: Vitis vinifera

<400> SEQUENCE: 255

```
atgggtcgag ctccatgctg tgacaaagcc aacgtgaaga agggaccatg gtccctgag      60 gaggatgcta agcttaaaac ttacattgag caatatggta ctggaggcaa ctggattgct     120
cttccccaga aaataggact taagagatgt ggaaaaagtt gcagactgag atggttgaat     180
tacttgagac ctaacatcaa gcatggtgga ttctctgaag aggaagacag catcatctgc     240
aacctctata agtattgt ttttttttt ttgtggtcgg taattgcagc ccaattgcct        300
ggaagaacag ataatgacat taagaactac tggaacacaa gactgaagaa gaagttgctt    360
ggaaagcgta acaatctca tttcaatcga ctttcggttg caggtcagga ccctaaagat     420
gcaactggtg tagaagataa tccatattca caggccttaa gcaattctgc ccttgaaaga    480
ctgcagctcc atatgcagct tcagagcctg caacaccct ttgctttcta caataatcct     540
```

-continued

```
gcactgtggc ccaagctgca tcccctccaa gaaaagctga tccagaacct ccagaatgag    600
ctccccagcc ctctgatgca acataccca cctagttctg acccgatggg acaagaacag    660
aagtctgggt tctatgaacc gcccactgct tccatcacac ttcaacaaga gtatccgaaa    720
accaacaatc caagggaga tgaatttgag aaatctttaa atgttttgcc ctcctcagac    780
agttcgatgg cctacaacag cgaaaatatg gtgggtgcac ctattatgtc taaaccagat    840
ggtgtagacc aatccaacat tgcacaacaa gcagtatcaa cctttcaagc tgagcttgat    900
gacttcctta ataacaaaat ggttggtttc ctcccacagg aagagcagat gactgaaata    960
gatggctcca aggacagctt ggcttggtgg tctaatgact ttgacacaaa atcggcatcc   1020
tcacactctt gggattccac ttctgttatt cagtctgagg ggatgttcca agattatgta   1080
ttaggttaca atctgcagtg a                                             1101
```

<210> SEQ ID NO 256
<211> LENGTH: 366
<212> TYPE: PRT
<213> ORGANISM: Vitis vinifera

<400> SEQUENCE: 256

```
Met Gly Arg Ala Pro Cys Cys Asp Lys Ala Asn Val Lys Lys Gly Pro
1               5                   10                  15

Trp Ser Pro Glu Glu Asp Ala Lys Leu Lys Thr Tyr Ile Glu Gln Tyr
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Gly Phe Ser Glu Glu Asp Ser Ile Ile Cys
65                  70                  75                  80

Asn Leu Tyr Ile Ser Ile Val Phe Phe Phe Leu Trp Ser Val Ile Ala
                85                  90                  95

Ala Gln Leu Pro Gly Arg Thr Asp Asn Asp Ile Lys Asn Tyr Trp Asn
            100                 105                 110

Thr Arg Leu Lys Lys Lys Leu Leu Gly Lys Arg Lys Gln Ser His Phe
        115                 120                 125

Asn Arg Leu Ser Val Ala Gly Gln Asp Pro Lys Asp Ala Thr Gly Val
    130                 135                 140

Glu Asp Asn Pro Tyr Ser Gln Ala Leu Ser Asn Ser Ala Leu Glu Arg
145                 150                 155                 160

Leu Gln Leu His Met Gln Leu Gln Ser Leu Gln His Pro Phe Ala Phe
                165                 170                 175

Tyr Asn Asn Pro Ala Leu Trp Pro Lys Leu His Pro Leu Gln Glu Lys
            180                 185                 190

Leu Ile Gln Asn Leu Gln Asn Glu Leu Pro Ser Pro Leu Met Gln His
        195                 200                 205

Thr Pro Pro Ser Ser Asp Pro Met Gly Gln Glu Gln Lys Ser Gly Phe
    210                 215                 220

Tyr Glu Pro Pro Thr Ala Ser Ile Thr Leu Gln Gln Glu Tyr Pro Lys
225                 230                 235                 240

Thr Asn Asn Pro Lys Gly Asp Glu Phe Glu Lys Ser Leu Asn Val Leu
                245                 250                 255

Pro Ser Ser Asp Ser Ser Met Ala Tyr Asn Ser Glu Asn Met Val Gly
            260                 265                 270
```

Ala Pro Ile Met Ser Lys Pro Asp Gly Val Asp Gln Ser Asn Ile Ala
            275                 280                 285

Gln Gln Ala Val Ser Thr Phe Gln Ala Glu Leu Asp Asp Phe Leu Asn
        290                 295                 300

Asn Lys Met Val Gly Phe Leu Pro Gln Glu Gln Met Thr Glu Ile
305                 310                 315                 320

Asp Gly Ser Lys Asp Ser Leu Ala Trp Trp Ser Asn Asp Phe Asp Thr
                325                 330                 335

Lys Ser Ala Ser His Ser Trp Asp Ser Thr Ser Val Ile Gln Ser
            340                 345                 350

Glu Gly Met Phe Gln Asp Tyr Val Leu Gly Tyr Asn Leu Gln
        355                 360                 365

<210> SEQ ID NO 257
<211> LENGTH: 1023
<212> TYPE: DNA
<213> ORGANISM: Vitis vinifera

<400> SEQUENCE: 257
atggggaggg caccttgctg tgacaaagcc aacgtcaaga aaggcccatg gtcgcctgaa      60
gaagatgcca agctcaagtc atatattgag cagcatggcc ctggtggtaa ttggatcgct     120
ttgccacaaa aaattggcct caagagatgt gggaagagct gccgccttag atggttaaac     180
tatctccgcc aaatatcag gcacggagga ttctctgaag aagaagataa catcatctgt     240
agcctgtata aagtattgg aagcaggtgg tctgttattg cagcacaatt accaggacga     300
actgacaatg atataaagaa ctactggaat acgagactga agaagaagct ccttggtaag     360
cagcgcaaag aacaacaggc tcgcagaggt agctgcccga agcaagagat gaaaagagca     420
agtgggaacg ccatggtttc tgataatgaa aacttaaacc cttactggcc tgagttgccc     480
gtgccagcac caataccgta cccaaacgaa gaaccacgct caacgatca ttcatccatc     540
agaagattgt tgatcaggct tgggggaaga ttttctgatg acggacaacc actccaaaac     600
gggacaaatc ttcagctccc gattgatatt tcatccgttc aacaaccttt tgaccactca     660
gtaaactttc tgtcttcttc tcctatgaat gccctaaaca ccctcgttc tgaatttcca     720
aacgctgagt acaatatgga agggggaggg ctacacatgc tacaaggaca gaacagtttt     780
ttagctgagc tggaggagat ggcttgtagc aacccacaaa gattagatgg ctggagttc     840
ttatatgcgc aggacatggc caataacaaa cccggatcaa ctgcttatga gcaaagtctc     900
agttggggtg agacgagctc tctggtttat cctcctgttg cttccaacta tgaaggtctt     960
caacagcaag gggtgacgca agaacatgac tttgatgagt tgaggtaccc taccccgcga    1020
taa                                                                  1023

<210> SEQ ID NO 258
<211> LENGTH: 340
<212> TYPE: PRT
<213> ORGANISM: Vitis vinifera

<400> SEQUENCE: 258

Met Gly Arg Ala Pro Cys Cys Asp Lys Ala Asn Val Lys Lys Gly Pro
1               5                   10                  15

Trp Ser Pro Glu Glu Asp Ala Lys Leu Lys Ser Tyr Ile Glu Gln His
            20                  25                  30

Gly Thr Gly Gly Asn Trp Ile Ala Leu Pro Gln Lys Ile Gly Leu Lys
        35                  40                  45

```
Arg Cys Gly Lys Ser Cys Arg Leu Arg Trp Leu Asn Tyr Leu Arg Pro
 50                  55                  60

Asn Ile Arg His Gly Gly Phe Ser Glu Glu Asp Asn Ile Ile Cys
 65                  70                  75                  80

Ser Leu Tyr Ile Ser Ile Gly Ser Arg Trp Ser Val Ile Ala Ala Gln
                 85                  90                  95

Leu Pro Gly Arg Thr Asp Asn Asp Ile Lys Asn Tyr Trp Asn Thr Arg
                100                 105                 110

Leu Lys Lys Lys Leu Leu Gly Lys Gln Arg Lys Glu Gln Gln Ala Arg
                115                 120                 125

Arg Gly Ser Cys Pro Lys Gln Glu Met Lys Arg Ala Ser Gly Asn Ala
130                 135                 140

Met Val Ser Asp Asn Glu Asn Leu Asn Pro Tyr Trp Pro Glu Leu Pro
145                 150                 155                 160

Val Pro Ala Pro Ile Pro Tyr Pro Asn Glu Glu Pro Arg Phe Asn Asp
                165                 170                 175

His Ser Ser Ile Arg Arg Leu Leu Ile Arg Leu Gly Gly Arg Phe Ser
                180                 185                 190

Asp Asp Gly Gln Pro Leu Gln Asn Gly Thr Asn Leu Gln Leu Pro Ile
                195                 200                 205

Asp Ile Ser Ser Val Gln Gln Pro Phe Asp His Ser Val Asn Phe Leu
210                 215                 220

Ser Ser Ser Pro Met Asn Ala Leu Asn Asn Pro Arg Ser Glu Phe Pro
225                 230                 235                 240

Asn Ala Glu Tyr Asn Met Glu Gly Gly Leu His Met Leu Gln Gly
                245                 250                 255

Gln Asn Ser Phe Leu Ala Glu Leu Glu Glu Met Ala Cys Ser Asn Pro
                260                 265                 270

Gln Arg Leu Asp Gly Leu Glu Phe Leu Tyr Ala Gln Asp Met Ala Asn
                275                 280                 285

Asn Lys Pro Gly Ser Thr Ala Tyr Glu Gln Ser Leu Ser Trp Gly Glu
                290                 295                 300

Thr Ser Ser Leu Val Tyr Pro Pro Val Ala Ser Asn Tyr Glu Gly Leu
305                 310                 315                 320

Gln Gln Gln Gly Val Thr Gln Glu His Asp Phe Asp Glu Leu Arg Tyr
                325                 330                 335

Pro Thr Pro Arg
                340

<210> SEQ ID NO 259
<211> LENGTH: 510
<212> TYPE: DNA
<213> ORGANISM: Vitis vinifera

<400> SEQUENCE: 259
atgggaagag ctccttgctg tgacaaggca aatgtgaaga aaggcccatg gtcacctgaa      60
gaagactcaa agcttaagga gtatattgag aaatatggga ctgggggaaa ttggattgct     120
ctcccacaaa aagctggtct taagagatgt gggaaaagct gcagattgag atggttgaac     180
tatctcagac ccaacattaa acatggagaa ttctctgatg atgaagatag gatcatctgc     240
agcgtctttg ctagcattgg aagcaagtgg tcagtaatag caaattactt gccggggagg     300
actgataacg atatcaagaa ctactggaac accaagctga agaagaaact catggggatg     360
gtgcctgtat ctcagagaaa accccatcaa gctaccttct ctcatcatct tcaaacctat     420
```

```
tcatcgttat catcacctto acatgcggta acaacaacag caacttcatc atcatatgaa        480
agcaacagca gcaacccctta ttacactcca                                        510
```

<210> SEQ ID NO 260
<211> LENGTH: 170
<212> TYPE: PRT
<213> ORGANISM: Vitis vinifera

<400> SEQUENCE: 260

```
Met Gly Arg Ala Pro Cys Cys Asp Lys Ala Asn Val Lys Lys Gly Pro
1               5                   10                  15

Trp Ser Pro Glu Glu Asp Ser Lys Leu Lys Glu Tyr Ile Glu Lys Tyr
            20                  25                  30

Gly Thr Gly Gly Asn Trp Ile Ala Leu Pro Gln Lys Ala Gly Leu Lys
        35                  40                  45

Arg Cys Gly Lys Ser Cys Arg Leu Arg Trp Leu Asn Tyr Leu Arg Pro
    50                  55                  60

Asn Ile Lys His Gly Glu Phe Ser Asp Glu Asp Arg Ile Ile Cys
65                  70                  75                  80

Ser Val Phe Ala Ser Ile Gly Ser Lys Trp Ser Val Ile Ala Asn Tyr
                85                  90                  95

Leu Pro Gly Arg Thr Asp Asn Asp Ile Lys Asn Tyr Trp Asn Thr Lys
            100                 105                 110

Leu Lys Lys Lys Leu Met Gly Met Val Pro Val Ser Gln Arg Lys Pro
        115                 120                 125

His Gln Ala Thr Phe Ser His His Leu Gln Thr Tyr Ser Ser Leu Ser
    130                 135                 140

Ser Pro Ser His Ala Val Thr Thr Thr Ala Thr Ser Ser Ser Tyr Glu
145                 150                 155                 160

Ser Asn Ser Ser Asn Pro Tyr Tyr Thr Pro
                165                 170
```

<210> SEQ ID NO 261
<211> LENGTH: 944
<212> TYPE: DNA
<213> ORGANISM: Zea mays

<400> SEQUENCE: 261

```
atggggagag ctccgtgctg cgacaaggct actgtgaaga agggcccgtg gtcaccggag        60
gaggacgcca agctcaagtc ctacatcgag cagaacggca ccggcggtaa ctggatagcc       120
ctgccgcaga agataggttt gaagaggtgc ggcaagagct gccgcctccg gtggctcaac       180
tacctccggc caaacatcag gcacggcggg ttctcggagg aggaggacag gataatcctt       240
agcctctaca tcagcatagg cagcaggtgg tcgataatag cggcgcagct gccggggagg       300
acggacaatg acataaagaa ctactggaac acgaagctca agaagaagct cttcggcaag       360
cagtcccgca gggatcagcg gcagcatcag ttcatgcgcc aggcagcggc ggcaagcgat       420
gggatgatga agcaagaagc ggcaaccggg gaggcagcgg gaagcagtag catggcggtg       480
gccaactaca actggcacca ccaccatcaa gccatggcgg ccgtgcctgt gcaaccaata       540
ctaggctcga taatgaaggg ccatcgcgca ggggatgagg tagatgagtc gattcggaag       600 cttcttttata agctaggagg agcaggccct tccacagcac tctcggttcc tcagtgtgtt       660
cctccaatgt actgtggaag tccagccctc atgccgccgc cgccgccgtc atgcccagca       720
gtggacaccg gcacatcgct tgatgaaggc ggcgtgcagg gctccggcgt gctgccggcg       780
```

```
ctggagatgg accatagctt ccacttcaac caggttaagc tagatggcct ggaaagcttc      840
ttcggcatga gtactgatca gagcatgcgg tggagtgagg tgagcccatt ggtttgccct      900
agcagtctgg ttgttgatga gccaggaaac cttgggatga agta                      944
```

<210> SEQ ID NO 262
<211> LENGTH: 314
<212> TYPE: PRT
<213> ORGANISM: Zea mays

<400> SEQUENCE: 262

```
Met Gly Arg Ala Pro Cys Cys Asp Lys Ala Thr Val Lys Lys Gly Pro
1               5                   10                  15

Trp Ser Pro Glu Glu Asp Ala Lys Leu Lys Ser Tyr Ile Glu Gln Asn
            20                  25                  30

Gly Thr Gly Gly Asn Trp Ile Ala Leu Pro Gln Lys Ile Gly Leu Lys
        35                  40                  45

Arg Cys Gly Lys Ser Cys Arg Leu Arg Trp Leu Asn Tyr Leu Arg Pro
    50                  55                  60

Asn Ile Arg His Gly Gly Phe Ser Glu Glu Glu Asp Arg Ile Ile Leu
65                  70                  75                  80

Ser Leu Tyr Ile Ser Ile Gly Ser Arg Trp Ser Ile Ile Ala Ala Gln
                85                  90                  95

Leu Pro Gly Arg Thr Asp Asn Asp Ile Lys Asn Tyr Trp Asn Thr Lys
            100                 105                 110

Leu Lys Lys Lys Leu Phe Gly Lys Gln Ser Arg Arg Asp Gln Arg Gln
        115                 120                 125

His Gln Phe Met Arg Gln Ala Ala Ala Ser Asp Gly Met Met Lys
    130                 135                 140

Gln Glu Ala Ala Thr Gly Glu Ala Gly Ser Ser Met Ala Val
145                 150                 155                 160

Ala Asn Tyr Asn Trp His His His Gln Ala Met Ala Ala Val Pro
                165                 170                 175

Val Gln Pro Ile Leu Gly Ser Ile Met Glu Gly His Arg Ala Gly Asp
            180                 185                 190

Glu Val Asp Glu Ser Ile Arg Lys Leu Leu Tyr Lys Leu Gly Gly Ala
        195                 200                 205

Gly Pro Ser Thr Ala Leu Ser Val Pro Gln Cys Val Pro Pro Met Tyr
    210                 215                 220

Cys Gly Ser Pro Ala Leu Met Pro Pro Pro Pro Ser Cys Pro Ala
225                 230                 235                 240

Val Asp Thr Gly Thr Ser Leu Asp Glu Gly Val Gln Ser Gly
                245                 250                 255

Val Leu Pro Ala Leu Glu Met Asp His Ser Phe His Phe Asn Gln Val
            260                 265                 270

Lys Leu Asp Gly Leu Glu Ser Phe Phe Gly Met Ser Thr Asp Gln Ser
        275                 280                 285

Met Arg Trp Ser Glu Val Ser Pro Leu Val Cys Pro Ser Ser Leu Val
    290                 295                 300

Val Asp Glu Pro Gly Asn Leu Gly Met Lys
305                 310
```

<210> SEQ ID NO 263
<211> LENGTH: 1083
<212> TYPE: DNA
<213> ORGANISM: Zea mays

<400> SEQUENCE: 263

```
atggggaggg cgccgtgctg cgacaaggcg agcgtgaaga aggggccgtg gtcgccggac      60
gaggacgcca agctcaaggc ctacatcgag gagcacggca ccggcggcaa ctggatcgcg     120
ctaccgcaca agattgggct gaagagatgc gggaaaagct gcaggctgag atggctcaat     180
tatctgaggc ccaatattaa gcatggtgac ttcacagaag aagaggagca tatcatttgc     240
agcctctaca ttagcattgg aagcaggtgg tccatcattg cagcgcagct gccggggcga     300
acggacaacg acatcaagaa ctactggaac accaagctga agaagaagct cctcggaaag     360
cgcgcgccgt ccaggcgcgc gaggacgaac caggatccct gctacctcgc cgcgggagcc     420
gccagcagca gcagcagcag cagcgccgcg acggccacgc aagccctaag cgcgtcggct     480
ctcgagcgga tccagctcca catgcggctc caaggcatct acggcgcgtt agcttgcagc     540
ggcggcaacg acgacagcaa cgctgccttc gggtcggcgg cggcggcgcc gccgcagtgg     600
ccgaagcttg aggcgctgtc gcaggccaac aggctgctcc cggggtcgct gccggcggac     660
gccatggcca caaccgtgag cgtgcagccg cacccacagc atctggtcga ggtcgaccac     720
caccagagcc tcgccgccgc cgcactcgag ggcgagcaac agctcagctc tgccggtgaa     780
ggaggctttt tcgagcggcc caaggtagat ttttactctc catcagccga ggtcgccgcc     840
gccgccgccg ccagcgtaga gatgaactcg gtcgccccga tggttgttgg cggctacgcg     900
ggcgccgccg gattcgggcc tcagcaccat cacgacgagc tctacgactt cctgtacagc     960
aagtacggat cagtgggcgg gctggcgcac gacggcgggg atgttccaac gttgccagag    1020
ctgcagtgcc cggacggcgc tgccgccgtc gtcggagccg acgagaagtt ctcggcgtgg    1080
acc                                                                  1083
```

<210> SEQ ID NO 264
<211> LENGTH: 361
<212> TYPE: PRT
<213> ORGANISM: Zea mays

<400> SEQUENCE: 264

```
Met Gly Arg Ala Pro Cys Cys Asp Lys Ala Ser Val Lys Lys Gly Pro
1               5                   10                  15
Trp Ser Pro Asp Glu Asp Ala Lys Leu Lys Ala Tyr Ile Glu Glu His
            20                  25                  30
Gly Thr Gly Gly Asn Trp Ile Ala Leu Pro His Lys Ile Gly Leu Lys
        35                  40                  45
Arg Cys Gly Lys Ser Cys Arg Leu Arg Trp Leu Asn Tyr Leu Arg Pro
    50                  55                  60
Asn Ile Lys His Gly Asp Phe Thr Glu Glu Glu His Ile Ile Cys
65                  70                  75                  80
Ser Leu Tyr Ile Ser Ile Gly Ser Arg Trp Ser Ile Ile Ala Ala Gln
                85                  90                  95
Leu Pro Gly Arg Thr Asp Asn Asp Ile Lys Asn Tyr Trp Asn Thr Lys
            100                 105                 110
Leu Lys Lys Lys Leu Leu Gly Lys Arg Ala Pro Ser Arg Arg Ala Arg
        115                 120                 125
Thr Asn Gln Asp Pro Cys Tyr Leu Ala Ala Gly Ala Ala Ser Ser Ser
    130                 135                 140
Ser Ser Ser Ser Ala Ala Thr Ala Thr Gln Ala Leu Ser Ala Ser Ala
145                 150                 155                 160
```

-continued

```
Leu Glu Arg Ile Gln Leu His Met Arg Leu Gln Gly Ile Tyr Gly Ala
            165                 170                 175

Leu Ala Cys Ser Gly Gly Asn Asp Asp Ser Asn Ala Ala Phe Gly Ser
        180                 185                 190

Ala Ala Ala Pro Pro Gln Trp Pro Lys Leu Glu Ala Leu Ser Gln
        195                 200                 205

Ala Asn Arg Leu Leu Pro Gly Ser Leu Pro Ala Asp Ala Met Ala Thr
        210                 215                 220

Thr Val Ser Val Gln Pro His Pro Gln His Leu Val Glu Val Asp His
225                 230                 235                 240

His Gln Ser Leu Ala Ala Ala Leu Glu Gly Glu Gln Gln Leu Ser
            245                 250                 255

Ser Ala Gly Glu Gly Gly Phe Phe Glu Arg Pro Lys Val Asp Phe Tyr
            260                 265                 270

Ser Pro Ser Ala Glu Val Ala Ala Ala Ala Ala Ser Val Glu Met
        275                 280                 285

Asn Ser Val Ala Pro Met Val Val Gly Gly Tyr Ala Gly Ala Ala Gly
        290                 295                 300

Phe Gly Pro Gln His His His Asp Glu Leu Tyr Asp Phe Leu Tyr Ser
305                 310                 315                 320

Lys Tyr Gly Ser Val Gly Gly Leu Ala His Asp Gly Gly His Val Pro
            325                 330                 335

Thr Leu Pro Glu Leu Gln Cys Pro Asp Gly Ala Ala Ala Val Val Gly
            340                 345                 350

Ala Asp Glu Lys Phe Ser Ala Trp Thr
            355                 360
```

<210> SEQ ID NO 265
<211> LENGTH: 1259
<212> TYPE: DNA
<213> ORGANISM: Oryza sativa

<400> SEQUENCE: 265

```
atggggagag cgccgtgctg cgacaaggcg agcgtgaaga aggggccatg gtcaccggag      60
gaggacgcga agctcaaatc ctacatcgag cagaacggca ccggcggcaa ctggatcgcc     120
ctgccccaga gatcggtat gtgttggcaa ttctcatgag tcatgagtcg atgtggtggt     180
tgtggcagca gcagcagcga tagtggtaga agaaagctaa tcaagtgcat gtgtgtcttt     240
gttggtttgg gtttgtacat gtaggtttga aaaggtgcgg caagagctgc cgcctccggt     300
ggctgaacta cctccggccg aacatcaagc acggcgggtt ctcggaggag aagacagga     360
tcatcctcag cctctacatc agcataggaa gcaggtatac ttgctaattc agctgggcac     420
acacaagtct agtcactcct atgatcaact caactgtaga attagctgcg aaaccggtag     480
gcaggcaggc aggttgcaca tggggcatga gagtgtagta caatctatga tctgacatga     540
ccatatatgc atggcacagg tggtcgataa tagcagcgca gctgccgggg cggacggaca     600
atgacatcaa gaactattgg aacacgaggc tcaagaagaa gctctttggc aagcagtcgc     660
gcaaggatca gaggcagcag cagcaccctgg cgcgccaggc ggcagcagct gccagcgact     720
tgcagatcaa acaagaagcg agcaggggtg caaacgaagc gatggcttg gctgccggtg     780
ccaattacac ttggcatcac caccacgcca tggccgtgcc tgtgcacccg atgtcggcac     840
caatggtggt ggaaggaggc cgtgtgggag acgatgtcga tgagtcgatc cggaagcttc     900
tgttcaagct cggagggaac ccattcgcgg cctcgccggc accgccatgc ataccctccac    960
```

-continued

```
caccaatgta cgaggaagcc ccaagcttcg tgccaccatt ggcgcacggc gtgccgctca   1020
acgaaggcgg catgcagtgc tccagcgtgc tgccggcgct ggagctggac gagaacttcc   1080
acttcaacca tgtcaagctg acgggctcg agtgcctctt cgggatggga gatcaccaaa    1140
acatgagatg gaatgaggtg agcccgttgg tttgccctaa taacgctgtg gcgtccagct   1200
cccaagggat gcagcagtac tgcctagttg aagaaccagc tgacctcggg atgcagtag    1259
```

<210> SEQ ID NO 266
<211> LENGTH: 116
<212> TYPE: PRT
<213> ORGANISM: Arabidopsis Thaliana
<220> FEATURE:
<221> NAME/KEY: MISC_FEATURE
<222> LOCATION: (4)..(4)
<223> OTHER INFORMATION: X at position 4 can be any amino acid
<220> FEATURE:
<221> NAME/KEY: MISC_FEATURE
<222> LOCATION: (9)..(9)
<223> OTHER INFORMATION: X at position 9 can be lysine or arginine
<220> FEATURE:
<221> NAME/KEY: MISC_FEATURE
<222> LOCATION: (10)..(11)
<223> OTHER INFORMATION: X at positions 10 and 11 can be any amino acid
<220> FEATURE:
<221> NAME/KEY: MISC_FEATURE
<222> LOCATION: (12)..(12)
<223> OTHER INFORMATION: X at position 12 can be methionine or valine
<220> FEATURE:
<221> NAME/KEY: MISC_FEATURE
<222> LOCATION: (14)..(14)
<223> OTHER INFORMATION: X at position 14 can be arginine or lysine
<220> FEATURE:
<221> NAME/KEY: MISC_FEATURE
<222> LOCATION: (16)..(16)
<223> OTHER INFORMATION: X at position 16 can be any amino acid
<220> FEATURE:
<221> NAME/KEY: MISC_FEATURE
<222> LOCATION: (18)..(18)
<223> OTHER INFORMATION: X at position 18 can be serine or alanine
<220> FEATURE:
<221> NAME/KEY: MISC_FEATURE
<222> LOCATION: (19)..(19)
<223> OTHER INFORMATION: X at position 19 can be any amino acid
<220> FEATURE:
<221> NAME/KEY: MISC_FEATURE
<222> LOCATION: (20)..(20)
<223> OTHER INFORMATION: X at position 20 can be aspartic acid,
      glutamine or glutamic acid
<220> FEATURE:
<221> NAME/KEY: MISC_FEATURE
<222> LOCATION: (23)..(24)
<223> OTHER INFORMATION: X at positions 23 and 24 can be any amino acid
<220> FEATURE:
<221> NAME/KEY: MISC_FEATURE
<222> LOCATION: (25)..(25)
<223> OTHER INFORMATION: X at position 25 can be isoleucine or leucine
<220> FEATURE:
<221> NAME/KEY: MISC_FEATURE
<222> LOCATION: (26)..(26)
<223> OTHER INFORMATION: X at position 26 can be arginine or lysine
<220> FEATURE:
<221> NAME/KEY: MISC_FEATURE
<222> LOCATION: (27)..(27)
<223> OTHER INFORMATION: X at position 27 can be any amino acid
<220> FEATURE:
<221> NAME/KEY: MISC_FEATURE
<222> LOCATION: (28)..(28)
<223> OTHER INFORMATION: X at position 28 can be phenylalanine or
      tyrosine
<220> FEATURE:
<221> NAME/KEY: MISC_FEATURE
<222> LOCATION: (29)..(32)
<223> OTHER INFORMATION: X at positions 29-32 can be any amino acid
<220> FEATURE:
<221> NAME/KEY: MISC_FEATURE

```
<222> LOCATION: (34)..(36)
<223> OTHER INFORMATION: X at positions 34-36 can be any amino acid
<220> FEATURE:
<221> NAME/KEY: MISC_FEATURE
<222> LOCATION: (37)..(37)
<223> OTHER INFORMATION: X at position 37 can be serine or asparagine
<220> FEATURE:
<221> NAME/KEY: MISC_FEATURE
<222> LOCATION: (40)..(41)
<223> OTHER INFORMATION: X at positions 40-41 can be any amino acid
<220> FEATURE:
<221> NAME/KEY: MISC_FEATURE
<222> LOCATION: (43)..(43)
<223> OTHER INFORMATION: X at position 43 can be any amino acid
<220> FEATURE:
<221> NAME/KEY: MISC_FEATURE
<222> LOCATION: (44)..(44)
<223> OTHER INFORMATION: X at position 44 can be arginine or lysine
<220> FEATURE:
<221> NAME/KEY: MISC_FEATURE
<222> LOCATION: (45)..(45)
<223> OTHER INFORMATION: X at position 45 can be any amino acid
<220> FEATURE:
<221> NAME/KEY: MISC_FEATURE
<222> LOCATION: (47)..(47)
<223> OTHER INFORMATION: X at position 47 can be isoleucine or leucine
<220> FEATURE:
<221> NAME/KEY: MISC_FEATURE
<222> LOCATION: (48)..(48)
<223> OTHER INFORMATION: X at position 48 can be any amino acid
<220> FEATURE:
<221> NAME/KEY: MISC_FEATURE
<222> LOCATION: (52)..(52)
<223> OTHER INFORMATION: X at position 52 can be lysine or arginine
<220> FEATURE:
<221> NAME/KEY: MISC_FEATURE
<222> LOCATION: (59)..(59)
<223> OTHER INFORMATION: X at position 59 can be isoleucine or leucine
<220> FEATURE:
<221> NAME/KEY: MISC_FEATURE
<222> LOCATION: (65)..(65)
<223> OTHER INFORMATION: X at position 65 can be any amino acid
<220> FEATURE:
<221> NAME/KEY: MISC_FEATURE
<222> LOCATION: (66)..(66)
<223> OTHER INFORMATION: X at position 66 can be isoleucine or leucine
<220> FEATURE:
<221> NAME/KEY: MISC_FEATURE
<222> LOCATION: (67)..(67)
<223> OTHER INFORMATION: X at position 67 can be arginine or lysine
<220> FEATURE:
<221> NAME/KEY: MISC_FEATURE
<222> LOCATION: (70)..(70)
<223> OTHER INFORMATION: X at position 70 can be any amino acid
<220> FEATURE:
<221> NAME/KEY: MISC_FEATURE
<222> LOCATION: (71)..(71)
<223> OTHER INFORMATION: X at position 71 can be phenylalanine or
      tyrosine
<220> FEATURE:
<221> NAME/KEY: MISC_FEATURE
<222> LOCATION: (72)..(72)
<223> OTHER INFORMATION: X at position 72 can be serine or threonine
<220> FEATURE:
<221> NAME/KEY: MISC_FEATURE
<222> LOCATION: (73)..(74)
<223> OTHER INFORMATION: X at positions 73-74 can be any amino acid
<220> FEATURE:
<221> NAME/KEY: MISC_FEATURE
<222> LOCATION: (76)..(76)
<223> OTHER INFORMATION: X at position 76 can be aspartic acid or
      glutamic acid
<220> FEATURE:
<221> NAME/KEY: MISC_FEATURE
<222> LOCATION: (77)..(78)
<223> OTHER INFORMATION: X at positions 77-78 can be any amino acid
<220> FEATURE:
<221> NAME/KEY: MISC_FEATURE
<222> LOCATION: (79)..(79)
```

```
<223> OTHER INFORMATION: X at position 79 can be isoleucine or valine
<220> FEATURE:
<221> NAME/KEY: MISC_FEATURE
<222> LOCATION: (80)..(82)
<223> OTHER INFORMATION: X at positions 80-82 can be any amino acid
<220> FEATURE:
<221> NAME/KEY: MISC_FEATURE
<222> LOCATION: (83)..(83)
<223> OTHER INFORMATION: X at position 83 can be phenylalanine or
      tyrosine
<220> FEATURE:
<221> NAME/KEY: MISC_FEATURE
<222> LOCATION: (84)..(86)
<223> OTHER INFORMATION: X at positions 84-86 can be any amino acid
<220> FEATURE:
<221> NAME/KEY: MISC_FEATURE
<222> LOCATION: (89)..(89)
<223> OTHER INFORMATION: X at position 89 can be lysine or arginine
<220> FEATURE:
<221> NAME/KEY: MISC_FEATURE
<222> LOCATION: (92)..(92)
<223> OTHER INFORMATION: X at position 92 can be any amino acid
<220> FEATURE:
<221> NAME/KEY: MISC_FEATURE
<222> LOCATION: (93)..(93)
<223> OTHER INFORMATION: X at position 93 can be methionine or
      isoleucine
<220> FEATURE:
<221> NAME/KEY: MISC_FEATURE
<222> LOCATION: (95)..(96)
<223> OTHER INFORMATION: X at positions 95-96 can be any amino acid
<220> FEATURE:
<221> NAME/KEY: MISC_FEATURE
<222> LOCATION: (97)..(97)
<223> OTHER INFORMATION: X at position 97 can be methionine or leucine
<220> FEATURE:
<221> NAME/KEY: MISC_FEATURE
<222> LOCATION: (98)..(99)
<223> OTHER INFORMATION: X at positions 98-99 can be any amino acid
<220> FEATURE:
<221> NAME/KEY: MISC_FEATURE
<222> LOCATION: (105)..(105)
<223> OTHER INFORMATION: X at position 105 can be isoleucine, leucine or
      valine
<220> FEATURE:
<221> NAME/KEY: MISC_FEATURE
<222> LOCATION: (108)..(108)
<223> OTHER INFORMATION: X at position 108 can be histidine or tyrosine
<220> FEATURE:
<221> NAME/KEY: MISC_FEATURE
<222> LOCATION: (110)..(110)
<223> OTHER INFORMATION: X at position 110 can be aspartic acid or
      asparagine
<220> FEATURE:
<221> NAME/KEY: MISC_FEATURE
<222> LOCATION: (111)..(111)
<223> OTHER INFORMATION: X at position 111 can be serine or threonine
<220> FEATURE:
<221> NAME/KEY: MISC_FEATURE
<222> LOCATION: (112)..(112)
<223> OTHER INFORMATION: X at position 112 can be arginine or lysine
<220> FEATURE:
<221> NAME/KEY: MISC_FEATURE
<222> LOCATION: (114)..(114)
<223> OTHER INFORMATION: X at position 114 can be arginine or lysine
<220> FEATURE:
<221> NAME/KEY: MISC_FEATURE
<222> LOCATION: (115)..(115)
<223> OTHER INFORMATION: X at position 115 can be arginine or lysine
<220> FEATURE:
<221> NAME/KEY: MISC_FEATURE
<222> LOCATION: (116)..(116)
<223> OTHER INFORMATION: X at position 116 can be arginine or lysine

<400> SEQUENCE: 266

Met Gly Arg Xaa Pro Cys Cys Asp Xaa Xaa Xaa Xaa Lys Xaa Gly Xaa
1               5                   10                  15
```

```
Trp Xaa Xaa Xaa Glu Asp Xaa Xaa Xaa Xaa Xaa Xaa
        20                  25                  30

Gly Xaa Xaa Xaa Xaa Trp Ile Xaa Xaa Pro Xaa Xaa Gly Xaa Xaa
            35                  40                  45

Arg Cys Gly Xaa Ser Cys Arg Leu Arg Trp Xaa Asn Tyr Leu Arg Pro
 50                  55                  60

Xaa Xaa Xaa His Gly Xaa Xaa Xaa Xaa Glu Xaa Xaa Xaa Xaa
 65              70                  75                  80

Xaa Xaa Xaa Xaa Xaa Gly Ser Xaa Trp Ser Xaa Xaa Ala Xaa Xaa
                85                  90                  95

Xaa Xaa Xaa Arg Thr Asp Asn Asp Xaa Lys Asn Xaa Trp Xaa Xaa Xaa
        100                 105                 110

Leu Xaa Xaa Xaa
        115

<210> SEQ ID NO 267
<211> LENGTH: 87
<212> TYPE: PRT
<213> ORGANISM: Arabidopsis thaliana
<220> FEATURE:
<221> NAME/KEY: MISC_FEATURE
<222> LOCATION: (1)..(1)
<223> OTHER INFORMATION: X at position 1 can be arginine or lysine
<220> FEATURE:
<221> NAME/KEY: MISC_FEATURE
<222> LOCATION: (2)..(10)
<223> OTHER INFORMATION: X at positions 2-10 can be any amino acid
<220> FEATURE:
<221> NAME/KEY: MISC_FEATURE
<222> LOCATION: (12)..(13)
<223> OTHER INFORMATION: X at positions 12-13 can be any amino acid
<220> FEATURE:
<221> NAME/KEY: MISC_FEATURE
<222> LOCATION: (15)..(42)
<223> OTHER INFORMATION: X at positions 15-42 can be any amino acid
<220> FEATURE:
<221> NAME/KEY: MISC_FEATURE
<222> LOCATION: (44)..(57)
<223> OTHER INFORMATION: X at positions 44-57 can be any amino acid
<220> FEATURE:
<221> NAME/KEY: MISC_FEATURE
<222> LOCATION: (58)..(58)
<223> OTHER INFORMATION: X at position 58 can be tyrosine or
      phenylalanine
<220> FEATURE:
<221> NAME/KEY: MISC_FEATURE
<222> LOCATION: (59)..(62)
<223> OTHER INFORMATION: X at positions 59-62 can be any amino acid
<220> FEATURE:
<221> NAME/KEY: MISC_FEATURE
<222> LOCATION: (64)..(86)
<223> OTHER INFORMATION: X at positions 64-86 can be any amino acid
<220> FEATURE:
<221> NAME/KEY: MISC_FEATURE
<222> LOCATION: (87)..(87)
<223> OTHER INFORMATION: X at position 87 can be arginine or lysine

<400> SEQUENCE: 267

Xaa Xaa Xaa Xaa Xaa Xaa Xaa Xaa Xaa Gly Xaa Xaa Ile Xaa Xaa
 1               5                  10                  15

Xaa Xaa Xaa Xaa Xaa Xaa Xaa Xaa Xaa Xaa Xaa Xaa Xaa Xaa
        20                  25                  30

Xaa Xaa Xaa Xaa Xaa Xaa Xaa Xaa His Xaa Xaa Xaa Xaa
        35                  40                  45

Xaa Xaa Xaa Xaa Xaa Xaa Xaa Xaa Xaa Xaa Xaa Xaa Ser Xaa
    50                  55                  60

Xaa Xaa Xaa Xaa Xaa Xaa Xaa Xaa Xaa Xaa Xaa Xaa Xaa Xaa Xaa
```

```
                65                  70                  75                  80
Xaa Xaa Xaa Xaa Xaa Xaa Xaa
                85

<210> SEQ ID NO 268
<211> LENGTH: 87
<212> TYPE: PRT
<213> ORGANISM: Arabidopsis thaliana
<220> FEATURE:
<221> NAME/KEY: MISC_FEATURE
<222> LOCATION: (2)..(2)
<223> OTHER INFORMATION: X at position 2 can be any amino acid
<220> FEATURE:
<221> NAME/KEY: MISC_FEATURE
<222> LOCATION: (4)..(6)
<223> OTHER INFORMATION: X at positions 4-6 can be any amino acid
<220> FEATURE:
<221> NAME/KEY: MISC_FEATURE
<222> LOCATION: (9)..(10)
<223> OTHER INFORMATION: X at positions 9-10 can be any amino acid
<220> FEATURE:
<221> NAME/KEY: MISC_FEATURE
<222> LOCATION: (11)..(11)
<223> OTHER INFORMATION: X at position 11 can be isoleucine or leucine
<220> FEATURE:
<221> NAME/KEY: MISC_FEATURE
<222> LOCATION: (12)..(12)
<223> OTHER INFORMATION: X at position 12 can be arginine or lysine
<220> FEATURE:
<221> NAME/KEY: MISC_FEATURE
<222> LOCATION: (13)..(18)
<223> OTHER INFORMATION: X at positions 13-18 can be any amino acid
<220> FEATURE:
<221> NAME/KEY: MISC_FEATURE
<222> LOCATION: (20)..(42)
<223> OTHER INFORMATION: X at positions 20-42 can be any amino acid
<220> FEATURE:
<221> NAME/KEY: MISC_FEATURE
<222> LOCATION: (45)..(45)
<223> OTHER INFORMATION: X at position 45 can be isoleucine or leucine
<220> FEATURE:
<221> NAME/KEY: MISC_FEATURE
<222> LOCATION: (51)..(51)
<223> OTHER INFORMATION: X at position 51 can be any amino acid
<220> FEATURE:
<221> NAME/KEY: MISC_FEATURE
<222> LOCATION: (52)..(52)
<223> OTHER INFORMATION: X at position 52 can be isoleucine or leucine
<220> FEATURE:
<221> NAME/KEY: MISC_FEATURE
<222> LOCATION: (53)..(53)
<223> OTHER INFORMATION: X at position 53 can be arginine or lysine
<220> FEATURE:
<221> NAME/KEY: MISC_FEATURE
<222> LOCATION: (56)..(56)
<223> OTHER INFORMATION: X at position 56 can be any amino acid
<220> FEATURE:
<221> NAME/KEY: MISC_FEATURE
<222> LOCATION: (57)..(57)
<223> OTHER INFORMATION: X at position 57 can be phenylalanine or
      tyrosine
<220> FEATURE:
<221> NAME/KEY: MISC_FEATURE
<222> LOCATION: (58)..(60)
<223> OTHER INFORMATION: X at positions 58-60 can be any amino acid
<220> FEATURE:
<221> NAME/KEY: MISC_FEATURE
<222> LOCATION: (62)..(62)
<223> OTHER INFORMATION: X at position 62 can be aspartic acid or
      glutamic acid
<220> FEATURE:
<221> NAME/KEY: MISC_FEATURE
<222> LOCATION: (63)..(75)
<223> OTHER INFORMATION: X at positions 63-75 can be any amino acid
<220> FEATURE:
<221> NAME/KEY: MISC_FEATURE
<222> LOCATION: (77)..(79)
```

<223> OTHER INFORMATION: X at positions 77-79 can be any amino acid
<220> FEATURE:
<221> NAME/KEY: MISC_FEATURE
<222> LOCATION: (81)..(85)
<223> OTHER INFORMATION: X at positions 81-85 can be any amino acid

<400> SEQUENCE: 268

Gly Xaa Trp Xaa Xaa Xaa Glu Asp Xaa Xaa Xaa Xaa Xaa Xaa Xaa
1               5                   10                  15

Xaa Xaa Gly Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Arg Trp Xaa Asn Tyr Leu
        35                  40                  45

Arg Pro Xaa Xaa Xaa His Gly Xaa Xaa Xaa Xaa Xaa Glu Xaa Xaa Xaa
    50                  55                  60

Xaa Xaa Xaa Xaa Xaa Xaa Xaa Xaa Xaa Xaa Trp Xaa Xaa Xaa Ala
65                  70                  75                  80

Xaa Xaa Xaa Xaa Xaa Arg Thr
                85

<210> SEQ ID NO 269
<211> LENGTH: 10
<212> TYPE: PRT
<213> ORGANISM: Arabidopsis thaliana

<400> SEQUENCE: 269

Ser Phe Ser Gln Leu Leu Leu Asp Pro Asn
1               5                   10

<210> SEQ ID NO 270
<211> LENGTH: 15
<212> TYPE: PRT
<213> ORGANISM: Arabidopsis thaliana

<400> SEQUENCE: 270

Thr Ser Thr Ser Ala Asp Gln Ser Thr Ile Ser Trp Glu Asp Ile
1               5                   10                  15

<210> SEQ ID NO 271
<211> LENGTH: 30
<212> TYPE: DNA
<213> ORGANISM: artificial sequence
<220> FEATURE:
<223> OTHER INFORMATION: synthetic primer

<400> SEQUENCE: 271
acgttctaga atgggaagag caccgtgttg                                        30

<210> SEQ ID NO 272
<211> LENGTH: 32
<212> TYPE: DNA
<213> ORGANISM: artificial sequence
<220> FEATURE:
<223> OTHER INFORMATION: synthetic primer

<400> SEQUENCE: 272
atcgggatcc ttacacatga tttggcgcat tg                                     32

<210> SEQ ID NO 273
<211> LENGTH: 30
<212> TYPE: DNA
<213> ORGANISM: artificial sequence
<220> FEATURE:
<223> OTHER INFORMATION: synthetic primer

```
<400> SEQUENCE: 273
acgttctaga atgggaagag caccgtgttg                                    30

<210> SEQ ID NO 274
<211> LENGTH: 37
<212> TYPE: DNA
<213> ORGANISM: artificial sequence
<220> FEATURE:
<223> OTHER INFORMATION: synthetic primer

<400> SEQUENCE: 274
atcgggatcc ttaaaaaaat tgctttgaat cagaata                            37

<210> SEQ ID NO 275
<211> LENGTH: 27
<212> TYPE: DNA
<213> ORGANISM: artificial sequence
<220> FEATURE:
<223> OTHER INFORMATION: synthetic primer

<400> SEQUENCE: 275
acgtaagctt tcgtaaaatc tctcatg                                       27

<210> SEQ ID NO 276
<211> LENGTH: 40
<212> TYPE: DNA
<213> ORGANISM: artificial sequence
<220> FEATURE:
<223> OTHER INFORMATION: synthetic primer

<400> SEQUENCE: 276
gtcactcgag cctaggtttc ttgattcttg attcttgatc                         40

<210> SEQ ID NO 277
<211> LENGTH: 35
<212> TYPE: DNA
<213> ORGANISM: artificial sequence
<220> FEATURE:
<223> OTHER INFORMATION: synthetic primer

<400> SEQUENCE: 277
aaagtcgacg catctttaca atgtaaagct tttct                              35

<210> SEQ ID NO 278
<211> LENGTH: 27
<212> TYPE: DNA
<213> ORGANISM: artificial sequence
<220> FEATURE:
<223> OTHER INFORMATION: synthetic primer

<400> SEQUENCE: 278
aaatctagat gttcgttgct tttcggg                                       27

<210> SEQ ID NO 279
<211> LENGTH: 38
<212> TYPE: DNA
<213> ORGANISM: artificial sequence
<220> FEATURE:
<223> OTHER INFORMATION: synthetic primer

<400> SEQUENCE: 279
aaagtcgaca gaagacaaat gagagttggt ttatattt                           38

<210> SEQ ID NO 280
```

```
-continued

<211> LENGTH: 29
<212> TYPE: DNA
<213> ORGANISM: artificial sequence
<220> FEATURE:
<223> OTHER INFORMATION: synthetic primer

<400> SEQUENCE: 280
aaatctagac gcaacgaact ttgattcaa                                29

<210> SEQ ID NO 281
<211> LENGTH: 30
<212> TYPE: DNA
<213> ORGANISM: artificial sequence
<220> FEATURE:
<223> OTHER INFORMATION: synthetic primer

<400> SEQUENCE: 281
atgggaagag caccgtgttg tgataaggcc                               30

<210> SEQ ID NO 282
<211> LENGTH: 35
<212> TYPE: DNA
<213> ORGANISM: artificial sequence
<220> FEATURE:
<223> OTHER INFORMATION: synthetic primer

<400> SEQUENCE: 282
ttaatttggc gcattgaagt aacttgcatc ttcgg                         35

<210> SEQ ID NO 283
<211> LENGTH: 28
<212> TYPE: DNA
<213> ORGANISM: artificial sequence
<220> FEATURE:
<223> OTHER INFORMATION: synthetic primer

<400> SEQUENCE: 283
acgttctaga atggggagag cgccgtgc                                 28

<210> SEQ ID NO 284
<211> LENGTH: 29
<212> TYPE: DNA
<213> ORGANISM: artificial sequence
<220> FEATURE:
<223> OTHER INFORMATION: synthetic primer

<400> SEQUENCE: 284
tgcaggatcc tactgcatcc cgaggtcag                                29

<210> SEQ ID NO 285
<211> LENGTH: 30
<212> TYPE: DNA
<213> ORGANISM: artificial sequence
<220> FEATURE:
<223> OTHER INFORMATION: synthetic primer

<400> SEQUENCE: 285
acgttctaga atggggagag ctccttgttg                               30

<210> SEQ ID NO 286
<211> LENGTH: 29
<212> TYPE: DNA
<213> ORGANISM: artificial sequence
<220> FEATURE:
<223> OTHER INFORMATION: synthetic primer

<400> SEQUENCE: 286
```
acgtggatcc ctattgcgct cctcctggg                                    29

<210> SEQ ID NO 287
<211> LENGTH: 29
<212> TYPE: DNA
<213> ORGANISM: artificial sequence
<220> FEATURE:
<223> OTHER INFORMATION: synthetic primer

<400> SEQUENCE: 287
acgttctaga atggggaggg caccttgct                                    29

<210> SEQ ID NO 288
<211> LENGTH: 29
<212> TYPE: DNA
<213> ORGANISM: artificial sequence
<220> FEATURE:
<223> OTHER INFORMATION: synthetic primer

<400> SEQUENCE: 288
acgttctaga atggggagag ctccgtgct                                    29

<210> SEQ ID NO 289
<211> LENGTH: 28
<212> TYPE: DNA
<213> ORGANISM: artificial sequence
<220> FEATURE:
<223> OTHER INFORMATION: synthetic primer

<400> SEQUENCE: 289
actgtctaga atggggaggg cgccgtgc                                     28

<210> SEQ ID NO 290
<211> LENGTH: 31
<212> TYPE: DNA
<213> ORGANISM: artificial sequence
<220> FEATURE:
<223> OTHER INFORMATION: synthetic primer

<400> SEQUENCE: 290
actgtctaga atgggaagag ctccttgctg t                                 31

<210> SEQ ID NO 291
<211> LENGTH: 29
<212> TYPE: DNA
<213> ORGANISM: artificial sequence
<220> FEATURE:
<223> OTHER INFORMATION: synthetic primer

<400> SEQUENCE: 291
acgttctaga atggggagag ctccgtgct                                    29

<210> SEQ ID NO 292
<211> LENGTH: 31
<212> TYPE: DNA
<213> ORGANISM: artificial sequence
<220> FEATURE:
<223> OTHER INFORMATION: synthetic primer

<400> SEQUENCE: 292
actgtctaga atgggaagag ctccatgttg t                                 31

<210> SEQ ID NO 293
<211> LENGTH: 35
<212> TYPE: DNA

```
<213> ORGANISM: artificial sequence
<220> FEATURE:
<223> OTHER INFORMATION: synthetic primer

<400> SEQUENCE: 293
gactggatcc ttagtaataa aacatcccta tctca                              35

<210> SEQ ID NO 294
<211> LENGTH: 30
<212> TYPE: DNA
<213> ORGANISM: artificial sequence
<220> FEATURE:
<223> OTHER INFORMATION: synthetic primier

<400> SEQUENCE: 294
acgttctaga atggggagag ctccttgctg                                    30

<210> SEQ ID NO 295
<211> LENGTH: 31
<212> TYPE: DNA
<213> ORGANISM: artificial sequence
<220> FEATURE:
<223> OTHER INFORMATION: synthetic primer

<400> SEQUENCE: 295
gactggatcc tcattgtggc ccaaagaagc t                                  31

<210> SEQ ID NO 296
<211> LENGTH: 35
<212> TYPE: DNA
<213> ORGANISM: artificial sequence
<220> FEATURE:
<223> OTHER INFORMATION: synthetic primer

<400> SEQUENCE: 296
aaagtcgacg catctttaca atgtaaagct tttct                              35

<210> SEQ ID NO 297
<211> LENGTH: 27
<212> TYPE: DNA
<213> ORGANISM: artificial sequence
<220> FEATURE:
<223> OTHER INFORMATION: synthetic primer

<400> SEQUENCE: 297
aaatctagat gttcgttgct tttcggg                                       27

<210> SEQ ID NO 298
<211> LENGTH: 38
<212> TYPE: DNA
<213> ORGANISM: artificial sequence
<220> FEATURE:
<223> OTHER INFORMATION: synthetic primer

<400> SEQUENCE: 298
aaagtcgaca gaagacaaat gagagttggt ttatattt                           38

<210> SEQ ID NO 299
<211> LENGTH: 29
<212> TYPE: DNA
<213> ORGANISM: artificial sequence
<220> FEATURE:
<223> OTHER INFORMATION: synthetic primer

<400> SEQUENCE: 299
aaatctagac gcaacgaact ttgattcaa                                     29
```

<210> SEQ ID NO 300
<211> LENGTH: 29
<212> TYPE: DNA
<213> ORGANISM: artificial sequence
<220> FEATURE:
<223> OTHER INFORMATION: synthetic primer

<400> SEQUENCE: 300
aaaggatcca tgggaagagc accgtgttg                              29

<210> SEQ ID NO 301
<211> LENGTH: 32
<212> TYPE: DNA
<213> ORGANISM: artificial sequence
<220> FEATURE:
<223> OTHER INFORMATION: synthetic primer

<400> SEQUENCE: 301
aaaggatccc cactccctaa agacacagat tt                          32

<210> SEQ ID NO 302
<211> LENGTH: 28
<212> TYPE: DNA
<213> ORGANISM: artificial sequence
<220> FEATURE:
<223> OTHER INFORMATION: synthetic primer

<400> SEQUENCE: 302
aaatctagaa tgggaagagc accgtgtt                               28

<210> SEQ ID NO 303
<211> LENGTH: 29
<212> TYPE: DNA
<213> ORGANISM: artificial sequence
<220> FEATURE:
<223> OTHER INFORMATION: synthetic primer

<400> SEQUENCE: 303
aaaggatcct tacacatgat ttggcgcat                              29

<210> SEQ ID NO 304
<211> LENGTH: 30
<212> TYPE: DNA
<213> ORGANISM: artificial sequence
<220> FEATURE:
<223> OTHER INFORMATION: synthetic primer

<400> SEQUENCE: 304
actgtctaga atgggaagag ctccatgctg                             30

<210> SEQ ID NO 305
<211> LENGTH: 32
<212> TYPE: DNA
<213> ORGANISM: artificial sequence
<220> FEATURE:
<223> OTHER INFORMATION: synthetic primer

<400> SEQUENCE: 305
cagtggatcc ttaaacactg tggtagctca tc                          32

<210> SEQ ID NO 306
<211> LENGTH: 30
<212> TYPE: DNA
<213> ORGANISM: artificial sequence
<220> FEATURE:

<223> OTHER INFORMATION: synthetic primer

<400> SEQUENCE: 306
actgtctaga atgggaagag ctccgtgttg                                30

<210> SEQ ID NO 307
<211> LENGTH: 31
<212> TYPE: DNA
<213> ORGANISM: artificial sequence
<220> FEATURE:
<223> OTHER INFORMATION: synthetic primer

<400> SEQUENCE: 307
acgtggatcc taggagtaga aatagggcaa g                              31

<210> SEQ ID NO 308
<211> LENGTH: 31
<212> TYPE: DNA
<213> ORGANISM: artificial sequence
<220> FEATURE:
<223> OTHER INFORMATION: synthetic primer

<400> SEQUENCE: 308
actgtctaga atgggtaggg ctccatgttg t                              31

<210> SEQ ID NO 309
<211> LENGTH: 34
<212> TYPE: DNA
<213> ORGANISM: artificial sequence
<220> FEATURE:
<223> OTHER INFORMATION: synthetic primer

<400> SEQUENCE: 309
acgtggatcc tcagtagtac aacatgaact tatc                           34

<210> SEQ ID NO 310
<211> LENGTH: 28
<212> TYPE: DNA
<213> ORGANISM: artificial sequence
<220> FEATURE:
<223> OTHER INFORMATION: synthetic primer

<400> SEQUENCE: 310
aaaatctaga atgggaagag caccgtgc                                  28

<210> SEQ ID NO 311
<211> LENGTH: 31
<212> TYPE: DNA
<213> ORGANISM: artificial sequence
<220> FEATURE:
<223> OTHER INFORMATION: synthetic primer

<400> SEQUENCE: 311
aaaaagatct ctactcatta tcgtatagag g                              31

<210> SEQ ID NO 312
<211> LENGTH: 30
<212> TYPE: DNA
<213> ORGANISM: artificial sequence
<220> FEATURE:
<223> OTHER INFORMATION: synthetic primer

<400> SEQUENCE: 312
acgtgtcgac gaagcagcag aagccttgat                                30

```
<210> SEQ ID NO 313
<211> LENGTH: 32
<212> TYPE: DNA
<213> ORGANISM: artificial sequence
<220> FEATURE:
<223> OTHER INFORMATION: synthetic primer

<400> SEQUENCE: 313
acgttctaga ggtagagaaa agagaaagcc tc                                  32

<210> SEQ ID NO 314
<211> LENGTH: 30
<212> TYPE: DNA
<213> ORGANISM: artificial sequence
<220> FEATURE:
<223> OTHER INFORMATION: synthetic primer

<400> SEQUENCE: 314
acgttctaga atggggagag cgccgtgctg                                     30

<210> SEQ ID NO 315
<211> LENGTH: 32
<212> TYPE: DNA
<213> ORGANISM: artificial sequence
<220> FEATURE:
<223> OTHER INFORMATION: synthetic primer

<400> SEQUENCE: 315
tgcaggatcc ctactgcatc ccgaggtcag ct                                  32

<210> SEQ ID NO 316
<211> LENGTH: 29
<212> TYPE: DNA
<213> ORGANISM: artificial sequence
<220> FEATURE:
<223> OTHER INFORMATION: synthetic primer

<400> SEQUENCE: 316
acgttctaga atggggaggg caccttgct                                      29

<210> SEQ ID NO 317
<211> LENGTH: 28
<212> TYPE: DNA
<213> ORGANISM: artificial sequence
<220> FEATURE:
<223> OTHER INFORMATION: synthetic primer

<400> SEQUENCE: 317
acgtggatcc tattgcgccc ccgggtag                                       28

<210> SEQ ID NO 318
<211> LENGTH: 34
<212> TYPE: DNA
<213> ORGANISM: artificial sequence
<220> FEATURE:
<223> OTHER INFORMATION: synthetic primer

<400> SEQUENCE: 318
aaatctagaa tggggagagc tccgtgctgc gaca                                34

<210> SEQ ID NO 319
<211> LENGTH: 34
<212> TYPE: DNA
<213> ORGANISM: artificial sequence
<220> FEATURE:
<223> OTHER INFORMATION: synthetic primer
```

```
<400> SEQUENCE: 319
aaaggatccc tacttcatcc caaggtttcc tggc                          34

<210> SEQ ID NO 320
<211> LENGTH: 30
<212> TYPE: DNA
<213> ORGANISM: artificial sequence
<220> FEATURE:
<223> OTHER INFORMATION: synthetic primer

<400> SEQUENCE: 320
acgttctaga atggggagag ctccttgttg                               30

<210> SEQ ID NO 321
<211> LENGTH: 29
<212> TYPE: DNA
<213> ORGANISM: artificial sequence
<220> FEATURE:
<223> OTHER INFORMATION: synthetic primer

<400> SEQUENCE: 321
acgtggatcc ctattgcgct cctcctggg                                29

<210> SEQ ID NO 322
<211> LENGTH: 39
<212> TYPE: DNA
<213> ORGANISM: artificial sequence
<220> FEATURE:
<223> OTHER INFORMATION: synthetic primer

<400> SEQUENCE: 322
aaatctagaa tgggaagagc accgtgttgt gataaggcc                     39

<210> SEQ ID NO 323
<211> LENGTH: 42
<212> TYPE: DNA
<213> ORGANISM: artificial sequence
<220> FEATURE:
<223> OTHER INFORMATION: synthetic primer

<400> SEQUENCE: 323
aaaggatcct tacacattat ttggcccatt gaagtatctt gc                 42

<210> SEQ ID NO 324
<211> LENGTH: 39
<212> TYPE: DNA
<213> ORGANISM: artificial sequence
<220> FEATURE:
<223> OTHER INFORMATION: synthetic primer

<400> SEQUENCE: 324
aaatctagaa tgggaagagc accgtgttgt gacaaggct                     39

<210> SEQ ID NO 325
<211> LENGTH: 42
<212> TYPE: DNA
<213> ORGANISM: artificial sequence
<220> FEATURE:
<223> OTHER INFORMATION: synthetic primer

<400> SEQUENCE: 325
aaaggatcct tacaaatgat ttgccccatt gaagtaactt gc                 42
```

PLANTS HAVING INCREASED TOLERANCE TO HEAT STRESS

REFERENCE TO RELATED APPLICATIONS

This non-provisional patent application is a continuation of pending U.S. patent application Ser. No. 12/148,548, filed Apr. 18, 2008, which claims priority under 35 U.S.C. § 119(e) to U.S. Ser. No. 60/925,312, filed Apr. 18, 2007, and U.S. Ser. No. 60/965,582, filed Aug. 20, 2007, the contents of each of which are herein incorporated by reference in their entireties.

INCORPORATION BY REFERENCE OF SEQUENCE LISTING

The contents of the text file named "PREP-014C01US Sequence Listing.txt", which was created on Jan. 26, 2017 and is 439 KB in size, are hereby incorporated by reference in their entireties.

FIELD OF THE INVENTION

The invention is in the field of plant molecular biology and relates to transgenic plants having novel phenotypes, methods of producing such plants and polynucleotides and polypeptides useful in such methods. More specifically, the invention relates to the use of MYB polynucleotides and transgenic plants expressing these polynucleotides and polypeptides.

BACKGROUND OF THE INVENTION

Environmental stresses are responsible for significant yield reduction in agricultural crops. In addition to many reports published previously, the relation between climate variation and production of corn and soybean throughout the United States for the period 1982-1998 was studied in recent years (Lobell and Asner, 2003). Gradual temperature changes have made a measurable impact on crop yield. In corn and soybean it has been estimated that yield is reduced by 17% per degree as the growth temperature rises above the season optimum. With a predicted temperature increase of 1.4° C. to 5.8° C. between the years 1990 and 2010 (IPCC Working Group I, 2001), improvement of high temperature tolerance in crop plants has become one of the major focuses of agricultural biotechnology development.

Both monocots and dicots are particularly sensitive to heat stress during flowering and seed development and therefore heat stress has a significant impact on seed yield (Young et al., 2004; Sato et al., 2002; Angadi et al., 2000; Carlson, 1990; Wahid, A., Gelani, S., Ashraf, M., and Foolad, M. R. (2007)). It has been suggested that plants possess an inherent ability for basal and acquired thermotolerance and that a common heat response mechanisms is present in diverse plant species (Kapoor et al., 1990; Vierling, 1991; Flahaut et al., 1996; Burke et al., 2000; Hong and Vieling, 2000; Massie et al., 2003; Larkindale et al., 2005). Basal thermotolerance allows plants survive from exposure to temperature above optimal for growth, whereas acquired thermotolerance is induced by a short acclimation period at a sub-lethal heat stress which enables a plant to survive a subsequent heat stress that would be otherwise lethal. A number of studies have been conducted to identify and characterize genes and pathways that are involved in plant thermotolerance. For example, heat shock transcription factors (HSF) and heat shock proteins (HSP) have received much attention to elucidate the roles and effects of these genes in response to heat stress as have plant growth hormones such as abscisic acid and ethylene.

Transcription factors are DNA binding proteins that interact with specific promoter or enhancer sequences and alter the gene expression of the associated gene. Where the specific sequence that binds the transcription factor is associated with a suite of genes whole pathways can be coordinately regulated with various component genes being simultaneously up-regulated or down-regulated. A transcription factors may coordinately alter a suite of genes in response to a stimulus such as an environmental stress, nutritional status or pathogen attack, for example, or can be a component of a signaling pathway, such as a hormone signaling pathway for example. Transcription factors posses a modular structure and are classified primarily on the basis of the DNA binding domain.

The MYB family of transcription factors is composed of at least 198 genes (Yanhui et al. 2006) and has been proposed to have regulatory functions in a wide array of processes ranging from growth and development to defense responses. Plant MYB proteins are classified based on the presence and number of imperfect MYB repeats each composed of about 52 amino acids. The MYB domain forms a helix-turn-helix conformation and represents the DNA binding domain. Three major groups of MYB proteins have been classified as R1R2R3-MYB, R2R3-MYB and MYB-related proteins.

The R2R3-MYB family of proteins in *Arabidopsis* consists of 125 proteins and is characterized by having a R2R3 DNA binding domain at their N-terminus (Kranz et al., 1998, and Stracke et al., 2001). These genes are involved in a number of biological processes including mediating hormone actions, secondary metabolism (Paz-Ares et al., 1987), control of cell morphogenesis (Oppenheimer et al., 1991), meristem, floral and seed development (Kirik et al., 1998, Schmitz et al., 2002) and response to various environmental factors (Kranz et al., 1998; Jin and Martin, 1999; Meissner et al, 1999).

MYB sequences have been further classified into a number of subgroups based on sequence (Krantz et al 1998, Stracke et al 2001). MYB68 falls within subgroup14 as does MYB36 and MYB84 as identified by Krantz et al 1998. However, Stracke et al 2001, have additionally include the MYB37, MYB38 and MYB87 in subgroup14. Stracke further notes that there are several cases of functional conservation of genes that cluster together in the dendrogram.

Classification of the R2R3-MYB family has identified 125 MYB proteins in *Arabidopsis thaliana* (At). A R2R3 MYB gene is characterized by a MYB domain containing two imperfect repeats of 53 aa (R2, and R3). Each repeat contains three helix-turn-helix structures. The R2 and R3 domains are located near the N-terminus of the proteins. The last two helices on each repeat with a loop between them form a DNA-binding motif structure similar to HLH proteins. The third helix directly binds to DNA, and the first and second helices contribute to the conformation of the HLH motif that appears to be important in recognition of a specific gene target (Ogata et al., 1994; William and Grotewold, 1997; Jia et al., 2004). The R2R3-MYB proteins were further characterized into 22 subgroups according to their phylogenetic relationship based on at least one of the shared amino acid motifs in addition to the MYB domain (Kranz et al., 1998). AtMYB68, AtMYB84, and AtMYB36 were categorized as subgroup14 based on two shared motifs: S1: SFSQLLLDPN SEQ ID NO:266 and S2: TSTSADQS-TISWEDI SEQ ID NO:267, at the C-terminus of the proteins. The homology at these motifs was limited, for example, *Arabidopsis* MYB36 has only 20% identity. Subsequently, AtMYB87, AtMYB37 and AtMYB38 were also included in subgroup14, on the basis of sequence conservation in the MYB DNA domain: R2 and R3 helix-turn-helix repeats (Stracke et al., 2001).

The R2R3 domains may be indicative of specific DNA binding through the unique amino acid sequence of the third helix of the R3 domain and minor conformational changes associated with the structural interaction between the first two helices. It suggests that subgroup14 members may be functionally redundant orthologous. For example, lateral meristem initiation in *Arabidopsis* was studied with respect to MYB-subgroup14 (Muller et al., 2006). All members of MYB-subgroup14 showed high similarity to the tomato Blind (B1) gene, a regulator of axillary meristems. Transcripts of four members: AtMYB37, AtMYB38, AtMYB84 and AtMYB87 were detected by RT-PCR in tissues including shoot tip, internode, leaf, flower bud, open flower, and root, whereas AtMYB36 and AtMYB68 expression was expressed in root tissue. Phenotypic analysis using knockouts of AtMYB37, AtMYB38 and AtMYB84 indicated that these members of MYB-subgroup14 at least partially redundant for regulating axillary bud formation.

MYB68 is a R2R3 type MYB gene, and a member of MYB-subgroup14, that has been identified in a transposon gene trapping study (Feng et al., 2004). Expression of this gene has been demonstrated to be specific to root pericycle cells. In the null mutant, no MYB68 mRNA was detectable; however, no mutant phenotype was exhibited when plants were grown under standard conditions. In the evaluation of MYB68 under a variety of growth conditions the only phenotype discerned was reduced plant leaf area when plants were grown under hot greenhouse conditions (30-40° C.). This phenotype was rescued by transformation of the myb68 mutant background with a wild-type MYB68 gene. Examination root tissue of the myb68 mutant grown in root cultures indicated increased biomass and lignin levels. The authors conclude that MYB68 is involved in root development (Feng et al., 2004).

Transcriptional activation is primarily mediated through transcription factors that interact with enhancer and promoter elements. Binding of transcription factors to such DNA elements constitutes a crucial step in transcriptional initiation. Each transcription factor binds to its specific binding sequence in a promoter and activates expression of the linked coding region through interactions with coactivators and/or proteins that are a part of the transcription complex.

SUMMARY OF THE INVENTION

This invention relates to a method for enhancing the heat stress tolerance of plants by means of increasing the expression of a MYB subgroup-14 polypeptide. Enhanced heat stress tolerance includes improved seed set during and following conditions of heat stress. Improved seed set results in increased yield. A MYB-subgroup-14 polypeptide includes for example a MYB68, a MYB36, a MYB84, a MYB37, a MYB38 or a MYB87 polypeptide. Preferably, the MYB-subgroup-14 polypeptide is a MYB68, a MYB36 or a MYB84 polypeptide. The MYB subgroup-14 polypeptide expression is ectopic, or constitutive. Alternatively, expression of the MYB subgroup-14 polypeptide in its typical place of expression, e.g. root tissue.

A heat stress heat stress tolerant plant is produced by providing a nucleic acid construct that increases the expression of a Myb subgroup-14 polypeptide, inserting the nucleic construct into a vector, transforming a plant, tissue culture, or a plant cell with the vector to obtain a plant, tissue culture or a plant cell with increased expression of the Myb subgroup-14 polypeptide and growing said plant or regenerating a plant from the tissue culture or plant cell. A nucleic acid construct that increases the expression of a Myb subgroup-14 polypeptide includes for example an enhancer element. An enhancer is a sequence found in eukaryotes and certain eukaryotic viruses which can increase transcription of a gene when located, in either orientation, up to several kilobases from the gene concerned. These sequences act as enhancers when on the 5' side (upstream) of the gene in question. However, some enhancers are active when placed on the 3' side (downstream) of the gene. The enhancer elements can activate transcription of a gene and alter the normal expression pattern of the endogenous gene. Enhancer elements are known to those skilled in the art. For example the enhancer element is a 35S enhancer element.

Additionally, a nucleic acid construct that increases the expression of a Myb subgroup-14 polypeptide includes for example a nucleic acid encoding a Myb subgroup-14 polypeptide. Exemplary, MYB polypeptides and nucleic acids include those of SEQ ID NO: 1-265. The nucleic acid encoding a Myb subgroup-14 polypeptide is operably linked to a promoter. The promoter is a heterologous promoter or a homologous promoter. Additionally, the promoter is a constitutive or an inducible promoter.

By increasing the expression of a MYB subgroup-14 polypeptide is meant that the amount produced by the cell transformed with the nucleic acid construct is greater than a cell, e.g. control cell that is not transformed with the nucleic acid construct. A control cell includes for example a cell that endogenously expresses a MYB subgroup-14 polypeptide such a plant root cell, alternatively a control cell is a non transformed cell of the same cell-type as the transformed cell, be it a leaf cell a meristem cell or a flower or seed cell. An increase is a 1-fold, 2-fold, 3 fold or greater increase. An increase of expression is also meant to include expression of a MYB subgroup-14 polypeptide in a cell that does not typically produced by a cell.

Also included in the invention is a method of identifying a heat stress tolerant plant. The plants identified by these methods have reduced flower abortion and increased yield as compared to a control plant. Heat stress tolerant plants are identified by exposing a population of flowering plants to a heat stress treatment and selecting a plant from the population of plants that has reduced flower abortion. Heat stress treatment includes for example exposing the plant to a temperature that is hot enough for a sufficient amount of time such that damage to plant functions or development results. By reduced flower abortion is meant that a plant does not loss as many flowers, due to flower abortion, or has a greater seed yield compared to another plant that is exposed to a similar level of heat stress. Plants with a reduced flower abortion have a 5, 10, 20, 25, 30% or more increase in seed yield as compared to a control plant.

The invention further includes the plants produced by the methods of the invention and the seed produced by the plants which produce a plant that has an increase tolerance to heat stress.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention is based upon the surprising discovery of plants that have an increased tolerance to heat stress which results in an increased yield relative to a wild-type control. More specifically, the invention is based upon the discovery that increasing the expression of a MYB-subgroup14 polypeptide (e.g., MYB68) results in a plant having an increased resistance to heat stress.

Expression of a MYB-subgroup 14 polypeptide can be accomplished for example by increasing the expression of an endogenous MYB-subgroup 14 polypeptide (e.g., activation tag insertion) or by expression of an exogenous gene construct encoding for a MYB-subgroup 14 polypeptide. The gene encoding for the MYB-subgroup 14 polypeptide may be endogenous or exogenous to the transformed species. As shown in the EXAMPLES plants having an increases resistance to heat stress were produced not only transforming a plant with its native MYB-subgroup 14 polypeptide but also with a MYB-subgroup 14 polypeptide from another plant species.

Accordingly the invention provides methods of enhancing (e.g., increasing) the heat stress tolerance of plants by increasing the expression of a MYB subgroup-14 polypeptide. Also included in the invention is a method of identifying a heat stress tolerant plant. The plants identified by these methods have reduced flower abortion and increased yield as compared to a control plant. Heat stress tolerant plants are identified by exposing the population of flowering plants to a heat stress treatment and selecting a plant from the population of plants that has reduced flower abortion. The invention also includes the transgenic plants produced by the methods of the invention and the seeds produced by the transgenic plants that produce a heat stress tolerant plant.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

For convenience, before further description of the present invention, certain terms employed in the specification, examples and appended claims are defined herein. These definitions should be read in light of the remainder of the disclosure and as understood by a person of ordinary skill in the art.

The term "constitutive expression" means expression of a gene in any cell at constant levels in a non-regulated manner.

The terms "cMYB" and "MYB" refer to a cDNA clone of MYB and are used interchangeably. Where a genomic sequence has been used or referred to, it is identified and differentiated by the term "gMYB" or "genomic MYB" thereby referring to a genomic MYB sequence.

The term "ectopic expression" means expression of a gene in an abnormal place in an organism relative to the endogenous gene expression. Ectopic expression may include constitutively expressed genes depending on the native expression patterns of a given gene.

The term "expression cassette" means a vector construct wherein a gene is transcribed. Additionally, the expressed mRNA may be translated into a polypeptide.

The terms "expression" or "over-expression" are used interchangeably and means the expression of a gene such that the transgene is expressed. The total level of expression in a cell may be elevated relative to a wild-type cell.

"Flower abortion" means a flower that fails to develop and produce a fruit or seed. In addition to premature senescence of a flower, flower abortion may refer to loss of pollen production, altered pollination or fertilization and subsequent seed development. Altered growth and development of meristem tissue, a flower meristem in particular, is further included within the meaning of flower abortion.

The term "heat tolerance" is defined as a phenotype where a first plant, or plant line, has increased capacity to withstand elevated temperature and produce a yield that is in excess of a second plant or plant line, the second plant line being a control plant such as a wild-type control plant line.

A "promoter sequence", or "promoter", means a nucleic acid sequence capable of inducing transcription of an operably linked gene sequence in a plant cell.

The term "seed set" is seed formation as a result of flower pollination followed by egg cell fertilization and zygote development. Reductions in seed set which can occur due to interruption in any of the above processes will produce a net reduction in seed number produced.

The term "substantially similar" refers to nucleic acids where a change in one or more nucleotides does not alter the functional properties of the nucleic acid or the encoded polypeptide. Due to the degeneracy of the genetic code, a base pair change can result in no change in the encoded amino acid sequence. For example, the codons ACT, ACC, ACA and ACG all encode a threonine amino acid. Alternatively one or more base pair changes may alter the encoded amino acid however if the substituted amino acid has similar chemical properties functionality of the encoded protein is likely to be unaffected. For example, threonine codons ACT and ACC when changed to AGT or AGC respectively encode for serine, a chemically and biologically similar amino acid. Additionally, certain amino acids within a polypeptide are non essential and alterations may be made in these locations without an effect on the functionality of the polypeptide. Substantially similar also refers to sequences having changes at one or more nucleotide bases wherein the changes do not affect the ability of the sequence to alter gene expression by various gene silencing methodologies such as antisense, RNAi or co-suppression. The term "substantially similar" refers to polypeptides wherein a change in one or more amino acids does not alter the functional properties of the polypeptide as discussed above.

The term "yield" refers to seed number, seed weight, seed size, total plant biomass, increased biomass of a plant organ, such as stems or leaves or roots, fruit production, and flower production, The term "yield protection" is defined as the positive difference, expressed as a % value, between the yield of the transgenic or mutant and the control, where the yield is expressed as a % of optimal, following an imposed stress.

The calculation is done by comparing the optimal yield with that after the stress treatment (stress yield/optimal yield× 100).

The MYB gene family is classified based on sequence homology and the presence of defined domains and motifs such as an R2R3 domain. The classification in all cases is not absolute and varies depending on the criteria selected for the analysis (Krantz et al 1998, Stracke et al 2001).

Herein we define the MYB-subgroup14 to include at least the following members, MYB68, MYB36, MYB84, MYB37, MYB38 and MYB87. The *Arabidopsis* MYB68, MYB36, MYB84, MYB37, MYB38 and MYB87 sequences are used to identify homologues from other species according to the methods herein, examples of which are included in Table 1

The term "MYB sequence" refers to a polynucleotide sequence or a polypeptide sequence as contextually appropriate.

Sequences

The following sequences from the MYB-subgroup14 family, and corresponding sequence identifiers, are employed throughout the specification, examples and appended claims:

TABLE 1

| SEQ ID NO: | SPECIES | Accession Number Reference | MYB Identification | |
|---|---|---|---|---|
| 1 | ARABIDOPSIS THALIANA | NM_125976.2 | MYB68 | NT |
| 2 | ARABIDOPSIS THALIANA | NP_201380.1 | MYB68 | AA |
| 3 | ARABIDOPSIS THALIANA | NM_114829.3 | MYB84 | NT |
| 4 | ARABIDOPSIS THALIANA | NP_190538.1 | MYB84 | AA |
| 5 | ARABIDOPSIS THALIANA | NM_125143.3 | MYB36 | NT |
| 6 | ARABIDOPSIS THALIANA | NP_200570.1 | MYB36 | AA |
| 7 | BRASSICA RAPA | | MYB68 | NT |
| 8 | BRASSICA RAPA | | MYB68 | AA |
| 9 | ORYZA SATIVA | NM_001057941.1 | MYB36 | NT |
| 10 | ORYZA SATIVA | AAT85046.1 | MYB36 | AA |
| 11 | GOSSYPIUM | TC34239 | MYB68 | NT |
| 12 | GOSSYPIUM | TC34239_ORF | MYB68 | AA |
| 13 | GLYCINE MAX | DQ822965.1 | MYB84 | NT |
| 14 | GLYCINE MAX | ABH02906.1 | MYB84 | AA |
| 15 | GLYCINE MAX | | MYB84 | NT |
| 16 | GLYCINE MAX | | MYB84 | AA |
| 17 | ZEA MAYS | TC370133 | MYB84 | NT |
| 18 | ZEA MAYS | TC370133_ORF | MYB84 | AA |
| 19 | SORGHUM BICOLOR | AF474127 | MYB36 | NT |
| 20 | SORGHUM BICOLOR | AAL84760.1 | MYB36 | AA |
| 21 | TRITICUM AESTIVUM | BQ483726 | MYB84 | NT |
| 22 | TRITICUM AESTIVUM | BQ483726_ORF | MYB84 | AA |
| 23 | POPULUS | TC54478 | MYB84 | NT |
| 24 | POPULUS | TC54478_ORF | MYB84 | AA |
| 25 | MEDICAGO TRUNCATULA | TC97441 | MYB68 | NT |
| 26 | MEDICAGO TRUNCATULA | TC97441_ORF | MYB68 | AA |
| 27 | SOLANUM LYCOPERSICUM | AF426174.1 | MYB36 | NT |
| 28 | SOLANUM LYCOPERSICUM | AAL69334.1 | MYB36 | AA |
| 29 | SOLANUM LYCOPERSICUM | BG134669 | MYB36 | NT |
| 30 | SOLANUM LYCOPERSICUM | BG134669_ORF | MYB36 | AA |
| 31 | ARABIDOPSIS THALIANA | NM_119940.3 | MYB87 | NT |
| 32 | ARABIDOPSIS THALIANA | NP_195492.2 | MYB87 | AA |
| 33 | ARABIDOPSIS THALIANA | NM_122206.3 | MYB37 | NT |
| 34 | ARABIDOPSIS THALIANA | NP_197691.1 | MYB37 | AA |
| 35 | ARABIDOPSIS THALIANA | NM_129245.2 | MYB38 | NT |
| 36 | ARABIDOPSIS THALIANA | NP_181226.1 | MYB38 | AA |
| 37 | AEGILOPS SPELTOIDES | BQ841600.1 | MYB36 | NT |
| 38 | ANTIRRHINUM MAJUS | AJ794728.1 | MYB68 | NT |
| 39 | ANTIRRHINUM MAJUS | AJ794728.1_ORF | MYB68 | AA |
| 40 | AQUILEGIA | TC13008 | MYB84 | NT |
| 41 | AQUILEGIA | TC13008_ORF | MYB84 | AA |
| 42 | AQUILEGIA | TC11167 | MYB36 | NT |
| 43 | AQUILEGIA | TC11167_ORF | MYB36 | AA |
| 44 | ARACHIS HYPOGAEA | CD038321.1 | MYB68 | NT |
| 45 | ARACHIS HYPOGAEA | CD038321.1_ORF | MYB68 | AA |
| 46 | ARACHIS HYPOGAEA | ES761155.1 | MYB68 | NT |
| 47 | ARACHIS HYPOGAEA | ES761155.1_ORF | MYB68 | AA |
| 48 | ARACHIS STENOSPERMA | EH046152.1 | MYB36 | NT |
| 49 | ARACHIS STENOSPERMA | EH046152.1_ORF | MYB36 | AA |
| 50 | BRACHYPODIUM DISTACHYON | DV486330.1 | MYB38 | NT |
| 51 | BRACHYPODIUM DISTACHYON | DV486330.1_ORF | MYB38 | AA |
| 52 | BRACHYPODIUM DISTACHYON | DV488965.1 | MYB38 | NT |

TABLE 1-continued

| SEQ ID NO: | SPECIES | Accession Number Reference | MYB Identification | |
|---|---|---|---|---|
| 53 | BRACHYPODIUM DISTACHYON | DV488965.1_ORF | MYB38 | AA |
| 54 | BRASSICA NAPUS (bud) | | MYB68 | NT |
| 55 | BRASSICA NAPUS (bud) | | MYB68 | AA |
| 56 | BRASSICA NAPUS (root) | | MYB68 | NT |
| 57 | BRASSICA NAPUS (root) | | MYB68 | AA |
| 58 | BRASSICA NAPUS | TC40384 | MYB68 | NT |
| 59 | BRASSICA NAPUS | ES900275.1 | MYB68 | NT |
| 60 | BRASSICA NAPUS | ES900275.1_ORF | MYB68 | AA |
| 61 | BRASSICA NAPUS | TC55899 | MYB38 | NT |
| 62 | BRASSICA NAPUS | TC55899_ORF | MYB38 | AA |
| 63 | BRASSICA RAPA | EX134980.1 | MYB68 | NT |
| 64 | BRASSICA RAPA | EX134980.1_ORF | MYB68 | AA |
| 65 | BRASSICA RAPA | EX137439.1 | MYB68 | NT |
| 66 | BRASSICA RAPA | EX137439.1_ORF | MYB68 | AA |
| 67 | CARTHAMUS TINCTORIUS | EL384492.1 | MYB36 | NT |
| 68 | CARTHAMUS TINCTORIUS | EL384492.1_ORF | MYB36 | AA |
| 69 | CARTHAMUS TINCTORIUS | EL392277.1 | MYB36 | NT |
| 70 | CARTHAMUS TINCTORIUS | EL392277.1_ORF | MYB36 | AA |
| 71 | CENTAUREA MACULOSA | EH724496.1 | MYB36 | NT |
| 72 | CENTAUREA MACULOSA | EH724496.1_ORF | MYB36 | AA |
| 73 | CENTAUREA MACULOSA | EH719165.1 | MYB36 | NT |
| 74 | CENTAUREA MACULOSA | EH719165.1_ORF | MYB36 | AA |
| 75 | CENTAUREA MACULOSA | EH724438.1 | MYB68 | NT |
| 76 | CENTAUREA MACULOSA | EH724438.1_ORF | MYB68 | AA |
| 77 | CENTAUREA SOLSTITIALIS | EH774519.1 | MYB68 | NT |
| 78 | CENTAUREA SOLSTITIALIS | EH774519.1_ORF | MYB68 | AA |
| 79 | CENTAUREA SOLSTITIALIS | EH771972.1 | MYB68 | NT |
| 80 | CENTAUREA SOLSTITIALIS | EH771972.1_ORF | MYB68 | AA |
| 81 | CENTAUREA SOLSTITIALIS | EH768792.1 | MYB84 | NT |
| 82 | CENTAUREA SOLSTITIALIS | EH768792.1_ORF | MYB84 | AA |
| 83 | CICHORIUM ENDIVIA | EL361859.1 | MYB84 | NT |
| 84 | CICHORIUM ENDIVIA | EL361859.1_ORF | MYB84 | AA |
| 85 | CICHORIUM INTYBUS | EH681135.1 | MYB38 | NT |
| 86 | CICHORIUM INTYBUS | EH681135.1_ORF | MYB38 | AA |
| 87 | CICHORIUM INTYBUS | EH694860.1 | MYB68 | NT |
| 88 | CITRUS SINENSIS | CK936024.1 | MYB68 | NT |
| 89 | CITRUS SINENSIS | CK936024.1_ORF | MYB68 | AA |
| 90 | COFFEA CANEPHORA | DV692261.1 | MYB37 | NT |
| 91 | COFFEA CANEPHORA | DV691112.1 | MYB37 | NT |
| 92 | CUCUMIS MELO | AM727197.2 | MYB36 | NT |
| 93 | CUCUMIS MELO | AM727197.2_ORF | MYB36 | AA |
| 94 | CUCUMIS MELO | AM716075.2 | MYB36 | NT |
| 95 | CUCUMIS MELO | AM716075.2_ORF | MYB36 | AA |
| 96 | DAUCUS CAROTA | AB298508.1 | MYB68 | NT |
| 97 | DAUCUS CAROTA | BAF49444.1 | MYB68 | AA |
| 98 | ELAEIS GUINEENSIS | EL690464.1 | MYB84 | NT |
| 99 | ELAEIS GUINEENSIS | EL690464.1_ORF | MYB84 | AA |
| 100 | ELAEIS OLEIFERA | ES370938.1 | MYB84 | NT |
| 101 | ELAEIS OLEIFERA | ES370938.1_ORF | MYB84 | AA |
| 102 | ESCHSCHOLZIA CALIFORNICA | CD480801.1 | MYB68 | NT |
| 103 | ESCHSCHOLZIA CALIFORNICA | CD480801.1_ORF | MYB68 | AA |
| 104 | EUPHORBIA ESULA | DV138530.1 | MYB84 | NT |
| 105 | EUPHORBIA ESULA | DV138530.1_ORF | MYB84 | AA |
| 106 | EUPHORBIA ESULA | DV126436.1 | MYB36 | NT |
| 107 | EUPHORBIA ESULA | DV126436.1_ORF | MYB36 | AA |
| 108 | EUPHORBIA TIRUCALLI | BP958179.1 | MYB84 | NT |
| 109 | GINKGO BILOBA | EX940876.1 | MYB68 | NT |
| 110 | GLYCINE MAX | | MYB84 | NT |
| 111 | GLYCINE MAX | | MYB84 | AA |
| 112 | GLYCINE MAX | TC213651 | MYB84 | NT |
| 113 | GLYCINE MAX | TC213651_ORF | MYB84 | AA |
| 114 | GLYCINE MAX | DQ822971.1 | MYB36 | NT |
| 115 | GLYCINE MAX | ABH02912.1 | MYB36 | AA |
| 116 | GLYCINE MAX | TC211227 | MYB36 | NT |

TABLE 1-continued

| SEQ ID NO: | SPECIES | Accession Number Reference | MYB Identification | |
|---|---|---|---|---|
| 117 | GLYCINE MAX | TC211227_ORF | MYB36 | AA |
| 118 | GOSSYPIUM | TC62721 | MYB68 | NT |
| 119 | GOSSYPIUM | TC62721_ORF | MYB68 | AA |
| 120 | GOSSYPIUM | DW491290.1 | MYB36 | NT |
| 121 | GOSSYPIUM | DW491290.1_ORF | MYB36 | AA |
| 122 | HEDYOTIS TERMINALIS | CB077617.1 | MYB84 | NT |
| 123 | HEDYOTIS TERMINALIS | CB077617.1_ORF | MYB84 | AA |
| 124 | HELIANTHUS ANNUUS | BQ967558 | MYB36 | NT |
| 125 | HELIANTHUS ARGOPHYLLUS | EE621630.1 | MYB36 | NT |
| 126 | HELIANTHUS ARGOPHYLLUS | EE621630.1_ORF | MYB36 | AA |
| 127 | HELIANTHUS ARGOPHYLLUS | EE619500.1 | MYB36 | NT |
| 128 | HELIANTHUS ARGOPHYLLUS | EE619500.1_ORF | MYB36 | AA |
| 129 | HELIANTHUS CILIARIS | EL422629.1 | MYB68 | NT |
| 130 | HELIANTHUS EXILIS | EE645503.1 | MYB68 | NT |
| 131 | HELIANTHUS EXILIS | EE645503.1_ORF | MYB68 | AA |
| 132 | HELIANTHUS EXILIS | EE646813.1 | MYB36 | NT |
| 133 | HELIANTHUS EXILIS | EE646813.1_ORF | MYB36 | AA |
| 134 | HELIANTHUS PARADOXUS | EL474327.1 | MYB84 | NT |
| 135 | HELIANTHUS PETIOLARIS | DY942970.1 | MYB84 | NT |
| 136 | HELIANTHUS PETIOLARIS | DY942970.1_ORF | MYB84 | AA |
| 137 | HELIANTHUS PETIOLARIS | DY953493.1 | MYB68 | NT |
| 138 | HELIANTHUS PETIOLARIS | DY953493.1_ORF | MYB68 | AA |
| 139 | HELIANTHUS TUBEROSUS | EL445341.1 | MYB36 | NT |
| 140 | HELIANTHUS TUBEROSUS | EL445341.1_ORF | MYB36 | AA |
| 141 | HORDEUM VULGARE | BY845215.1 | MYB38 | NT |
| 142 | HORDEUM VULGARE | BY845215.1_ORF | MYB38 | AA |
| 143 | HUMULUS LUPULUS | AJ876882.1 | MYB36 | NT |
| 144 | HUMULUS LUPULUS | CAI46244.1 | MYB36 | AA |
| 145 | LACTUCA PERENNIS | DW092247.1 | MYB84 | NT |
| 146 | LACTUCA PERENNIS | DW092247.1_ORF | MYB84 | AA |
| 147 | LACTUCA SALIGNA | DW065247.1 | MYB68 | NT |
| 148 | LACTUCA SALIGNA | DW065247.1_ORF | MYB68 | AA |
| 149 | LACTUCA SATIVA | DY960463.1 | MYB38 | NT |
| 150 | LACTUCA SATIVA | DY960463.1_ORF | MYB38 | AA |
| 151 | LACTUCA SATIVA | DY969483.1 | MYB38 | NT |
| 152 | LACTUCA SATIVA | DY969483.1_ORF | MYB38 | AA |
| 153 | LACTUCA SATIVA | DY980672.1 | MYB38 | NT |
| 154 | LACTUCA SATIVA | DY980672.1_ORF | MYB38 | AA |
| 155 | LACTUCA SERRIOLA | DW108054.1 | MYB38 | NT |
| 156 | LACTUCA VIROSA | DW160139.1 | MYB84 | NT |
| 157 | LACTUCA VIROSA | DW160139.1_ORF | MYB84 | AA |
| 158 | LACTUCA VIROSA | DW160891.1 | MYB38 | NT |
| 159 | LACTUCA VIROSA | DW160891.1_ORF | MYB38 | AA |
| 160 | LIRIODENDRON TULIPIFERA | CO998829.1 | MYB38 | NT |
| 161 | LIRIODENDRON TULIPIFERA | CO998829.1_ORF | MYB38 | AA |
| 162 | MALUS DOMESTICA | DT002401.1 | MYB36 | NT |
| 163 | MALUS DOMESTICA | DT002401.1_ORF | MYB36 | AA |
| 164 | MALUS DOMESTICA | DQ074472.1 | MYB38 | NT |
| 165 | MALUS DOMESTICA | AAZ20440.1 | MYB38 | AA |
| 166 | MANIHOT ESCULENTA | DB936694.1 | MYB68 | NT |
| 167 | MANIHOT ESCULENTA | DB936694.1_ORF | MYB68 | AA |
| 168 | MARCHANTIA POLYMORPHA | BJ846153.1 | MYB84 | NT |
| 169 | MARCHANTIA POLYMORPHA | BJ846153.1_ORF | MYB84 | AA |
| 170 | MEDICAGO TRUNCATULA | TC110497 | MYB36 | NT |
| 171 | MEDICAGO TRUNCATULA | TC110497_ORF | MYB36 | AA |
| 172 | MEDICAGO TRUNCATULA | BF634640 | MYB84 | NT |
| 173 | MEDICAGO TRUNCATULA | BF634640_ORF | MYB84 | AA |
| 174 | NUPHAR ADVENA | CD472544.1 | MYB36 | NT |
| 175 | NUPHAR ADVENA | CD472544.1_ORF | MYB36 | AA |
| 176 | ORYZA SATIVA | LOC_Os01g09590.1_cds | MYB38 | NT |
| 177 | ORYZA SATIVA | LOC_Os01g09590.1 | MYB38 | AA |
| 178 | ORYZA SATIVA | LOC_Os01g49160.1_cds | MYB36 | NT |

TABLE 1-continued

| SEQ ID NO: | SPECIES | Accession Number Reference | MYB Identification | |
|---|---|---|---|---|
| 179 | ORYZA SATIVA | LOC_Os01g49160.1 | MYB36 | AA |
| 180 | ORYZA SATIVA | LOC_Os01g52410.1_cds | MYB38 | NT |
| 181 | ORYZA SATIVA | LOC_Os01g52410.1 | MYB38 | AA |
| 182 | ORYZA SATIVA | LOC_Os02g54520.1_cds | MYB36 | NT |
| 183 | ORYZA SATIVA | LOC_Os02g54520.1 | MYB36 | AA |
| 184 | ORYZA SATIVA | LOC_Os05g48010.1_cds | MYB36 | NT |
| 185 | ORYZA SATIVA | LOC_Os05g48010.1 | MYB36 | AA |
| 186 | ORYZA SATIVA | LOC_Os08g15020.1_cds | MYB36 | NT |
| 187 | ORYZA SATIVA | LOC_Os08g15020.1 | MYB36 | AA |
| 188 | ORYZA SATIVA | LOC_Os09g26170.1_cds | MYB36 | NT |
| 189 | ORYZA SATIVA | LOC_Os09g26170.1 | MYB36 | AA |
| 190 | ORYZA SATIVA | LOC_Os10g35660.1_cds | MYB36 | NT |
| 191 | ORYZA SATIVA | LOC_Os10g35660.1 | MYB36 | AA |
| 192 | PICEA | EX361512.1 | MYB68 | NT |
| 193 | PICEA | EX361512.1_ORF | MYB68 | AA |
| 194 | PICEA | TC20498 | MYB68 | NT |
| 195 | PICEA | TC20498_ORF | MYB68 | AA |
| 196 | PINUS | DR015810 | MYB84 | NT |
| 197 | PINUS | DR015810_ORF | MYB84 | AA |
| 198 | PINUS | TC66643 | MYB68 | NT |
| 199 | PINUS | TC66643_ORF | MYB68 | AA |
| 200 | PONCIRUS TRIFOLIATA | CD575120.1 | MYB38 | NT |
| 201 | PONCIRUS TRIFOLIATA | CD575120.1_ORF | MYB38 | AA |
| 202 | POPULUS | Gw1.II.96.1 | MYB68 | NT |
| 203 | POPULUS | Gw1.II.96.1_ORF | MYB68 | AA |
| 204 | POPULUS | DB879439.1 | MYB84 | NT |
| 205 | POPULUS | DB879439.1_ORF | MYB84 | AA |
| 206 | POPULUS | TC74579 | MYB36 | NT |
| 207 | POPULUS | TC74579_ORF | MYB36 | AA |
| 208 | QUERCUS PETRAEA | CU639795.1 | MYB36 | NT |
| 209 | QUERCUS PETRAEA | CU639795.1_ORF | MYB36 | AA |
| 210 | QUERCUS SUBER | EE743680.1 | MYB84 | NT |
| 211 | RAPHANUS RAPHANISTRUM | FD544184.1 | MYB68 | NT |
| 212 | RAPHANUS RAPHANISTRUM | FD544184.1_ORF | MYB68 | AA |
| 213 | RAPHANUS RAPHANISTRUM | EY915531.1 | MYB68 | NT |
| 214 | RAPHANUS RAPHANISTRUM | FD540311.1 | MYB68 | NT |
| 215 | RAPHANUS RAPHANISTRUM | FD540311.1_ORF | MYB68 | AA |
| 216 | RAPHANUS RAPHANISTRUM | EV548164.1 | MYB38 | NT |
| 217 | RAPHANUS SATIVUS | FD580369.1 | MYB68 | NT |
| 218 | ROSA HYBRID | EC587279.1 | MYB68 | NT |
| 219 | ROSA HYBRID | EC587279.1_ORF | MYB68 | AA |
| 220 | SACCHARUM OFFICINARUM | CA150911 | MYB36 | NT |
| 221 | SACCHARUM OFFICINARUM | CA150911_ORF | MYB36 | AA |
| 222 | SACCHARUM OFFICINARUM | CA258665 | MYB84 | NT |
| 223 | SACCHARUM OFFICINARUM | CA258665_ORF | MYB84 | AA |
| 224 | SACCHARUM OFFICINARUM | TC44677 | MYB36 | NT |
| 225 | SACCHARUM OFFICINARUM | TC44677_ORF | MYB36 | AA |
| 226 | SECALE CEREALE | BE495537 | MYB38 | NT |
| 227 | SECALE CEREALE | BE495537_ORF | MYB38 | AA |
| 228 | SOLANUM LYCOPERSICUM | TC182203 | MYB36 | NT |
| 229 | SOLANUM LYCOPERSICUM | TC182203_ORF | MYB36 | AA |
| 230 | SOLANUM TUBEROSUM | AM907873.1 | MYB36 | NT |
| 231 | SOLANUM TUBEROSUM | AM907873.1_ORF | MYB36 | AA |
| 232 | SORGHUM BICOLOR | TC98185 | MYB36 | NT |
| 233 | SORGHUM BICOLOR | TC98185_ORF | MYB36 | AA |
| 234 | SORGHUM BICOLOR | TC101637 | MYB36 | NT |
| 235 | SORGHUM BICOLOR | TC101637_ORF | MYB36 | AA |
| 236 | SORGHUM PROPINQUUM | BG560270.1 | MYB36 | NT |
| 237 | SORGHUM PROPINQUUM | BG560270.1_ORF | MYB36 | AA |
| 238 | TARAXACUM OFFICINALE | DY830100.1 | MYB68 | NT |
| 239 | TARAXACUM OFFICINALE | DY830100.1_ORF | MYB68 | AA |

TABLE 1-continued

| SEQ ID NO: | SPECIES | Accession Number Reference | MYB Identification | |
|---|---|---|---|---|
| 240 | TRIPHYSARIA PUSILLA | EY172046.1 | MYB68 | NT |
| 241 | TRIPHYSARIA PUSILLA | EY172046.1_ORF | MYB68 | AA |
| 242 | TRIPHYSARIA PUSILLA | EY179359.1 | MYB36 | NT |
| 243 | TRIPHYSARIA PUSILLA | EY179359.1_ORF | MYB36 | AA |
| 244 | TRIPHYSARIA PUSILLA | EY174724.1 | MYB38 | NT |
| 245 | TRIPHYSARIA PUSILLA | EY174724.1_ORF | MYB38 | AA |
| 246 | TRIPHYSARIA VERSICOLOR | EX989121.1 | MYB38 | NT |
| 247 | TRIPHYSARIA VERSICOLOR | EY018825.1 | MYB38 | NT |
| 248 | TRIPHYSARIA VERSICOLOR | EY018825.1_ORF | MYB38 | AA |
| 249 | TRITICUM AESTIVUM | | MYB84 | NT |
| 250 | TRITICUM AESTIVUM | | MYB84 | AA |
| 251 | VACCINIUM CORYMBOSUM | CV090776.1 | MYB36 | NT |
| 252 | VACCINIUM CORYMBOSUM | CV090776.1_ORF | MYB36 | AA |
| 253 | VITIS VINIFERA | CAO70108.1_cds | MYB84 | NT |
| 254 | VITIS VINIFERA | CAO70108.1 | MYB84 | AA |
| 255 | VITIS VINIFERA | CAO43296.1_cds | MYB36 | NT |
| 256 | VITIS VINIFERA | CAO43296.1 | MYB36 | AA |
| 257 | VITIS VINIFERA | CAO61524.1_cds | MYB84 | NT |
| 258 | VITIS VINIFERA | CAO61524.1 | MYB84 | AA |
| 259 | VITIS VINIFERA | DT006424 | MYB36 | NT |
| 260 | VITIS VINIFERA | DT006424_ORF | MYB36 | AA |
| 261 | ZEA MAYS | | MYB36 | NT |
| 262 | ZEA MAYS | | MYB36 | AA |
| 263 | ZEA MAYS | TC320820 | MYB36 | NT |
| 264 | ZEA MAYS | TC320820_ORF | MYB36 | AA |
| 265 | ORYZA SATIVA | | MYB36 | NT |

Determining Homology Between Two or More Sequences

To determine the percent homology of two amino acid sequences or of two nucleic acids, the sequences are aligned for optimal comparison purposes (e.g., gaps can be introduced in either of the sequences being compared for optimal alignment between the sequences). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch 1970 *J Mol Biol* 48: 443-453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the coding sequence (encoding) part of the DNA sequence shown in Table 1.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region. The term "percentage of positive residues" is calculated by comparing two optimally aligned sequences over that region of comparison, determining the number of positions at which the identical and conservative amino acid substitutions, as defined above, occur in both sequences to yield the number of matched positions, dividing the number of matched positions by the total number of positions in the region of comparison (i.e., the window size), and multiplying the result by 100 to yield the percentage of positive residues.

Recombinant Expression Vectors and Host Cells

Another aspect of the invention pertains to vectors, preferably expression vectors, containing a nucleic acid encoding a MYB-subgroup14 protein, gene, analogs or homologs thereof. The sequence encoding a MYB-subgroup14 polypeptide may be a genomic sequence or a cDNA sequence. As used herein the term expression vector includes vectors which are designed to provide transcription of the nucleic acid sequence. The transcribed nucleic acid may be translated into a polypeptide or protein product. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication). Other vectors are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors or plant transformation vectors, binary or otherwise, which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to include promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences) or inducible promoters (e.g., induced in response to abiotic factors such as environmental conditions, heat, drought, nutrient status or physiological status of the cell or biotic such as pathogen responsive). Examples of suitable promoters include for example constitutive promoters, ABA inducible promoters, tissue specific promoters and abiotic or biotic inducible promoters. It will be appreciated by those skilled in the art that the design of the expression vector can depend on such factors as the choice of the host cell to be transformed, the level of expression of protein desired as well as timing and location of expression, etc. The expression vectors of the invention can be introduced into host cells to thereby produce proteins or peptides, including fusion proteins or peptides, encoded by nucleic acids as described herein (e.g., MYB-subgroup14 proteins such as MYB68 proteins, mutant forms of MYB68 proteins, fusion proteins, etc.).

The recombinant expression vectors of the invention can be designed for expression of a MYB-subgroup14 gene or a MYB-subgroup14 protein in prokaryotic or eukaryotic cells. For example, a MYB-subgroup14 gene or a MYB-subgroup14 protein can be expressed in bacterial cells such as *Escherichia coli*, insect cells (using baculovirus expression vectors) yeast cells, plant cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

In one embodiment, a nucleic acid of the invention is expressed in plants cells using a plant expression vector. Examples of plant expression vectors systems include tumor inducing (Ti) plasmid or portion thereof found in *Agrobacterium*, cauliflower mosaic virus (CAMV) DNA and vectors such as pBI121, a pCAMBA series vector or one of preferred choice to a person skilled in the art.

For expression in plants, the recombinant expression cassette will contain in addition to a MYB-subgroup14 polynucleotide, a promoter region functional in a plant cell, a transcription initiation site (if the coding sequence to transcribed lacks one), and a transcription termination/polyadenylation sequence. The termination/polyadenylation region may be obtained from the same gene as the promoter sequence or may be obtained from different genes. Unique restriction enzyme sites at the 5' and 3' ends of the cassette are typically included to allow for easy insertion into a pre-existing vector.

Examples of suitable plant expressible promoters include promoters from plant viruses such as the 35S promoter from cauliflower mosaic virus (CaMV) (Odell, et al., Nature, 313: 810-812 (1985)), promoters from genes such as rice actin (McElroy, et al., Plant Cell, 163-171 (1990)), ubiquitin (Christensen, et al., Plant Mol. Biol., 12: 619-632 (1992); and Christensen, et al., Plant Mol. Biol., 18: 675-689 (1992)), pEMU (Last, et al., Theor. Appl. Genet., 81: 581-588 (1991)), MAS (Velten, et al., EMBO J., 3: 2723-2730 (1984)), maize 113 histone (Lepetit, et al., Mol. Gen. Genet., 231: 276-285 (1992); and Atanassvoa, et al., Plant Journal, 2(3): 291-300 (1992)), the 5'- or 3'-promoter derived from T-DNA of *Agrobacterium tumefaciens*, the Smas promoter, the cinnamyl alcohol dehydrogenase promoter (U.S. Pat. No. 5,683,439), the Nos promoter, the rubisco promoter, the GRP1-8 promoter, ALS promoter, (WO 96/30530), a synthetic promoter, such as Rsyn7, SCP and UCP promoters, ribulose-1,3-diphosphate carboxylase, fruit-specific promoters, heat shock promoters, seed-specific promoters and other transcription initiation regions from various plant genes, for example, including the various opine initiation regions, such as for example, octopine, mannopine, and nopaline. Useful promoters also include heat inducible promoters such as the HSP18.2 or HSP81.1 promoters (Takahashi et al. 1992, Plant J. 2, 751-761; Yoshida et al., 1995, Appl. Microbiol. Biotechnol. 44, 466-472; Ueda et al., 1996, Mol Gen Genet. 250, 533-539). Cryptic promoters are also useful for chimeric constructs useful in the invention. Cryptic gene regulatory elements are inactive at their native locations in the genome but are fully functional when positioned adjacent to genes in transgenic plants.

In addition to chimeric promoter-gene constructs the use of a native MYB-subgroup14 promoter is contemplated. Expression characteristics of a native promoter may be modified by inclusion of regulatory elements such that expression levels are elevated and or expressed ectopically and or constitutively. For example, a 4×35S enhancer sequence (Wiegel et al., 2000) may be included in a construct to enhance expression. Alternatively a population of plants may be produced by transformation with a construct having a 4×35S enhancer sequence, such as, a pSKI15 vector as per Wiegel et al., 2000. The transformed population can be screened for plants having increased expression of a MYB-subgroup14 sequence, or screened for plants having increased heat tolerance and reduced flower abortion, or a combination of such screens to identify a plant of interest.

Additional regulatory elements that may be connected to a MYB-subgroup14 encoding nucleic acid sequence for expression in plant cells include terminators, polyadenylation sequences, and nucleic acid sequences encoding signal peptides that permit localization within a plant cell or secretion of the protein from the cell. Such regulatory elements and methods for adding or exchanging these elements with the regulatory elements of a MYB-subgroup14 gene are known, and include, but are not limited to, 3' termination and/or polyadenylation regions such as those of the *Agrobacterium tumefaciens* nopaline synthase (nos) gene (Bevan, et al., Nucl. Acids Res., 12: 369-385 (1983)); the potato proteinase inhibitor II (PINII) gene (Keil, et al., Nucl. Acids Res., 14: 5641-5650 (1986) and hereby incorporated by reference); and An, et al., Plant Cell, 1: 115-122 (1989)); and the CaMV 19S gene (Mogen, et al., Plant Cell, 2: 1261-1272 (1990)).

Plant signal sequences, including, but not limited to, signal-peptide encoding DNA/RNA sequences which target proteins to the extracellular matrix of the plant cell (Dratewka-Kos, et al., J. Biol. Chem., 264: 4896-4900 (1989)) and the *Nicotiana plumbaginifolia* extension gene (DeLoose, et al., Gene, 99: 95-100 (1991)), or signal peptides which target proteins to the vacuole like the sweet potato sporamin gene (Matsuka, et al., Proc. Nat'l Acad. Sci. (USA), 88: 834 (1991)) and the barley lectin gene (Wilkins, et al., Plant Cell, 2: 301-313 (1990)), or signals which cause proteins to be secreted such as that of PIM (Lind, et al., Plant Mol. Biol., 18: 47-53 (1992)), or those which target proteins to the plastids such as that of rapeseed enoyl-ACP reductase (Verwaert, et al., Plant Mol. Biol., 26: 189-202 (1994)) are useful in the invention.

In another embodiment, the recombinant expression vector is capable of directing expression of the nucleic acid preferentially in a particular cell type (e.g., tissue-specific regulatory elements are used to express the nucleic acid). Tissue-specific regulatory elements are known in the art. Especially useful in connection with the nucleic acids of the present invention are expression systems which are operable in plants. These include systems which are under control of a tissue-specific promoter, as well as those which involve promoters that are operable in all plant tissues.

Organ-specific promoters are also well known. For example, the chalcone synthase-A gene (van der Meer et al., 1990, *Plant Molecular Biology* 15(1):95-109) or the dihydroflavonol-4-reductase (dfr) promoter (Elomaa et al., The Plant Journal, 16(1) 93-99) direct expression in specific floral tissues. Also available are the patatin class I promoter is transcriptionally activated only in the potato tuber and can be used to target gene expression in the tuber (Bevan, M., 1986, *Nucleic Acids Research* 14:4625-4636). Another potato-specific promoter is the granule-bound starch synthase (GBSS) promoter (Visser, R. G. R, et al., 1991, *Plant Molecular Biology* 17:691-699).

Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, P., 1986, Trans. R. Soc. London B314:343).

The resulting expression system or cassette is ligated into or otherwise constructed to be included in a recombinant vector which is appropriate for plant transformation. The vector may also contain a selectable marker gene by which transformed plant cells can be identified in culture. The marker gene may encode antibiotic resistance. These markers include resistance to G418, hygromycin, bleomycin, kanamycin, and gentamicin. Alternatively the marker gene may encode a herbicide tolerance gene that provides tolerance to glufosinate or glyphosate type herbicides. After transforming the plant cells, those cells having the vector will be identified by their ability to grow on a medium containing the particular antibiotic or herbicide. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as kanamycin or tetracycline.

Other DNA sequences encoding additional functions may also be present in the vector, as is known in the art. For instance, in the case of *Agrobacterium* transformations, T-DNA sequences will also be included for subsequent transfer to plant chromosomes.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell.

A host cell of the invention, such as a prokaryotic or eukaryotic host cell in culture, can be used to produce (i.e., express) a polypeptide of the invention encoded in an open reading frame of a polynucleotide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

A number of cell types may act as suitable host cell for expression of a polypeptide encoded by an open reading frame in a polynucleotide of the invention. Plant host cells include, for example, plant cells that could function as suitable hosts for the expression of a polynucleotide of the invention include epidermal cells, mesophyll and other ground tissues, and vascular tissues in leaves, stems, floral organs, and roots from a variety of plant species, for example *Arabidopsis, Brassica, Oryza, Zea, Sorghum, Gossypium, Triticum, Glycine, Pisum, Phaseolus, Lycopersicon, Trifolium, Cannabis, Cucurbita, Rosa, Vitis, Juglans, Fragaria, Lotus, Medicago, Onobrychis, Trigonella, Vigna, Citrus, Linum, Geranium, Manihot, Daucus, Raphanus, Sinapis, Atropa, Capsicum, Datura, Hyoscyamus, Nicotiana, Solanum, Petunia, Digitalis, Majorana, Ciahorium,*

*Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Lolium, Avena, Hordeum, Secale, Picea, Caco,* and *Populus.*

Conservative Mutations

In addition to naturally-occurring allelic variants of a MYB-subgroup14 or a MYB68 sequence that may exist in the population, the skilled artisan will further appreciate that changes can be introduced by mutation into the nucleotide sequence of SEQ ID NO:1, 3, 5, 7, 9, 11, 13, 15, 17, 19, 21, 23, 25, 27, 29, 31, 33, 35, 37, 38, 40, 42, 44, 46, 48, 50, 52, 54, 56, 58, 59, 61, 63, 65, 67, 69, 71, 73, 75, 77, 79, 81, 83, 85, 87, 88, 90, 91, 92, 94, 96, 98, 100, 102, 104, 106, 108, 109, 110, 112, 114, 116, 118, 120, 122, 124, 125, 127, 129, 130, 132, 134, 135, 137, 139, 141, 143, 145, 147, 149, 151, 153, 155, 156, 158, 160, 162, 164, 166, 168, 170, 172, 174, 176, 178, 180, 182, 184, 186, 188, 190, 192, 194, 196, 198, 200, 202, 204, 206, 208, 210, 211, 213, 214, 216, 217, 218, 220, 222, 224, 226, 228, 230, 232, 234, 236, 238, 240, 242, 244, 246, 247, 249, 251, 253, 255, 257, 259, 261, 263 and 265 thereby leading to changes in the amino acid sequence of the encoded MYB-subgroup14 or a MYB68 protein, without altering the functional ability of the MYB-subgroup14 or a MYB68 protein. For example, nucleotide substitutions leading to amino acid substitutions at "non-essential" amino acid residues can be made in the sequence of SEQ ID NO:2, 4, 6, 8, 10, 12, 14, 16, 18, 20, 22, 24, 26, 28, 30, 32, 34, 36, 39, 41, 43, 45, 47, 49, 51, 53, 55, 57, 60, 62, 64, 66, 68, 70, 72, 74, 76, 78, 80, 82, 84, 86, 89, 93, 95, 97, 99, 101, 103, 105, 107, 111, 113, 115, 117, 119, 121, 123, 126, 128, 131, 133, 136, 138, 140, 142, 144, 146, 148, 150, 152, 154, 157, 159, 161, 163, 165, 167, 169, 171, 173, 175, 177, 179, 181, 183, 185, 187, 189, 191, 193, 195, 197, 199, 201, 203, 205, 207, 209, 212, 215, 219, 221, 223, 225, 227, 229, 231, 233, 235, 237, 239, 241, 243, 245, 248, 250, 252, 254, 256, 258, 260, 262 and 264. A "non-essential" amino acid residue is a residue that can be altered from the wild-type sequence of a MYB-subgroup14 or a MYB68 without altering the biological activity, whereas an "essential" amino acid residue is required for biological activity. For example, amino acid residues that are conserved among MYB-subgroup14 or MYB68 proteins of the present invention are predicted to be poor candidates for alteration. Alignments and identification of conserved regions are described herein and provide further guidance as to identification of essential amino acids and conserved amino acids.

Another aspect of the invention pertains to nucleic acid molecules encoding a MYB-subgroup14 or MYB68 protein that contain changes in amino acid residues that are not essential for activity. Such MYB-subgroup14 or MYB68 proteins differ in amino acid sequence from SEQ ID NO: 2, 4, 6, 8, 10, 12, 14, 16, 18, 20, 22, 24, 26, 28, 30, 32, 34, 36, 39, 41, 43, 45, 47, 49, 51, 53, 55, 57, 60, 62, 64, 66, 68, 70, 72, 74, 76, 78, 80, 82, 84, 86, 89, 93, 95, 97, 99, 101, 103, 105, 107, 111, 113, 115, 117, 119, 121, 123, 126, 128, 131, 133, 136, 138, 140, 142, 144, 146, 148, 150, 152, 154, 157, 159, 161, 163, 165, 167, 169, 171, 173, 175, 177, 179, 181, 183, 185, 187, 189, 191, 193, 195, 197, 199, 201, 203, 205, 207, 209, 212, 215, 219, 221, 223, 225, 227, 229, 231, 233, 235, 237, 239, 241, 243, 245, 248, 250, 252, 254, 256, 258, 260, 262 and 264 yet retain biological activity. In one embodiment, the isolated nucleic acid molecule comprises a nucleotide sequence encoding a protein, wherein the protein comprises an amino acid sequence at least about 75% homologous to the amino acid sequence of SEQ ID NO: 2, 4, 6, 8, 10, 12, 14, 16, 18, 20, 22, 24, 26, 28, 30, 32, 34, 36, 39, 41, 43, 45, 47, 49, 51, 53, 55, 57, 60, 62, 64, 66, 68, 70, 72, 74, 76, 78, 80, 82, 84, 86, 89, 93, 95, 97, 99, 101, 103, 105, 107, 111, 113, 115, 117, 119, 121, 123, 126, 128, 131, 133, 136, 138, 140, 142, 144, 146, 148, 150, 152, 154, 157, 159, 161, 163, 165, 167, 169, 171, 173, 175, 177, 179, 181, 183, 185, 187, 189, 191, 193, 195, 197, 199, 201, 203, 205, 207, 209, 212, 215, 219, 221, 223, 225, 227, 229, 231, 233, 235, 237, 239, 241, 243, 245, 248, 250, 252, 254, 256, 258, 260, 262 and 264. Preferably, the protein encoded by the nucleic acid is at least about 80% homologous to SEQ ID NO: 2, 4, 6, 8, 10, 12, 14, 16, 18, 20, 22, 24, 26, 28, 30, 32, 34, 36, 39, 41, 43, 45, 47, 49, 51, 53, 55, 57, 60, 62, 64, 66, 68, 70, 72, 74, 76, 78, 80, 82, 84, 86, 89, 93, 95, 97, 99, 101, 103, 105, 107, 111, 113, 115, 117, 119, 121, 123, 126, 128, 131, 133, 136, 138, 140, 142, 144, 146, 148, 150, 152, 154, 157, 159, 161, 163, 165, 167, 169, 171, 173, 175, 177, 179, 181, 183, 185, 187, 189, 191, 193, 195, 197, 199, 201, 203, 205, 207, 209, 212, 215, 219, 221, 223, 225, 227, 229, 231, 233, 235, 237, 239, 241, 243, 245, 248, 250, 252, 254, 256, 258, 260, 262 and 264 more preferably at least about 90%, 95%, 98%, and most preferably at least about 99% homologous to SEQ ID NO: 2, 4, 6, 8, 10, 12, 14, 16, 18, 20, 22, 24, 26, 28, 30, 32, 34, 36, 39, 41, 43, 45, 47, 49, 51, 53, 55, 57, 60, 62, 64, 66, 68, 70, 72, 74, 76, 78, 80, 82, 84, 86, 89, 93, 95, 97, 99, 101, 103, 105, 107, 111, 113, 115, 117, 119, 121, 123, 126, 128, 131, 133, 136, 138, 140, 142, 144, 146, 148, 150, 152, 154, 157, 159, 161, 163, 165, 167, 169, 171, 173, 175, 177, 179, 181, 183, 185, 187, 189, 191, 193, 195, 197, 199, 201, 203, 205, 207, 209, 212, 215, 219, 221, 223, 225, 227, 229, 231, 233, 235, 237, 239, 241, 243, 245, 248, 250, 252, 254, 256, 258, 260, 262 and 264.

An isolated nucleic acid molecule encoding a MYB-subgroup14 or a MYB68 protein homologous to the protein of SEQ ID NO: 2, 4, 6, 8, 10, 12, 14, 16, 18, 20, 22, 24, 26, 28, 30, 32, 34, 36, 39, 41, 43, 45, 47, 49, 51, 53, 55, 57, 60, 62, 64, 66, 68, 70, 72, 74, 76, 78, 80, 82, 84, 86, 89, 93, 95, 97, 99, 101, 103, 105, 107, 111, 113, 115, 117, 119, 121, 123, 126, 128, 131, 133, 136, 138, 140, 142, 144, 146, 148, 150, 152, 154, 157, 159, 161, 163, 165, 167, 169, 171, 173, 175, 177, 179, 181, 183, 185, 187, 189, 191, 193, 195, 197, 199, 201, 203, 205, 207, 209, 212, 215, 219, 221, 223, 225, 227, 229, 231, 233, 235, 237, 239, 241, 243, 245, 248, 250, 252, 254, 256, 258, 260, 262 and 264 can be created by introducing one or more nucleotide substitutions, additions or deletions into the nucleotide sequence of SEQ ID NO:1, 3, 5, 7, 9, 11, 13, 15, 17, 19, 21, 23, 25, 27, 29, 31, 33, 35, 37, 38, 40, 42, 44, 46, 48, 50, 52, 54, 56, 58, 59, 61, 63, 65, 67, 69, 71, 73, 75, 77, 79, 81, 83, 85, 87, 88, 90, 91, 92, 94, 96, 98, 100, 102, 104, 106, 108, 109, 110, 112, 114, 116, 118, 120, 122, 124, 125, 127, 129, 130, 132, 134, 135, 137, 139, 141, 143, 145, 147, 149, 151, 153, 155, 156, 158, 160, 162, 164, 166, 168, 170, 172, 174, 176, 178, 180, 182, 184, 186, 188, 190, 192, 194, 196, 198, 200, 202, 204, 206, 208, 210, 211, 213, 214, 216, 217, 218, 220, 222, 224, 226, 228, 230, 232, 234, 236, 238, 240, 242, 244, 246, 247, 249, 251, 253, 255, 257, 259, 261, 263 and 265 such that one or more amino acid substitutions, additions or deletions are introduced into the encoded protein.

Mutations can be introduced into the nucleotide sequence of SEQ ID NO:1, 3, 5, 7, 9, 11, 13, 15, 17, 19, 21, 23, 25, 27, 29, 31, 33, 35, 37, 38, 40, 42, 44, 46, 48, 50, 52, 54, 56, 58, 59, 61, 63, 65, 67, 69, 71, 73, 75, 77, 79, 81, 83, 85, 87, 88, 90, 91, 92, 94, 96, 98, 100, 102, 104, 106, 108, 109, 110, 112, 114, 116, 118, 120, 122, 124, 125, 127, 129, 130, 132, 134, 135, 137, 139, 141, 143, 145, 147, 149, 151, 153, 155, 156, 158, 160, 162, 164, 166, 168, 170, 172, 174, 176, 178, 180, 182, 184, 186, 188, 190, 192, 194, 196, 198, 200, 202, 204, 206, 208, 210, 211, 213, 214, 216, 217, 218, 220, 222, 224, 226, 228, 230, 232, 234, 236, 238, 240, 242, 244, 246, 247, 249, 251, 253, 255, 257, 259, 261, 263 and 265 by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in MYB68 is replaced with another amino acid residue from the same side chain family. Alternatively, in another embodiment, mutations can be introduced randomly along all or part of a MYB-subgroup14 or a MYB68 coding sequence, such as by saturation mutagenesis, and the resultant mutants can be screened for biological activity to identify mutants that retain activity and the desired phenotypes. Following mutagenesis of SEQ ID NO:1, 3, 5, 7, 9, 11, 13, 15, 17, 19, 21, 23, 25, 27, 29, 31, 33, 35, 37, 38, 40, 42, 44, 46, 48, 50, 52, 54, 56, 58, 59, 61, 63, 65, 67, 69, 71, 73, 75, 77, 79, 81, 83, 85, 87, 88, 90, 91, 92, 94, 96, 98, 100, 102, 104, 106, 108, 109, 110, 112, 114, 116, 118, 120, 122, 124, 125, 127, 129, 130, 132, 134, 135, 137, 139, 141, 143, 145, 147, 149, 151, 153, 155, 156, 158, 160, 162, 164, 166, 168, 170, 172, 174, 176, 178, 180, 182, 184, 186, 188, 190, 192, 194, 196, 198, 200, 202, 204, 206, 208, 210, 211, 213, 214, 216, 217, 218, 220, 222, 224, 226, 228, 230, 232, 234, 236, 238, 240, 242, 244, 246, 247, 249, 251, 253, 255, 257, 259, 261, 263 and 265 the encoded protein can be expressed by any recombinant technology known in the art and the activity of the protein can be determined.

Transformed Plants Cells and Transgenic Plants

The invention includes a protoplast, plants cell, plant tissue and plant (e.g., monocot or dicot) transformed with a MYB-subgroup14 nucleic acid, a vector containing a MYB-subgroup14 nucleic acid or an expression vector containing a MYB-subgroup14 nucleic acid. As used herein, "plant" is meant to include not only a whole plant but also a portion thereof (i.e., cells, and tissues, including for example, leaves, stems, shoots, roots, flowers, fruits and seeds).

The plant can be any plant type including, for example, species from the genera *Arabidopsis, Brassica, Oryza, Zea, Sorghum, Gossypium, Triticum, Glycine, Pisum, Phaseolus, Lycopersicon, Trifolium, Cannabis, Cucurbita, Rosa, Vitis, Juglans, Fragaria, Lotus, Medicago, Onobrychis, Trigonella, Vigna, Citrus, Linum, Geranium, Manihot, Daucus, Raphanus, Sinapis, Atropa, Capsicum, Datura, Hyoscyamus, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Lolium, Avena, Hordeum, Secale, Picea, Caco,* and *Populus*.

The invention also includes cells, tissues, including for example, leaves, stems, shoots, roots, flowers, fruits and seeds and the progeny derived from the transformed plant.

Numerous methods for introducing foreign genes into plants are known and can be used to insert a gene into a plant host, including biological and physical plant transformation protocols (See, for example, Miki et al., (1993) "Procedure for Introducing Foreign DNA into Plants", In: Methods in Plant Molecular Biology and Biotechnology, Glick and Thompson, eds., CRC Press, Inc., Boca Raton, pages 67-88; and Andrew Bent in, Clough S J and Bent A F, (1998) "Floral dipping: a simplified method for *Agrobacterium*-mediated transformation of *Arabidopsis thaliana*"). The methods chosen vary with the host plant, and include chemical transfection methods such as calcium phosphate, polyethylene glycol (PEG) transformation, microorganism-mediated gene transfer such as *Agrobacterium* (Horsch, et al., Science, 227: 1229-31 (1985)), electroporation, protoplast transformation, micro-injection, flower dipping and biolistic bombardment.

Agrobacterium-Mediated Transformation

The most widely utilized method for introducing an expression vector into plants is based on the natural transformation system of *Agrobacterium tumefaciens* and *A. rhizogenes* which are plant pathogenic bacteria which genetically transform plant cells. The Ti and Ri plasmids of *A. tumefaciens* and *A. rhizogenes*, respectfully, carry genes responsible for genetic transformation of plants (See, for example, Kado, Crit. Rev. Plant Sci., 10: 1-32 (1991)). Descriptions of the *Agrobacterium* vector systems and methods for *Agrobacterium*-mediated gene transfer are provided in Gruber et al., supra; and Moloney, et al, Plant Cell Reports, 8: 238-242 (1989).

Transgenic *Arabidopsis* plants can be produced easily by the method of dipping flowering plants into an *Agrobacterium* culture, based on the method of Andrew Bent in, Clough S J and Bent A F, 1998. Floral dipping: a simplified method for *Agrobacterium*-mediated transformation of *Arabidopsis thaliana*. Wild type plants are grown until the plant has both developing flowers and open flowers. The plants are inverted for 1 minute into a solution of *Agrobacterium* culture carrying the appropriate gene construct. Plants are then left horizontal in a tray and kept covered for two days to maintain humidity and then righted and bagged to continue growth and seed development. Mature seed is bulk harvested.

Direct Gene Transfer

A generally applicable method of plant transformation is microprojectile-mediated transformation, where DNA is carried on the surface of microprojectiles measuring about 1 to 4 µm. The expression vector is introduced into plant tissues with a biolistic device that accelerates the microprojectiles to speeds of 300 to 600 m/s which is sufficient to penetrate the plant cell walls and membranes. (Sanford, et al., Part. Sci. Technol., 5: 27-37 (1987); Sanford, Trends Biotech, 6: 299-302 (1988); Sanford, Physiol. Plant, 79: 206-209 (1990); Klein, et al., Biotechnology, 10: 286-291 (1992)).

Plant transformation can also be achieved by the Aerosol Beam Injector (ABI) method described in U.S. Pat. Nos. 5,240,842, 6,809,232. Aerosol beam technology is used to accelerate wet or dry particles to speeds enabling the particles to penetrate living cells Aerosol beam technology employs the jet expansion of an inert gas as it passes from a region of higher gas pressure to a region of lower gas pressure through a small orifice. The expanding gas accelerates aerosol droplets, containing nucleic acid molecules to be introduced into a cell or tissue. The accelerated particles are positioned to impact a preferred target, for example a plant cell. The particles are constructed as droplets of a sufficiently small size so that the cell survives the penetration. The transformed cell or tissue is grown to produce a plant by standard techniques known to those in the applicable art.

Regeneration of Transformants

The development or regeneration of plants from either single plant protoplasts or various explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by *Agrobacterium* from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983). In particular, U.S. Pat. No. 5,349,124 (specification incorporated herein by reference) details the creation of genetically transformed lettuce cells and plants resulting therefrom which express hybrid crystal proteins conferring insecticidal activity against Lepidopteran larvae to such plants.

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, or pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A preferred transgenic plant is an independent segregant and can transmit the MYB68 gene and its activity to its progeny. A more preferred transgenic plant is homozygous for the gene, and transmits that gene to all offspring on sexual mating. Seed from a transgenic plant may be grown in the field or greenhouse, and resulting sexually mature transgenic plants are self-pollinated to generate true breeding plants. The progeny from these plants become true breeding lines that are evaluated for increased expression of the MYB68 transgene.

Method of Producing Transgenic Plants

Included in the invention are methods of producing a transgenic plant. The method includes introducing into one or more plant cells a compound that alters expression or activity of a MYB-subgroup14 in the plant to generate a transgenic plant cell and regenerating a transgenic plant from the transgenic cell. The compound increases MYB-subgroup14 expression or activity. The increased expression and or activity can additionally be directed to occur ectopically or constitutively or in a tissue specific manner. The compound can be, e.g., (i) a MYB-subgroup14 polypeptide; (ii) a MYB-subgroup14 nucleic acid and analogs and homologs thereof; (iii) a nucleic acid that increases expression of a MYB-subgroup14 nucleic acid. A nucleic acid that increases expression of a MYB-subgroup14 nucleic acid may include promoters or enhancer elements. The promoter is a heterologous promoter or a homologous promoter. Additionally, the promoter is a constitutive or an inducible promoter. Promoters include for example, organ specific promoter or tissue specific promoter. Promoter suitable for directing gene expression are know in the art and are described herein. Enhancer elements are known to those skilled in the art. For example the enhancer element is a 35S enhancer element.

By increasing the expression of a MYB subgroup-14 polypeptide is meant that the amount produced by the cell transformed with the nucleic acid construct is greater than a cell, e.g. control cell that is not transformed with the nucleic acid construct. A control cell includes for example a cell that endogenously expresses a MYB subgroup-14 polypeptide such as a plant root cell, alternatively a control cell is a non transformed cell of the same cell-type as the transformed cell, be it a leaf cell a meristem cell or a flower or seed cell. An increase is a 1-fold, 2-fold, 3 fold or greater increase. An increase of expression is also meant to include expression of a MYB subgroup-14 polypeptide in a cell that does not typically express a MYB subgroup-14 polypeptide.

The nucleic acid can be either endogenous or exogenous. Preferably, the compound is a MYB-subgroup14 polypeptide or a MYB-subgroup14 nucleic acid encoding a MYB-subgroup14 polypeptide. For example the compound comprises the nucleic acid sequence of SEQ ID NO: 1, 3, 5, 7, 9, 11, 13, 15, 17, 19, 21, 23, 25, 27, 29, 31, 33, 35, 37, 38, 40, 42, 44, 46, 48, 50, 52, 54, 56, 58, 59, 61, 63, 65, 67, 69, 71, 73, 75, 77, 79, 81, 83, 85, 87, 88, 90, 91, 92, 94, 96, 98, 100, 102, 104, 106, 108, 109, 110, 112, 114, 116, 118, 120, 122, 124, 125, 127, 129, 130, 132, 134, 135, 137, 139, 141, 143, 145, 147, 149, 151, 153, 155, 156, 158, 160, 162, 164, 166, 168, 170, 172, 174, 176, 178, 180, 182, 184, 186, 188, 190, 192, 194, 196, 198, 200, 202, 204, 206, 208, 210, 211, 213, 214, 216, 217, 218, 220, 222, 224, 226, 228, 230, 232, 234, 236, 238, 240, 242, 244, 246, 247, 249, 251, 253, 255, 257, 259, 261, 263 and 265. Preferably, the compound is a MYB-subgroup14 nucleic acid sequence from an endogenous source to the species being transformed. Alternatively, the compound is a MYB-subgroup14 nucleic acid sequence from an exogenous source to the species being transformed.

Also included in the invention are methods of producing a transgenic plant. The method includes introducing into one or more plant cells a compound that alters a MYB-subgroup14 nucleic acid expression or activity in the plant to generate a transgenic plant cell and regenerating a transgenic plant from the transgenic cell. The compound increases a MYB-subgroup14 sequence expression or activity. The compound can be, e.g., (i) a MYB-subgroup14 polypeptide; (ii) a MYB-subgroup14 nucleic acid and analogs and homologs thereof; (iii) a nucleic acid that increases expression of a MYB-subgroup14 nucleic acid. A nucleic acid that increases expression of a MYB-subgroup14 nucleic acid may include promoters or enhancer elements. The nucleic acid can be either endogenous or exogenous. Preferably, the compound is a MYB-subgroup14 polypeptide or a MYB-subgroup14 nucleic acid. For example the compound comprises the nucleic acid sequence of SEQ ID NO: 1, 3, 5, 7, 9, 11, 13, 15, 17, 19, 21, 23, 25, 27, 29, 31, 33, 35, 37, 38, 40, 42, 44, 46, 48, 50, 52, 54, 56, 58, 59, 61, 63, 65, 67, 69, 71, 73, 75, 77, 79, 81, 83, 85, 87, 88, 90, 91, 92, 94, 96, 98, 100, 102, 104, 106, 108, 109, 110, 112, 114, 116, 118, 120, 122, 124, 125, 127, 129, 130, 132, 134, 135, 137, 139, 141, 143, 145, 147, 149, 151, 153, 155, 156, 158, 160, 162, 164, 166, 168, 170, 172, 174, 176, 178, 180, 182, 184, 186, 188, 190, 192, 194, 196, 198, 200, 202, 204, 206, 208, 210, 211, 213, 214, 216, 217, 218, 220, 222, 224, 226, 228, 230, 232, 234, 236, 238, 240, 242, 244, 246, 247, 249, 251, 253, 255, 257, 259, 261, 263 and 265. Preferably, the compound is a MYB-subgroup14 nucleic acid sequence endogenous to the species being transformed. Alternatively, the compound is a MYB-subgroup14 nucleic acid sequence exogenous to the species being transformed.

An exogenous MYB-subgroup14 sequence expressed in a host species need not be identical to the endogenous MYB-subgroup14 sequence. For example, sequences of three *Arabidopsis* GAMYB-like genes were obtained on the basis of sequence similarity to GAMYB genes from barley, rice, and *L. temulentum*. These three *Arabidopsis* genes were determined to encode transcription factors (AtMYB33, AtMYB65, and AtMYB101) and could substitute for a barley GAMYB and control alpha-amylase expression (Gocal et al. (2001) Plant Physiol. 127: 1682 1693).

Maize, *petunia* and *Arabidopsis* MYB transcription factors that regulate flavonoid biosynthesis are very genetically similar and affect the same trait in their native species, therefore sequence and function of these MYB transcription factors correlate with each other in these diverse species (Borevitz et al. (2000) Plant Cell 12: 2383-2394).

Therefore an expressed MYB-subgroup14 need only be functionally recognized in the host cell. Expression of MYB-subgroup14 encoding nucleic acids in *Arabidopsis* provides the basis of a functionally equivalent assay. For example expression of a MYB-subgroup14 from a *Brassica*, soybean, cotton or corn source in *Arabidopsis* and assessment of the heat tolerance demonstrates functional equivalence and provides a sound basis for prediction that the exogenous sequence is a MYB-subgroup14 gene and functions accordingly.

Disclosed herein is a description of expression of MYB-subgroup14 sequences from *Arabidopsis, Brassica* and soybean that have been demonstrated to be functional in *Arabidopsis* in that the resulting plants have increased heat tolerance as indicated by reduced flower abortion and increased seed set under heat stress conditions during flowering.

In various aspects the transgenic plant has an altered phenotype as compared to a wild type plant (i.e., untransformed). By altered phenotype is meant that the plant has a one or more characteristics that is different from the wild type plant. For example, when the transgenic plant has been contacted with a compound that increases the expression or activity of a MYB-subgroup14 nucleic acid, the plant has a phenotype such as increased heat tolerance as compared to a wild type plant and manifests this trait in phenotypes such as decreased flower abortion, increased seed set and development, increased yield protection and protection of pollen development and protection of meristems, particularly flower meristems, from heat damage, drought tolerance and salt tolerance for example. Plants with a reduced flower abortion have a 5, 10, 20, 25, 30% or more increase in seed yield as compared to a control plant.

The plant can be any plant type including, for example, species from the genera *Arabidopsis, Brassica, Oryza, Zea, Sorghum, Gossypium, Triticum, Glycine, Pisum, Phaseolus, Lycopersicon, Trifolium, Cannabis, Cucurbita, Rosa, Vitis, Juglans, Fragaria, Lotus, Medicago, Onobrychis, Trigonella, Vigna, Citrus, Linum, Geranium, Manihot, Daucus, Raphanus, Sinapis, Atropa, Capsicum, Datura, Hyoscyamus, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Lolium, Avena, Hordeum, Secale, Picea, Caco*, and *Populus*.

Method of Identifying a Heat Stress Tolerant Plant

Also included in the invention is a method of identifying a heat stress tolerant plant. The plants identified by these methods have reduced flower abortion and increased yield as compared to a control plant. Heat stress tolerant plants are identified by exposing a population of flowering plants to a heat stress treatment and selecting a plant from the population of plants that has reduced flower abortion. Heat stress treatment includes for example exposing the plant to a temperature that is hot enough for a sufficient amount of time such that damage to plant functions or development results. By reduced flower abortion is meant that a plant does not loss as many flowers, due to flower abortion, or has a greater seed yield compared to another plant that is exposed to a similar level of heat stress. Plants with a reduced flower abortion have a 5, 10, 20, 25, 30% or more increase in seed yield as compared to a control plant.

EXAMPLES

The invention will be further illustrated in the following non-limiting examples.

Example 1: Identification of Heat Tolerant Mutant

*Arabidopsis thaliana* var. Columbia was transformed with pSKI15 vector containing a 4×35S enhancer sequence (Wiegel et al., 2000). A T3 population of *Arabidopsis* seed was obtained from ABRC and used to produce a T4-generation that was used in genetic screen experiments. The *Arabidopsis* h138 mutant was identified as having reduced or no flower abortion, relative to a wild type control, when exposed to a heat stress during flowering of about 45° C. for about 30 to 60 minutes. Initial isolates were retested by having flowering plants subjected to a 1 hour temperature ramp-up from 22° C. to 45° C. followed by a 2 hour heat stress of 45° C., flower production, seed set and seed development was monitored and heat tolerant lines selected.

Example 2: Identification of the Heat Tolerant MYB68 Gene

Genome walking to localize the T-DNA activation tag insertion was performed as follows. Genomic DNA was purified by phenol:chloroform extraction using 10-day-old seedlings of mutant h138. The isolated DNA was subsequently digested by the restriction enzymes such as EcoRV, PvuII, NruI, or StuI to generate DNA fragments with blunt ends. The resulting fragments from each digestion were ligated to an adaptor that was formed by the annealing of two oligos: Adaptor 1 and Adaptor 2. The addition of the adaptor to the DNA fragments enables PCR amplification using primers specific to the adaptor and a T-DNA insertion site.

Two rounds of PCR were used to generate DNA fragments for further sequencing analysis. Primer HeatL1 (SEQ) that is specific to the T-DNA left border, and primer CAP1 (SEQ) that is specific to the adaptor, were used for the $1^{st}$ PCR. The resulted PCR products were diluted 50 folds to serve as templates for $2^{nd}$ PCR. A confirmed DNA fragment was then amplified by two nested primers HeatL2 (SEQ) and CAP2 (SEQ). PCR programs TOUCH1 (6 cycles of 94° C., 25 sec; 72° C., 7 min; 32 cycles of 94° C., 25 sec; 67° C., 7 min and 1 cycle of 67° C., 10 min) and TOUCH2 (4 cycles of 94° C., 25 sec; 72° C., 7 min; 20 cycles of 94° C., 25 sec; 67° C., 7 min and 1 cycle of 67° C., 10 min) were used for the two rounds of PCR. All PCR was carried out using Ex-Taq as DNA polymerase and a Biometra® thermocycler. The PCR products were sequenced, and the flanking genomic sequences identified. The 4×35S enhancers were inserted into an intergenic region that is 5 kb down stream of 3' end of genomic AtMYB68 (AT5G65790) on chromosome 5. Northern analysis and real-time PCR showed that the expression of MYB68 in h138 was induced to more than 2 fold relative to wild type.

Example 3: Physiological Characterization of the h138 Mutant (Myb68)

Plants were assessed for heat tolerance during flowering and scored based on the number of aborted flowers or pods and final seed yield. Plants were grown in controlled environment chambers where optimal growth conditions were 16 hr light 200 uE and 8 hr dark, 22° C. and 70% relative humidity. Three groups of plants were used in the experimental design; 1) A control group grown under optimal conditions; 2) a 3-hour heat treatment group and; 4) a 4-hour heat treatment group. Heat treatment was performed 6 days after first open flower and the temperature was ramped from 22° C. to 44° C. over a 1-hour period. Each group of plants contained the myb68 mutant and its wild type control (myb68-null) with 10 replicate pots per entry per treatment with each pot containing 5 plants. Plants were assessed for flower abortion a week following the heat stress treatments then left to grow under optimal conditions until maturity. Final seed yield per pot was determined for all 3 groups of plants.

Following heat stress the seed yield of myb68 was lower than that of the myb68-null control in both the 3-hour (25%) and 4-hour (17%) stress treatments however the difference was only statistically significant for the 3-hour treatment. The 3-hour treatment resulted in 32% fewer aborted pods relative to myb68-null and the final seed yield was increased by 16% relative to myb68 plants grown in optimal conditions. The 4-hour treatment also resulted in a 16% increase in seed yield relative to optimally grown myb68 plants. In contrast, the myb68-null showed 15% and 23% reductions in seed yield relative to optimally grown plants. The overall yield protection provided by the myb68 mutation was 31% and 39%, relative to the wild-type. Additional experiments have shown results of yield protection ranging from 5% to 44% depending on the experimental conditions.

Example 4: Constructs Useful for Expression of MYB-Subgroup14 Sequences Including MYB68

According to the methods described below, expression vector constructs can be produced using appropriate promoters and a MYB gene of the invention. For example any of the gene sequences described by the SEQ ID NO: 1, 3, 5, 7, 9, 11, 13, 15, 17, 19, 21, 23, 25, 27, 29, 31, 33, 35, 37, 38, 40, 42, 44, 46, 48, 50, 52, 54, 56, 58, 59, 61, 63, 65, 67, 69, 71, 73, 75, 77, 79, 81, 83, 85, 87, 88, 90, 91, 92, 94, 96, 98, 100, 102, 104, 106, 108, 109, 110, 112, 114, 116, 118, 120, 122, 124, 125, 127, 129, 130, 132, 134, 135, 137, 139, 141, 143, 145, 147, 149, 151, 153, 155, 156, 158, 160, 162, 164, 166, 168, 170, 172, 174, 176, 178, 180, 182, 184, 186, 188, 190, 192, 194, 196, 198, 200, 202, 204, 206, 208, 210, 211, 213, 214, 216, 217, 218, 220, 222, 224, 226, 228, 230, 232, 234, 236, 238, 240, 242, 244, 246, 247, 249, 251, 253, 255, 257, 259, 261, 263 and 265. Such vector constructs are useful to produce a MYB68 gene, operably linked to a sequence that functions as a promoter in a plant cell and to operably express said gene and protein encoded by the gene.

Vectors to over-express MYB68 under regulatory control of either constitutive or conditional promoters may be constructed, as described below. The sequence encoding a MYB68 open reading frame has been operably linked to the promoter sequences of the 35S CaMV constitutive promoter, the P18.2 or P81.1 heat inducible promoters and its endogenous PMYB68 promoter. Additionally the genomic sequence of MYB68 has been cloned behind the 35S CaMV constitutive promoter in a pEGAD vector backbone.

35S-Genomic AtMYB68 (in pEGAD Vector (35S-gAtMYB68)

A 1.4 kb of MYB68 genomic DNA including 83 bps of 3' UTR was amplified by PCR using primers: MYB68FW-BamH3 (5'-AAAGGATCCATGG-GAAGAGCACCGTGTTG-3') (SEQ ID NO:300) and MYB68RV-BamH4 (5'-AAAGGATCCC-CACTCCCTAAAGACACAGATTT-3') (SEQ ID NO:301), and subsequently digested with BamHI. The resulting DNA fragment was ligated into pBluescript II SK (+/−), and then subcloned into pEGAD at the same site to obtain 35S-gemonicAtMYB68 (35S-gAtMYB68) in pEGAD.

35S AtMYB68, 35S-AtMYB84, 35S-AtMYB36, 35S-AtMYB37, 35S AtMYB38, 35S-AtMYB87

AtMYB84 (At3g49690), AtMYB36 (At5g57620), AtMYB37 (At5g23000), AtMYB38 (At2g36890) and AtMYB87 (At4g37780) are classified as members of the MYB-subgroup14 family along with AtMYB68 (Stracke et al., 2001), therefore it is possible that their functions are redundant. These MYB genes are over-expressed in *Arabidopsis* to test their functionality as an AtMYB68 orthologue with respect to heat tolerance. The cDNA sequences are amplified by RT-PCR, and cloned into pBI121 without GUS to generate constructs of 35S-AtMYB84, 35S-AtMYB36, 35S-AtMYB37, 35S-AtMYB38 and 35S-AtMYB87.

A 1.1 kb of AtMYB68 cDNA was produced by RT-PCR using primers HG2F (5'-AAATCTAGAATGG-GAAGAGCACCGTGTT-3') (SEQ ID NO:302) and HG2R (5'-AAAGGATCCTTACACATGATTTGGCGCAT-3') (SEQ ID NO:303), and digested with XbaI and BamHI. The resulting DNA fragment was cloned into pBluescript II SK (+/−), and then into pBI121 without GUS to generate 35S-MYB68. pBI121 without GUS was obtained by SmaI and EcolcR1 double digestion and followed by self-ligation of the remaining vector.

The coding sequence of AtMYB84 (933 bp, AtMYB84, At3g49690) was amplified by RT-PCR using forward primer 690M84-Xba-FW containing an XbaI site (5'-acgt TCTAGA ATG GGA AGA GCA CCG TGT TG-3') (SEQ ID NO:273) and reverse primer 690M84-Bam-Re containing a BamHI site (5'-atcg GGATCC TTA AAA AAA TTG CTT TGA ATC AGA ATA-3') (SEQ ID NO:274). The PCR product was cloned at the XbaI-BamHI sites in pBI121, generating construct of 35S-AtMYB84.

The coding sequence of AtMYB36 (1002 bp, AtMYB36, At5g57620) was amplified by RT-PCR using forward primer M36-Xb-FW containing an XbaI site (5'-actg TCTAGA ATG GGA AGA GCT CCA TGC TG-3') (SEQ ID NO:304) and reverse primer M36-Bm-Re containing a BamHI site (5'-cagt GGATCC TTA AAC ACT GTG GTA GCT CAT C-3') (SEQ ID NO:305). The PCR product was cloned at the XbaI-BamHI sites in pBI121, generating construct of 35S-AtMYB36.

The coding sequence of AtMYB37 (990 bp, AtMYB37, At5g23000) was amplified by RT-PCR using forward primer AM37-Xb-FW containing an XbaI site (5'-actg TCTAGA ATG GGA AGA GCT CCG TGT TG-3') (SEQ ID NO:306) and reverse primer AM37-Bm-Re containing a BamH I site (5'-acgt GGATC CTA GGA GTA GAA ATA GGG CAA G-3') (SEQ ID NO:307). The PCR product was cloned at the XbaI-BamHI sites in pBI121, generating construct of 35S-AtMYB37.

The coding sequence of AtMYB38 (897 bp, AtMYB38, At2g36890) was amplified by RT-PCR using forward primer AM38-Xb-FW containing an XbaI site (5'-actg TCTAGA ATG GGT AGG GCT CCA TGT TGT-3') (SEQ ID NO:308) and reverse primer AM38-Bm-Re containing a BamH I site (5'-acgt GGATCC TCA GTA GTA CAA CAT GAA CTT ATC-3') (SEQ ID NO:309). The PCR product was cloned at the XbaI-BamHI sites in pBI121, generating construct of 35S-AtMYB38.

The coding sequence of AtMYB87 (918 bp, AtMYB87, At4g37780) will be amplified by RT-PCR using forward primer M87-Xb-FW containing an XbaI site (5'-aaaa TCTAGA ATG GGA AGA GCA CCG TGC-5') (SEQ ID NO:310) and reverse primer M87-Bg-Re containing a Bgl2 site (5'-aaaa AGATCT CTA CTC ATT ATC GTA TAG AGG-3') (SEQ ID NO:311). The PCR product will be cloned at the XbaI-BamHI sites in pBI121, generating construct of 35S-AtMYB87.

P18.2-MYB68, and P81.1-MYB68

The construction involved 4-steps; 1) a 869 bp of Hsp18.2 promoter, and a 406 bp of Hsp81.1 promoter were amplified by PCR using primer sets: HP1F (SEQ ID NO: 277) and HP1R (SEQ ID NO:278), and HP2F (SEQ ID NO:279) and HP2R (SEQ ID NO:280), respectively, and digested with SalI and XbaI. The resulting DNA fragments were cloned into pBI101 at the same sites to generate the new vectors: P18.2pBI101 and P81.1pBI101; 2) a MCS2-oligo (including restriction sites of XbaI, HpaI, AgeII, KpnI, XhoI, ScaI, SpeI, SalI, BamHI and SmaI) was cloned into the new vectors at XbaI and SmaI sites. The resulting vectors were named P18.2pBI101MCS and P81.1pBI101MCS; 3) the GUS gene was removed by SmaI and EcolcR1 double digestion and followed by self-ligation of the remaining vector to give vectors P18.2pBI101MCS without GUS and P81.1pBI101MCS without GUS; 4) the 1.1 kb of MYB68 cDNA fragment was ligated into the two newer vectors at XbaI and BamHI sites to complete the construction of P18.2pBI101MCS without GUS for P18.2-MYB68, and P81.1MCSpBI121 without GUS for P81.1-MYB68.

pHSP81.1-AtMYB68

The coding sequence of AtMYB68 was isolated by restriction digestion with XbaI and BamHI from plasmid pHSP18.2-AtMYB68, and cloned at the XbaI-BamHI sites in pHSP81.1.

pHPR-AtMYB68

The promoter sequence (−1 to −506 bp, relative to ATG start codon) of the Arabidopsis hydroxy pyruvate reductase gene (HPR, At1g68010) was amplified by PCR from Arabidopsis genomic DNA using a forward primer containing a Sal I site (HPR-Sal-FW, acgt gtcgac GAAGCAGCAGAAGCCTTGAT) (SEQ ID NO:312) and a reverse primer containing an Xba I site (HPR-Xb-R2, acgt tctaga GGT AGA GAA AAG AGA aag cct c) (SEQ ID NO:313). The digested fragment was cloned into the vector pHSP81.1-AtMYB68 that was pre-digested with SalI and XbaI to remove the HSP81.1 promoter. This generates a recombinant plasmid with the HPR promoter placed in front of AtMYB68.

PMYB68-AtMYB68

The AtMYB68 promoter (−1 through −1034 with respect to the MYB68 ATG start codon) was amplified by PCR using primers: Pm68-H3-FW (SEQ ID NO:275) and Pm68-Av-Xh-Re (SEQ ID NO:276), and digested by restriction enzymes: HindIII and XhoI. The resulting promoter fragment was cloned into P81.1MCSpBI121 without GUS at the same sites, replacing the Hsp81.1 promoter. This vector is then named PMYB68pBI121, and used for further cloning of AtMYB68 cDNA (1.1 kb) at Avr II and BamHI sites to obtain PMYB68-AtMYB68. The AvrII-BamHI fragment of MYB cDNA was recovered from the plasmid 18.2-MYB68.

pM68-AtMYB84

The coding sequence of AtMYB84 (933 bp, AtMYB84, At3g49690) was amplified by RT-PCR using forward primer 690M84-Xba-FW containing an XbaI site (5'-acgt TCTAGA ATG GGA AGA GCA CCG TGT TG-3') (SEQ ID NO:273) and reverse primer 690M84-Bam-Re containing a BamHI site (5'-atcg GGATCC TTA AAA AAA TTG CTT TGA ATC AGA ATA-3') (SEQ ID NO:274). The PCR product was cloned at the AvRII-BamHI sites in pB-Pm68, generating construct of AtMYB84 under control of the AtMYB68 promoter.

pM68-AtMYB36

The coding sequence of AtMYB36 (1002 bp, At5g57620) was amplified from RNA isolated from young Arabidopsis seedlings (leaves and roots) by RT-PCR using forward primer M36-Xb-FW containing an XbaI site (5'-actg TCTAGA ATG GGA AGA GCT CCA TGC TG-3') (SEQ ID NO:305) and reverse primer M36-Bm-Re containing a BamHI site (5'-cagt GGATCC TTA AAC ACT GTG GTA GCT CAT C-3') (SEQ ID NO:306). The PCR product was cloned at the Avr II and BamHI sites in pBI-Pm68 described above. This generated a construct of AtMYB36 under control of the AtMYB68 promoter.

35S-OsMYB36

Rice MYB36 cDNA homolog: The coding sequence (966 bp) of a rice MYB36 gene (SEQ ID NO:9), encoding a protein identified as SEQ ID NO:10 was amplified by RT-PCR from rice root RNA using forward primer rM-Xb-FW2 containing an XbaI site (5'-acgt TCTAGA ATG GGG AGA GCG CCG TGC TG-3') (SEQ ID NO:314) and reverse primer rM-Bm-Re2 containing a BamH I site (5'-tgca GGATCC CTA CTG CAT CCC GAG GTC AG CT-3') (SEQ ID NO:315). The PCR product was cloned at the XbaI-BamHI sites in pBI121, generating construct 35S-Os MYB36.

35S-gOs MYB36

Rice MYB genomic homolog clone: Using the same primers described above forward primer rM-Xb-FW2 (SEQ ID NO:314) and reverse primer rM-Bm-Re2 (SEQ ID NO:315), the genomic sequence of the rice MYB36 gene (SEQ ID NO:265) was amplified (1259 bp). The PCR product was cloned at the XbaI-BamHI sites in pBI121, generating construct 35S-gOsMYB36.

35S-GmMYB84

The soybean MYB161 is a homolog of Arabidopsis MYB84. Herein the term 'soybean MYB84' is used interchangeably with Soybean MYB161. The 1068 bp coding sequence of a soybean MYB161 was cloned by RT-PCR from soybean root RNA using forward primer soybM-Xba-FW2 containing an XbaI site (5'-acgt TCTAGA ATG GGG AGG GCA CCT TGC T-3') (SEQ ID NO:316) and reverse primer soybM-Bm-Re containing a BamHI site (5'-acgt GGATC CTA TTG CGC CCC CGG GTA G-3') (SEQ ID NO:317). The PCR product was cloned at the XbaI-BamHI sites in pBI121, generating construct 35S-GmMYB84.

35S-ZmMYB36

The corn MYB36 cDNA (SEQ ID NO:261) was amplified by PCR using primers: ZmYYBFW-XbaI (5'-aaatctagaATGGGGAGAGCTCCGTGCTGCGACA-3') (SEQ ID NO:318) and ZmMYBRV-BamHI2 (5'-aaaggatccCTACTTCATCCCAAGGTTTCCTGGC-3') (SEQ ID NO:319). The DNA fragment was digested by XbaI and BamHI and subsequently ligated to the same sites at pBluescript II SK (+), and then subcloned into the same sites of pBI121 replacing GUS.

35S-GhMYB68 or 35SS-CotMYB68

The cotton MYB68 cDNA was amplified by PCR using primers: CotM-Xb-Fw (5'-acgt TCTAGA ATG GGG AGA GCT CCT TGT TG-3') (SEQ ID NO:320) and CotM-Bm-Re (5'-acgt GGATCC CTA TTG CGC TCC TCC TGG G-3') (SEQ ID NO:321). The DNA fragment was digested by XbaI and BamHI. It was ligated to the same sites at pBluescript II SK (+), and then subcloned into the same sites in pBI121 replacing GUS.

35S-BnMYB68r

The canola root MYB cDNA was amplified by PCR using primers: Bn68root-FW-XbaI (5'-aaatctagaATGG-GAAGAGCACCGTGTTGTGATAAGGCC-3') (SEQ ID NO:322) and Bn68root-RV-BamHI (5'-aaaggatccTTACA-CATTATTTGGCCCATTGAAGTATCTTGC-3') (SEQ ID NO:323). The DNA fragment was digested by XbaI and BamHI. It was ligated to the same sites at pBluescript II SK (+). The same fragment was then subcloned to the same sites in pBI121 replacing GUS.

35S-BnMYB68b

The canola bud MYB cDNA was amplified by PCR using primers: Bn68Bud-FW-XbaI (5'-aaatctagaATGG-GAAGAGCACCGTGTTGTGACAAGGCT-3') (SEQ ID NO:324) and Bn68Bud-RV-BamHI (5'-aaaggatccTTA-CAAATGATTTGCCCCATTGAAGTAACTTGC-3') (SEQ ID NO:325). The DNA fragment was digested by XbaI and BamHI. It was ligated to the same sites at pBluescript II SK (+). The same fragment was then subcloned to the same sites in pBI121 replacing GUS.

Table 2 below describes oligonucleotide primers used to make the vector constructs described above, and additional primers useful for cloning AtMYB homologues.

TABLE 2

Oligonucleotide primers synthesized for cloning AtMYB68 homologues

| SEQ ID NO | Primer name | Restriction site | Sequence (5'-3') | Remark |
|---|---|---|---|---|
| 271 | 790M68-Xba-FW | XbaI | ACGT TCTAGA ATG GGA AGA GCA CCG TGT TG | AtMYB68 (at5g65790) |
| 272 | 790M68-Bam-Re | BamHI | ATCG GGATCC TTA CAC ATG ATT TGG CGC ATT G | AtMYB68 (at5g65790) |
| 273 | 690M84-Xba-FW | Xba I | ACGT TCTAGA ATG GGA AGA GCA CCG TGT TG | AtMYB84 (at3g49690) |
| 274 | 690M84-Bam-Re | Bam HI | ATCG GGATCC TTA AAA AAA TTG CTT TGA ATC AGA ATA | AtMYB84 (at3g49690) |
| 275 | Pm68-H3-FW | Hind III | ACGT AAGCTT TCG TAA AAT CTC TCA TG | AtMYB68 Promoter |
| 276 | Pm68-Av-Xh-Re | Avr II and Xho I | GTCA CTCGAG CCTAGG TTT CTT GAT TCT TGA TTC TTG ATC | AtMYB68 Promoter |
| 277 | HP1f | | AAAGTCGACGCATCTTTACAATGT AAAGCTTTTCT | |
| 278 | HP1R | | AAATCTAGATGTTCGTTGCTTTTC GGG | |
| 279 | HP2F | | AAAGTCGACAGAAGACAAATGAG AGTTGGTTTATATTT | |
| 280 | HP2R | | AAATCTAGACGCAACGAACTTTG ATTCAA | |
| 281 | BnMYB68FW2 | | ATGGGAAGAGCACCGTGTTGTGA TAAGGCC | Canola MYB68 (AC189266.1) |
| 282 | BnMYB68RV2 | | TTAATTTGGCGCATTGAAGTAACT TGCATCTTCGG | Canola MYB68 (AC189266.1) |
| 283 | rM-Xb-FW | Xba I | ACGT TCTAGA ATG GGG AGA GCG CCG TGC | Rice MYB (AAT85046) |
| 284 | rM-Bm-Re | BamH I | TGCA GGATC CTA CTG CAT CCC GAG GTC AG | Rice MYB (AAT85046) |
| 285 | cotM-Xb-FW | Xba I | ACGT TCTAGA ATG GGG AGA GCT CCT TGT TG | Cotton MYB (TC34239) |
| 286 | cotM-Bm-Re | BamH I | ACGT GGATCC CTA TTG CGC TCC TCC TGG G | |

TABLE 2-continued

Oligonucleotide primers synthesized for cloning AtMYB68 homologues

| SEQ ID NO | Primer name | Restriction site | Sequence (5'-3') | Remark |
|---|---|---|---|---|
| 287 | soybM-Xba-FW2 | XbaI | ACGT TCTAGA ATG GGG AGG GCA CCT TGC T | Soybean MYB (ABH02906) |
| 288 | cornM-Xba-FW2 | XbaI I | ACGT TCTAGA ATG GGG AGA GCT CCG TGC T | Corn MYB (TC370133) |
| 289 | wheatM-Xba-FW | XbaI | ACTG TCTAGA ATG GGG AGG GCG CCG TGC | Wheat MYB (BQ483726) |
| 290 | MedtM-Xba-FW | XbaI | ACTG TCTAGA ATG GGA AGA GCT CCT TGC TGT | *M. truncatula* MYB (TC97441) |
| 291 | sorgM-Xb-FW | XbaI | ACGTTCTAGA ATGGGGAGAG CTCCGTGCT | *sorghum* MYB (AAL84760) |
| 292 | toM-Xb-FW | XbaI | ACTGTCTAGAATGGGAAGAGCTC CATGTTGT | Tomato blind (AAL69334) |
| 293 | toM-Bm-Re | BamtII | GACT GGATCC TTA GTA ATA AAA CAT CCC TAT CTC A | |
| 294 | popM-Xb-FW | Xba I | ACGT TCTAGA ATG GGG AGA GCT CCT TGC TG | Poplar MYB (TC54478) |
| 295 | popM-Bm-Re | BamtII | GACT GGATCC TCA TTG TGG CCC AAA GAA GCT | Poplar MYB (TC54478) |
| 296 | HSP18.2 | HP1F | AAAGTCGACGCATCTTTACAATGT AAAGCTTTTCT | |
| 297 | HSP18.2 | HP1R | AAATCTAGATGTTCGTTGCTTTTC GGG | |
| 298 | HSP81.1 | HP2F | AAAGTCGACAGAAGACAAATGAG AGTTGGTTTATATTT | |
| 299 | HSP81.1 | HP2R | AAATCTAGACGCAACGAACTTTG ATTCAA | |

Note:
1. FW: Forward primer with gene specific sequence starting from the ATG start codon.
2. Re: Reverse primer with gene specific sequence starting at the stop codon.
3. Restriction sites at the 5' end are underlined.

The expression vector constructs of the invention can be introduced into *Arabidopsis*, the plant of origin or any species of choice. For example an *Arabidopsis* MYB gene may be over expressed in a *Brassica* species or alternatively a soybean, maize, rice or cotton species.

Example 5: Amino Acid Sequence Analysis of MYB68

The tables below provide a comparison of amino acid sequences from the MYB gene family across different plant species, under different settings for multiple sequence alignment and amino acid sequence analysis. Note: Different MYB naming and numbering systems are used in the literature and databases for different plant species. In the tables below, (*) indicates the predicted ORF genomic DNA sequence was edited according to peptide sequence alignments to generate a putative coding sequence sequence. The (P) designation indicates a partial sequence. Sequence homology and multiple sequence alignments were compared by ClustalW.

TABLE 3

| Species | Name | Sequence file | Protein size (a.a.) | Multi-alignment scores to AtMYBs (%, Clustal) | | |
|---|---|---|---|---|---|---|
| | | | | MYB68 | MYB84 | MYB36 |
| | AtMYB68 | | | 100 | | |
| | AtMYB84 | At3g49690 SEQ ID NO: 4 | 310 | 64 | 100 | |
| | AtMYB36 | At5g57650 SEQ ID NO: 6 | 333 | 35 | 39 | 100 |

TABLE 3-continued

| Species | Name | Sequence file | Protein size (a.a.) | Multi-alignment scores to AtMYBs (%, Clustal) | | |
|---|---|---|---|---|---|---|
| | | | | MYB68 | MYB84 | MYB36 |
| Canola | | AC189266 SEQ ID NO: 8 | 364 (*) | 88 | 59 | 33 |
| Rice | Rice MYB s8137 | | 360 | 34 | 36 | |
| | Rice MYB s3656 | AAT85046 SEQ ID NO: 10 | 321 | 39 | 40 | 39 |
| Soybean | Soybean MYB84 | ABH02831 | 259 | 21 | 20 | |
| | Soybean MYB84 | ABH02839 | 317 | 22 | 20 | |
| | Soybean MYB161 | ABH02906 SEQ ID NO: 14 | 198 (P) | 63 | 65 | 58 |
| | Soybean MYB71 | ABH02912 | 209 (P) | 58 | 56 | |
| Corn | | TC32080 | 361 | 33 | 38 | |
| | | TC32080 | 131 | 79 | 80 | |
| | ZmMYB-IP30 | AF099429 | 43 (P) | 86 | 86 | |
| | ZmMYB-IP30 | TC370133 SEQ ID NO: 18 | 131 (P) | 82 | 83 | 83 |
| | ZmMYB-HX43 | AF099383 | 43 (P) | 81 | 81 | |
| | Corn MYB8 | CAJ42201 | 226 | 33 | 35 | |
| | Corn MYB31 | CAJ42202 | 275 | 26 | 26 | |
| | Corn MYB38 | P20025 | 255 | 30 | 30 | |
| Cotton | Cotton MYB | TC34239 SEQ ID NO: 12 | 356 | 40 | 41 | 34 |
| | Cotton GHMYB25 | AAK19616 | 309 | 32 | 27 | |
| | Cotton GHMYB9 | AAK19619 | 264 | 28 | 25 | |
| | Cotton GHMYB30 | AAZ83352 | 307 | 31 | 29 | |
| Sorghum | Sorghum MYB68 | AAL90639 | 87 (P) | 60 | 62 | |
| | Sorghum MYB86 | AAQ54875 | 157 (P) | 69 | 70 | |
| | Sorghum MYB20 | AAL84760 SEQ ID NO: 20 | 157 (P) | 69 | 70 | 75 |
| | Sorghum MYB34 | AAL84761 | 203 | 46 | 40 | |
| | | Sbi_042749 | 318 | 38 | 37 | |
| | | | 203 | 55 | 53 | |
| | | | 157 | 63 | 63 | |
| Medicago truncatula | | ABE78637 | 336 | 28 | 31 | |
| | | ABE90877 | 319 | 24 | 24 | |
| | | TC97441 SEQ ID NO: 26 | 178 (P) | 70 | 70 | 66 |
| Tomato | Blind | AAL69334 SEQ ID NO: 28 | 315 | 39 | | |
| | | EST467561 SEQ ID NO: 30 | 237 | 51 | 51 | |
| | | TC182203 | 185 (P) | 60 | 54 | 64 |
| | | AAL69334 | 185 | 62 | 58 | 62 |
| | | EST467561 | 185 | 61 | 58 | 59 |
| Wheat | | BQ483726 SEQ ID NO: 22 | 175 (P) | 66 | 65 | 70 |
| Poplar | | TC54478 SEQ ID NO: 24 | 345 | 39 | 44 | 38 |

TABLE 4

ATMYB68 Homologues from Different Crops/Species

| Name | Sequence file | Protein size (a.a.) | Multi-alignment scores to AtMYBs (%, ClustalW) | | |
|---|---|---|---|---|---|
| | | | AtMYB68 | AtMYB84 | AtMYB36 |
| AtMYB68 | At5g65790 SEQ ID NO: 2 | 374 | 100 | | |
| AtMYB84 | At3g49690 | 310 | 64 | 100 | |
| AtMYB36 | At5g57620 | 333 | 35 | 39 | 100 |
| Canola | AC189266 | 364 ((*)) | 88 | 59 | 33 |
| Soybean | ABH02906 | 198 (P) | 63 | 65 | 58 |
| Cotton | TC34239 | 356 | 40 | 41 | 34 |
| Tomato | Blind AAL69334 | 315 | 39 | | |
| Medicago truncatula | TC97441 | 178 (P) | 70 | 70 | 66 |
| Rice | AAT85046 | 321 | 39 | 40 | 38 |
| Corn | TC370133 | 131 (P) | 82 | 83 | 83 |
| Wheat | BQ483726 | 175 (P) | 66 | 65 | 70 |
| Sorghum | AAL84760 | 157 (P) | 69 | 70 | 75 |
| Poplar | TC54478 | 345 | 39 | 44 | 38 |

In Table 4 above, sequence homology and multiple sequence alignments were compared by ClustalW at http://www.ebi.ac.uk/clustalw/ with the following default settings:
Matrix: Gonnet 250
GAP OPEN: 10.0
END GAPS: −1
GAP EXTENSION: 0.2
GAP DISTANCES: 4

TABLE 5

ATMYB68 Homologues from Different Crops/Species

| Species | Sequence file | Protein size (a.a.) | Sequence homology (%) to AtMYB68 | |
|---|---|---|---|---|
| | | | Protein | DNA |
| AtMYB68 | At5g65790 SEQ ID NO: 2 | 374 | 100 | 100 |
| AtMYB84 | At3g49690 | 310 | 64 | 68 |
| AtMYB36 | At5g57620 | 333 | 37 | 29 |
| Canola | AC189266 | 364 ((*)) | 88 | 90 |
| Soybean | ABH02906 | 198 (P) | 63 | 53 |
| Cotton | TC34239 | 356 | 40 | 30 |
| Tomato | Blind (AAL69334) | 315 | 39 | 28 |
| Medicago truncatula | TC97441 | 178 (P) | 70 | 58 |
| Rice | AAT85046 | 321 | 39 | 28 |
| Corn | TC370133 | 131 (P) | 82 | 67 |
| Wheat | BQ483726 | 175 (P) | 66 | 53 |
| Sorghum | AAL84760 | 157 (P) | 69 | 59 |
| Poplar | TC54478 | 345 | 39 | 30 |

In Table 5 above, sequence homology and multiple sequence alignments were compared by ClustalW at http://www.ebi.ac.uk/clustalw/ with the following default settings:
Matrix: Protein: Gonnet 250
GAP OPEN: DNA: 15.0 Protein: 10.0
END GAPS: −1
GAP EXTENSION: DNA: 6.66 Protein: 0.2
GAP DISTANCES: 4

Example 6: Physiological Characterization of the 35S-MYB68 Expression Lines

Within a population of transgenic lines a gradation of expression levels and physiological response will exist. In part, the gradation of variation is a result of the site of integration of the gene construct and the local environment for gene expression at that locus. Therefore, lines must be screened and evaluated in order to select the best performing lines. This process is one of routine to one skilled in the art.

Homozygous lines expressing a 35S-MYB68 expression construct have been evaluated in a heat and flower abortion experiment. The experimental set up included 8 replicate plants per line with 1 plant per 3″ pot and grown under optimal conditions in a controlled environment chamber (18 hr light at 200 uE, 6 hr dark, 22° C., 70% relative humidity). Three days after the appearance of the first flower, plants were exposed to a heat shock of 1 hour at 42° C. and returned to optimal conditions for a further 7 days. Plants were assessed for flower abortion on the main stem. Lines were identified that demonstrated reduced flower abortion rates from 34% to 60% relative to wild type controls.

Seed yields and yield protection, expressed as a percent relative to wild type, was determined for nine independent 35S-MYB68 transgenic lines. The experimental set up included 3 plants per 3″ pot which were grown as above with 22 replicates per line. Three days after the appearance of the first flower, 12 replicates per line were exposed to a 3-hour heat stress at 45° C. with a 1 hour ramp up from 22° C. Three days later the heat stress was applied again. The remaining 10 replicates the plants per line were maintained under optimal conditions throughout their life cycle. The final seed yield was determined for all the plants. Wild type plants showed a 40% reduction in yield due to the applied heat stress whereas transgenic lines, while still having a reduced yield due to heat stress the reduction was less severe resulting in a 10% to 12% yield protection.

Selected lines were re-evaluated and stressed as follows. Plants were exposed to a 1-hour ramp up period from 22° C. to 45° C. and a heat stress of 45° C. for 1.5 to 1.8 hours was maintained. Heat stress was applied daily for five consecutive days followed by a five day recovery period and then a sixth heat treatment. The heat treatment resulted in 11% reduction in yield in WT plants and in four of the transgenic lines a yield increase was observed ranging from 2% to 17%. As shown in Table 6, six transgenic lines (68, 80, 93, 73, 83, 30) showed yield protection relative to WT following the heat stress. This protection ranged from 3 to 31%. Two of these transgenic lines (30 and 73) have been shown to have yield protection in the previous experiment and two lines (93 and 83) showed reduction in flower abortion.

TABLE 6

| Line | Heat seed yield | Yield protection relative to WT |
|---|---|---|
| 68 | 0.816 | 31% |
| 80 | 0.714 | 26% |
| 93 | 0.781 | 17% |
| 73 | 0.820 | 14% |
| 83 | 0.719 | 5% |
| 30 | 0.801 | 3% |
| WT | 0.784 | — |
| myb68 | 0.577 | 15% |
| WT (myb68-null) | 0.779 | — |

Characterization of *Arabidopsis* Lines Expressing the PMYB68-AtMYB68 Construct

Fourteen homozygous transgenic lines at T3 were evaluated in a flower abortion experiment. Plants (fourteen replicates per entry) were grown under optimal conditions (18 hr light, 200 uE, 22 C, 60% RH) in 2.25″ pots until three days from first open flower. At that point plants were exposed to 1 hr treatment at 43 C. Following the heat treatment plants were returned to optimal conditions for 7 more days. The impact of heat treatment on the pod formation was assessed at that point by counting the aborted and damaged (short) pods in the region that was exposed to the heat stress. Six transgenic lines showed a reduction in the total number of damaged pods as compared to controls (wild type-Colombia and the null-n11-8) (see Table 7 below). The best line showed only 70% of the heat damage as the control. Two of the transgenic lines examined here also showed reduced flower abortion at the T2 stage of screening. The myb68 mutant, included as a positive control also showed a reduction in the total number of damaged pods as compared to its segregating null control (myb68-null).

TABLE 7

| Entry | # of damaged pods | | total damaged pods as % of col |
|---|---|---|---|
| | Mean | Std Err | |
| 15-8 | 2.3 | 0.4 | 70% |
| 3-3 | 2.4 | 0.4 | 72% |
| 4-4 | 2.9 | 0.4 | 87% |
| 8-1 | 2.9 | 0.4 | 89% |
| 27-1 | 3.1 | 0.4 | 93% |
| 20-4 | 3.2 | 0.4 | 98% |
| n-11-8 | 4.1 | 0.4 | 126% |
| col | 3.3 | 0.4 | 100% |
| myb68 | 1.9 | 0.5 | 60% |
| myb68-null | 3.2 | 0.4 | 100% |

Example 7: Physiological Assessment of Transgenic Plants Expressing MYB68

*Arabidopsis* Myb68 Mutant Shows Drought Tolerance

Five plants per 3" pot with 6 replicates per entry were grown under optimal conditions of 16 hr light (180 uE), 22 C, 70% RH in a growth chamber until first open flower. A drought treatment was started equalizing the amount of water in all pots and cessation of watering. Water loss was measured daily by weighing the pots. Soil water content (SWC) was calculated as a % of initial. Plants were harvested on days 0, 2 and 4 of the drought treatment. Water lost relative to shoot dry biomass of the plants was calculated. The myb68 plants show trends towards greater SWC than that of control throughout the drought treatment. Shoot biomass was not different or slightly larger than that of control. The ratio of water lost in 2 days over shoot dry weight on day 2 was lower for the myb68 mutant than control indicating trends towards drought tolerance.

TABLE 8

Soil water content (% of initial) on days of the drought treatment and water lost in 2 days relative to shoot dry weight on day 2.

| Entry | SWC-d2 (% Initial) | | SWC-d4 (% Initial) | | Water lost in 2d/ Shoot DW-d2 | |
|---|---|---|---|---|---|---|
| | Mean | S.E. | Mean | S.E. | Mean | S.E. |
| myb68 | 36.3 | 1.0 | 9.1 | 0.2 | 161.6 | 4.9 |
| WT | 32.3 | 0.8 | 8.5 | 0.2 | 185.3 | 8.6 |

Myb68 Mutant and 35S-gMYB68 and 35S-MYB68 *Arabidopsis* Transgenic Lines Show Salt Tolerance at Seedling Stage Seeds were sterilized and placed on agar plates with ½ MS growth media containing salt (200 mM NaCl) or no salt (optimal plates) with 6 plates per entry and 30 seeds per plate. After 3 days at 4 C plates were placed in the growth room at 22 C, and 18 hr lights (100 uE) for 16 days. After 7 days plates were scored for germination and after additional 9 days seedlings were scored for bleaching (% white seedling indicative of stress). No differences were found between controls and transgenic lines or the mutant in germination on optimal plates and on salt plates. But after 16 days of salt exposure seedlings showed signs of stress by becoming bleached. Results indicated that the myb68 mutant and the transgenic 35S-Myb68 expressing lines had fewer bleached seedlings which are indicative of lower sensitivity to salt stress.

TABLE 9

Bleached seedlings (% of white seedling) scored after 16 days on 200 mM NaCl containing agar and ½ MS plates.

| construct | Entry | % White Seedlings | |
|---|---|---|---|
| | | Mean | Std Err |
| myb68 (mutant) | myb68 | 51.3 | 6.5 |
| | myb68-null | 60.1 | 7.0 |
| 35S-gMYB68 | 30 | 29.3 | 5.0 |
| | 73 | 29.8 | 4.7 |
| | control | 41.6 | 4.6 |
| 35S-MYB68 | 104-3 | 56.7 | 4.9 |
| | 22-7 | 62.1 | 5.4 |

Constitutive Expression of MYB68 in *Arabidopsis* Results in Yield Protection Following Heat Stress.

The 35S-Myb68 *Arabidopsis* plants were grown in 3" pots with 3 plants per pot and 10 replicates per optimal treatment and 12 replicates per heat treatment. All plants were grown under optimal conditions until 2 days into flowering. At that point optimal plants remained in optimal conditions (22 C, 18 hr light of 200 uE, 70% RH) and the test group had a daily heat treatment applied by increasing temperature from 22° C. to 45° C. over a 1 hr ramp period and maintaining that temperature for 1.5 to 2.5 hr for five consecutive days. Plants recovered for a two day period without applied stress after which stress was applied again for an additional three days (total of eight days of heat treatment). Following the heat treatments plants were maintained in optimal conditions till maturity together with the optimal group and final seed yield of both groups was determined. The results indicate that four 35S-Myb68 transgenic lines (22-7, 20-11, 35-1 and 8-6) showed yield protection following the heat stress treatments that ranged from 8 to 21% relative to controls.

TABLE 10

Seed yield per pot from plants grown under optimal and heat stress conditions as described above. Yield protection was calculated as the difference between the seed yield following stress and expressed as % of optimal in transgenic lines and col.

| | | optimal | | | heat | | | yield Protection |
|---|---|---|---|---|---|---|---|---|
| | | seed yield (g) | | | seed yield (g) | | % of | relative to |
| Entry | n | Mean | Std Err | n | Mean | Std Err | opt | col |
| 22-7 | 8 | 0.449 | 0.034 | 12 | 0.470 | 0.018 | 105% | 21% |
| 20-11 | 10 | 0.194 | 0.025 | 11 | 0.201 | 0.014 | 104% | 20% |
| 35-1 | 8 | 0.500 | 0.033 | 12 | 0.465 | 0.023 | 93% | 10% |
| 8-6 | 9 | 0.517 | 0.028 | 12 | 0.473 | 0.011 | 91% | 8% |
| 28-12 | 10 | 0.572 | 0.025 | 12 | 0.503 | 0.012 | 88% | 4% |
| 33-3 | 8 | 0.155 | 0.016 | 11 | 0.133 | 0.012 | 86% | 2% |
| 25-6 | 10 | 0.395 | 0.027 | 12 | 0.335 | 0.013 | 85% | 1% |
| 20-7 (null) | 10 | 0.571 | 0.021 | 12 | 0.484 | 0.010 | 85% | |
| 33-10 (null) | 10 | 0.546 | 0.018 | 12 | 0.456 | 0.016 | 84% | |
| Col | 10 | 0.548 | 0.029 | 12 | 0.457 | 0.020 | 83% | |

Example 8: Functional Confirmation of *Arabidopsis* MYB-Subgroup14 Sequences and Homologues from Other Species Produce the Desired Phenotypes Such as Heat Tolerance Constitutive Expression of BnMYB68 in *Arabidopsis* Results in Reduced Flower Abortion Following Heat Stress.

Two closely related Myb68 sequences were identified from *Brassica*. Their expression patterns differ in that one is expressed predominately in the roots (SEQ ID NO:54), the other in flower buds (SEQ ID NO:56). Plants having constructs expressing either of the BnMyb68 were produced and evaluated. Plants were grown in 2.25" pots (1/pot) under optimal conditions (22 C, 50% RH, 17 hr light of 200 uE) until 3 days from first open flower. Plants were transferred from 22 C to 43 C for 2-2.5 hr (see tables below). Following this heat stress plants were returned to optimal conditions at 22 C for a week. One week following the heat stress number of aborted flowers was counted. Transgenic lines of 35S-BnMyb68(root) construct showed fewer aborted pods than its control (null). Two transgenic lines of 35S-BnMyb68 (bud) construct showed reduced flower abortion following heat stress than their control (null line).

TABLE 11

Number of aborted flowers following 2 hr heat stress at 43 C.-35S-BnMYB68 (root)

| | # | # Aborted pods | | |
|---|---|---|---|---|
| Entry | Reps | Mean | Std Err | % Null |
| 36-1 | 10 | 6.6 | 0.9 | 79% |
| 49-1 | 12 | 6.6 | 0.9 | 79% |
| 61-4 | 11 | 6.8 | 0.7 | 82% |
| 70-2 | 11 | 7.5 | 1.1 | 89% |
| 73-3 | 12 | 7.5 | 0.7 | 90% |
| 75-7 | 11 | 5.9 | 1.0 | 71% |
| 78-8 | 11 | 6.5 | 0.9 | 77% |
| 80-8 | 12 | 6.5 | 0.9 | 78% |
| null 75-5 | 11 | 8.4 | 0.9 | |

TABLE 12

Number of aborted flowers following 2.5 hr heat stress at 43 C.-35S-BnMYB68 (bud)

| | # | # Aborted pods | | |
|---|---|---|---|---|
| Entry | Reps | Mean | Std Err | % Null |
| 11-6 | 11 | 4.6 | 0.4 | 73% |
| 61-12 | 12 | 5.8 | 0.8 | 92% |
| Null 97-1 | 12 | 6.3 | 0.6 | |

Constitutive Expression of Soybean MYB84 or *Arabidopsis* MYB84 or *Arabidopsis* MYB36 in *Arabidopsis* Results in Reduced Flower Abortion Following Heat Stress.

Over-expression constructs of soybean-Myb84 (Gm-Myb84) or *Arabidopsis* Myb84 (AtMyb84) or *Arabidopsis* Myb36 (AtMyb36) were made and transformed into *Arabidopsis* plants functionally confirm the Myb-subgroup14 homologues resulted in heat tolerance as demonstrated by reduced flower abortion under heat stress. Transgenic plants were produced and the T2 generation was used for an initial screen of heat tolerance. Subsequently, T3 homozygous transgenic plants are used for detailed physiological assessment and confirmation of initial results.

The T2 seeds were plated on 0.5× MS agar plates with vitamins (1 plate/flat). Each test group included a positive control, the original heat tolerant mutant myb68, and a corresponding wild type. Seedlings were transplanted to soil on day ten post germination. At the early flowering stage, plants were placed into a heating chamber at 45° C., 65% humidity) for 24-30 minutes. The plants were then placed back into the growing chamber under normal growth conditions (17 h light/7 h dark, 200 µE, 22° C., 70% humidity). Plants were examined on day thirty-two and scored for aborted siliques, partially aborted siliques, dead meristems or normal siliques. A heat stress was deemed effective if a majority of wild type plants had significant flower abortion Transgenic lines were assessed for gene expression by RT-PCR and demonstrated to have elevated expression levels.

Constructs and transgenic plants are produced using homologous of Myb-subgroup14 sequences from desired crop species, for example, rice, corn, wheat, soybean and cotton and evaluated for heat tolerance.

TABLE 13

| Construct | flower abortion as % of control |
|---|---|
| 35S-Bn MYB68-bud | 84 |
| 35S-Bn-MYB68-root | 82 |
| 35S-GmMYB84 | 58 |
| 35S-AtMYB84 | 77 |
| 35S-AtMYB36 | 81 |

This example demonstrates that *Arabidopsis* can be used as a model system to assess and provide conformation that a Mub-subgroup14 sequence can provide heat tolerance and that sequences identified from other plant species are functional in *Arabidopsis*.

Characterization of *Arabidopsis* Lines Expressing a 35S-AtMYB36 Construct

Fifteen homozygous transgenic lines at T3 were evaluated in a flower abortion experiment. Plants (fourteen replicates per entry) were grown under optimal conditions (18 hr light, 200 uE, 22 C, 60% RH) in 2.25" pots until four days from first open flower. At that point plants were exposed to 1 hr treatment at 43 C. Following the heat treatment plants were returned to optimal conditions for 7 more days. The impact of heat treatment on the pod formation was assessed at that point by counting the aborted and damaged (short) pods in the region that was exposed to the heat stress. Nine transgenic lines showed reduction in the total number of damaged pods as compared to controls (wild type-Columbia and the null-n77-4) (see table below). Three of the lines examined here also showed reduced flower abortion at the T2 stage of screening. The myb68 mutant, included as a positive control also showed a reduction in the total number of damaged pods as compared to its segregating null control (myb68-null).

TABLE 14

| entry | total # of damaged pods | | total damaged pods as % of col |
|---|---|---|---|
| | Mean | Std Err | |
| 108-2 | 3.2 | 0.6 | 65% |
| 14-3 | 3.7 | 0.5 | 76% |
| 36-2 | 3.8 | 0.4 | 78% |
| 103-7 | 3.8 | 0.4 | 78% |
| 43-6 | 3.8 | 0.4 | 78% |
| 23-4 | 3.9 | 0.4 | 81% |
| 67-7 | 4.0 | 0.4 | 82% |
| 82-7 | 4.4 | 0.4 | 90% |
| 40-4 | 4.5 | 0.6 | 93% |
| n77-4 | 4.1 | 0.5 | 85% |
| col | 4.9 | 0.6 | 100% |
| myb68 | 3.1 | 0.4 | 72% |
| myb68-null | 4.3 | 0.5 | 100% |

Constitutive or Inducible Expression in *Brassica napus* of an *Arabidopsis* MYB68 Shows Reduced Flower Abortion Following Heat Stress Five transgenic lines having an *Arabidopsis* Myb68 gene sequence under the control of a constitutive promoter or a heat inducible promoter were evaluated for heat stress tolerance under growth chamber conditions. These lines were at the T2 stage and were heterozygous, with the exception of the 01-105G-1-E line. Analysis of heterozygous lines typically produces greater variation than the same analysis performed on homozygous lines. However, early analysis allows for screening and subsequent analysis of the derived homozygous lines. Segregating nulls and the parent DH12075 were included as controls. The experiment was arranged in a split-plot design with temperature as main factor and transgenic line as subfactor. The plants were grown in 15 cm plastic pots filled with "Sunshine Mix #3" under approximately 500 μmol m$^{-2}$ s$^{-1}$ photosynthetically active radiation at the top of the crop canopy. Molecular analysis was performed to confirm transgene presence. Two groups of plants were included in the test; one group was grown under optimum conditions (22/18° C. day/night temperature, 16-h photoperiod) throughout the growing period, while the second group was subjected to heat stress at 31° C. for 5 hr. per day (ramped-up from 18 to 31° C., then back down to 18° C.). Heat stress conditions were initiated on the third day following the first flower opening and for seven days thereafter. The heat-stressed plants were then returned to optimum conditions until maturity. All racemes on the stressed plants were marked at the beginning and end of the heat stress period, to indicate which flowers had been subjected to heat stress. Viable and aborted pods on the marked racemes were counted and the pod abortion rate calculated as the ratio of aborted pods to aborted plus viable pods under heat-stress conditions, expressed as percent. Seed yield was determined after harvest.

There were significant differences in flower abortion among different lines, with two 35S-Myb68 lines showing significantly reduced abortion rate under heat stress compared to the parental line. Line 02-104G-4-A had a significantly lower abortion rate (33%) than its segregating null (48%) and DH12075 (61%). The abortion rate for line 02-104G-3-K (47%) was also significantly lower than that of the segregating null (66%) and DH12075. The homozygous line (01-105G-1-E) had a slightly lower abortion rate (53%) than its segregating null (58%) and the parental control. Within a population of transgenic lines a gradation of expression levels and physiological response will exist. In part, the gradation of variation is a result of the site of integration of the gene construct and the local environment for gene expression at that locus. This gradation is expected and therefore, lines must be screened and evaluated in order to select the best performing lines. This process is one of routine to one skilled in the art.

Seed yield differed among the tested lines. The yield of three transgenic lines, 02-104G-3-K, 02-104G-4-A and 01-105G-1-E, was similar to that of the parental line, however compared to it's own null the three lines showed between 10% and 22% increase in seed yield. Two transgenic lines (02-33H-1-V and 01-105G-3-G) appeared to under perform compared to the DH12075 parent however, compared to appropriate nulls, one line was significantly lower. Due to the zygosity of these lines such variability is not unexpected.

A similar trend was found for seed number per raceme under heat stress conditions. Lines 02-104G-3-K, 02-104G-4-A and 01-105G-1-E had a slightly higher seed number per raceme but the other transgenic lines (02-33H-1-V and 01-105G-3-G) had significantly lower seed number per raceme compared the parent line. There were no significant differences in 100 seed weight among the tested lines.

In general, two transgenic lines expressing the *Arabidopsis* Myb68 gene demonstrated significant protection against flower abortion during heat stress imposed at flowering. Additionally, three transgenic lines indicated a trend of increased seed yield.

TABLE 15

| Construct | Line | abortion rate % | S.E. | Ab % null | Yield | S.E. | Yield % Null |
|---|---|---|---|---|---|---|---|
| 35S-MYB68 | 02-104G-3-K | 47 | 4.8 | 71 | 0.71 | 0.188 | 122 |
| | 02-104G-3-G null | 66 | 3.7 | | 0.58 | 0.091 | |
| | 02-104G-4-A | 33 | 7.6 | 69 | 0.75 | 0.153 | 110 |
| | 02-104G-4-F null | 48 | 2.8 | | 0.68 | 0.090 | |
| | 02-33H-1-V | 79 | 1.9 | 116 | 0.31 | 0.159 | 44 |
| | 02-33H-1-F null | 68 | 4.3 | | 0.71 | 0.090 | |

TABLE 15-continued

| Construct | Line | abortion rate % | S.E. | Ab % null | Yield | S.E. | Yield % Null |
|---|---|---|---|---|---|---|---|
| P18.2-MYB68 | 01-105G-1-E | 53 | 4.1 | 91 | 0.73 | 0.097 | 116 |
| | 01-105G-1-B null | 58 | 3.0 | | 0.63 | 0.090 | |
| | 01-105G-3-G | 75 | 4.9 | 94 | 0.31 | 0.099 | 96 |
| | 01-105G-3-J null | 80 | 3.6 | | 0.32 | 0.097 | |
| Control | DH12075 parent | 61 | 2.4 | | 0.62 | 0.106 | |

Example 9: Identification of MYB-Subgroup14 Sequences and Homologues

Methods for identification of *Arabidopsis* MYB sequences, classification of MYB sequences into designated subgroups and identification of MYB-subgroup14 sequences are further described in Stracke et al., 2001 and Kranz et al., 1998. MYB-subgroup14 sequences have been is defined as a nucleotide or protein sequence comprising an *Arabidopsis* the characteristics described herein. The MYB-subgroup14 is a R2R3 MYB sequence that additionally comprises a conserved motif or motifs as described by the following patterns.

The general pattern (SEQ ID NO:266) provides a sequence that can be used to identify a candidate MYB-subgroup14 sequence. At some positions multiple amino acid residues are permitted at a given location. Where multiple amino acids are permitted, the optional residues are indicated within square brackets. Where a R2R3 MYB protein sequence fits the general pattern it is likely to be a MYB-subgroup14 sequence. A MYB-subgroup14 sequence may be less than identical to the general pattern, for example it may be 90%, 95% or 99% identical.

If a candidate MYB-subgroup14 sequence, matching the general pattern further includes a match to the exclusive pattern (SEQ ID NO:267) then the sequence is a strong candidate for inclusion as a MYB-subgroup14 sequence. The exclusive sequence (SEQ ID NO:267) defines the pattern of amino acids that are present in MYB-subgroup14 sequences but may differ in other R2R3 MYB proteins. Presence of the exclusive pattern within a MYB protein is a strong indicator that the MYB is a member of the MYB-subgroup14 family.

If a candidate MYB-subgroup14 sequence, matching the general pattern further includes a match to the absolute pattern (SEQ ID NO:268) then the sequence is a strong candidate for inclusion as a MYB-subgroup 14 sequence. The Absolute pattern (SEQ ID NO:268) represents sequence residues present in all MYB-subgroup14 sequences analyzed to date.

For the general, exclusive, and absolute patterns (SEQ ID NOs:266-268) listed below, "X" denotes any amino acid, "X(N)", where N is any number, denotes a string of the indicated number of "X"s, (i.e., X(23) denotes a string of 23 "X"s), where X is any amino acid. At some positions multiple amino acid residues are permitted at a given location. Where multiple amino acids are permitted, the optional residues are indicated within square brackets.

```
General Pattern
                                    (SEQ ID NO: 266)
M-G-R-X-P-C-C-D-[KR]-X-X-[MV]-K-[RK]-G-X W-[SA]-X-

[DQE]-E-D-X-X-[IL]-[RK]-X-[FY]-X-X-X-X-G-X-X-X-
```

```
                -continued
[SN]-W-I-X-X-P-X-[RK]-X-G-[IL]-X-R-C-G-[KR]-S-C-R-

L-R-W-[IL]-N-Y-L-R-P-X-[IL]-[RK]-H-G-X-[FY]-[ST]-

X-X-E-[DE]-X-X-[IV]-X-X-X-[FY]-X-X-X-G-S-[KR]-W-S-

X-[MI]-A-X-X-[ML]-X-X-R-T-D-N-D-[ILV]-K-N-[HY]-W-

[DN]-[ST]-[RK]-L-[RK]-[RK]-[RK]

Exclusive Pattern
                                    (SEQ ID NO: 267)
[RK]-X(9)G-X-X-I-X(28)-H-X(14)-[YF]-X(4)-S-X(23)-

[RK]

Absolute Pattern
                                    (SEQ ID NO: 268)
G-X-W-X-X-X-E-D-X-X-[IL]-[RK]-X-X-X-X-X-G-X(23)-

R-W-[IL]-N-Y-L-R-P-X-[IL]-[RK]-H-G-X-[FY]-X-X-X-E-

[DE]-X(13)-W-X-X-X-A-X-X-X-X-R-T
```

MYB-subgroup14 sequences can be defined by the consensus sequence of SEQ ID NO:266. Positions have been identified in which the amino acid residues are found exclusively or predominately in the MYB-subgroup14 sequences. In the following description all position numbers are in reference to *Arabidopsis* MYB68 protein (SEQ ID NO:2) which correlates to the general consensus sequence above, SEQ ID NO:266.

Within the R2 domain at position 26, a positively charged (K or R) residue is conserved in MYB-subgroup14. Although this amino acid is not exclusive to this subgroup at this position, the tendency for the rest of the *Arabidopsis* MYB proteins is for a hydrophobic residue, with over 50% of all MYB proteins having a hydrophobic isoleucine or valine residue (Stracke et al., 2001).

At position 36, all members of subgroup 14 contain an insertion, resulting in an extra amino acid residue. This appears to be exclusive to MYB-subgroup14. Glycine (G), a small hydrophobic residue, is the extra residue in all cases except in MYB87 (SEQ ID NO:32), which contains an asparagine residue at this position and a rice homologue (SEQ ID NO:194) which contains an argentine at this position.

At position 39, members of the MYB-subgroup14 predominantly contain a hydrophobic isoleucine residue. One exception to this is a rice homologue identified as SEQ ID NO:191, which possesses a glutamine at this position. Although other hydrophobic residues are generally found in MYB proteins at this position, isoleucine appears to be exclusive to MYB-subgroup14. Additionally, positively charged residues (39% R), and polar residues (23% N) are most prevalent at this position.

Within the R3 domain at position 68, all MYB-subgroup14 members contain the positively charged histadine residue. A positively charged residue appears at this position in all MYB proteins; however in contrast to the MYB-subgroup14, in other MYB proteins 73% contain an arginine (R) and 17% contain a lysine residue.

At position 83, most members of MYB-subgroup14 contain an aromatic hydrophobic residue (tyrosine Y, or phenylalanine F). The appearance of an aromatic hydrophobic residue at this position seems to be exclusive to MYB-subgroup14. The majority of MYB proteins have a histidine residue (87%). This histidine has been suggested to be a crucial residue in the hydrophobic core of the helix (Ogata et al., 1992). Through NMR analysis, it appears to be in contact with two of the critical tryptophan residues. The absence of a histidine at position 83 does not necessarily exclude it as a member of MYB-subgroup14 as members have been identified that do possess a histidine residue, for example SEQ ID NO:169 and SEQ ID NO:225.

At position 88, members of MYB-subgroup14 contain the polar serine residue, while almost all other MYB proteins (91%) contain the polar asparagine residue. A serine residue appears to be exclusive to this subgroup. The absence of a serine at position 88 does not necessarily exclude it as a member of MYB-subgroup14 as at least one MYB-subgroup14 member has been identified that possesses a phenylalanine residue in position 88, for example SEQ ID NO:256.

At position 112, members of MYB-subgroup14 contain a positively charged arginine or lysine residue. The majority of MYB proteins also contain positively charged residues at this position, however, histadine (48%) is the most prevalent residue found. The absence of a arginine at position 112 does not necessarily exclude it as a member of MYB-subgroup14 as at least one MYB-subgroup14 member has been identified that possesses a glutamic acid residue in position 112, for example SEQ ID NO:68 contains a glutamic acid residue and SEQ ID NO:191 contains a threonine.

Variation within a R2R3 domain is permissible as shown in the identified consensus sequences. A R2R3 domain of a MYB-subgroup14 sequence may be 90% homologous, preferably 95% homologous or more preferably 99% homologous to the consensus sequence presented.

The Addition of S1 and S2 Motifs

Within MYB-subgroup14 the MYB68 and MYB84 sequences contain two further conserved motifs identified as S1 (SFSQLLLDPN) (SEQ ID NO:269) and S2 (TSTSADQSTISWEDI) (SEQ ID NO:270). These motifs are found in both *Arabidopsis* and *Brassica* MYB68, MYB36 and MYB84 sequences and show at least 70% homology within the amino acid sequence. Additionally, homology to the S1 or S2 motifs was found to exist in orthologs in *Brassica napus* (Canola), *Brassica rapa* (Cabbage), *Brassica oleracea, Raphanus raphanistrum* (Radish), and homology to the S2 region in *Poncirus trifoliate* (Orange), and weak homology in a *Medicago trunculata* homologue and *Vitis vinifera* (Grape) homologue within the S2 region.

For inclusion as a S1 or S2 motif target sequences show homology of at least 70%, more preferably 80% and most preferably 95%.

The MYB68 and MYB84 sequences from species other than *Arabidopsis* and *Brassica* may not contain a 51 and S2 motif but may still be classified as a MYB subgroup-14 sequence based on sequence analysis and inclusion of other criteria.

Identification of MYB-Subgroup14 Members, Including MYB68, Homologues

Homologues of an *Arabidopsis* MYB-subgroup14 sequence (Table 1) or a desired MYB68 (SEQ ID NO:1, SEQ ID NO:2), can be found using a variety of public or commercial software that is known to those skilled in the art.

Blast alignments can be performed and putative sequences identified. Searches can be performed as outlined herein. The top homologues are determined using programs such as tblastn, tblastp, searches against available databases in NCBI, such as the EST, GSS, HTG and chromosomal databases, as well as other genomic databases, such as the TIGR unigene database, Cucurbit genomics database, Sunflower and Lettuce, *Medicago truncatula* (International Medicago Genome Annotation Group), SGN, and Orange. In instances where species were more highly divergent, the alignment parameters such as Gap costs, matrix values can be appropriately changed.

To confirm the top hit to AtMYB68 in each species is in fact a MYB68 homologue, a reciprocal blast can be performed, in which the homologue is blasted against all *Arabidopsis* proteins. In many cases the homologue's closest *Arabidopsis* hit is to one of MYB68's gene family members (a MYB subgroup-14), instead of MYB68 itself. In cases where the homologue is closest to an *Arabidopsis* protein outside of the MYB68 gene family, the homologue is assessed not to be a MYB-subgroup14 member.

Open reading frames may be determined using programs such as "getorf" from the EMBOSS program, or ESTScan.

Methods for identification of MYB sequences, classification of MYB sequences into designated subgroups and identification of MYB-subgroup14 sequences are further described in Stracke et al., 2001 and Kranz et al., 1998.

Weakly conserved homologues between highly divergent species are often not found using traditional blast methods. In such cases, conserved motifs, domains and fingerprints will exist between homologues, and are good predictors of functional homology. Many programs exist that are proficient at finding conserved domains across species using hidden markov models, position-specific-scoring matrices, and patterns. PSI-Blast, PRATT, PHI-Blast, and HMM-Build/HMMSearch.

PRATT is a tool provided by the PROSITE database. It generates conserved patterns from a group of conserved proteins. PRATT was used to determine a conserved pattern between MYB68 and its closest homologues. ScanProsite and PHI-BLAST was then used to look for the conserved pattern in the Swiss-Prot and NCBI protein databases respectively. The search results are limited to alignments that also contain the pattern.

HMMBuild was used to build a hidden markov model using the MYB68 and its homologues. HMMSearch was used to scan NCBI's protein database using the hidden markov model. Similar proteins to the basic blastp search were found.

Utilizing the above methods, MYB68 homologues were found in over 50 different plant species. Homology was restricted in most cases to the N-terminal MYB DNA binding domain. Homology in the less conserved C-terminal region existed in genes found in *Brassica napus* (Canola), *Brassica rapa* (Cabbage), *Brassica oleracea, Raphanus raphanistrum* (Radish), *Poncirus trifoliate* (Orange), and weak homology in genes found in *Medicago trunculata* homologue and *Vitis vinifera* (Grape) within the S2 region.

The *Poncirus trifoliate* and *Brassica rapa* genes were identified by downloading strong EST hits, and assembling them using CAP3. The resulting contigs did not code for a complete protein. The contig sequence from Orange coded for a partial protein spanning only the S2 region, and in *Brassica rapa*, a partial 202 aa protein spanning from 1-202 in AtMYB68 was found.

A variety of programs have characterized the MYB domain with profiles, patterns, and hidden markov models.

To confirm the presence of the MYB domain in a unknown sequence, a sequence can be searched against these profiles. InterProScan is particularly useful as it provides an interface to query 13 programs simultaneously. The databases incorporated in InterPro include a) ProDom: a database of protein domain families. Built by clustering homologous segments from Swiss-Prot/Trembl database, followed by recursive PSI-BLAST searches.
b) HMMTIGR: Protein families represented by Hidden Markov Models.
c) TMHMM: Predicton of transmembrane helices in proteins.
d) FPrintScan: Searches the PRINTS database of fingerprints. Fingerprints are protein families represented by multiple motifs.
e) ProfileScan: Profiles from family related sequences.
f) HMMPanther: A database of hidden markov models
g) HMMPIR: Hidden markov models based on evolutionary relationship of whole proteins.
h) ScanRegExp: Scans the prosite database of patterns and profiles
i) Gene3D: a database of proteins containing functional information
j) HMMPfam: Protein domain families represented by hidden markov models.
k) Superfamily: a database of structural and functional protein annotations for all completely sequenced organisms.
l) HMMSmart: Allows the identification of mobile domains based on hidden markov models.
m) SignalIP: predicts the presence and location of signal peptide cleavage sites in amino acid sequences.

Blocks are multiply aligned ungapped segments corresponding to the most highly conserved regions of proteins. The MYB domain is represented by three blocks. As expected AtMYB68 contained each of these three blocks, as well as 1 of the 5 Wos2 blocks.

The invention is based in part on the discovery of plants that are heat stress tolerant. The gene responsible for the heat tolerant phenotype has been determined and shown to be a MYB68 gene. Methods of producing a heat tolerant transgenic plant are disclosed herein. Specifically the invention identifies a transcription factor gene family, specifically the MYB gene family, and in particular a MYB-subgroup14 that when expressed in plants results in plants that are heat stress tolerant and have an increased yield following a heat stress or display tolerance to drought stress or salt stress.

Example 10: Identification of MYB68 Homologues

Homologues from the same plant, different plant species or other organisms were identified using database sequence search tools, such as the Basic Local Alignment Search Tool (BLAST) (Altschul et al. (1990) J. Mol. Biol. 215:403-410; and Altschul et al. (1997) Nucl. Acid Res. 25: 3389-3402). The tblastn or blastn sequence analysis programs were employed using the BLOSUM-62 scoring matrix (Henikoff, S. and Henikoff, J. G. (1992) Proc. Natl. Acad. Sci. USA 89: 10915-10919). The output of a BLAST report provides a score that takes into account the alignment of similar or identical residues and any gaps needed in order to align the sequences. The scoring matrix assigns a score for aligning any possible pair of sequences. The P values reflect how many times one expects to see a score occur by chance. Higher scores are preferred and a low threshold P value threshold is preferred. These are the sequence identity criteria. The tblastn sequence analysis program was used to query a polypeptide sequence against six-way translations of sequences in a nucleotide database. Hits with a P value less than −25, preferably less than −70, and more preferably less than −100, were identified as homologous sequences (exemplary selected sequence criteria). The blastn sequence analysis program was used to query a nucleotide sequence against a nucleotide sequence database. In this case too, higher scores were preferred and a preferred threshold P value was less than −13, preferably less than −50, and more preferably less than −100.

Alternatively, a fragment of a sequence from SEQ ID NO: 1, 3, 5, 7, 9, 11, 13, 15, 17, 19, 21, 23, 25, 27, 29, 31, 33, 35, 37, 38, 40, 42, 44, 46, 48, 50, 52, 54, 56, 58, 59, 61, 63, 65, 67, 69, 71, 73, 75, 77, 79, 81, 83, 85, 87, 88, 90, 91, 92, 94, 96, 98, 100, 102, 104, 106, 108, 109, 110, 112, 114, 116, 118, 120, 122, 124, 125, 127, 129, 130, 132, 134, 135, 137, 139, 141, 143, 145, 147, 149, 151, 153, 155, 156, 158, 160, 162, 164, 166, 168, 170, 172, 174, 176, 178, 180, 182, 184, 186, 188, 190, 192, 194, 196, 198, 200, 202, 204, 206, 208, 210, 211, 213, 214, 216, 217, 218, 220, 222, 224, 226, 228, 230, 232, 234, 236, 238, 240, 242, 244, 246, 247, 249, 251, 253, 255, 257, 259, 261, 263 and 265 is $^{32}$P-radiolabeled by random priming (Sambrook et al., (1989) Molecular Cloning. A Laboratory Manual, $2^{nd}$ Ed., Cold Spring Harbor Laboratory Press, New York) and used to screen a plant genomic library (the exemplary test polynucleotides) As an example, total plant DNA from *Arabidopsis thaliana*, *Nicotiana tabacum*, *Lycopersicon pimpinellifolium*, *Prunus avium*, *Prunus cerasus*, *Cucumis sativus*, or *Oryza sativa* are isolated according to Stockinger al (Stockinger, E. J., et al., (1996), J. Heredity, 87:214-218). Approximately 2 to 10 µs of each DNA sample are restriction digested, transferred to nylon membrane (Micron Separations, Westboro, Mass.) and hybridized. Hybridization conditions are: 42.degree. C. in 50% formamide, 5×SSC, 20 mM phosphate buffer 1×Denhardt's, 10% dextran sulfate, and 100 µg/ml herring sperm DNA. Four low stringency washes at RT in 2×SSC, 0.05% sodium sarcosyl and 0.02% sodium pyrophosphate are performed prior to high stringency washes at 55° C. in 0.2.times.SSC, 0.05% sodium sarcosyl and 0.01% sodium pyrophosphate. High stringency washes are performed until no counts are detected in the washout according to Walling et al. (Walling, L. L., et al., (1988) Nucl. Acids Res. 16:10477-10492).

Example 11: Identification of MYB68 Technical Features

A MYB68 gene can be identified by identifying genes that have high homology to an *Arabidopsis* MYB68 (SEQ ID NO:1). In addition to having homology of the nucleotide or amino acid sequence, one may identify candidate genes that share conformational protein structure. Such structural motifs may assist in identification of related proteins and their structure and function relationships.

Example 12: Functional Confirmation of Homologues

Candidate homologues are introduced into *Arabidopsis* and assessed for heat tolerance. Genes disclosed as SEQ ID NO: 1, 3, 5, 7, 9, 11, 13, 15, 17, 19, 21, 23, 25, 27, 29, 31, 33, 35, 37, 38, 40, 42, 44, 46, 48, 50, 52, 54, 56, 58, 59, 61, 63, 65, 67, 69, 71, 73, 75, 77, 79, 81, 83, 85, 87, 88, 90, 91, 92, 94, 96, 98, 100, 102, 104, 106, 108, 109, 110, 112, 114, 116, 118, 120, 122, 124, 125, 127, 129, 130, 132, 134, 135, 137, 139, 141, 143, 145, 147, 149, 151, 153, 155, 156, 158, 160, 162, 164, 166, 168, 170, 172, 174, 176, 178, 180, 182, 184, 186, 188, 190, 192, 194, 196, 198, 200, 202, 204, 206, 208, 210, 211, 213, 214, 216, 217, 218, 220, 222, 224, 226, 228, 230, 232, 234, 236, 238, 240, 242, 244, 246, 247, 249, 251, 253, 255, 257, 259, 261, 263 and 265 are expressed in *Arabidopsis* plants and heat tolerance assessed as described herein. Optionally, the expression of If a candidate MYB-subgroup14 sequence, matching the general pattern further includes a match to the exclusive pattern then the sequence is a strong candidate for inclusion as a MYB-subgroup14 genes or MYB68 genes can be evaluated in any transformable species, for example, *Brassica*, maize, cotton, soybean or rice. Examples of such functional testing have been provided in this disclosure.

It is noted that some of the sequences disclosed herein are not full length. Full length sequences can be obtained by standard molecular methods known to those of skill in the art. The full length sequences can then be expressed as described herein.

What is claimed is:

1. A method of producing a heat stress tolerant plant, comprising:
    a) providing a nucleic acid encoding a plant MYB subgroup-14 polypeptide, wherein said plant MYB subgroup-14 polypeptide is MYB68;
    b) inserting said nucleic acid into a vector;
    c) transforming a plant, a tissue culture, or a plant cell with said vector to obtain a transformed plant, tissue culture, or plant cell;
    d) increasing expression of said plant MYB subgroup-14 polypeptide in said transformed plant, tissue culture, or plant cell as compared to a wild type plant of the same species not transformed with said vector;
    e) growing said transformed plant or regenerating a plant from said transformed tissue culture or plant cell, wherein a heat stress tolerant plant is produced which has an increased heat stress tolerance as compared to a wild type plant of the same species not transformed with said vector; and
    f) selecting the heat stress tolerant plant by exposing the plant to heat stress conditions.

2. The method according to claim 1, wherein said vector comprises a constitutive promoter or an inducible promoter.

* * * * *